United States Patent
Siliphaivanh et al.

(10) Patent No.: US 9,884,048 B2
(45) Date of Patent: Feb. 6, 2018

(54) ERK INHIBITORS

(71) Applicant: Merck Sharp & Dohme Corp., Rahway, NJ (US)

(72) Inventors: Phieng Siliphaivanh, Newton, MA (US); Joey Methot, Westwood, MA (US); Kathryn Ann Lipford, Boston, MA (US); Danielle Molinari, Brookline, MA (US); David L. Sloman, Brookline, MA (US); David Witter, Norfolk, MA (US); Hua Zhou, Acton, MA (US); Christopher Boyce, Flemington, NJ (US); Xianhai Huang, Warren, NJ (US); Jongwon Lim, Lexington, MA (US); David Guerin, Natick, MA (US); Ganesh Babu Karunakaran, Tamil Nadu (IN); Raman Kumar Bakshi, Edison, NJ (US); Ziping Liu, Beijing (CN); Jianmin Fu, Beijing (CN); Zhilong Wan, Beijing (CN); Wei Liu, Beijing (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 15/531,759

(22) PCT Filed: Dec. 10, 2015

(86) PCT No.: PCT/US2015/064860
§ 371 (c)(1),
(2) Date: May 31, 2017

(87) PCT Pub. No.: WO2016/100050
PCT Pub. Date: Jun. 23, 2016

(65) Prior Publication Data
US 2017/0266167 A1 Sep. 21, 2017

(30) Foreign Application Priority Data
Dec. 15, 2014 (WO) .............. PCT/CN2014/093860

(51) Int. Cl.
*A61K 31/437* (2006.01)
*A61K 31/4545* (2006.01)
*A61K 31/444* (2006.01)
*C07D 471/04* (2006.01)
*C07D 519/00* (2006.01)

(52) U.S. Cl.
CPC .......... *A61K 31/437* (2013.01); *A61K 31/444* (2013.01); *A61K 31/4545* (2013.01); *C07D 471/04* (2013.01); *C07D 519/00* (2013.01)

(58) Field of Classification Search
CPC .................................................... A61K 31/437
See application file for complete search history.

(56) References Cited

U.S. PATENT DOCUMENTS

| | | | |
|---|---|---|---|
| 9,546,168 B2 * | 1/2017 | Lipford | ............... A61K 31/437 |
| 2010/0249096 A1 | 9/2010 | Aay et al. | |
| 2013/0039906 A1 | 2/2013 | Do et al. | |
| 2014/0031360 A1 | 1/2014 | Wang et al. | |

FOREIGN PATENT DOCUMENTS

| | | |
|---|---|---|
| WO | 2007070398 A1 | 6/2007 |
| WO | 2008153858 A1 | 12/2008 |
| WO | 2009105500 A1 | 8/2009 |
| WO | 2014186313 A1 | 11/2014 |

* cited by examiner

*Primary Examiner* — Rebecca L Anderson
*Assistant Examiner* — Karen Cheng
(74) *Attorney, Agent, or Firm* — Catherine D. Fitch; Richard S. Parr

(57) ABSTRACT

The present invention provides a compound of Formula (I) or the pharmaceutically acceptable salts, esters, and prodrugs thereof, which are ERK2 inhibitors. The invention also provides a pharmaceutical composition comprising an effective amount of at least one compound of Formula (I) and a pharmaceutically acceptable carrier. The invention also provides a pharmaceutical composition comprising an effective amount of at least one compound of Formula (I) and an effective amount of at least one other pharmaceutically active ingredient (such as, for example, a chemotherapeutic agent), and a pharmaceutically acceptable carrier.

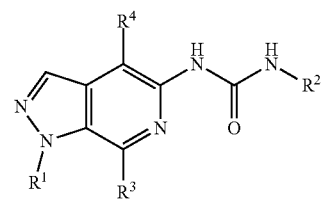

I

6 Claims, No Drawings

ERK INHIBITORS

This application is a National Stage application of PCT/US2015/064860, filed Dec. 10, 2015, which claims the benefit of PCT Application Serial No. PCT/CN2014/093860, filed Dec. 15, 2014, which is incorporated herein by reference in its entirety.

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumors. Therefore, a welcome contribution to the art would be small-molecules (i.e., compounds) that inhibit ERK activity (ERK2 activity), which small-molecules may be useful for treating a broad spectrum of cancers, such as, for example, melanoma, pancreatic cancer, thryroid cancer, colorectal cancer, lung cancer, breast cancer, and ovarian cancer.

SUMMARY OF THE INVENTION

This invention provides compounds of the Formula I:

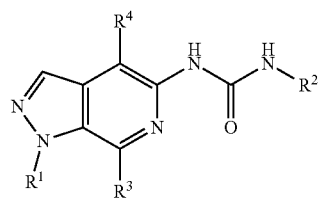

I or the pharmaceutically acceptable salts, esters, and prodrugs thereof, which are ERK2 inhibitors.

DETAILED DESCRIPTION OF THE INVENTION

One embodiment of the invention is compounds of formula I

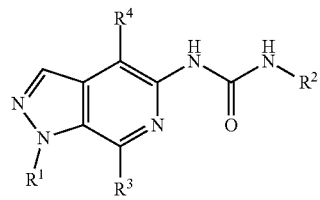

I or a pharmaceutically acceptable salt thereof, wherein
$R^1$ is
  1) a $C_{4-8}$ monocyclic or bicyclic carbocycle, wherein the monocyclic carbocycle is saturated or unsaturated, and wherein the bicyclic carbocycle comprises 2 fused rings which are independently saturated or unsaturated, wherein the monocyclic or bicyclic carbocycle is unsubstituted or monosubstituted with halogen,
  2) a 5-10 membered monocyclic or bicyclic heterocycle having 1-3 heteroatoms independently selected from N, S and O, wherein the monocyclic heterocycle is saturated or unsaturated, and wherein the bicyclic heterocycle comprises 2 fused rings which are independently saturated or unsaturated, wherein the monocyclic or bicyclic heterocycle is unsubstituted or substituted with $C_{1-4}$alkyl, =O, or $C(O)OC(C_{1-4}alkyl)_3$,
  3) —$CH_2R^5$, wherein $R^5$ is H, $C_{1-4}$alkyl, pyridine, $C_{3-5}$cycloalkyl, —$CH_2OH$, $CH_2OCH_3$, $CF_3$, $CH_2CN$, $CH_2CH_2OC_{1-4}$alkyl, $CH(C_{1-4}alkyl)_2$, or a 4-6 membered unsubstituted monocyclic saturated heterocycle having 1 O atom,
  4) hydrogen,
  5) $C(O)R^6$, wherein $R^6$ is —$NHC_{1-4}$alkyl,
  6) —$CHR^7R^8$, wherein $R^7$ and $R^8$ are independently $C_{1-4}$alkyl, or
  7) $C_{1-4}$alkyl;
$R^2$ is
  1) $CH_2R^9$, where $R^9$ is
    a) unsubstituted phenyl or phenyl substituted one, two or three times independently selected from
      1) halogen, 2) —$OC_{1-4}$alkyl, 3) 5-membered saturated or unsaturated heterocycle which is unsubstituted or substituted with =O having 1 or 2 heteroatoms selected from O and N,
      4)

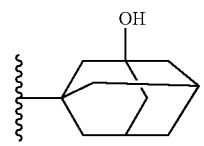 [SMILES: *C12CC3CC(C1)CC(O)(C3)C2]

5) —$SO_2C_{1-4}$alkyl, 6) —$C(O)NHC_{1-4}$alkyl, 7) —$C(C_{1-4}alkyl)_2OH$, or
      8) —$NHSO_2C_{1-4}$alkyl,
    b) —$CH_2R^{13}$ wherein $R^{13}$ is
      1) $C_6H_5$, 2) $N(C_{1-4}alkyl)_2$, 3) $C_6H_4F$, 4) halogen, 5) —$OC_{1-4}$alkyl, 6) $CF_3$, 7) O—$C_6H_4F$, 8) $OCH_2C_6H_5$, 9) $NHCH_2C_6H_5$, 10) 6-membered saturated heterocycle which is unsubstituted or substituted with —$CH_2OC_6H_5$ having 1 or 2 heteroatoms selected from O and N, 11) 5-membered saturated heterocycle which is unsubstituted having 1 heteroatom which is O, 12) 5-membered unsaturated heterocycle which is unsubstituted or mono- or di-substituted with $C_{1-4}$alkyl having 1 or 2 heteroatoms independently selected from N and O, or

12)

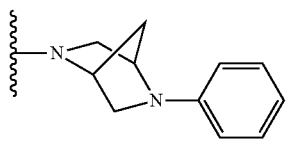 [SMILES: *N1CC2CC1CN2c1ccccc1]

c) $C_{3-6}$cycloalkyl unsubstituted or substituted with —N($C_{1-4}$alkyl)$_2$, d) 10-membered bicyclic carbocycle comprising two fused rings, wherein one ring is unsaturated, e) —CHR$^{19}$R$^{10}$, wherein R$^{19}$ and R$^{10}$ are independently selected from
  1) pyridine, 2) 6-membered saturated heterocycle, having 1 or 2 heteroatoms selected from O and N, which is unsubstituted or substituted with one or two F, 3) —CH$_2$OH, 4) phenyl, 5) piperidine, 6) $C_6H_4F$, 7) $CH_3$, 8) OH, or 9) $C_6H_4CF_3$, f) a 4-10 membered monocyclic or bicyclic heterocycle having 1-3 heteroatoms independently selected from N, S and O, wherein the monocyclic heterocycle is saturated or unsaturated, and wherein the bicyclic heterocycle is saturated or unsaturated, wherein the monocyclic or bicyclic heterocycle is unsubstituted or independently mono-, di- or tri-substituted with —CHCF$_3$CH$_3$, $C_6H_4F$, $C_6H_4FCl$, $CH_2CF_3$, $C_{1-4}$alkyl, =O, $C_6H_5$, or halogen, g) $CF_2C_6H_5$, or h)

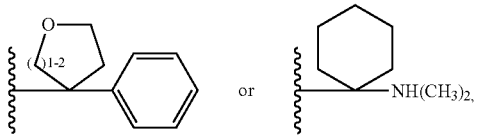

2) —CHR$^{11}$R$^{12}$, where R$^{11}$ and R$^{12}$ are independently selected from
  a) $C_{1-4}$alkyl, b) —O$C_{1-4}$alkyl, c) $CF_3$,
  d) $C_6H_4R^{12'}$ where R$^{12'}$ is halogen, —OCF$_3$, —SO$_2C_{1-4}$alkyl, H, or a 5-membered unsaturated unsubstituted heterocycle or heterocycle substituted with $C_{1-4}$alkyl having 2 or 3 heteroatoms selected from O, N and S,
  e) $CH_2CH_2$N($C_{1-4}$alkyl)$_2$,
  f) $CH_2CH_2R^{12''}$ where R$^{12''}$ is a 6-membered saturated or unsaturated heterocycle which heterocycle is unsubstituted or mono- or di- substituted with halogen,
  g) $CH_2NH_2$, h) $CH_2OH$, i) $C_6H_5SO_2C_{1-4}$alkyl, j) $CHF_2$, k) $CH_2CH_2OH$,
  l) $CH_2OC_{1-4}$alkyl, m) —O$C_{1-4}$alkyl, n) —CH$_2$N(CH$_3$)$_2$,
  o) —CH$_2$R$^{12'''}$ where R$^{12'''}$ is a
    1) 5-membered unsaturated unsubstituted heterocycle having 2 N atoms, 2) —O$C_{1-4}$ alkyl, 3) N($C_{1-4}$alkyl)$_2$, 4) —CH$_2$OCH$_2$CH$_2$O$C_{1-4}$alkyl,
    5) C(O)O$C_{1-4}$alkyl, 6) NH$_2$, 7) NHC(O)CH=CH$_2$, 8) C($C_{1-4}$alkyl)$_2$OH,
    9) OH, 10) a 6-membered saturated heterocycle having 2 heteroatoms independently selected from N and O,
  p) C(O)NH$C_{1-4}$alkyl, q) C(O)N($C_{1-4}$alkyl)$_2$, r) $C_6H_3FCl$,
  s) C($C_{1-4}$alkyl)$_2$OH, t) $C_6H_3Cl_2$, u) C($C_{1-4}$alkyl)$_2$OH, v) CH($C_{1-4}$alkyl)OH, w) C($C_{1-4}$alkyl)$_3$, x) —C($C_{1-4}$alkyl)$_2$OH,
  y) a 5-membered unsaturated or saturated heterocycle having one or two heteroatoms independently selected from N, O and S atoms, which heterocycle is unsubstituted or substituted with $C_{1-4}$alkyl,
  z) a 6-membered unsaturated heterocycle having one heteroatom which is N, which heterocycle is unsubstituted, or
  aa) C(O)OCH$_3$, 3) a $C_{4-10}$ monocyclic or bicyclic saturated or unsaturated carbocycle, wherein the bicyclic carbocycle comprises 2 fused rings, wherein the monocyclic or bicyclic carbocycle is unsubstituted or monosubstituted with
  a) NH$_2$, b) NHC(O)$C_{1-4}$alkyl, c) —O$C_{1-4}$alkyl, d) —N($C_{1-4}$alkyl)$_2$,
  e) —O$C_{1-4}$alkyl, f) $C_6H_5$, g) NHC(O)$C_6H_5$, h) $C_6H_4F$, i) —OCH$_2C_6H_5$, j) —CH$_2C_6H_5$, k) —O$C_6H_5$,
  l) —OCH$_2$CH$_2$CH$_2C_6H_5$, m) —O$C_6H_4F$, or n) —O-pyridine, 4) a 5-10 membered monocyclic or bicyclic saturated or unsaturated heterocycle having 1-3 heteroatoms independently selected from N and O, wherein the monocyclic or bicyclic heterocycle is unsubstituted or independently mono-, di-, tri- or tetra-substituted with
  a) $C_6H_4Cl$, b) $C_{1-4}$alkyl, c) =O, d) $C_6H_5$, e) $C_{3-6}$cycloalkyl, f) $C_6H_4F$,
  g) $CH_2C_6H_3(OC_{1-4}$alkyl)(F), h) $C_6H_4(C_{1-4}$alkyl), i) $CH_2CH_2C_6H_5$,
  j) $CH_2CH_2CH_2C_6H_5$, k) O$C_{1-4}$alkyl, l) —O$C_6H_5$, m) $CH_2C_6H_3F_2$,
  n) $CH_2C_6H_4CF_3$, o) $CH_2C_6H_4CN$, p) O$C_6H_4F$, q) —O$C_{1-4}$alkyl,
  r) a 5-6-membered heterocycle saturated or unsaturated, unsubstituted or substituted with $C_{1-4}$alkyl, $C_6H_5$ or $C_{3-6}$cycloalkyl, having 1 or 2 heteroatoms independently selected from O, N and S,
  s) —CH$_2$—R$^{2'}$, wherein R$^{2'}$ is a 5-6-membered unsaturated heterocycle, unsubstituted or substituted with halogen, having 1 or 2 heteroatoms independently selected from N and S, or
  t) —O—R$^{2''}$, wherein R$^{2''}$ is a 6-membered unsaturated heterocycle, unsubstituted or mono- or di-substituted with halogen, having 1 N heteroatom, 5) —CR$^{13}$R$^{14}$R$^{15}$ where R$^{13}$ and R$^{14}$ are independently $C_{1-4}$alkyl or together with the carbon atom to which they are attached form cyclopropyl, and R$^{15}$ is CN or $C_6H_5$, or

6)

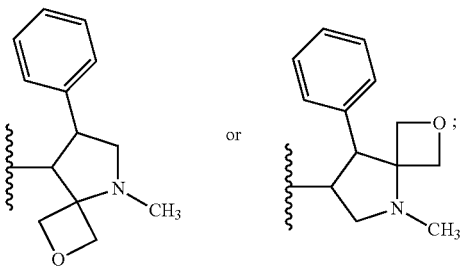 [SMILES: *C1C(c2ccccc2)CN(C)C12COC2 ; *C1CN(C)C2(COC2)C1c1ccccc1]

R[3] is hydrogen, —OC$_{1-4}$alkyl, —OC$_{1-4}$alkyl-OH, or —CH$_2$R[3'], wherein R[3'] is
  1) —OC$_{1-4}$alkyl, 2) 6-membered saturated unsubstituted heterocycle having 1 or 2 heteroatoms independently selected from N and O, 3) —NHC$_{1-4}$alkyl,
  4) —OC$_{1-4}$alkyleneR[3''] where R[3''] is a 4-6-membered saturated unsubstituted heterocycle having 1 or 2 heteroatoms selected from N and O,
  5) —OC$_{1-4}$alkylene-OH, 6) —OC$_{1-4}$alkylene-OCH$_3$, 7) hydrogen,
  8) —OC$_{1-4}$alkylene-OCH$_2$C$_6$H$_5$, 9) —OH, 10) —NHC$_{1-4}$alkyleneOC$_{1-4}$alkyl,
  11) NH$_2$, 12) —NHC$_{1-4}$alkyleneN(C$_{1-4}$alkyl)$_2$, 13) —NHC(O)CH=CH$_2$,
  14) —NHC(O)C$_{1-4}$alkyl, 15) —NHC(O)OC$_{1-4}$alkyl, 16) —OC(O)NHC$_{1-4}$alkyl, 17) —CH$_2$NHC(O)CH=CH$_2$,
  18) N(C$_{1-4}$alkyl)$_2$, or
  19)

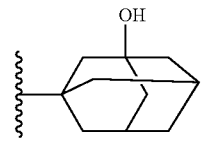

and
R[4] is hydrogen or halogen.
Another embodiment of the invention is compounds of Formula I, or a pharmaceutically acceptable salt thereof, wherein
R[1] is
  1) a C$_{4-8}$ monocyclic or bicyclic carbocycle, wherein the monocyclic carbocyle is saturated or unsaturated, and wherein the bicyclic carbocyle comprises 2 fused rings which are independently saturated or unsaturated, wherein the monocyclic or bicyclic carbocycle is unsubstituted or monosubstituted with F,
  2) a 5-10 membered monocyclic or bicyclic heterocycle having 1-3 heteroatoms independently selected from N, S and O, wherein the monocyclic heterocycle is saturated or unsaturated, and wherein the bicyclic heterocycle comprises 2 fused rings which are independently saturated or unsaturated, wherein the monocyclic or bicyclic heterocycle is unsubstituted or substituted with CH$_3$, =O, or C(O)OC(CH$_3$)$_3$,
  3) —CH$_2$R[5], wherein R[5] is H, CH$_3$, pyridine, cyclopentyl, cyclobutyl, CH$_2$CH$_3$, cyclopropyl, —CH$_2$OH, CH$_2$OCH$_3$, CF$_3$, CH$_2$CN, CH$_2$CH$_2$OCH$_3$, CH(CH$_3$)$_2$, or a 4-6 membered unsubstituted monocyclic saturated heterocycle having 1 O atom,
  4) hydrogen,
  5) C(O)R[6], wherein R[6] is —NHCH$_2$CH$_3$,
  6) —CHR[7]R[8], wherein R[7] and R[8] are independently CH$_3$, or
  7) C$_{1-4}$alkyl;
R[2] is
  1) CH$_2$R[9], where R[9] is
    a) unsubstituted phenyl or phenyl substituted one, two or three times independently selected from
      1) F, 2) —OCH$_3$ 3) Cl, 4) 5-membered saturated or unsaturated heterocycle which is unsubstituted or substituted with =O having 1 or 2 heteroatoms selected from O and N,
      5)

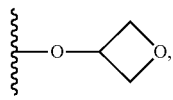

6) —SO$_2$CH$_3$, 7) —C(O)NHCH$_3$, 8) —C(CH$_3$)$_2$OH, or 9) —NHSO$_2$CH$_3$,
    b) —CH$_2$R[13] wherein R[13] is
      1) C$_6$H$_5$, 2) N(CH$_3$)$_2$, 3) C$_6$H$_4$F, 4) F, 5) —OCH$_3$, 6) CF$_3$, 7) O—C$_6$H$_4$F, 8) OCH$_2$C$_6$H$_5$, 9) NHCH$_2$C$_6$H$_5$, 10) 6-membered saturated heterocycle which is unsubstituted or substituted with —CH$_2$OC$_6$H$_5$ having 1 or 2 heteroatoms selected from O and N, 11) 5-membered saturated heterocycle which is unsubstituted having 1 heteroatom which is O, 12) 5-membered unsaturated heterocycle which is unsubstituted or mono- or di-substituted with CH$_3$ having 1 or 2 heteroatoms independently selected from N and O, or
      13)

c) cyclohexyl unsubstituted or substituted with —N(CH$_3$)$_2$,
    d) 10-membered bicyclic carbocycle comprising two fused rings, wherein one ring is unsaturated,
    e) —CHR[19]R[10], wherein R[19] and R[10] are independently selected from
      1) pyridine, 2) 6-membered saturated heterocycle which is unsubstituted having 1 or 2 heteroatoms selected from O and N, which is unsubstituted or substituted with one or two F, 3) —CH$_2$OH, 4) phenyl, 5) piperidine, 6) C$_6$H$_4$F, 7) CH$_3$, 8) OH, or 9) C$_6$H$_4$CF$_3$,
    f) a 4-10 membered monocyclic or bicyclic heterocycle having
      1-3 heteroatoms independently selected from N, S and O, wherein the monocyclic heterocycle is saturated or unsaturated, and wherein the bicyclic heterocycle is saturated or unsaturated, wherein the monocyclic or bicyclic heterocycle is unsubstituted or independently mono-, di- or tri-substituted with —CHCF$_3$CH$_3$, C$_6$H$_4$F, C$_6$H$_3$FCl, CH$_2$CF$_3$, CH$_2$CH$_2$CH$_3$, CH(CH$_3$)$_2$, =O, C$_6$H$_5$, CH$_3$, or F,
    g) CF$_2$C$_6$H$_5$, or h)

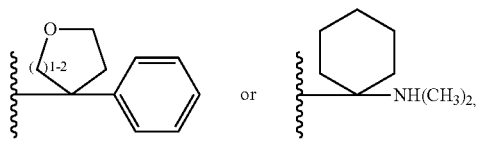

2) —CHR$^{11}$R$^{12}$, where R$^{11}$ and R$^{12}$ are independently selected from
   a) —CH$_3$, b) —OCH$_3$, c) CF$_3$,
   d) C$_6$H$_5$R$^{12'}$ where R$^{12'}$ is F, Cl, —OCF$_3$, —SO$_2$CH$_3$, H, or a 5-membered unsaturated unsubstituted heterocycle or heterocycle substituted with CH$_3$ having 2 or 3 heteroatoms selected from O, N and S,
   e) CH$_2$CH$_2$N(CH$_3$)$_2$,
   f) CH$_2$CH$_2$R$^{12''}$ where R$^{12''}$ is a 6-membered saturated or unsaturated heterocycle which heterocycle is di-substituted with F,
   g) CH$_2$NH$_2$, h) CH$_2$OH, i) C$_6$H$_5$SO$_2$CH$_3$, j) CHF$_2$, k) CH$_2$CH$_2$OH,
   l) CH$_2$OCH$_3$, m) —OCH$_2$CH$_3$, n) —CH$_2$N(CH$_3$)$_2$,
   o) —CH$_2$R$^{12'''}$ where R$^{12'''}$ is a
      1) 5-membered unsaturated unsubstituted heterocycle having 2 N atoms, 2) —OCH$_2$CH$_3$, 3) N(CH$_3$)$_2$, 4) —OCH(CH$_3$)$_2$, 5) —CH$_2$OCH$_2$CH$_2$OCH$_3$, 6) C(O)OCH$_3$, 7) NH$_2$, 8) NHC(O)CH=CH$_2$, 9) C(CH$_2$CH$_3$)$_2$OH, 10) OH, 11) 6-membered saturated heterocycle having 2 heteroatoms independently selected from N and O,
   p) C(O)NHCH$_2$CH$_3$, q) C(O)NHCH$_3$, r) C(O)N(CH$_2$CH$_3$)$_2$, s) C$_6$H$_3$FCl,
   t) C(CH$_3$)$_2$OH, u) C$_6$H$_3$Cl$_2$, v) C(CH$_3$)$_2$OH, w) CH(CH$_3$)OH, x) C(CH$_3$)$_3$, y) —C(CH$_2$CH$_3$)$_2$OH,
   z) a 5-membered unsaturated or saturated heterocycle having one or two heteroatoms independently selected from N, O and S atoms, which heterocycle is unsubstituted or substituted with CH$_3$,
   aa) a 6-membered unsaturated heterocycle having one heteroatom which is N, which heterocycle is unsubstituted, or
   bb) C(O)OCH$_3$,
3) a C$_{4-10}$ monocyclic or bicyclic saturated or unsaturated carbocycle, wherein the bicyclic carbocyle comprises 2 fused rings, wherein the monocyclic or bicyclic carbocycle is unsubstituted or monosubstituted with
   a) NH$_2$, b) NHC(O)CH$_3$, c) —OCH$_3$, d) —N(CH$_3$)$_2$, e) —OCH$_2$CH$_3$, f) C$_6$H$_5$, g) NHC(O)C$_6$H$_5$, h) C$_6$H$_4$F,
   i) —OCH$_2$C$_6$H$_5$, j) —CH$_2$C$_6$H$_5$, k) —OC$_6$H$_5$,
   l) —OCH$_2$CH$_2$CH$_2$C$_6$H$_5$, m) —OC$_6$H$_4$F, or n) —O-pyridine,
4) a 5-10 membered monocyclic or bicyclic saturated or unsaturated heterocycle having 1-3 heteroatoms independently selected from N and O, wherein the monocyclic or bicyclic heterocycle is unsubstituted or independently mono-, di-, tri- or tetra-substituted with
   a) C$_6$H$_4$Cl, b) CH$_3$, c) =O, d) C$_6$H$_5$, e) CH$_2$CH$_3$, f) CH$_2$CH$_2$CH$_3$,
   g) cyclopropyl, h) cyclohexyl, i) C$_6$H$_4$F, j) CH$_2$C$_6$H$_3$(OCH$_3$)(F),
   k) C$_6$H$_4$(CH$_3$), l) CH$_2$CH$_2$C$_6$H$_5$, m) CH$_2$CH$_2$CH$_2$C$_6$H$_5$, n) OCH$_3$,
   o) —OC$_6$H$_5$, p) cyclobutyl, q) CH(CH$_3$)$_2$, r) CH$_2$C$_6$H$_3$F$_2$, s) CH$_2$C$_6$H$_4$CF$_3$,
   t) CH$_2$C$_6$H$_4$CN, u) OC$_6$H$_4$F, v) —OCH$_2$CH$_3$,
   w) a 5-6-membered heterocycle saturated or unsaturated, unsubstituted or substituted with CH$_3$, C$_6$H$_5$ or cyclopropyl, having 1 or 2 heteroatoms independently selected from O, N and S,
   x) —CH$_2$—R$^{2'}$, wherein R$^{2'}$ is a 5-6-membered unsaturated heterocycle, unsubstituted or substituted with Cl, having 1 or 2 heteroatoms independently selected from N and S, or
   y) —O—R$^{2''}$, wherein R$^{2''}$ is a 6-membered unsaturated heterocycle, unsubstituted or mono- or di-substituted with F, having 1 N heteroatom,
5) —CR$^{13}$R$^{14}$R$^{15}$ where R$^{13}$ and R$^{14}$ are independently CH$_3$ or together with the carbon atom to which they are attached form cyclopropyl, and R$^{15}$ is CN or C$_6$H$_5$, or
6)

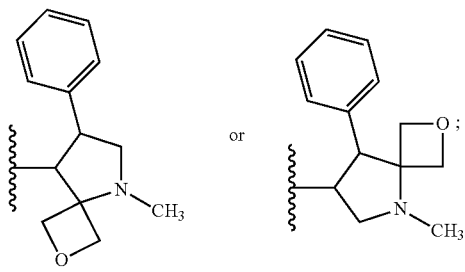 [SMILES: *C1C(c2ccccc2)CN(C)C12COC2 ; *C1CN(C)C2(COC2)C1c1ccccc1]

R$^3$ is hydrogen, —OC$_{1-4}$alkyl, —OC$_{1-4}$alkyl-OH, or —CH$_2$R$^{3'}$, wherein R$^{3'}$ is
   1) —OC$_{1-4}$alkyl, 2) 6-membered saturated unsubstituted heterocycle having 1 or 2 heteroatoms independently selected from N and O, 3) —NHC$_{1-4}$alkyl,
   4) —OC$_{1-4}$alkyleneR$^{3''}$ where R$^{3''}$ is a 4-6-membered saturated unsubstituted heterocycle having 1 or 2 heteroatoms selected from N and O,
   5) —OC$_{1-4}$alkylene-OH, 6) —OC$_{1-4}$alkylene-OCH$_3$, 7) hydrogen,
   8) —OC$_{1-4}$alkylene-OCH$_2$C$_6$H$_5$, 9) —OH, 10) —NHC$_{1-4}$alkyleneOC$_{1-4}$alkyl,
   11) NH$_2$, 12) —NHC$_{1-4}$alkyleneN(C$_{1-4}$alkyl)$_2$, 13) —NHC(O)CH=CH$_2$,
   14) —NHC(O)C$_{1-4}$alkyl, 15) —NHC(O)OC$_{1-4}$alkyl, 16) —OC(O)NHC$_{1-4}$alkyl, or 17) —CH$_2$NHC(O)CH=CH$_2$, 18) N(CH$_3$)$_2$, or
   19)

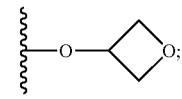

and
R$^4$ is hydrogen or halogen.

Another embodiment of the invention is compounds of Formula I, or a pharmaceutically acceptable salt thereof, wherein
R$^1$ is

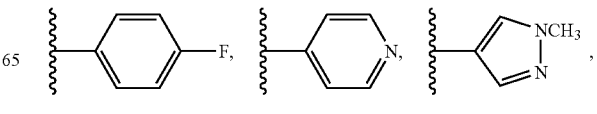

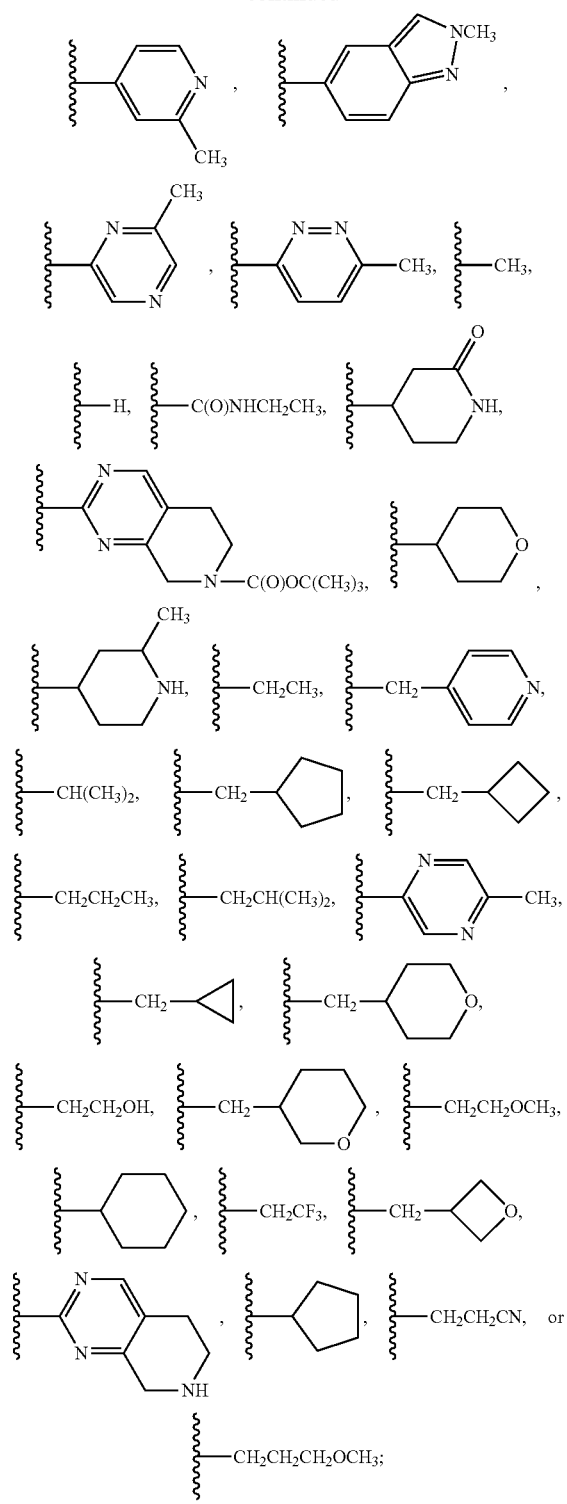
R² is
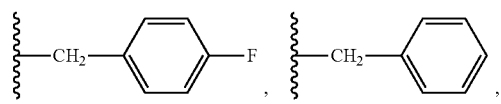

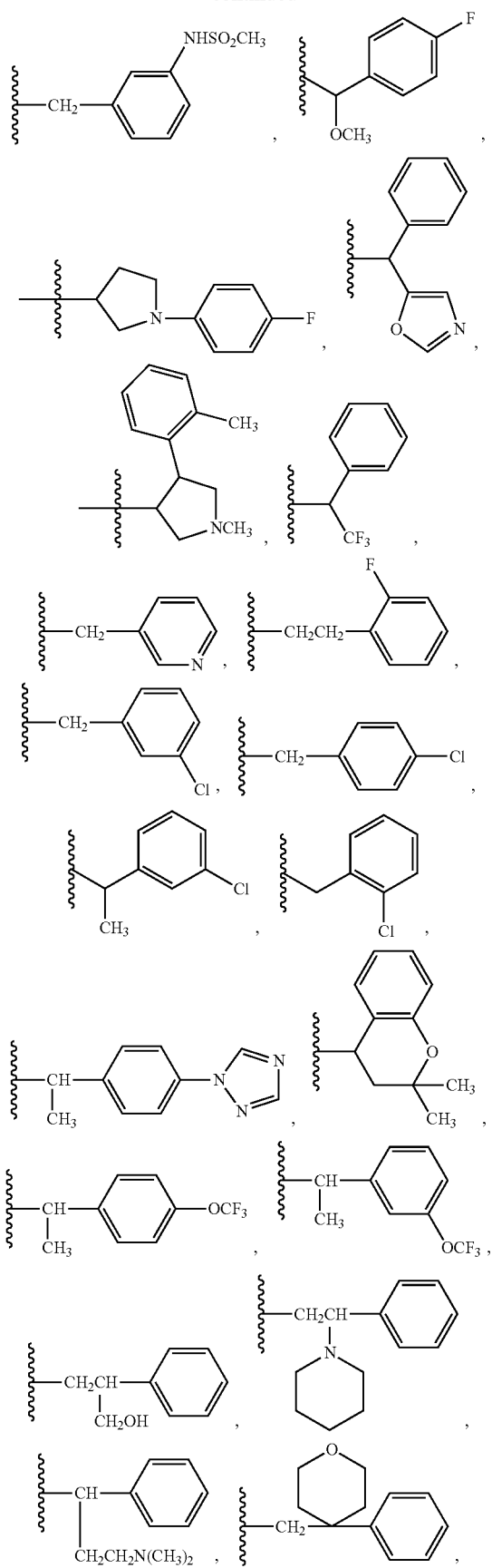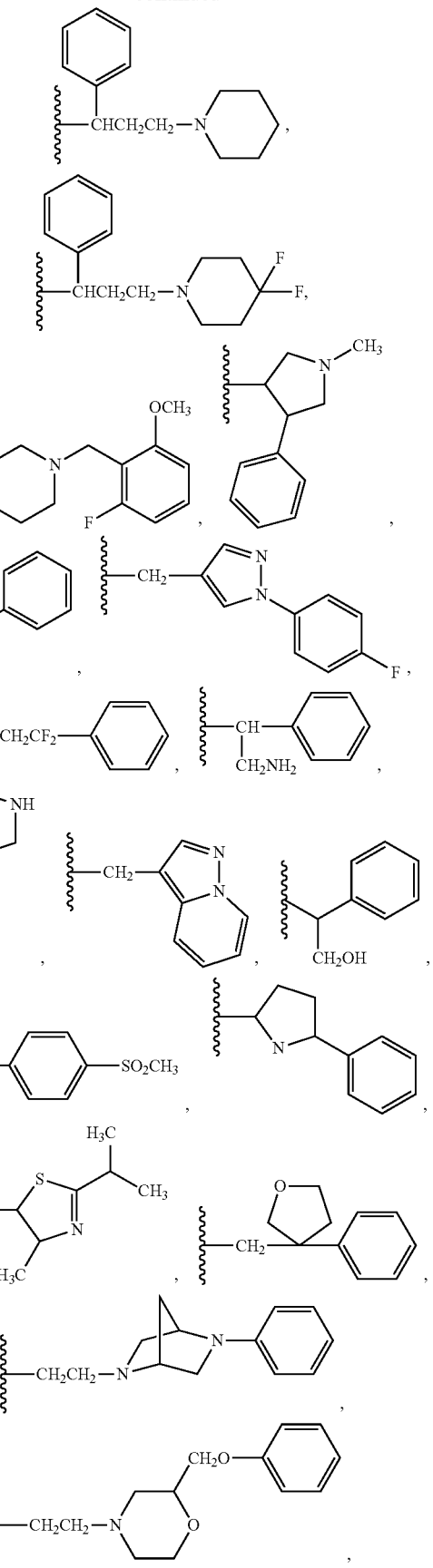

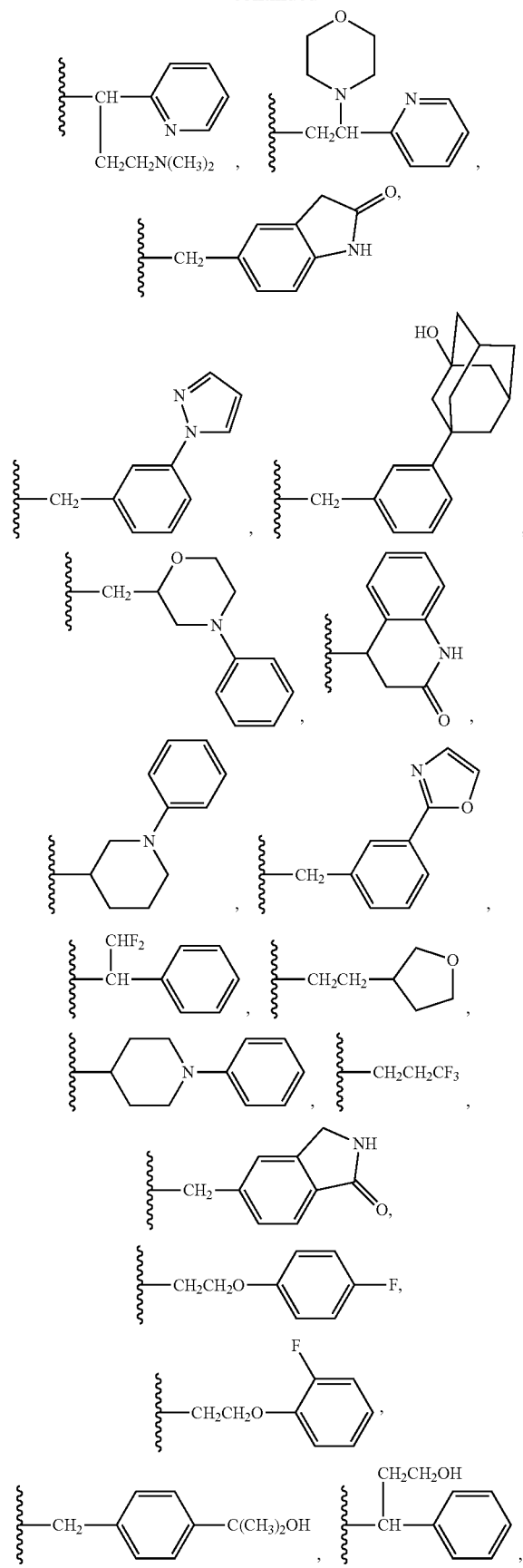
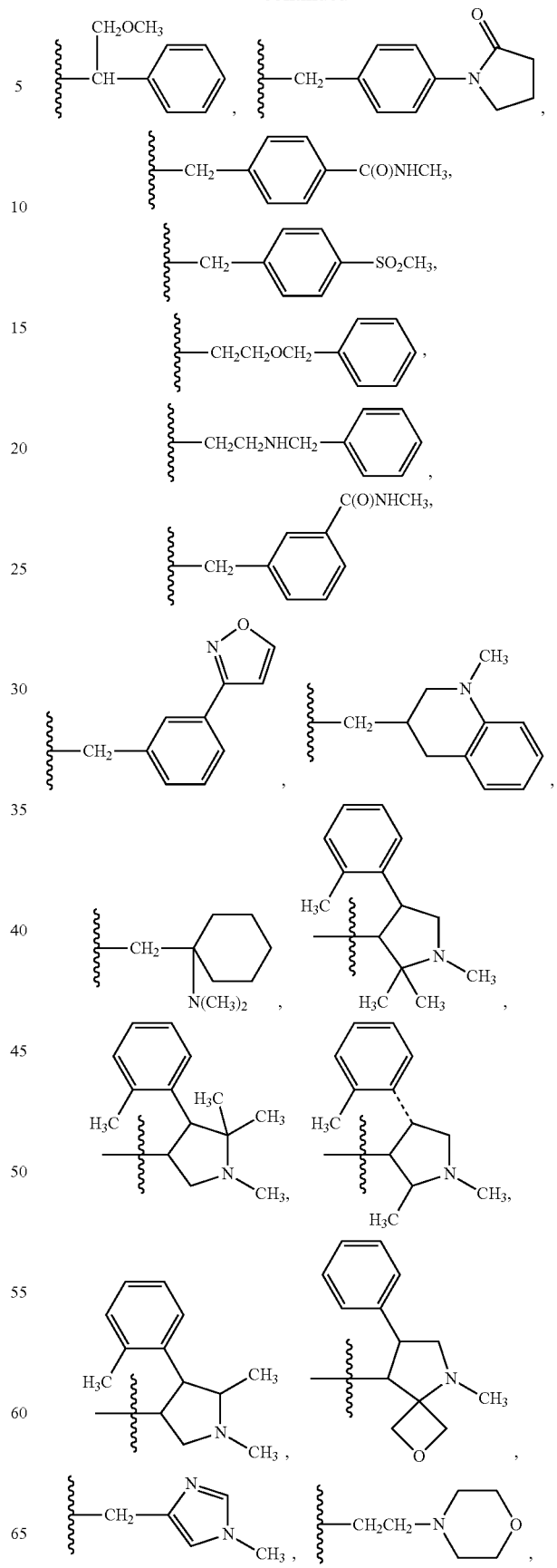

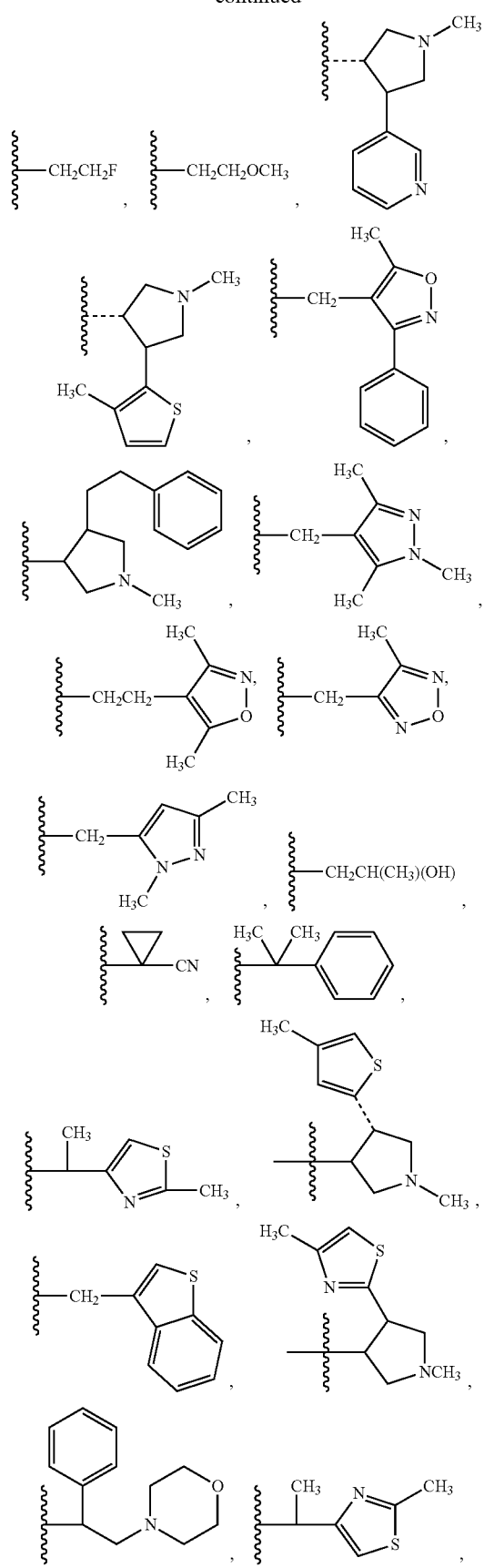
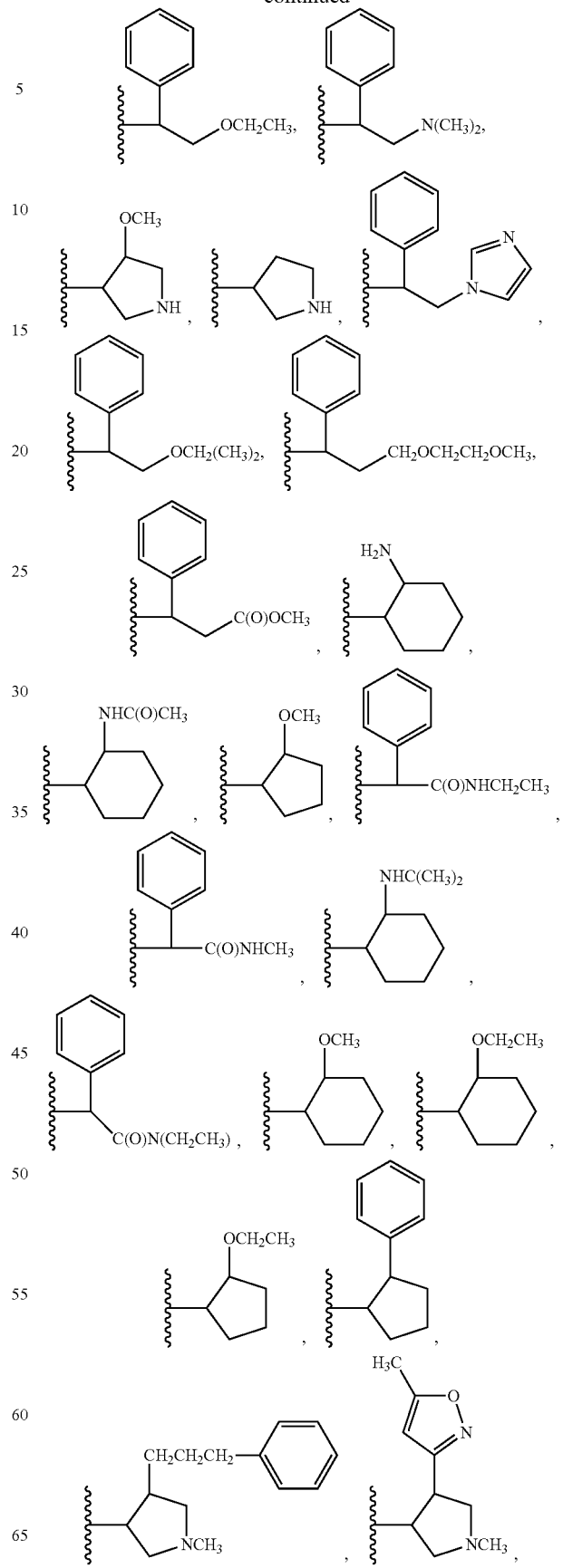

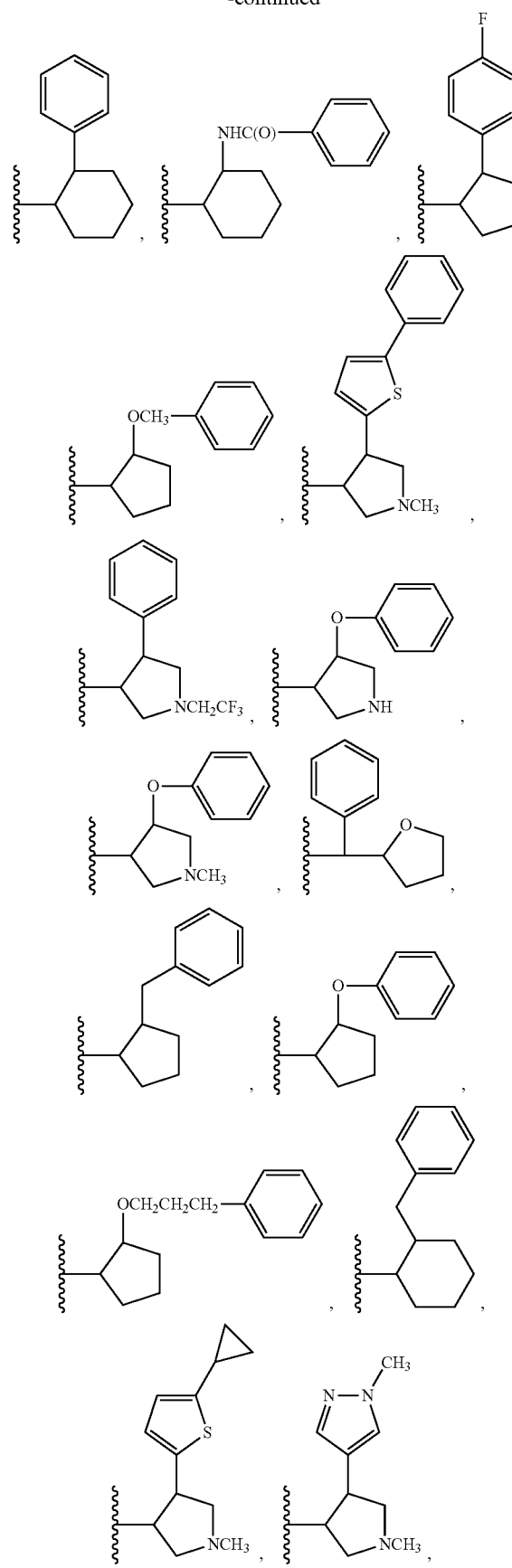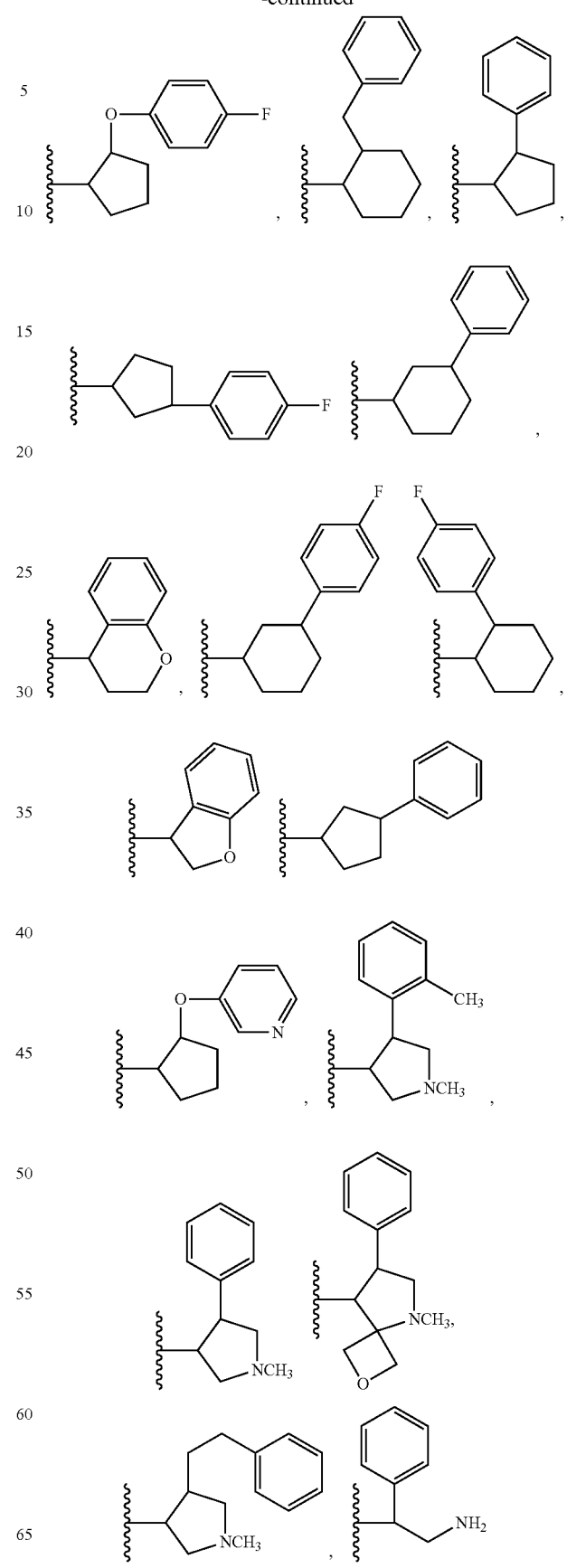

-continued
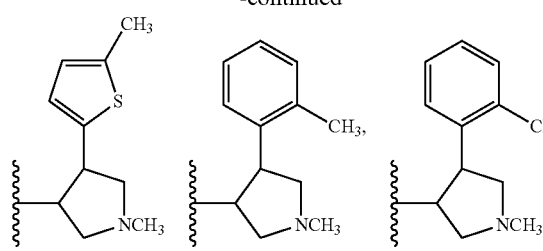
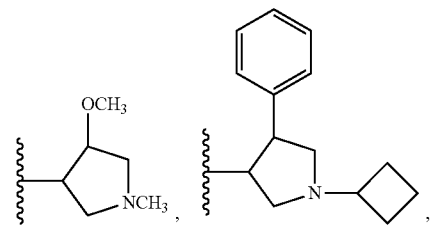
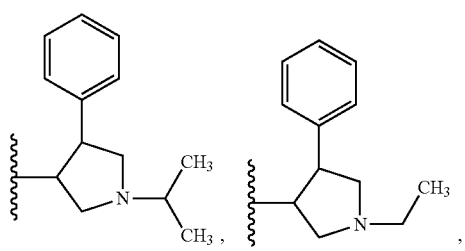
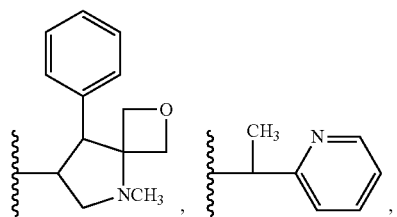
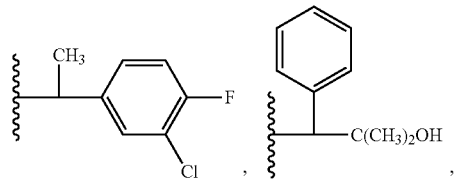
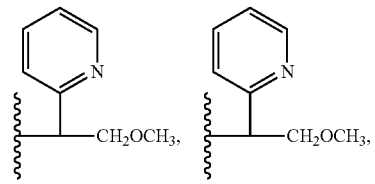
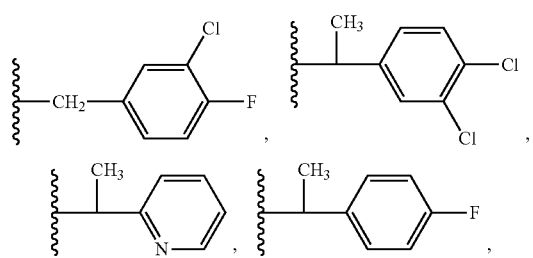
-continued
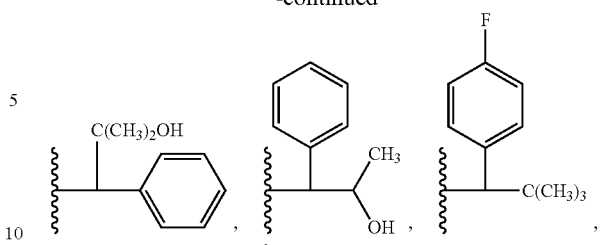
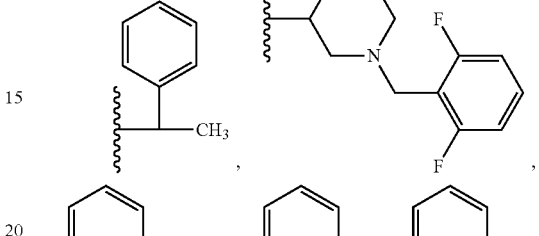
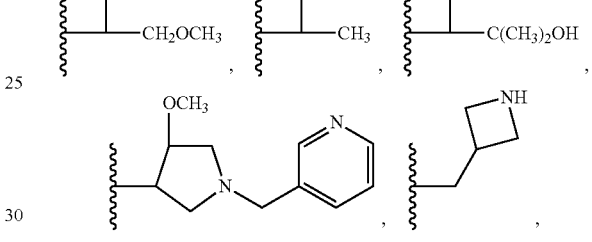
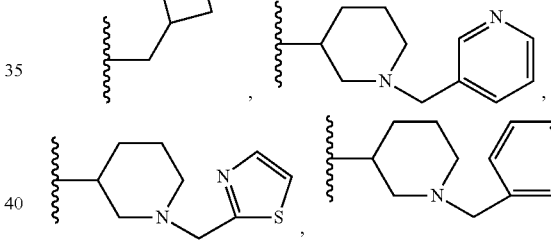
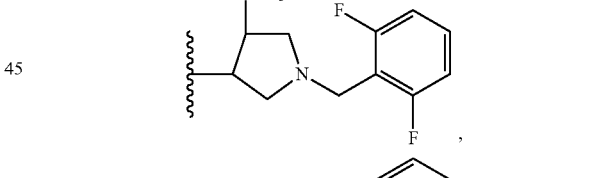
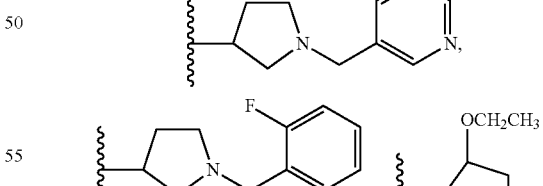
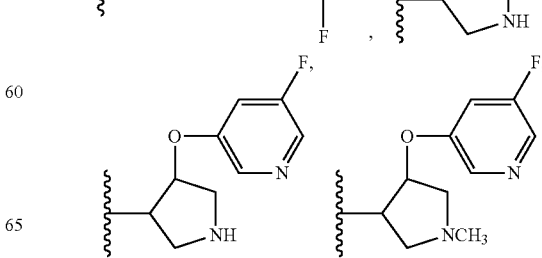

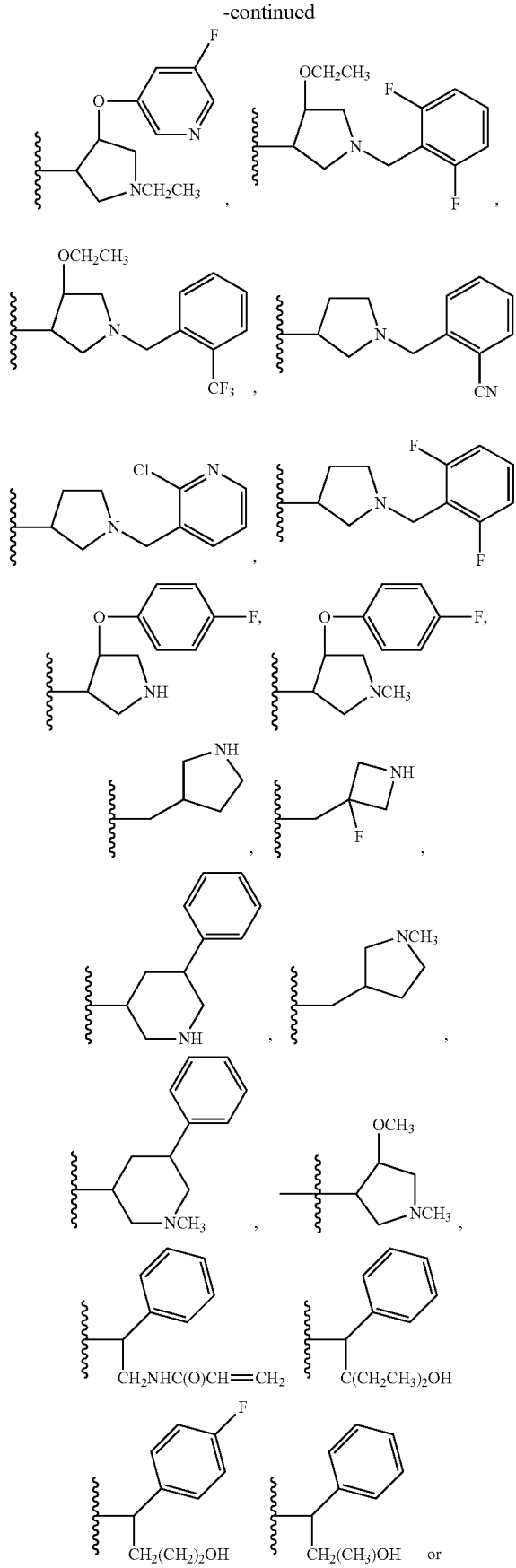

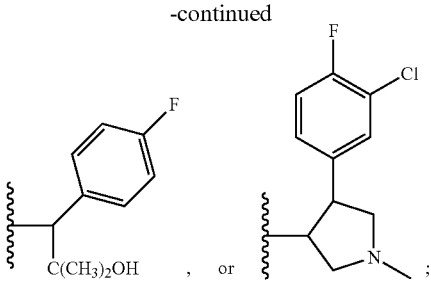

$R^3$ is

—H, —CH$_2$OCH$_3$, —CH$_2$—N(morpholine)O,

—CH$_2$NHCH$_3$, —CH$_2$OCH$_2$CH$_2$—N(morpholine)O,

—CH$_2$OCH$_2$CH$_2$OH, —CH$_2$OCH$_2$CH$_2$OCH$_3$,

—CH$_2$O-(oxetane)-O, —CH$_3$,

—CH$_2$OCH$_2$CH$_2$OCH$_2$-(phenyl), —CH$_2$OH, —OCH$_3$,

—OCH$_2$CH$_2$OH, —CH$_2$NHCH$_2$CH$_2$OCH$_3$, —CH$_2$NH$_2$,

—CH$_2$NHCH$_2$CH$_2$N(CH$_3$)$_2$, —CH$_2$NHC(O)CH=CH$_2$,

—CH$_2$NHC(O)CH$_3$, —CH$_2$NHC(O)OCH$_3$,

—CH$_2$OC(O)NHCH$_2$CH$_3$, —CH$_2$CH$_2$NHC(O)CH=CH$_2$, or

—CH$_2$N(CH$_3$)$_2$;

and
$R^4$ is H or F.

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient) for treating cancer. The term "antineoplastic agent" means a drug (medicament or pharmaceutically active ingredient) for treating cancer (i.e., a chemotherapeutic agent). The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "compound" with reference to the antineoplastic agents, includes the agents that are antibodies. The term "consecutively" means one following the other. The term "effective amount" includes a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, of an ERK inhibitor (i.e., a compound of the invention) is that amount which results in the reduction in ERK (ERK2) activity and phosphorylation. The reduction in ERK activity may be determined by the analysis of pharmacodynamic markers such as phosphorylated RSK1,2 using techniques well known in the art. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The invention also provides a pharmaceutical composition comprising an effective amount of at least one compound of Formula I and a pharmaceutically acceptable carrier. The invention also provides a pharmaceutical composition comprising an effective amount of at least one compound of Formula I and an effective amount of at least one other pharmaceutically active ingredient (such as, for example, a chemotherapeutic agent), and a pharmaceutically acceptable carrier.

The invention also provides a method of inhibiting ERK2 in a patient in need of such treatment comprising administering to said patient an effective amount of at least one compound of Formula I. The invention also provides a method for treating cancer in a patient in need of such treatment, said method comprising administering to said patient an effective amount of at least one compound of Formula I. The invention also provides a method for treating cancer in a patient in need of such treatment, said method comprising administering to said patient an effective amount of at least one compound of Formula I, in combination with an effective amount of at least one chemotherapeutic agent. The methods of the invention include the administration of a pharmaceutical composition comprising at least one compound of the invention and a pharmaceutically acceptable carrier. The invention also provides any of the above methods of treating cancer wherein the cancer is colorectal. The invention also provides any of the above methods of treating cancer wherein the cancer is melanoma. The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of the invention is directed to a method of treating cancer in a patient in need of such treatment, said method comprising administering an effective amount of a compound of Formula I. Another example of the invention is directed to a method of treating cancer in a patient in need of such treatment, said method comprising administering to said patient an effective amount of a compound of Formula I, and an effective amount of at least one chemotherapeutic agent.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians' Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), the Physicians' Desk Reference, 60$^{th}$ Edition, 2006 (published by Thompson PDR, Montvale, N.J. 07645-1742), and the Physicians' Desk Reference, 64$^{th}$ Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein may be useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of Formula I, or a pharmaceutically acceptable salt thereof, to said patient. Another example of the invention is directed to a method of treating colo-rectal cancer in a patient in need of such treatment, said method comprising administering to said patient an effective amount of a compound of Formula I, or a pharmaceutically acceptable salt thereof, and an effective amount of at least one chemotherapeutic agent.

In one example of the invention the cancer treated is melanoma. Thus, another example of the invention is directed to a method of treating melanoma in a patient in need of such treatment, said method comprising administering an effective amount of a compound of Formula I, or a pharmaceutically acceptable salt thereof, to said patient. Another example of the invention is directed to a method of treating melanoma in a patient in need of such treatment, said method comprising administering to said patient an effective amount of a compound of Formula I, or a pharmaceutically acceptable salt thereof, and an effective amount of at least one chemotherapeutic agent.

The compounds of the invention are also useful in preparing a medicament that may be useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

PD-1 inhibitors include pembrolizumab (lambrolizumab), nivolumab and MPDL3280A.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methyl sulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP 1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); *JNCI*, Vol. 69, p. 475 (1982); *Arch. Opthalmol.*, Vol. 108, p. 573 (1990); *Anat.*

Rec., Vol. 238, p. 68 (1994); *FEBS Letters*, Vol. 372, p. 83 (1995); *Clin, Orthop*. Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of the specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of the specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methyl sulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta5$ integrin, to compounds which antagonize, inhibit or counteract binding of a physiological ligand to both the $\alpha v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3, 9,10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy) propoxy)-2-ethylchromane-2-carboxylic acid.

Another example of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an example, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®);

Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with unsolvated and anhydrous forms.

Reference to the compounds of the invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH₃ or a symbol that is an extended bond as the terminal group, e.g.

ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

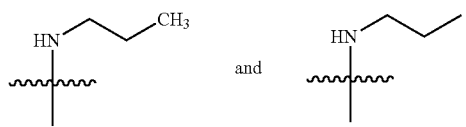

and have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of the invention which results in conversion in vivo to a compound within the scope of the invention is also within the scope of the invention. For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as prodrugs which can be hydrolyzed back to an acid (or —COO— depending on the pH of the fluid or tissue where conversion takes place) or hydroxy form particularly in vivo and as such are encompassed within the scope of the invention. Examples of pharmaceutically acceptable pro-drug modifications include, but are not limited to, —C$_{1-6}$alkyl esters and —C$_{1-6}$alkyl substituted with phenyl esters.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted herein, alkyl groups may be unsubstituted, or substituted with 1 to 3 substituents on any one or more carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$—, HS(O)$_{0-2}$—, (C$_1$-C$_6$ alkyl)S(O)$_{0-2}$(C$_1$-C$_6$ alkyl)-, HS(O)$_{0-2}$(C$_1$-C$_6$ alkyl)-, (C$_0$-C$_6$ alkyl)C(O)NH—, H$_2$N—C(NH)—, —O(C$_1$-C$_6$ alkyl)CF$_3$, HC(O)—, (C$_1$-C$_6$ alkyl)C(O)—, HOC(O)—, (C$_1$-C$_6$ alkyl)OC(O)—, HO(C$_1$-C$_6$ alkyl)-, (C$_1$-C$_6$ alkyl)O(C$_1$-C$_6$ alkyl)-, (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$—, HOC(O)NH—, (C$_1$-C$_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted, the term "halogen" means fluorine, chlorine, bromine or iodine.

Except where noted, the term saturated "heterocycle" refers to a stable 4- to 7-membered mono-cyclic or stable 7- to 12-membered bicyclic or stable 12- to 14-membered tricyclic heteroatom-containing ring system unsubstituted or substituted with C$_{1-4}$ alkyl or halogen, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane, and homopiperazine.

Except where noted herein, the term unsaturated "heterocycle" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Additional examples are pyridine, pyrimidine, thiophene, imidazole, isothiazole, oxadiazole, and isoxazole.

Except where noted herein, the term "unsaturated bicyclic heterocycle" or "unsaturated tricyclic heterocycle" refers to a heterocycle having fused rings in which at least one of the rings is not fully saturated, e.g.

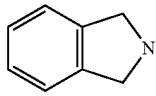

is a 9-membered unsaturated bicyclic heterocycle having one nitrogen atom.

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ monocyclic carbocycle, or a $C_9$ to $C_{12}$ bicyclic saturated or unsaturated ring, e.g., $C_{9-12}$ bicyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example, "aryl" rings. Unsaturated bicyclic carbocyclic ring systems include fused ring systems where all ring system members are carbon atoms and where at least one of the fused rings is not saturated.

Except where noted herein, the term "unsaturated bicyclic carbocycle" or "unsaturated tricyclic carbocycle" refers to a carbocycle having fused rings in which at least one of the rings is not fully saturated, e.g.

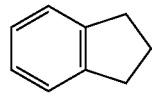

is a 9-membered unsaturated bicyclic carbocycle.

Except where noted, the term "aryl" refers to a stable 6- to 10-membered mono- or bicyclic unsaturated carbocyclic ring system such as phenyl, or naphthyl.

"Celite®" (Fluka) diatomite is diatomaceous earth, and can be referred to as "celite".

Except where noted herein, carbocycle groups may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, HS(O)$_{0-2}$—, $(C_1$-$C_6$ alkyl)S(O)$_{0-2}$—, $(C_1$-$C_6$ alkyl)S(O)$_{0-2}(C_1$-$C_6$ alkyl)-, HS(O)$_{0-2}(C_1$-$C_6$ alkyl)-, $(C_1$-$C_6$ alkyl)S(O)$_{0-2}$, $(C_1$-$C_6$ alkyl)C(O)NH—, HC(O)NH—, $H_2N$—C(NH)—, —$O(C_1$-$C_6$ alkyl)CF$_3$, $(C_1$-$C_6$ alkyl)C (O)—, HC(O)—, $(C_1$-$C_6$ alkyl)OC(O)—, HOC(O)—, $(C_1$-$C_6$ alkyl)O($C_1$-$C_6$ alkyl)-, HO($C_1$-$C_6$ alkyl)-, $(C_1$-$C_6$ alkyl)C(O)$_{1-2}$($C_1$-$C_6$ alkyl)-, $(C_1$-$C_6$ alkyl)C(O)$_{1-2}$—, HC(O)$_{1-2}$ ($C_1$-$C_6$ alkyl)-, $(C_1$-$C_6$ alkyl)OC(O)NH—, HOC(O)NH—, —P(O)(OH)$_2$, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heterocycles may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $(C_1$-$C_6$ alkyl)S(O)$_{0-2}$—, HS(O)$_{0-2}$—, $(C_1$-$C_6$ alkyl)S(O)$_{0-2}$ $(C_1$-$C_6$ alkyl)-, HS(O)$_{0-2}(C_1$-$C_6$ alkyl)-, $(C_1$-$C_6$ alkyl) S(O)$_{0-2}$—, $(C_1$-$C_6$ alkyl)C(O)NH—, HC(O)NH—, $H_2N$—C (NH)—, —$O(C_1$-$C_6$ alkyl)CF$_3$, HC(O)—, $(C_1$-$C_6$ alkyl)C (O)—, $(C_1$-$C_6$ alkyl)OC(O)—, HOC(O)—, $(C_1$-$C_6$ alkyl)O $(C_1$-$C_6$ alkyl)-, HO($C_1$-$C_6$ alkyl)-, $(C_1$-$C_6$ alkyl)O—, $(C_1$-$C_6$ alkyl)C(O)$_{1-2}$($C_1$-$C_6$ alkyl)-, HC(O)$_{1-2}$($C_1$-$C_6$ alkyl)-, $(C_1$-$C_6$ alkyl)C(O)$_{1-2}$, $(C_1$-$C_6$ alkyl)OC(O)NH—, HOC(O) NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O)NH$_2$, —$C_1$-$C_6$ alkylC(O)NH$_2$, —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For the, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula I hereinabove.

TLC is thin layer chromatography; Ts is tosyl; UV is ultraviolet; W is watts; wt. % is percentage by weight; xg is times gravity; α$_D$ is the specific rotation of polarized light at 589 nm; ° C. is degrees Celsius; % w/v is percentage in weight of the former agent relative to the volume of the latter agent.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Abbreviations

Bis(t-Bu)XPhos Precatalyst
Boc tert-butyloxycarbonyl
BOC$_2$O di-tert-butyl dicarbonate
BrettPhos Precatalyst
CDI 1,1'-carbonyldiimidazole
celite Celite® diatomaceous earth
DCM dichloromethane
DIEA Diisopropylethylamine
DIPEA diisopropylethylamine
DMA N,N-dimethylacetamide
DMAP 4-dimethylaminopyridine
DMF N,N-dimethylformamide
DMSO dimethyl sulfoxide
EDC  N-(3-dimethylaminopropyl)-N'-ethylcarbodiimide hydrochloride
EI electron ionization
EtOAc ethyl acetate
HATU  O-(7-azabenzotriazol-1-yl)-N,N,N',N'-tetramethyluronium hexafluorophosphate
HPLC high performance liquid chromatography
Hz hertz
J coupling constant
LC Liquid chromatography
LCMS liquid chromatography-mass spectrometry
MeCN acetonitrile
MeOH methanol
MS mass spectrometry
NMR nuclear magnetic resonance
Ph phenyl
SFC supercritical fluid chromatography
TEA triethanolamine
TBS-Cl
TLC analysis
TFA trifluoroacetic acid
THF tetrahydrofuran In the schemes and examples, unless otherwise indicated, Ar is unsubstituted or substituted unsaturated carbocycle or unsubstituted or unsubstituted or substituted unsaturated heterocycle, wherein substitution includes but is not limited to C$_{1-4}$ alkyl or halogen. In the schemes and examples, unless otherwise indicated, R is C$_{1-4}$ alkyl or Ar.

Intermediates

In the following tables, intermediates are identified by number in the column headed "Int. #". Unless otherwise indicated, Exact Mass [M+H]+ is represented in the tables by the heading "[M+H]+".

Scheme 1

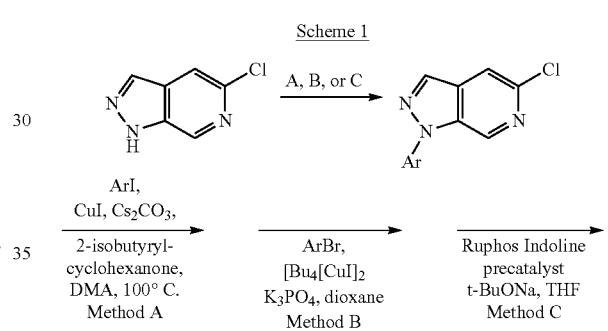

| ArI, CuI, Cs$_2$CO$_3$, 2-isobutyrylcyclohexanone, DMA, 100° C. Method A | ArBr, [Bu$_4$[CuI]$_2$ K$_3$PO$_4$, dioxane Method B | Ruphos Indoline precatalyst t-BuONa, THF Method C |

Intermediates were prepared according to Methods A, B or C.

Intermediate 1I:

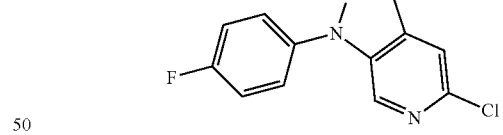

5-Chloro-1-(4-fluorophenyl)-1H-pyrazolo[3,4-c] pyridine

A suspension of 5-chloro-1H-pyrazolo[3,4-c]pyridine (100 mg, 0.651 mmol), 4-fluoro-1-iodobenzene (225 mg, 1.01 mmol), 2-isobutyrylcyclohexanone (50 mg, 0.297 mmol), copper(I) iodide (25 mg, 0.131 mmol) and cesium carbonate (400 mg, 1.23 mmol) in 5 mL of DMA was deoxygenated by bubbling nitrogen for 15 min. Next, the reaction mixture was warmed to 100° C. and stirred overnight. The reaction mixture was then cooled and diluted with DCM, washed with 1 N aqueous NaOH and water, dried (Na$_2$SO$_4$) and concentrated to dryness. The solid residue was suspended in ether, stirred for 30 min, and filtered to collect the desired intermediate, 5-chloro-1-(4-fluorophenyl)-1H-pyrazolo[3,4-c]pyridine: MS (EI) calc'd for $C_{12}H_8ClFN_3$ [M+H]$^+$ 248. found 248; $^1$H NMR (600 MHz, DMSO-d$_6$) δ 9.07 (s, 1H), 8.48 (s, 1H), 8.01 (s, 1H), 7.86 (dd, J=7.1, 5.0 Hz, 2H), 7.43 (t, J=8.8 Hz, 2H).

The following intermediate was made following similar protocol to intermediate 1I using appropriate reagent.

TABLE 1

| Int. # | Structure | IUPAC Name | [M + H]+ |
|---|---|---|---|
| 2I | 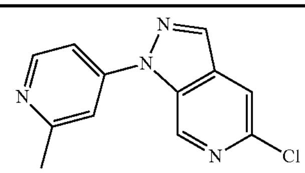 | 5-Chloro-1-(2-methylpyridin-4-yl)-1H-pyrazolo[3,4-c]pyridine | Calc'd 245, found 245 |

Intermediate 3I:

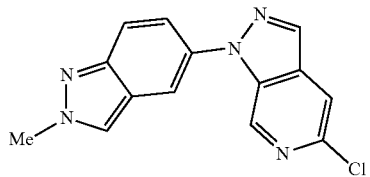 [SMILES: Cn1cc2cc(-n3ncc4cc(Cl)ncc43)ccc2n1]

5-chloro-1-(2-methyl-2H-indazol-5-yl)-1H-pyrazolo[3,4-c]pyridine 5-bromo-2-methyl-2H-indazole (515 mg, 2.44 mmol) and bis[(tetrabutylammonium iodide)copper(I) iodide] (456 mg, 0.407 mmol) were combined in a reaction vessel, followed by 5-chloro-1H-pyrazolo[3,4-c]pyridine (250 mg, 1.628 mmol), trans-N,N'-dimethylcyclohexane-1,2-diamine (0.257 ml, 1.628 mmol), and anhydrous K$_3$PO$_4$ (691 mg, 3.26 mmol). This mixture was then evacuated and backfilled with N$_2$ (3 times). Anhydrous degassed dioxane (20 ml) was added to this flask. This mixture was again evacuated and backfilled with N$_2$ (3 times) and then as heated at 110° C. for 22 h. LCMS showed a peak consistent with product. The reaction was diluted with EtOAc and water. The blue colored aqueous layer was separated from the green colored organic layer. The aqueous layer was extracted with EtOAc. The combined organics were filtered and concentrated. The residue was purified by column chromatography on silica gel (24 g), eluting with 1-100% EtOAc/hexanes to give 5-chloro-1-(2-methyl-2H-indazol-5-yl)-1H-pyrazolo[3,4-c]pyridine LCMS: M+H=284.

Intermediate 4I:

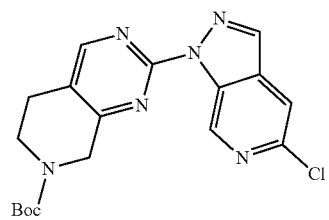 [SMILES: CC(C)(C)OC(=O)N1CCc2cnc(-n3ncc4cc(Cl)ncc43)nc2C1]

tert-butyl 2-(5-chloro-1H-pyrazolo[3,4-c]pyridin-1-yl)-5,6-dihydropyrido[3,4-d]pyrimidine-7(8H)-carboxylate In the reaction vessel Ruphos Indoline Precatalyst (19.77 mg, 0.027 mmol) and Sodium tert-butoxide (104 mg, 1.085 mmol) were combined, followed by tert-butyl 2-chloro-5,6-dihydropyrido[3,4-d]pyrimidine-7(8H)-carboxylate (146 mg, 0.543 mmol) and 5-chloro-1H-pyrazolo[3,4-c]pyridine (100 mg, 0.651 mmol). This mixture was then evacuated and backfilled with N$_2$ (3 times). Then dry, degassed Tetrahydrofuran (2713 μl) and was added to this flask. This mixture was then heated at 80° C. for 12 h. The mixture was cooled, brine (saturated, 20 mL) was added and the mixture was extracted with ethyl acetate (2×20 mL). The combined organic fractions were washed with brine (saturated, 1×20 mL), dried filtered and the solvent was evaporated under reduced pressure. The residue was purified by column chromatography on silica gel Isolute Flash Si; 20 g prepacked, eluting with EtOAc/isohexane to give tert-butyl 2-chloro-5,6-dihydropyrido[3,4-d]pyrimidine-7(8H)-carboxylate. Anal. Calcd. $C_{18}H_{19}ClN_6O_2$ [M+H] 387 found 387.

Scheme 2

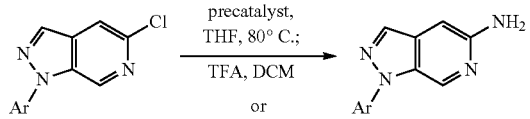

Intermediate 5I:

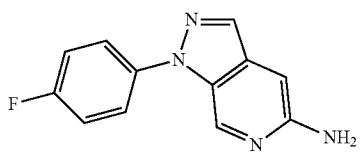 [SMILES: Nc1cc2cnn(-c3ccc(F)cc3)c2cn1]

1-(4-Fluorophenyl)-1H-pyrazolo[3,4-c]pyridin-5-amine

A solution of 5-chloro-1-(4-fluorophenyl)-1H-pyrazolo[3,4-c]pyridine (150 mg, 0.606 mmol) in DMA (5 mL) was treated with NH₂Boc (300 mg, 2.56 mmol), Cs₂CO₃ (600 mg, 1.842 mmol) and chloro[2-(dicyclohexylphosphino)-3,6-dimethoxy-2'-4'-6'-tri-i-propyl-1,1'-biphenyl][2-(2-aminoethyl)phenyl]-palladium(II) (50 mg, 0.063 mmol). The mixture was then deoxygenated by bubbling nitrogen for 15 min and stirred at 100° C. overnight. Diluted with 4:1 DCM/MeOH and washed with 1 N aqueous NaOH, then dried (Na₂SO₄) and concentrated. Chromatography on SiO₂ (0-100% EtOAc/DCM) gave the desired intermediate Boc-protected product which was dissolved in 2 M HCl in dioxane. The mixture was stirred for 30 min and concentrated to provide the bis-HCl salt, which was then dissolved in DCM and washed with sat'd NaHCO₃, dried (Na₂SO₄) and concentrated to provide 1-(4-fluorophenyl)-1H-pyrazolo[3,4-c]pyridin-5-amine: MS (EI) calc'd for $C_{12}H_{10}FN_4$ [M+H]⁺ 229. found 229; ¹H NMR (600 MHz, CD₃OD) δ 8.68 (s, 1H), 8.05 (s, 1H), 7.72 (dd, J=8.3, 5.0 Hz, 2H), 7.29 (t, J=8.5 Hz, 2H), 6.87 (s, 1H).

Intermediate 6I:

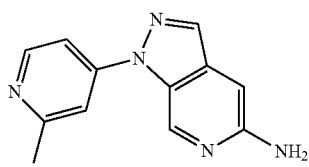 [SMILES: Cc1cc(-n2ncc3cc(N)ncc32)ccn1]

1-(2-Methylpyridin-4-yl)-1H-pyrazolo[3,4-c]pyridin-5-amine

A mixture of 5-chloro-1-(2-methylpyridin-4-yl)-1H-pyrazolo[3,4-c]pyridine (1.20 g, 4.90 mmol), NH₂Boc (1.50 g, 12.8 mmol), chloro(2-di-t-butylphosphino-2',4',6'-tri-i-propyl-1,1'-biphenyl)[2-(2-aminoethyl)phenyl] palladium(II) (300 mg, 0.437 mmol) in THF (5 mL) was deoxygenated by bubbling nitrogen and then treated with KOtBu as a 1 M solution in THF (8.00 mL, 8.00 mmol). The reaction was stirred overnight at 80° C., then diluted with DCM and washed with 1 N NaOH. The organic layer was dried (Na₂SO₄) and concentrated. Chromatography on SiO₂ (0-50% MeOH/DCM) gave the intermediate Boc-protected product. This intermediate was dissolved in 10 mL of DCM and 10 mL of TFA, and stirred for 3 hours. The reaction was concentrated, dissolved in DCM and washed with 1 N NaOH, the organic layer dried (Na₂SO₄), and concentrated to provide 1-(2-methylpyridin-4-yl)-1H-pyrazolo[3,4-c]pyridin-5-amine: MS (EI) calc'd for $C_{12}H_{12}N_5$[M+H]⁺ 226. found 226; ¹H NMR (600 MHz, DMSO-d₆) δ 9.02 (s, 1H), 8.47 (d, J=5.5 Hz, 1H), 8.26 (s, 1H), 7.68 (d, J=2.1 Hz, 1H), 7.63 (dd, J=5.6, 2.1 Hz, 1H), 6.72 (d, J=1.2 Hz, 1H), 5.78 (s, 2H), 2.53 (s, 3H).

Intermediate 7I:

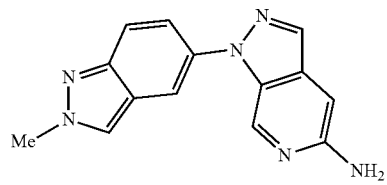 [SMILES: Cn1cc2cc(-n3ncc4cc(N)ncc43)ccc2n1]

1-(2-methyl-2H-indazol-5-yl)-1H-pyrazolo[3,4-c]pyridin-5-amine

A mixture of 5-chloro-1-(2-methyl-2H-indazol-5-yl)-1H-pyrazolo[3,4-c]pyridine (210 mg, 0.740 mmol) and SPHOS-Pd-Precatalyst (Generation 1, 56.3 mg, 0.074 mmol) were taken up in degassed THF (5 ml) and then degassed (vacuum/nitrogen) 3×. The mixture was treated with lithium bis(trimethylsilyl)amide (1.480 ml, 1.480 mmol) and heated at 60° C. The reaction was diluted with DCM (5 mL), treated with 1N HCl (2 mL), and stirred for 1 h. The mixture was then filtered through celite. The organic layer was again filtered and concentrated. The residue was purified by column chromatography on silica gel (24 g), eluting with 0-15% MeOH/DCM to give two products, of which the more polar was consistent with the desired product, 1-(2-methyl-2H-indazol-5-yl)-1H-pyrazolo[3,4-c]pyridin-5-amine. MS (ESI) calc'd for: for $C_{14}H_{12}N_6$[M+H]⁺=265 found 265.

Scheme 3

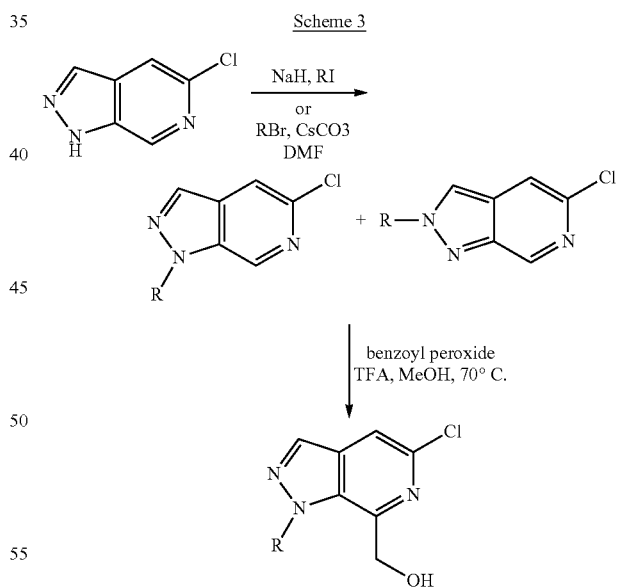

Intermediate 8I:

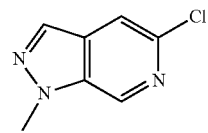

5-chloro-1-methyl-1H-pyrazolo[3,4-c]pyridine

At 0° C., to a suspension of NaH (0.31 g, 7.84 mmol) in anhydrous DMF (10 mL) was added 5-chloro-1H-pyrazolo[3,4-c]pyridine (1.0 g, 6.53 mmol) in anhydrous DMF (5 mL) dropwise and the contents were stirred at the same temperature for 15 min. MeI (1.01 g, 7.18 mmol) in DMF (2 mL) was added dropwise to the reaction mixture at the same temperature and the contents were warmed to ambient temperature. After 30 min, the reaction was quenched with H$_2$O (10 mL) and the organic contents were extracted with EtOAc (3×15 mL). The EtOAc layer was washed with brine (1×20 mL), dried over Na$_2$SO$_4$ and concentrated. The residue thus obtained was purified by flash column chromatography afforded the mixture of regio-isomers. 5-chloro-1-methyl-1H-pyrazolo[3,4-c]pyridine (8I) $^1$H NMR (CDCl$_3$, 400 MHz) δ 8.8 (s, 1H), 7.98 (s, 1H), 7.6 (s, 1H), 3.9 (s, 3H).

Intermediate 9I:

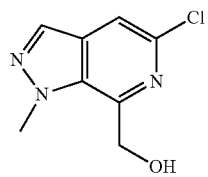

5-Chloro-1-(3-methoxypropyl)-1H-pyrazolo[3,4-c]pyridine

A solution of 5-chloro-1H-pyrazolo[3,4-c]pyridine (50 mg, 0.33 mmol) in DMF (1 mL) was treated with 1-bromo-3-methoxypropane (180 mg, 1.20 mmol) and Cs$_2$CO$_3$ (210 mg, 0.65 mmol). The mixture was warmed to 60° C. for 1.5 h and cooled to afford a crude mixture of isomers. The isomers were separated by chromatography on SiO$_2$ (5-60% EtOAc/hexanes) to yield the desired 5-chloro-1-(3-methoxypropyl)-1H-pyrazolo[3,4-c]pyridine: MS (EI) calc'd for C$_{10}$H$_{13}$ClN$_3$O [M+H]$^+$ 226. found 226; $^1$H NMR (600 MHz, CDCl$_3$) δ 8.75 (s, 1H), 7.99 (s, 1H), 7.61 (s, 1H), 4.56 (dt, J=6.5 Hz, 2H), 3.25 (s, 3H), 3.20 (t, J=5.6 Hz, 2H), 2.17 (dt, J=6.1 Hz, 2H).

Intermediate 10I:

(5-Chloro-1-methyl-1H-pyrazolo[3,4-c]pyridin-7-yl)methanol

5-Chloro-1-methyl-1H-pyrazolo[3,4-c]pyridine (Intermediate 8I, 543 mg, 3.24 mmol), benzoyl peroxide (2.3 g, 9.72 mmol), and TFA (0.300 mL, 3.89 mmol) was dissolved in methanol (30 mL) and stirred at 70° C. overnight. Additional benzoyl peroxide (1.2 g, 4.86 mmol) and methanol (5 mL) were added and the reaction mixture stirred at 70° C. overnight. DCM was added and the reaction was concentrated in vacuo while loading onto silica gel. Purification by flash chromatography (Biotage, 10-80% EtOAc/isohexane followed by 7-60% EtOAc/isohexanes) gave (5-chloro-1-methyl-1H-pyrazolo[3,4-c]pyridin-7-yl)methanol. MS ESI calc'd. for C$_8$H$_9$ClN$_3$O [M+1]$^+$ 198. found 198.

The following intermediate was made following similar protocol to intermediate 10I using appropriate reagent.

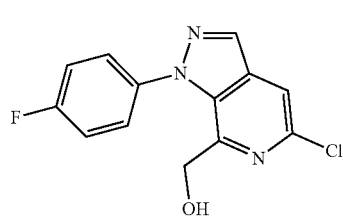

11I

(5-Chloro-1-(4-fluorophenyl)-1H-pyrazolo[3,4-c]pyridin-7-yl)methanol

Exact Mass [M+H]+ Calc'd 278. found 278.

Scheme 4

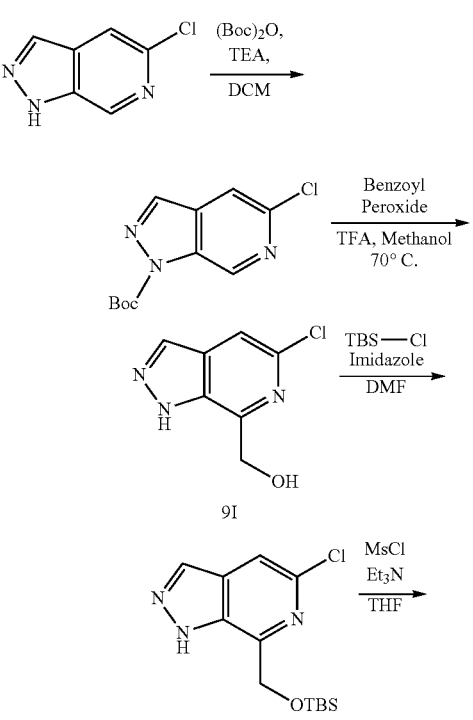

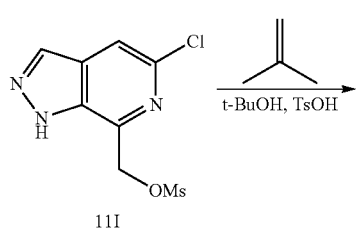

11I

55

-continued

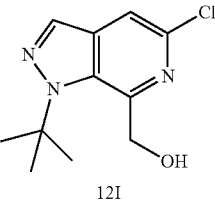

Intermediate 12I:

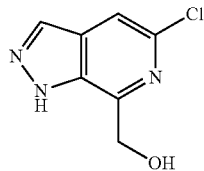 [SMILES: OCc1nc(Cl)cc2cn[nH]c12]

(5-Chloro-1H-pyrazolo[3,4-c]pyridin-7-yl)methanol

Step 1: tert-Butyl 5-chloro-1H-pyrazolo[3,4-c]pyridine-1-carboxylate

5-Chloro-1H-pyrazolo[3,4-c]pyridine (2.0 g, 13.02 mmol) and triethylamine (3.63 mL, 26.0 mmol) was dissolved in DCM (40 mL) and BOC$_2$O (4.54 ml, 19.54 mmol) was added. The reaction mixture was stirred at RT for 3 hours. DCM was added and the organic layer was washed with brine, dried over sodium sulfate, filtered, and concentrated in vacuo while loading onto silica gel. Purification by flash chromatography (Biotage, 2-30% EtOAc-Hexanes) gave tert-butyl 5-chloro-1H-pyrazolo[3,4-c]pyridine-1-carboxylate. MS ESI calc'd. for $C_{11}H_{13}ClN_3O_2$ [M+1]$^+$ 254. found 254.

Step 2: (5-Chloro-1H-pyrazolo[3,4-c]pyridin-7-yl)methanol

Tert-Butyl 5-chloro-1H-pyrazolo[3,4-c]pyridine-1-carboxylate (1.36 g, 5.36 mmol), benzoyl peroxide (3.90 g, 16.08 mmol), and TFA (0.496 mL, 6.43 mmol) were dissolved in methanol (68 mL) and was stirred at 70° C. overnight. The reaction mixture was concentrated in vacuo, TFA (5 mL) was added, and then stirred at RT for 3 hours. DCM was added and the mixture concentrated in vacuo while loading onto silica gel. Purification by flash chromatography (Biotage, 0-10% CH$_2$Cl$_2$/MeOH) gave (5-chloro-1H-pyrazolo[3,4-c]pyridin-7-yl)methanol. MS ESI calc'd. for $C_7H_7ClN_3O$ [M+1]$^+$ 184. found 184. $^1$H NMR (500 MHz, DMSO-d$_6$) δ 13.66 (s, 1H), 8.18 (s, 1H), 7.75 (s, 1H), 5.69 (s, 1H), 4.86 (s, 2H).

Intermediate 13I:

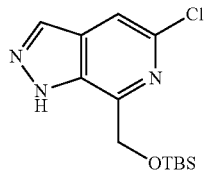 [SMILES: CC(C)(C)[Si](C)(C)OCc1nc(Cl)cc2cn[nH]c12]

56

7-(((tert-Butyldimethylsilyl)oxy)methyl)-5-chloro-1H-pyrazolo[3,4-c]pyridine (5-Chloro-1H-pyrazolo[3,4-c]pyridin-7-yl)methanol (Intermediate 12I, 376.2 mg, 2.049 mmol), TBS-Cl (371 mg, 2.459 mmol), and imidazole (167 mg, 2.459 mmol) was dissolved in DMF (5 mL) and stirred at room temperature for 2 hours. Additional TBS-Cl (92.75 mg, 0.6 mmol) and imidazole (41.75 mg, 0.6 mmol) was added and the reaction mixture stirred at RT for 1.5 hours. Ethyl acetate was added and the organic layer washed with sat. ammonium chloride and brine, dried over sodium sulfate, filtered, and concentrated in vacuo while loading onto silica gel. Purification by flash chromatography (Biotage, 2-20% EtOAc/isohexane) gave 7-(((tert-butyldimethylsilyl)oxy)methyl)-5-chloro-1H-pyrazolo[3,4-c]pyridine. MS ESI calc'd. for $C_{13}H_{21}ClN_3OSi$ [M+1]$^+$ 298. found 298.

Intermediate 14I:

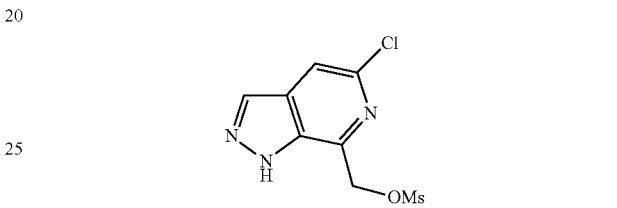

[5-chloro-1H-pyrazolo[3,4-c]pyridin-7-yl]methyl methanesulfonate

To a solution of [5-chloro-1H-pyrazolo[3,4-c]pyridin-7-yl]methanol, 12I, (1 g, 5.45 mmol) in THF (15 mL) was added TEA (552 mg, 5.46 mmol). Then methanesulfonyl chloride (623 mg, 5.44 mmol) was added dropwise with stirring at 0° C. and then stirred for 1 h at the same temperature. The resulting solution was diluted with EtOAc, washed with saturated NaHCO$_3$, brine, then dried (Na$_2$SO$_4$) and concentrated under reduced pressure to afford [5-chloro-1H-pyrazolo[3,4-c]pyridin-7-yl]methyl methanesulfonate. MS (EI) calc'd for $C_8H_9ClN_3O_3S$ [M+H]$^+$ 262. found 262.

Intermediate 15I:

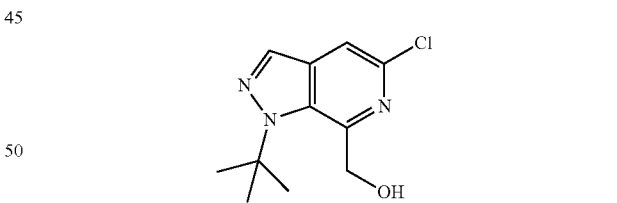

[1-tert-Butyl-5-chloro-1H-pyrazolo[3,4-c]pyridin-7-yl]methanol

To a solution of [5-chloro-1H-pyrazolo[3,4-c]pyridin-7-yl]methanol, 12I, (500 mg, 2.72 mmol) in tert-butanol (10 mL) was added 4-methylbenzene-1-sulfonic acid (560 mg, 3.25 mmol) and 2-methylprop-1-ene (760 mg, 13.55 mmol). The resulting solution was sealed in a tube and stirred for 16 h at 80° C. in an oil bath. The resulting mixture was concentrated under vacuum. The residue was diluted with EtOAc, washed with brine, then dried (Na$_2$SO$_4$) and concentrated under vacuum. The residue was purified by chromatography on SiO$_2$, eluted with petroleum ether/EtOAc (10:1) to afford [1-tert-butyl-5-chloro-1H-pyrazolo[3,4-c]pyridin-7-yl]methanol. MS (EI) calc'd for $C_{11}H_{15}ClN_3O$ [M+H]$^+$ 240. found 240.

Scheme 5

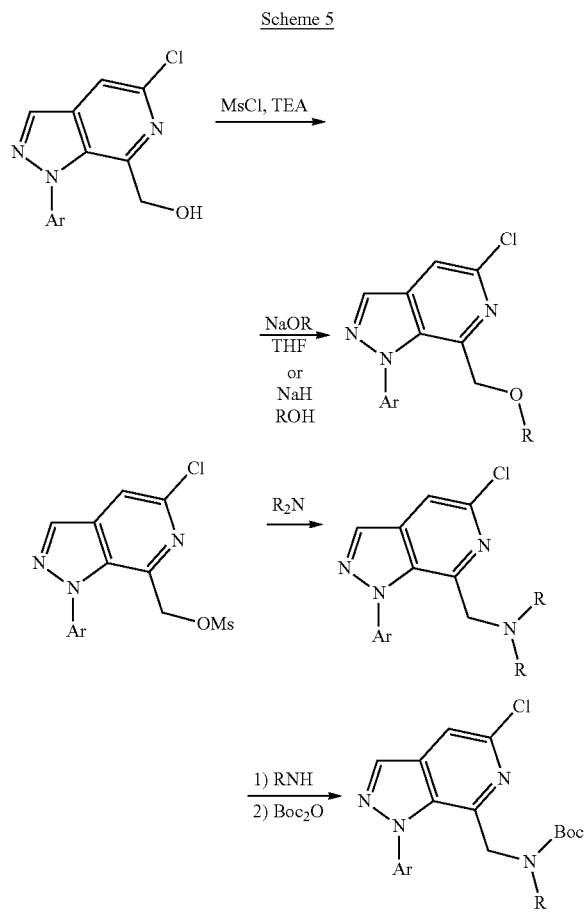

Intermediate 16I:

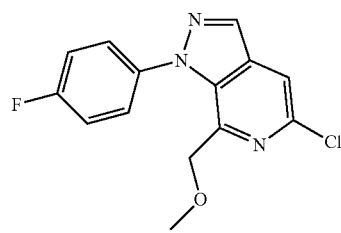 [SMILES: COCc1nc(Cl)cc2cnn(-c3ccc(F)cc3)c12]

5-Chloro-1-(4-fluorophenyl)-7-(methoxymethyl)-1H-pyrazolo[3,4-c]pyridine

Step 1: [5-Chloro-1-(4-fluorophenyl)-1H-pyrazolo[3,4-c] pyridin-7-yl] methyl methanesulfonate To a solution of [5-chloro-1-(4-fluorophenyl)-1H-pyrazolo[3,4-c]pyridin-7-yl]methanol (150 mg, 0.54 mmol) in THF (3 mL) was added TEA (164 mg, 1.62 mmol). Then methanesulfonyl chloride (92.8 mg, 0.81 mmol) was added dropwise with stirring at 0° C. The resulting solution was stirred for 2 h at 25° C. and then concentrated under reduced pressure. The residue was diluted with DCM, washed with saturated NaHCO$_3$, then dried (Na$_2$SO$_4$) and concentrated under reduced pressure to afford 200 mg (crude) of [5-chloro-1-(4-fluorophenyl)-1H-pyrazolo[3,4-c]pyridin-7-yl]methyl methanesulfonate as a solid, which was used in the next step without further purification. MS (EI) calc'd for $C_{14}H_{12}ClFN_3O_3S$ [M+H]$^+$ 356. found 356.

Step 2: 5-Chloro-1-(4-fluorophenyl)-7-(methoxymethyl)-1H-pyrazolo[3,4-c]pyridine To a solution of [5-chloro-1-(4-fluorophenyl)-1H-pyrazolo [3,4-c] pyridin-7-yl]methyl methanesulfonate (200 mg, 0.56 mmol, 1.00 equiv) in THF (5 mL) under nitrogen was added sodium methoxide (91 mg, 1.68 mmol). The resulting solution was stirred for 5 h at 25° C. and then quenched by the addition of water. The pH value of the solution was adjusted to 7 with 2 N aqueous HCl. The resulting solution was extracted with DCM, washed with saturated NaHCO$_3$, then dried (Na$_2$SO$_4$) and concentrated under reduced pressure to afford 5-chloro-1-(4-fluorophenyl)-7-(methoxymethyl)-1H-pyrazolo[3,4-c]pyridine. MS (EI) calc'd for $C_{14}H_{12}ClFN_3O$ [M+H]$^+$ 292. found 292.

Intermediate 17I:

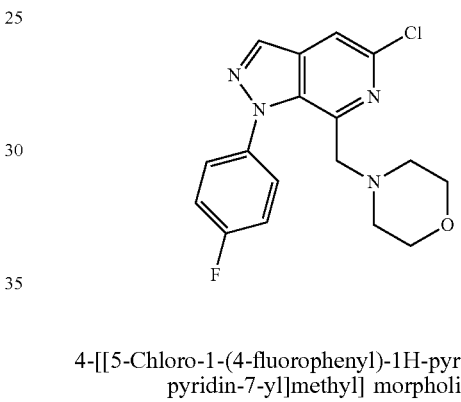

4-[[5-Chloro-1-(4-fluorophenyl)-1H-pyrazolo[3,4-c] pyridin-7-yl]methyl] morpholine To a solution of [5-chloro-1-(4-fluorophenyl)-1H-pyrazolo [3,4-c] pyridin-7-yl]methyl methanesulfonate (200 mg, 1.69 mmol, crude) in DCM (2 mL) was added morpholine (147 mg, 1.69 mmol). The resulting solution was stirred for 2 h at 30° C. and then concentrated under reduced pressure. The residue was diluted with DCM, washed with saturated NaHCO$_3$, brine, then dried (Na$_2$SO$_4$) and concentrated under reduced pressure to afford 4-[[5-chloro-1-(4-fluorophenyl)-1H-pyrazolo[3,4-c]pyridin-7-yl]methyl]morpholine, which was used in the next step without further purification. MS (EI) calc'd for $C_{17}H_{17}ClFN_4O$ [M+H]$^+$ 347. found 347. The following intermediate was made following similar protocol to intermediate 17I using appropriate reagent.

18I

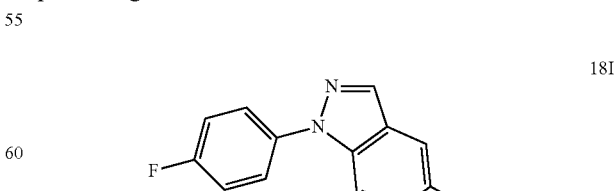

1-(5-chloro-1-(4-fluorophenyl)-1H-pyrazolo[3,4-c]pyridin-7-yl)-N,N-dimethylmethanamine Exact Mass [M+H]+ Calc'd 305. found 305.

Intermediate 19I:

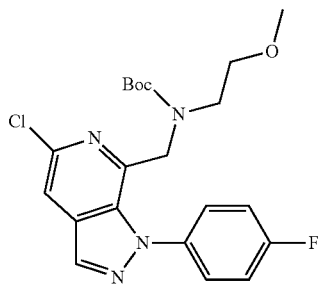 [SMILES: COCCN(Cc1nc(Cl)cc2cnn(-c3ccc(F)cc3)c12)C(=O)OC(C)(C)C]

tert-Butyl N-[[5-chloro-1-(4-fluorophenyl)-1H-pyrazolo[3,4-c]pyridin-7-yl]methyl]-N-(2-methoxyethyl)carbamate Step 1: 4-[[5-Chloro-1-(4-fluorophenyl)-1H-pyrazolo[3,4-c]pyridin-7-yl]methyl]morpholine To a solution of [5-chloro-1-(4-fluorophenyl)-1H-pyrazolo[3,4-c]pyridin-7-yl]methyl methanesulfonate (180 mg, 0.51 mmol) in MeCN (5 mL) was added 2-methoxyethan-1-amine (114 mg, 1.52 mmol). The resulting solution was stirred for 2 h at 80° C. in an oil bath, then concentrated under reduced pressure. The residue was diluted with DCM, washed with brine, then dried (Na$_2$SO$_4$) and concentrated to dryness. The crude product was purified by chromatography on SiO$_2$, eluted with DCM/MeOH (10:1) to afford [[5-chloro-1-(4-fluorophenyl)-1H-pyrazolo[3,4-c]pyridin-7-yl]methyl](2-methoxyethyl)amine. MS (EI) calc'd for C$_{16}$H$_{17}$ClFN$_4$O [M+H]$^+$ 335. found 335.

Step 2: tert-Butyl N-[[5-chloro-1-(4-fluorophenyl)-1H-pyrazolo[3,4-c]pyridin-7-yl]methyl]-N-(2-methoxyethyl)carbamate A solution of [[5-chloro-1-(4-fluorophenyl)-1H-pyrazolo[3,4-c]pyridin-7-yl]methyl](2-methoxyethyl)amine (140 mg, 0.42 mmol) in DCM (5 mL) was treated with (Boc)$_2$O (107 mg, 0.50 mmol) and TEA (127 mg, 1.26 mmol). The resulting solution was stirred for 2 h at 25° C. and then concentrated under reduced pressure. The residue was diluted with DCM, washed with brine, then dried (Na$_2$SO$_4$) and concentrated. The crude product was purified by chromatography on SiO$_2$, eluted with petroleum ether/EtOAc (5:1) to afford tert-butyl N-[[5-chloro-1-(4-fluorophenyl)-1H-pyrazolo[3,4-c]pyridin-7-yl]methyl]-N-(2-methoxyethyl)carbamate. MS (EI) calc'd for C$_{21}$H$_{25}$ClFN$_4$O$_3$[M+H]$^+$ 435. found 435.

The following intermediates were made following similar protocol to intermediate 19I using appropriate reagent.

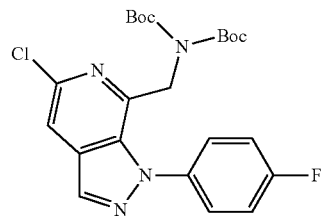

20I

Bis-tert-butyl ((5-chloro-1-(4-fluorophenyl)-1H-pyrazolo[3,4-c]pyridin-7-21I 21I yl)methyl)carbamate Exact Mass [M+H]+ Calc'd 477. found 477.

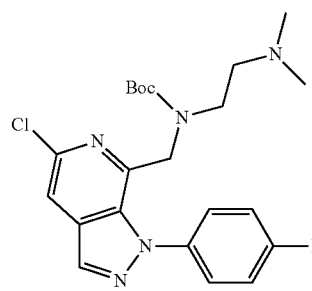

21I tert-butyl ((5-chloro-1-(4-fluorophenyl)-1H-pyrazolo[3,4-c]pyridin-7-yl)methyl)(2-(dimethylamino)ethyl)carbamate Exact Mass [M+H]+ Calc'd 448. found 448.

Intermediate 22I:

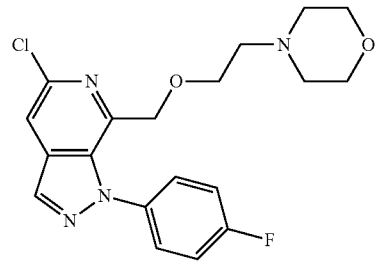 [SMILES: Fc1ccc(-n2ncc3cc(Cl)nc(COCCN4CCOCC4)c32)cc1]

4-(2-[[5-chloro-1-(4-fluorophenyl)-1H-pyrazolo[3,4-c] pyridin-7-yl] methoxy] ethyl) morpholine To a solution of 2-(morpholin-4-yl) ethan-1-ol (221 mg, 1.69 mmol) in THF (4 mL) under nitrogen was added sodium hydride (67.4 mg, 1.69 mmol, 60%) in portions at 0° C. The mixture was stirred for 1 h at 20° C. Then [5-chloro-1-(4-fluorophenyl)-1H-pyrazolo [3,4-c]pyridin-7-yl] methyl methanesulfonate (200 mg, 0.56 mmol) in THF (1 mL) was added and the resulting solution was stirred for 2 h at 20° C. The reaction was then quenched by the addition of water. The pH value of the mixture was adjusted to 7 with 2 N aqueous HCl. The resulting mixture was extracted with DCM, washed with brine, then dried (Na$_2$SO$_4$) and concentrated under reduced pressure. the residue was purified by chromatography on SiO$_2$, eluted with DCM/MeOH (10:1) to afford 4-(2-[[5-chloro-1-(4-fluorophenyl)-1H-pyrazolo [3,4-c] pyridin-7-yl] methoxy] ethyl) morpholine. MS (EI) calc'd for C$_{19}$H$_{21}$ClFN$_4$O$_2$[M+H]$^+$ 391. found 391. The following intermediate was made following protocol similar to intermediate 22I using the appropriate reagent.

TABLE 2
| Int. # | Structure | IUPAC Name | [M + H]+ |
|---|---|---|---|
| 23I | 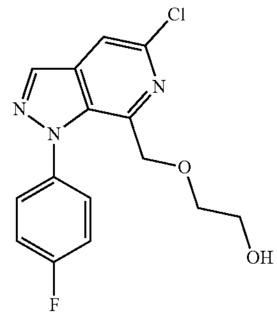 [SMILES: OCCOCc1nc(Cl)cc2cnn(-c3ccc(F)cc3)c12] | 2-((5-chloro-1-(4-fluorophenyl)-1H-pyrazolo[3,4-c]pyridin-7-yl)methoxy)ethanol | Calc'd 322, found 322 |
Scheme 6
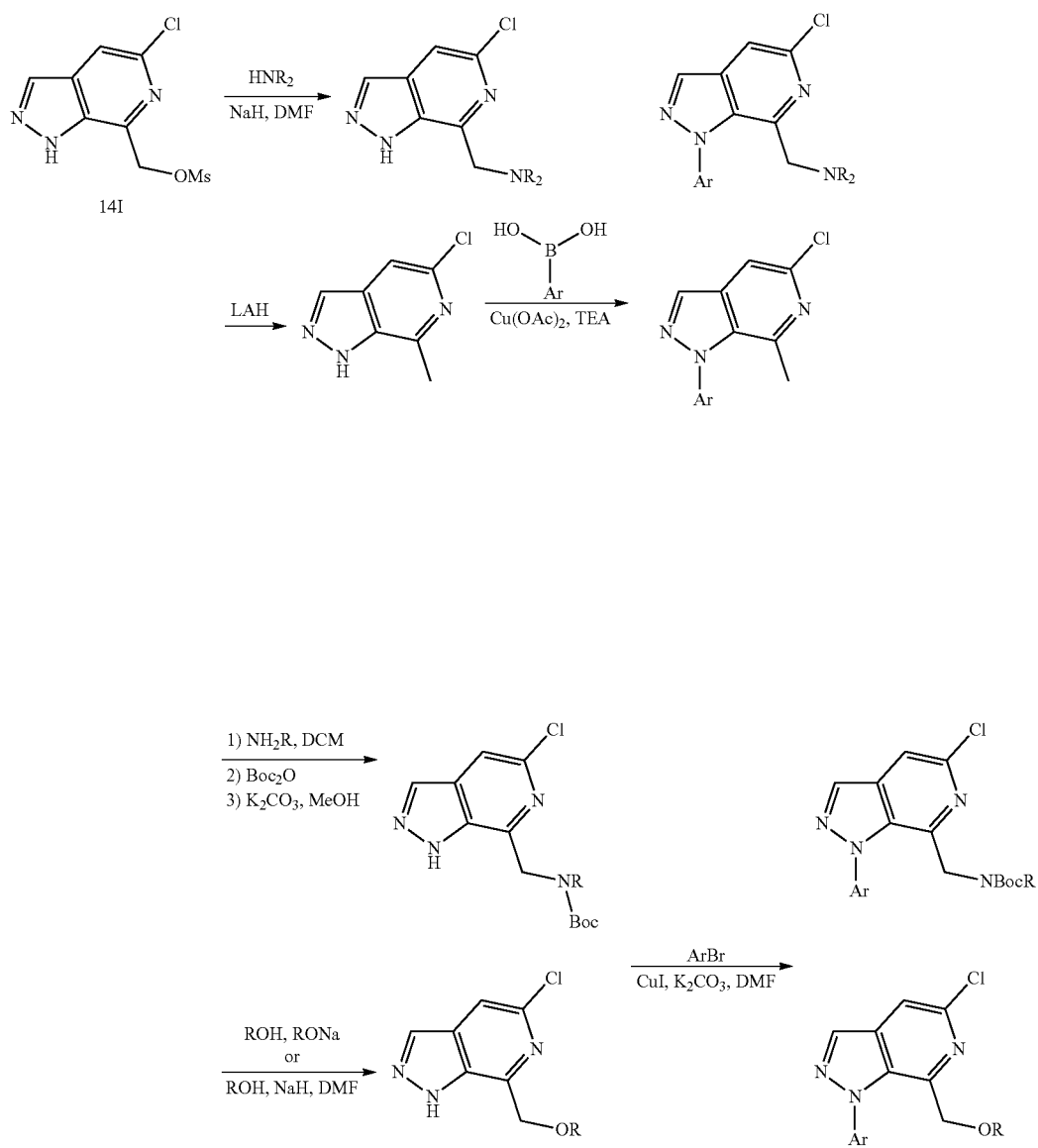

Intermediate 24I:

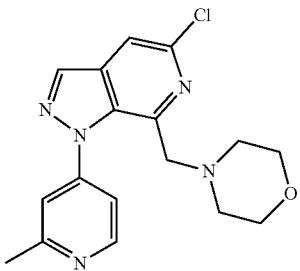 [SMILES: Cc1cc(-n2ncc3cc(Cl)nc(CN4CCOCC4)c32)ccn1]

4-[[5-chloro-1-(2-methylpyridin-4-yl)-1H-pyrazolo[3,4-c]pyridin-7-yl]methyl]morpholine Step 1: 4-([5-chloro-1H-pyrazolo[3,4-c]pyridin-7-yl]methyl)morpholine To a mixture of sodium hydride (37 mg, 1.50 equiv) in N,N-dimethylformamide (10 mL), under nitrogen was added morpholine (539 mg, 6.19 mmol) and stirred for 0.5 h at 20° C. Then [5-chloro-1-methanesulfonyl-1H-pyrazolo[3,4-c]pyridin-7-yl]methyl methanesulfonate, 14I, (210 mg, 0.62 mmol) was added and the resulting solution was stirred for 2 h at 20° C. The reaction was then quenched by the addition of saturated NH$_4$Cl (50 mL). The resulting mixture was extracted with EtOAc, washed with saturated NaHCO$_3$, brine, then dried (Na$_2$SO$_4$) and concentrated under reduced pressure. The residue was purified by chromatography on SiO$_2$, eluted with petroleum ether/EtOAc (10:1) to afford 4-([5-chloro-1H-pyrazolo[3,4-c]pyridin-7-yl]methyl)morpholine. MS (EI) calc'd for $C_{11}H_{14}ClN_4O$ [M+H]$^+$ 253. found 253.

Step 2: 4-[[5-chloro-1-(2-methylpyridin-4-yl)-1H-pyrazolo[3,4-c]pyridin-7-yl]methyl]morpholine To a mixture of 4-([5-chloro-1H-pyrazolo[3,4-c]pyridin-7-yl]methyl)morpholine (100 mg, 0.40 mmol) in dioxane (20 mL) were added (2-methylpyridin-4-yl)boronic acid (81.4 mg, 0.59 mmol), TEA (140 mg, 1.39 mmol), and Cu(OAc)$_2$ (123 mg, 0.68 mmol). The resulting mixture was stirred for 24 h at 60° C. The solids were filtered off and the filtrate was concentrated under vacuum. The residue was purified by chromatography on SiO$_2$, eluted with DCM/MeOH (40:1) to give 4-[[5-chloro-1-(2-methylpyridin-4-yl)-1H-pyrazolo[3,4-c]pyridin-7-yl]methyl]morpholine. MS (EI) calc'd for $C_{17}H_{19}ClN_5O$ [M+H]+ 344. found 344.

Intermediate 25I:

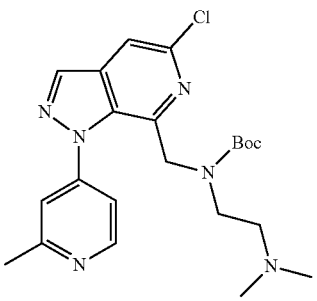

tert-Butyl N-[[5-chloro-1-(2-methylpyridin-4-yl)-1H-pyrazolo[3,4-c]pyridin-7-yl]methyl]-N-[2-(dimethylamino)ethyl]carbamate Step 1: ([5-Chloro-1H-pyrazolo[3,4-c]pyridin-7-yl]methyl)[2-(dimethylamino)ethyl]amine To a solution of [5-chloro-1H-pyrazolo[3,4-c]pyridin-7-yl]methyl methanesulfonate, 14I, (300 mg, 1.15 mmol) in DCM (3 mL) was added (2-aminoethyl)dimethylamine (303 mg, 3.44 mmol, 3.00 equiv). The resulting solution was stirred for 3 h at 30° C. and then concentrated under reduced pressure. The residue was purified by chromatography on SiO$_2$, eluted with DCM/MeOH (10:1) to afford of ([5-chloro-1H-pyrazolo[3,4-c]pyridin-7-yl]methyl)[2-(dimethylamino)ethyl]amine. MS (EI) calc'd for $C_{11}H_{17}ClN_5$ [M+H]$^+$ 254. found 254.

Step 2: tert-butyl 7-([[(tert-butoxy)carbonyl][2-(Dimethylamino)ethyl]amino]methyl)-5-chloro-1H-pyrazolo[3,4-c]pyridine-1-carboxylate To a solution of ([5-chloro-1H-pyrazolo[3,4-c]pyridin-7-yl]methyl)[2-(dimethylamino)ethyl]amine (120 mg, 0.47 mmol) in DCM (3 mL) was added TEA (239 mg, 2.36 mmol) and Boc$_2$O (227 mg, 1.04 mmol). The resulting solution was stirred for 5 h at 30° C. and then concentrated under reduced pressure. The residue was diluted with DCM, washed with Saturated NaHCO$_3$, brine, then dried (Na$_2$SO$_4$) and concentrated to afford tert-butyl 7-([[(tert-butoxy)carbonyl][2-(dimethylamino)ethyl]amino]methyl)-5-chloro-1H-pyrazolo[3,4-c]pyridine-1-carboxylate. MS (EI) calc'd for $C_{21}H_{33}ClN_5O_4$[M+H]$^+$ 454. found 454.

Step 3: tert-Butyl N-([5-chloro-1H-pyrazolo[3,4-c]pyridin-7-yl]methyl)-N-[2-(dimethylamino)ethyl]carbamate To a solution of tert-butyl 7-([[(tert-butoxy)carbonyl][2-(dimethylamino)ethyl]amino]methyl)-5-chloro-1H-pyrazolo[3,4-c]pyridine-1-carboxylate (220 mg, 0.48 mmol) in MeOH (5 mL) was added potassium carbonate (200.9 mg, 1.45 mmol). The resulting solution was stirred for 2 h at 20° C. and then concentrated under reduced pressure. The residue was purified by chromatography on SiO$_2$, eluted with DCM/MeOH (10:1) to afford tert-butyl N-([5-chloro-1H-pyrazolo[3,4-c]pyridin-7-yl]methyl)-N-[2-(dimethylamino)ethyl]carbamate. MS (EI) calc'd for $C_{16}H_{25}ClN_5O_2$[M+H]$^+$ 354. found 354.

Step 4: tert-Butyl N-[[5-chloro-1-(2-methylpyridin-4-yl)-1H-pyrazolo[3,4-c]pyridin-7-yl]methyl]-N-[2-(dimethylamino)ethyl]carbamate To a solution of tert-butyl N-([5-chloro-1H-pyrazolo[3,4-c]pyridin-7-yl]methyl)-N-[2-(dimethylamino)ethyl]carbamate (158 mg, 0.45 mmol) in N,N-dimethylformamide (10 mL) under nitrogen was added 4-bromo-2-methylpyridine (153 mg, 0.89 mmol), 2-acetylcyclohexan-1-one (38 mg, 0.27 mmol), CuI (26 mg, 0.14 mmol) and Cs$_2$CO$_3$ (292 mg, 0.90 mmol). The resulting mixture was stirred for 15 h at 120° C. in an oil bath. The solids were filtered out. The filtrate was concentrated under vacuum. The residue was purified by chromatography on SiO$_2$, eluted with DCM/MeOH (10:1) to afford tert-butyl N-[[5-chloro-1-(2-methylpyridin-4-yl)-1H-pyrazolo[3,4-c]pyridin-7-yl]methyl]-N-[2-(dimethylamino)ethyl]carbamate. MS (EI) calc'd for $C_{22}H_{30}ClN_6O_2$[M+H]$^+$ 445. found 445.

The following intermediate was made following protocol similar to intermediate 25I using the appropriate reagent.

TABLE 3

| Int. # | Structure | IUPAC Name | [M + H]+ |
|---|---|---|---|
| 26I | 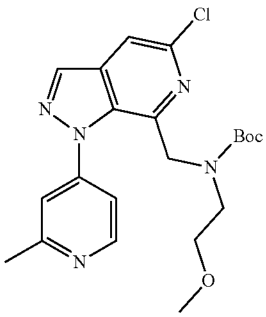 [SMILES: COCCN(Cc1nc(Cl)cc2cnn(-c3ccnc(C)c3)c12)C(=O)OC(C)(C)C] | tert-butyl ((5-chloro-1-(2-methylpyridin-4-yl)-1H-pyrazolo[3,4-c]pyridin-7-yl)methyl)(2-methoxyethyl)carbamate | Calc'd 432, found 432 |

Intermediate 27I:

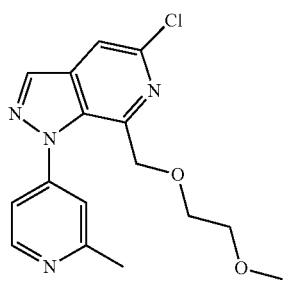 [SMILES: COCCOCc1nc(Cl)cc2cnn(-c3ccnc(C)c3)c12]

4-[5-Chloro-7-[(2-methoxyethoxy)methyl]-1H-pyrazolo[3,4-c]pyridin-1-yl]-2-methylpyridine Step 1: 5-Chloro-7-[(2-methoxyethoxy)methyl]-1H-pyrazolo[3,4-c]pyridine To a suspension of NaH (92 mg, 3.83 mmol, 60%) in N,N-dimethylformamide (10 mL), was added 2-methoxyethan-1-ol (874 mg, 11.49 mmol) at 0° C. After stirring for 30 min at 20° C., [5-chloro-1H-pyrazolo[3,4-c]pyridin-7-yl] methyl methanesulfonate (300 mg, 1.15 mmol) was added. The resulting mixture was stirred for 1 h at 20° C., quenched by the addition of saturated aqueous NH$_4$Cl and extracted with EtOAc. The combined organic phases was washed with brine, dried with Na$_2$SO$_4$ and concentrated. The residue was purified by chromatography on SiO$_2$, eluted with petroleum ether/EtOAc (2:1) to give 5-chloro-7-[(2-methoxyethoxy)methyl]-1H-pyrazolo[3,4-c]pyridine. MS (EI) calc'd for C$_{10}$H$_{13}$ClN$_3$O$_2$[M+H]$^+$ 242. found 242.

Step 2: 4-[5-Chloro-7-[(2-methoxyethoxy)methyl]-1H-pyrazolo[3,4-c]pyridin-1-yl]-2-methylpyridine This compound was synthesized by the same method as described in intermediate 25I at step 4 except 5-chloro-7-[(2-methoxyethoxy)methyl]-1H-pyrazolo[3,4-c]pyridine was used: MS (EI) calc'd for C$_{16}$H$_{18}$ClN$_4$O$_2$[M+H]$^+$ 333. found 333.

The following intermediates were made following protocol similar to intermediate 27I using the appropriate reagent.

TABLE 4

| Int. # | Structure | IUPAC Name | [M + H]+ |
|---|---|---|---|
| 28I | 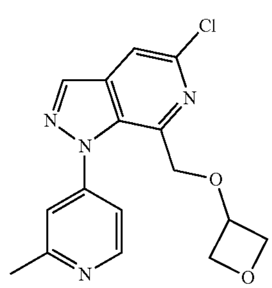 [SMILES: Cc1cc(-n2ncc3cc(Cl)nc(COC4COC4)c32)ccn1] | 5-chloro-1-(2-methylpyridin-4-yl)-7-((oxetan-3-yloxy)methyl)-1H-pyrazolo[3,4-c]pyridine | Calc'd 331, found 331 |

TABLE 4-continued

| Int. # | Structure | IUPAC Name | [M + H]+ |
|---|---|---|---|
| 29I | 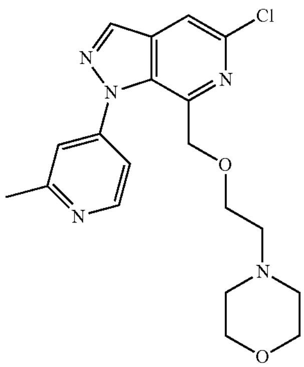 [SMILES: Cc1cc(-n2ncc3cc(Cl)nc(COCCN4CCOCC4)c32)ccn1] | 4-(2-((5-chloro-1-(2-methylpyridin-4-yl)-1H-pyrazolo[3,4-c]pyridin-7-yl)methoxy)ethyl)morpholine | Calc'd 388, found 388 |
| 30I | 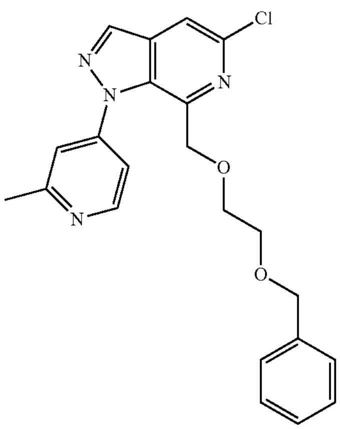 [SMILES: Cc1cc(-n2ncc3cc(Cl)nc(COCCOCc4ccccc4)c32)ccn1] | 7-((2-(benzyloxy)ethoxy)methyl)-5-chloro-1-(2-methylpyridin-4-yl)-1H-pyrazolo[3,4-c]pyridine | Calc'd 409, found 409 |
| 31I | 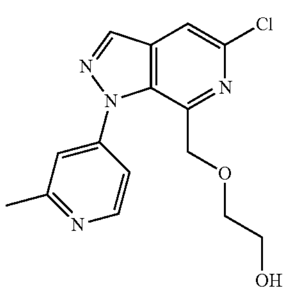 [SMILES: Cc1cc(-n2ncc3cc(Cl)nc(COCCO)c32)ccn1] | 2-((5-chloro-1-(2-methylpyridin-4-yl)-1H-pyrazolo[3,4-c]pyridin-7-yl)methoxy)ethanol | Calc'd 319, found 319 |

Intermediate 32I:

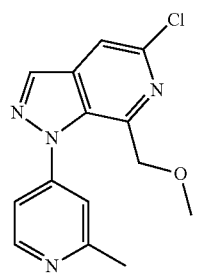 [SMILES: COCc1nc(Cl)cc2cnn(-c3ccnc(C)c3)c12]

5-Chloro-7-(methoxymethyl)-1-(2-methylpyridin-4-yl)-1H-pyrazolo[3,4-c]pyridine

Step 1: 5-Chloro-7-(methoxymethyl)-1H-pyrazolo[3,4-c]pyridine & 5-chloro-4-methoxy-7-methyl-1H-pyrazolo[3,4-c]pyridine To a solution of MeONa (383 mg, 8.3 mmol) in MeOH (5 mL) was added a solution of [5-chloro-1H-pyrazolo[3,4-c]pyridin-7-yl]methyl methanesulfonate (200 mg, 0.76 mmol) in MeOH (5 mL) dropwise with stirring. The resulting mixture was stirred for 2 h at 20° C. and then concentrated under vacuum. The residue was diluted with water, extracted with EtOAc, washed with brine, then dried (Na$_2$SO$_4$) and concentrated. The residue was purified by chromatography on SiO$_2$, eluted with petroleum ether/EtOAc (10:1) to afford a mixture of isomers of 5-chloro-7-(methoxymethyl)-1H-pyrazolo[3,4-c]pyridine. MS (EI) calc'd for C$_8$H$_9$ClN$_3$O [M+H]$^+$ 198. found 198.

Step 2: 5-Chloro-7-(methoxymethyl)-1-(2-methyl-pyridin-4-yl)-1H-pyrazolo[3,4-c]pyridine The mixture of 5-chloro-7-(methoxymethyl)-1H-pyrazolo [3,4-c]pyridine and 5-chloro-4-methoxy-7-methyl-1H-pyrazolo[3,4-c]pyridine (80 mg, 0.40 mmol) was dissolved in N,N-dimethylformamide (4 mL). Then 4-bromo-2-methyl-pyridine (90 mg, 0.52 mmol), 2-acetylcyclohexan-1-one (34 mg, 0.24 mmol), CuI (24 mg, 0.13 mmol) and Cs$_2$CO$_3$ (264 mg, 0.80 mmol) were added. The resulting solution was degassed with nitrogen and then stirred for 16 h at 110° C. The resulting mixture was concentrated under vacuum. The residue was purified by chromatography on SiO$_2$, eluted with DCM/MeOH (40:1) to afford a mixture of 5-chloro-7-(methoxymethyl)-1-(2-methylpyridin-4-yl)-1H-pyrazolo[3,4-c]pyridine. MS (EI) calc'd for C$_{14}$H$_{14}$ClN$_4$O [M+H]$^+$ 289. found 289.

Intermediate 33I:

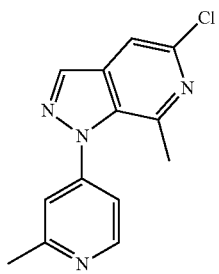 [SMILES: Cc1cc(-n2ncc3cc(Cl)nc(C)c32)ccn1]

5-chloro-7-methyl-1-(2-methylpyridin-4-yl)-1H-pyrazolo[3,4-c]pyridine

Step 1:
5-Chloro-7-methyl-1H-pyrazolo[3,4-c]pyridine

To a solution of [5-chloro-1H-pyrazolo[3,4-c]pyridin-7-yl]methyl methanesulfonate (300 mg, 1.15 mmol) in THF (10 mL) was added LiAlH$_4$ (87 mg, 2.29 mmol) in portions at 0° C. and the resulting solution was stirred for 1 h at 20° C. The reaction was quenched by the addition of saturated aqueous NH$_4$Cl. The resulting mixture was extracted with EtOAc, washed with brine, then dried (Na$_2$SO$_4$) and concentrated under vacuum to afford crude 5-chloro-7-methyl-1H-pyrazolo[3,4-c]pyridine. MS (EI) calc'd for C$_7$H$_7$ClO$_3$ [M+H]$^+$ 168. found 168.

Step 2. 5-chloro-7-methyl-1-(2-methylpyridin-4-yl)-1H-pyrazolo[3,4-c]pyridine

To a solution of 5-chloro-7-methyl-1H-pyrazolo[3,4-c] pyridine (400 mg, 2.39 mmol) in dioxane (30 mL) were added (2-methylpyridin-4-yl)boronic acid (656 mg, 4.79 mmol), TEA (847 mg, 8.37 mmol) and Cu(OAc)$_2$ (1.1 g, 6.04 mmol). The resulting mixture was stirred for 24 h at 65° C. The solids were filtered off and the filtrate was concentrated under vacuum. The residue was purified by chromatography on SiO$_2$, eluted with petroleum ether/EtOAc (2:1) to give 4-[5-chloro-7-methyl-1H-pyrazolo[3,4-c]pyridin-1-yl]-2-methylpyridine. MS (EI) calc'd for C$_{13}$H$_{12}$ClN$_4$ [M+H]$^+$ 259. found 259.

Scheme 7

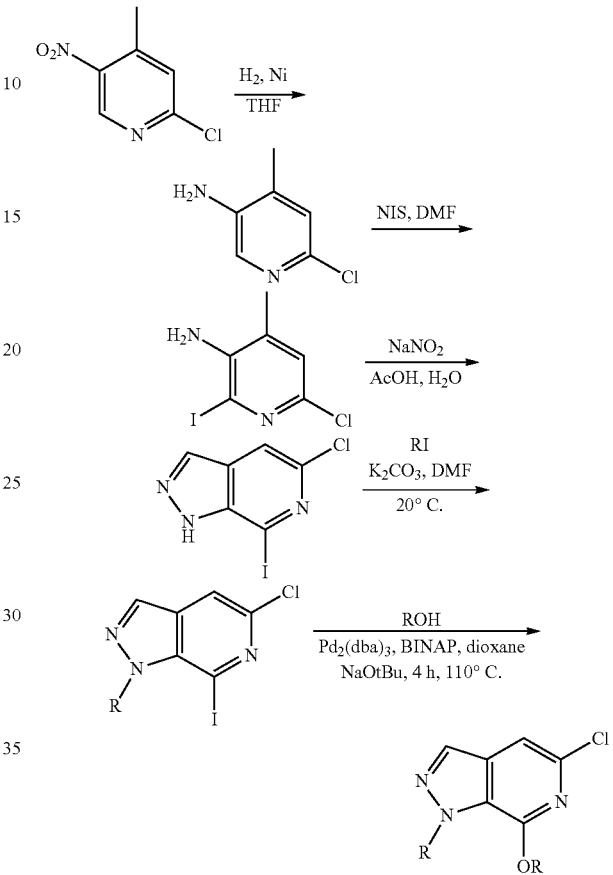

Intermediate 34I:

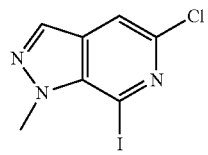

5-Chloro-1-methyl-7-iodo-1H-pyrazolo[3,4-c]pyridine

Step 1: 6-Chloro-4-methylpyridin-3-amine

To a solution of 2-chloro-4-methyl-5-nitropyridine (200 g, 1.16 mol) in THF (1000 mL) was added Raney-nickel (68.0 g, 1.16 mol) in portions. The resulting mixture was purged in 2-4 atm of hydrogen and stirred for 16 h at 25° C. under an atmosphere of hydrogen (2~4 atm.). The reaction mixture was filtered, and the filtrate was concentrated under vacuum to give 6-chloro-4-methylpyridin-3-amine, which was used directly for the next step without further purification. MS (EI) calc'd for C$_6$H$_8$ClN$_2$ [M+H]$^+$ 143. found 143.

Step 2: 6-Chloro-2-iodo-4-methylpyridin-3-amine

To a solution of 6-chloro-4-methylpyridin-3-amine (100 g, 701 mmol) in DMF (1000 mL) was added 1-iodopyrrolidine-2,5-dione (189 g, 842 mmol) in portions. The mixture was stirred for 10 h at 25° C. and then concentrated under reduced pressure. The residue was diluted with water and extracted with EtOAc, washed with brine, dried (Na$_2$SO$_4$), filtered and concentrated. The residue was purified by chromatography on SiO$_2$, eluted with petroleum ether/EtOAc (10:1) to give 6-chloro-2-iodo-4-methylpyridin-3-amine. MS (EI) calc'd for C$_6$H$_7$ClIN$_2$ [M+H]$^+$ 269. found 269.

Step 3: 5-Chloro-7-iodo-1H-pyrazolo[3,4-c]pyridine

To a solution of 6-chloro-2-iodo-4-methylpyridin-3-amine (80 g, 298 mmol) in AcOH (500 mL) was added a solution of sodium nitrite (22.6 g, 328 mmol) in water (200 mL) in portions at 0° C. The resulting mixture was stirred for 10 h at 25° C. and concentrated under vacuum and diluted with water. The pH value of the solution was adjusted to 7 with saturated NaHCO$_3$ and then extracted with DCM, washed with brine, dried (Na$_2$SO$_4$), and filtered. The filtrate was concentrated to give 5-chloro-7-iodo-1H-pyrazolo[3,4-c]pyridine. MS (EI) calc'd for C$_6$H$_4$ClIN$_3$ [M+H]$^+$ 280. found 280.

Step 4. 5-Chloro-1-methyl-7-iodo-1H-pyrazolo[3,4-c]pyridine

To a solution of 5-chloro-7-iodo-1H-pyrazolo[3,4-c]pyridine (20.0 g, 64.4 mmol) in DMF (100 mL) were added K$_2$CO$_3$ (17.8 g, 129 mmol) and iodomethane (9.14 g, 64.4 mmol). The resulting mixture was stirred for 2 h at 25° C. and then concentrated under vacuum. The residue was diluted with DCM, washed with water, dried (Na$_2$SO$_4$), filtered and concentrated. The residue was purified by chromatography on SiO$_2$, eluted with petroleum ether/EtOAc (10:1) to give the desired isomer 5-chloro-1-methyl-7-iodo-1H-pyrazolo[3,4-c]pyridine. MS (EI) calc'd for C$_7$H$_6$ClIN$_3$ [M+H]$^+$ 294. found 294. $^1$H NMR (300 MHz, CDCl$_3$) δ 7.94 (s, 1H), 7.56 (s, 1H), 4.47 (s, 3H).

The following intermediate was made following protocol similar to intermediate 34I using the appropriate reagent.

Intermediate 36I:

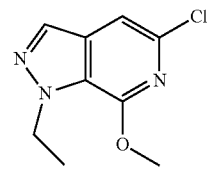

5-chloro-1-ethyl-7-methoxy-1H-pyrazolo[3,4-c]pyridine

To a solution of 5-chloro-1-ethyl-7-iodo-1H-pyrazolo[3,4-c]pyridine, intermediate 32I, (1 g, 3.25 mmol) in 1,4-dioxane (20 ml) was added Pd$_2$(dba)$_3$.CHCl$_3$ (0.17 g, 0.16 mmol), BINAP (0.04 g, 0.06 mmol), sodium tert-butoxide (0.88 g, 9.11 mmol) and MeOH (1.04 g, 32.5 mmol). The resulting solution was stirred for 4 h at 110° C. The solid was filtered out. The filtrate was concentrated under vacuum. The residue was purified by chromatography on SiO$_2$, eluted with petroleum ether/EtOAc (10:1) to afford 5-chloro-1-ethyl-7-methoxy-1H-pyrazolo[3,4-c]pyridine. MS (EI) calc'd for C$_9$H$_{11}$ClN$_3$O [M+H]$^+$ 212. found 212.

Intermediate 37I:

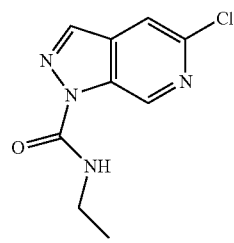

5-chloro-N-ethyl-1H-pyrazolo[3,4-c]pyridine-1-carboxamide

A solution of 5-chloro-1H-pyrazolo[3,4-c]pyridine (200 mg, 1.302 mmol) and Hunig's Base (1.137 ml, 6.51 mmol) in THF (10 ml) was cooled to 0° C. and then treated slowly with ethyl isocyanate (0.155 ml, 1.954 mmol). The reaction was slowly allowed to warm to room temperature overnight. The reaction was diluted with DCM and quenched with water. The layers were separated. The aqueous layer was extracted with DCM (2×). The combined organic fractions were washed with brine, filtered and concentrated to an off-white solid. The residue was purified by column chromatography on silica gel (24 g), eluting with 1-100% EtOAc/hexanes to give 5-chloro-N-ethyl-1H-pyrazolo[3,4-c]pyridine-1-carboxamide. LCMS (ESI) calc'd for C$_9$H$_9$ClN$_4$O [M+H]$^+$ 225. found 225.

TABLE 5

| Int. # | Structure | IUPAC Name | [M + H]+ |
|---|---|---|---|
| 35I | 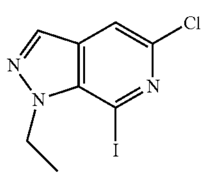 | 5-chloro-1-ethyl-7-iodo-1H-pyrazolo[3,4-c]pyridine | Calc'd 308, found 308 |

Scheme 8

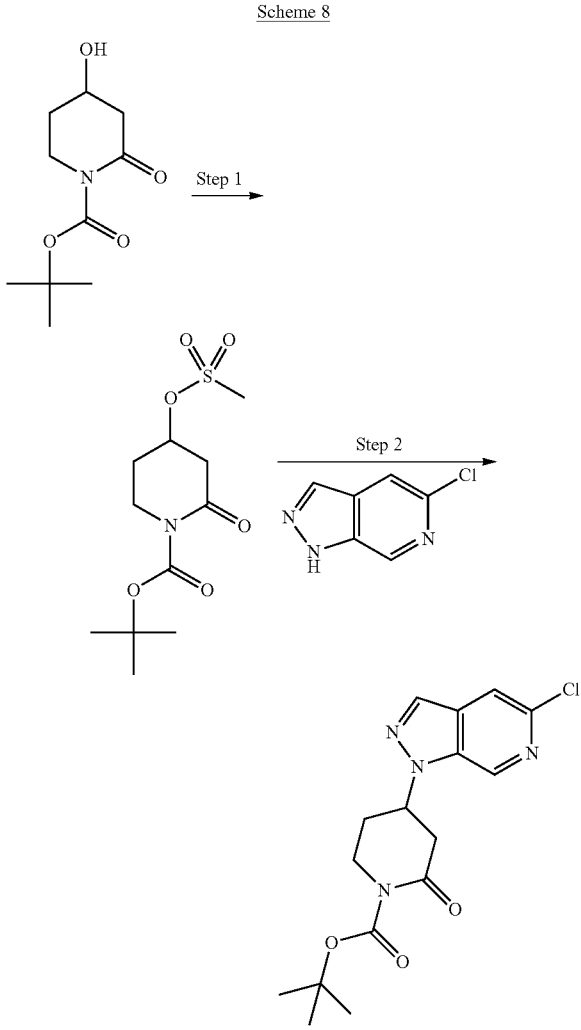

Intermediate 38I:

tert-butyl 4-(5-chloro-1H-pyrazolo[3,4-c]pyridin-1-yl)-2-oxopiperidine-1-carboxylate

Step 1: tert-butyl 4-((methylsulfonyl)oxy)-2-oxopiperidine-1-carboxylate

In a 40 mL vial with pressure relief cap, under an atmosphere of nitrogen gas, tert-butyl 4-hydroxy-2-oxopiperidine-1-carboxylate (200 mg, 0.929 mmol) and n,n-diisopropylethylamine (0.502 ml, 2.88 mmol) were dissolved in DCM (6.00 ml). After cooling to 0° C. the reaction mixture was treated with methanesulfonyl chloride (0.108 ml, 1.394 mmol) and stirred at room temperature overnight. The mixture was diluted with dichloromethane (60 mL) and brine (60 mL). The biphasic solution was separated and the aqueous layer was extracted with dichloromethane (2×60 mL). The combined organic phase was dried over sodium sulfate, filtered and concentrated to dryness under reduced pressure to provide tert-butyl 4-((methylsulfonyl)oxy)-2-oxopiperidine-1-carboxylate.

Step 2: tert-butyl 4-(5-chloro-1H-pyrazolo[3,4-c]pyridin-1-yl)-2-oxopiperidine-1-carboxylate To a solution of 5-chloro-1H-pyrazolo[3,4-c]pyridine (130 mg, 0.847 mmol) dissolved in N,N-dimethylformamide (5.00 ml) was added cesium carbonate (579 mg, 1.778 mmol) followed by tert-butyl 4-((methylsulfonyl)oxy)-2-oxopiperidine-1-carboxylate (273 mg, 0.931 mmol). The reaction mixture stirred at room temperature overnight. LC/MS analysis indicated that the desired product was not obtained. The reaction was heated to 65° C. and stirred overnight. The mixture was filtered through a 0.2 mm Millex syringe-driven filter unit, washed with methanol (2×6 mL) and concentrated to dryness under reduced pressure. The crude mixture was purified by reverse phase HPLC (10% to 90% Acetonitrile/Water+0.1% TFA, over 10 minutes) to provide the desired product tert-butyl 4-(5-chloro-1H-pyrazolo[3,4-c]pyridin-1-yl)-2-oxopiperidine-1-carboxylate. LCMS (ESI) calc'd for $C_{16}H_{19}ClN_4O_3$ $[M+H]^+=351$. found 351.

Scheme 9

Intermediate 39I:

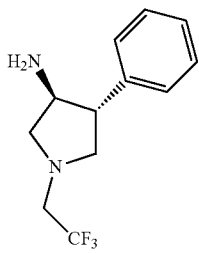 [SMILES: N[C@@H]1CN(CC(F)(F)F)C[C@H]1c1ccccc1]

(3S,4R)-4-phenyl-1-(2,2,2-trifluoroethyl)pyrrolidin-3-amine

Step 1: Synthesis of (E)-(2-nitrovinyl)benzene

At 0° C., to a solution of benzaldehyde (5.0 g, 47.16 mmol) and nitromethane (3.45 g, 56.6 mmol) in MeOH (50 mL) was added NaOH (1.98 g, 49.5 mmol) dissolved in minimum amount of water (5 mL). The resultant mixture was stirred at the same temperature for about an hour. A pre cooled 2N HCl (50 mL) was added dropwise to the reaction mixture and the resultant was stirred for additional 2 h. The product was extracted into ethyl acetate (3×25 mL). The combined extracts were washed with brine solution, dried over anhydrous $Na_2SO_4$ and concentrated to residue. The residue was purified by column chromatography using pet ether and ethyl acetate as mobile phase (9:1) afforded the title compound. $^1$H NMR (CDCl$_3$, 300 MHz): δ 8.03 (d, J=14.0 Hz, 1H), 7.44-7.63 (m, 6H).

Step 2: trans-1-benzyl-3-nitro-4-phenylpyrrolidine

At 0° C., to a solution of (E)-(2-nitrovinyl)benzene (0.4 g, 2.65 mmol) and N-benzyl-1-methoxy-N-((trimethylsilyl)methyl)methanamine (0.95 g, 4.02 mmol) in anhydrous $CH_2Cl_2$ (5 mL) was added TFA (0.029 g, 0.25 mmol) and the resultant was stirred at the same temperature. After 30 min, the reaction mixture was warmed and stirred at ambient temperature for additional 2 h. The organic volatiles were then removed under reduced pressure and the residue thus obtained was purified by flash column chromatography afforded the title compound. Anal. Calcd. $C_{17}H_{18}N_2O_2$ [M+H] 283 Found 283.

Step 3: Synthesis of trans-3-nitro-4-phenylpyrrolidine

A solution of trans-1-benzyl-3-nitro-4-phenylpyrrolidine (0.25 g, 0.886 mmol) in chloroethyl chloroformate (2 mL) was heated to reflux. After 7 h, the reaction mixture was cooled to ambient temperature, and the volatile was removed under reduced pressure. The residue thus obtained was taken up in MeOH (5 mL) and the contents were heated to reflux. After 2 h, MeOH was removed under reduced pressure, the residue thus obtained was triturated with $Et_2O$ afforded the title compound. Anal. Calcd. $C_{10}H_{12}N_2O_2$ [M+H] 193. Found 193.

Step 4: Trans-3-nitro-4-phenyl-1-(2,2,2-trifluoroethyl)pyrrolidine

At 0° C., to the solution of trans-3-nitro-4-phenylpyrrolidine (0.3 g, 1.57 mmol) in THF: DMF (1:1 mL) was added DIPEA (0.6 g, 4.71 mmol) followed by 2,2,2 trifluoroethyl trifluoromethanesulfonate (0.54 g, 2.35 mmol). The resultant mixture was stirred at RT for 2 h. The reaction mixture was quenched with $H_2O$ (3 mL) and was diluted with EtOAc (10 mL). The organic layer was separated and washed with brine solution (1×10 mL), dried over anhydrous $Na_2SO_4$ and the solvents were removed under reduced pressure. The residue thus obtained was purified by flash column chromatography using a mixture of pet ether and ethyl acetate as mobile phase afforded the title compound. Anal. Calcd. $C_{12}H_{13}F_3N_2O_2$[M+H] 275. Found 275.

Step 5: Trans-4-phenyl-1-(2,2,2-trifluoroethyl)pyrrolidin-3-amine

To a suspension of Zn dust (0.12 g, 1.82 mmol) in MeOH:AcOH (1:1 ratio, 4 mL) was added a solution of trans-3-nitro-4-phenyl-1-(2,2,2-trifluoroethyl)pyrrolidine (0.1 g, 0.364 mmol) in MeOH (1 mL) and the resultant mixture was heated to 80° C., After 6 h, the reaction mixture was brought back to ambient temperature and filtered through a pad of celite. The organic volatiles were then removed under reduced pressure and the residue thus obtained was basified by aqueous $NH_3$. The organic contents were then extracted with $CH_2Cl_2$ (3×15 mL) and was washed with brine solution, dried over anhydrous $Na_2SO_4$ and concentrated. The residue thus obtained was taken directly for next step without purification. Anal. Calcd. $C_{12}H_{15}F_3N_2$ [M+H] 245. Found 245.

Scheme 10

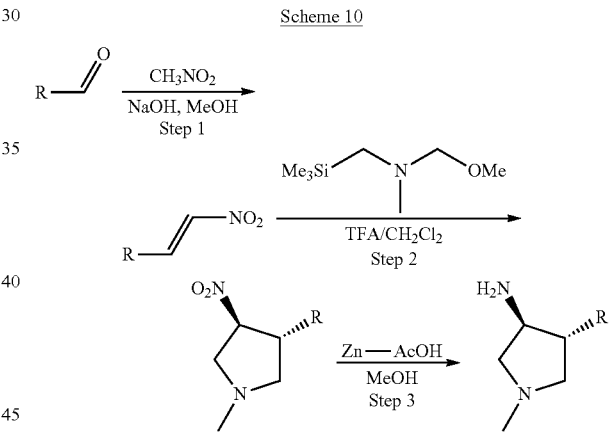

Intermediate 40I:

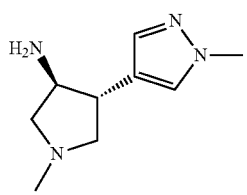

(3S,4R)-1-methyl-4-(1-methyl-1H-pyrazol-4-yl)pyrrolidin-3-amine

Step 1: Synthesis of (E)-1-methyl-4-(2-nitrovinyl)-1H-pyrazole

At 0° C., to a solution of 1-methyl 1H pyrzole-4-carbaldehyde (1.0 g, 9.1 mmol) and nitro methane (0.56 g, 9.1 mmol) in MeOH (10 mL) was added NaOH (0.364 g, 9.10 mmol) dissolved in minimum water (0.2 mL). The resultant mixture was stirred at the same temperature for about an hour. A pre cooled 2N HCl (10 mL) was added dropwise to the reaction mixture and the resultant was stirred for additional 2 h. The product that is crashed out from the solvent was filtered and washed successively with MeOH afforded the title compound. $^1$H NMR (300 MHz, CDCl$_3$): δ 7.93 (d, J=13.5 Hz, 1H), 7.75 (s, 1H), 7.69 (s, 1H), 7.43 (d, J=13.5 Hz, 1H), 3.96 (s, 3H).

Step 2: Synthesis of 1-methyl-trans-1-methyl-4-nitropyrrolidin-3-yl)-1H-pyrazole At 0° C., to a solution of (E)-1-methyl-4-(2-nitrovinyl)-1H-pyrazole (0.6 g, 3.92 mmol) and 1-methoxy-N-methyl-N-((trimethylsilyl)methyl)methanamine (0.76 g, 4.7 mmol) in anhydrous CH$_2$Cl$_2$ (5 mL) was added TFA (0.45 g, 0.39 mmol) and the resultant was stirred at the same temperature. After 30 min, the reaction mixture was warmed and stirred at ambient temperature for additional 2 h. The organic volatiles were then removed under reduced pressure and the residue thus obtained was purified by flash column chromatography afforded the title compound. Anal. Calcd. C$_9$H$_{14}$N$_4$O$_2$, [M+H] 211. Found 211.

Step 3: Trans-1-methyl-4-(1-methyl-1H-pyrazol-4-yl)pyrrolidin-3-amine

To a suspension of Zn dust (0.15 g, 2.37 mmol) in MeOH:AcOH (1:1 ratio, 4 mL) was added a solution of 1-methyl-trans-1-methyl-4-nitropyrrolidin-3-yl)-1H-pyrazole (0.1 g, 0.48 mmol) in MeOH (1 mL) and the resultant mixture was heated to 80° C., After 6 h, the reaction mass was brought back to ambient temperature and the suspension was filtered through a pad of celite. The organic volatiles were then removed under reduced pressure and the residue thus obtained was basified by aqueous NH$_3$. The organic contents were then extracted with CH$_2$Cl$_2$ (3×15 mL) and was washed with brine solution, dried over anhydrous Na$_2$SO$_4$ and concentrated. The residue thus obtained was taken as such for next step. The residue thus obtained was taken as such for next step.

The following intermediates were made following protocol similar to intermediate 40I using the appropriate aldehyde:

TABLE 6

| Int. # | Structure | IUPAC Name |
|---|---|---|
| 41I | 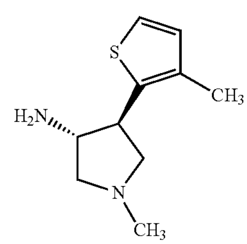 | (3R,4S)-1-methyl-4-(3-methylthiophen-2-yl)pyrrolidin-3-amine |
| 42I | 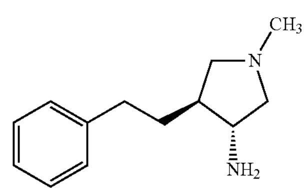 | (3R,4S)-1-methyl-4-phenethylpyrrolidin-3-amine |
| 43I | 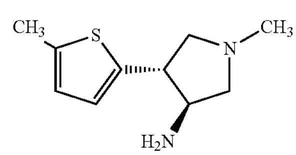 | (3S,4R)-1-methyl-4-(5-methylthiophen-2-yl)pyrrolidin-3-amine |
| 44I | 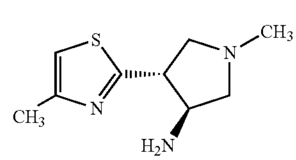 | (3S,4R)-1-methyl-4-(4-methylthiazol-2-yl)pyrrolidin-3-amine |
| 45I | 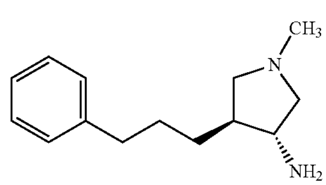 [SMILES: CN1C[C@H](CCCc2ccccc2)[C@@H](N)C1] | (3R,4S)-1-methyl-4-(3-phenylpropyl)pyrrolidin-3-amine |

TABLE 6-continued

| Int. # | Structure | IUPAC Name |
|---|---|---|
| 46I | 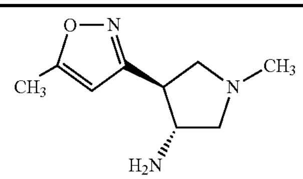 | (3R,4S)-1-methyl-4-(5-methylisoxazol-3-yl)pyrrolidin-3-amine |
| 47I | 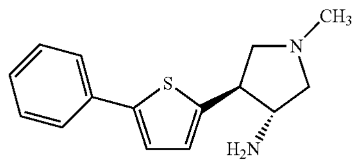 [SMILES: CN1C[C@H](c2ccc(-c3ccccc3)s2)[C@@H](N)C1] | (3R,4S)-1-methyl-4-(5-phenylthiophen-2-yl)pyrrolidin-3-amine |
| 48I | 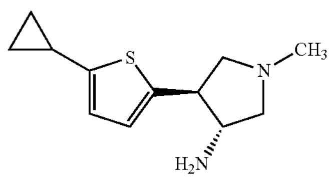 | (3R,4S)-4-(5-cyclopropylthiophen-2-yl)-1-methylpyrrolidin-3-amine |

Scheme 11

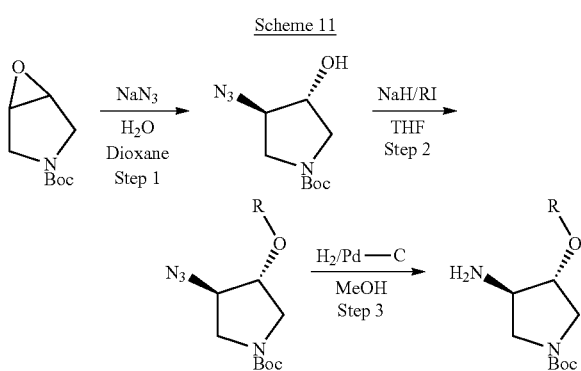

Intermediate 49I:

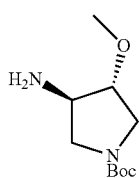

(3R,4R)-tert-butyl
3-amino-4-methoxypyrrolidine-1-carboxylate

Step 1: Synthesis of trans-tert-butyl 3-azido-4-hydroxypyrrolidine-1-carboxylate To a solution of tert-butyl 6-oxa-3-azabicyclo[3.1.0]hexane-3-carboxylate (4.0 g, 20 mmol) in 1:1 mixture of 1,4-dioxane-$H_2O$ mixture (40 mL) was added $NaN_3$ (5.7 g, 80 mmol) and the contents were heated at 80° C. After 4 h, the reaction mixture was cooled to ambient temperature, diluted with $H_2O$ (50 mL) and the organic contents were extracted with EtOAc (3×50 mL) and dried over $Na_2SO_4$. The volatiles were then removed under reduced pressure afforded the title compound. $^1H$ NMR (CDCl$_3$, 400 MHz): δ 4.27-4.25 (m, 1H), 3.9-3.92 (m, 1H), 3.72-3.34 (s, 4H), 2.7 (bs, 1H), 1.47 (s, 9H).

Step 2: Synthesis of trans-tert-butyl 3-azido-4-methoxypyrrolidine-1-carboxylate At 0° C., to a suspension of NaH (60% dispersion in mineral oil, 1.2 g, 30 mmol) in anhydrous THF (30 mL) was added a solution of trans-tert-butyl 3-azido-4-hydroxypyrrolidine-1-carboxylate (4.5 g, 20 mmol) in anhydrous THF (20 mL). A vigorous effervescence was noticed and after 10 min, a solution of MeI (3.3 g, 20 mmol) in anhydrous THF (10 mL) was added dropwise. The contents were stirred at ambient temperature for 2 h, and the reaction mixture was then quenched with ice cold $H_2O$ (10 mL) and the organic contents were extracted with EtOAc (2×50 mL). The organic layer was dried over anhydrous $Na_2SO_4$ and concentrated under reduced pressure. The residue thus obtained was purified by flash column chromatography using 15% EtOAc/hexanes mixture afforded the title compound. $^1H$ NMR (CDCl$_3$, 400 MHz): δ 4.99 (bs, 1H), 4.3-4.1 (m, 1H), 3.78-3.40 (m, 4H), 3.11 (s, 3H), 1.49 (s, 9H).

Step 3: Synthesis of trans-tert-butyl 3-amino-4-methoxypyrrolidine-1-carboxylate To a solution of trans-tert-butyl 3-azido-4-methoxypyrrolidine-1-carboxylate (3.0 g, 10 mmol) in anhydrous MeOH (20 mL) was added Pd—C (0.3 g, 10 mol %) and the contents were stirred at ambient temperature under the atmosphere of $H_2$ (balloon pressure). After 16 h, the reaction mixture was filtered through a pad of celite and the filtrate thus obtained was concentrated under reduced pressure afforded the title compound and the material was taken directly for the next step without further purification and characterization.

The following intermediates were made following protocol similar to intermediate 49I using the appropriate alkylating agent in step 2:

TABLE 7

| Int. # | Structure | IUPAC Name |
|---|---|---|
| 50I | 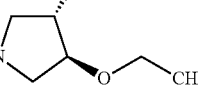 | (3S,4S)-tert-butyl 3-amino-4-ethoxypyrrolidine-1-carboxylate |
| 51I | 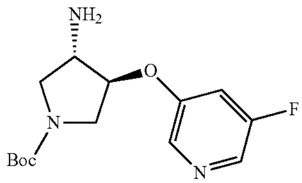 [SMILES: CC(C)(C)OC(=O)N1C[C@H](Oc2cncc(F)c2)[C@@H](N)C1] | (3S,4S)-tert-butyl 3-amino-4-(5-fluoropyridin-3-yl)oxy)pyrrolidine-1-carboxylate |
| 52I | 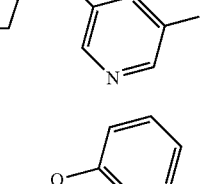 | (3S,4S)-tert-butyl 3-amino-4-phenoxypyrrolidine-1-carboxylate |
| 53I | 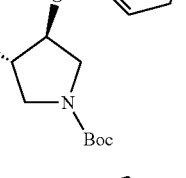 | (3S,4S)-tert-butyl 3-amino-4-(4-fluorophenoxy)pyrrolidine-1-carboxylate |

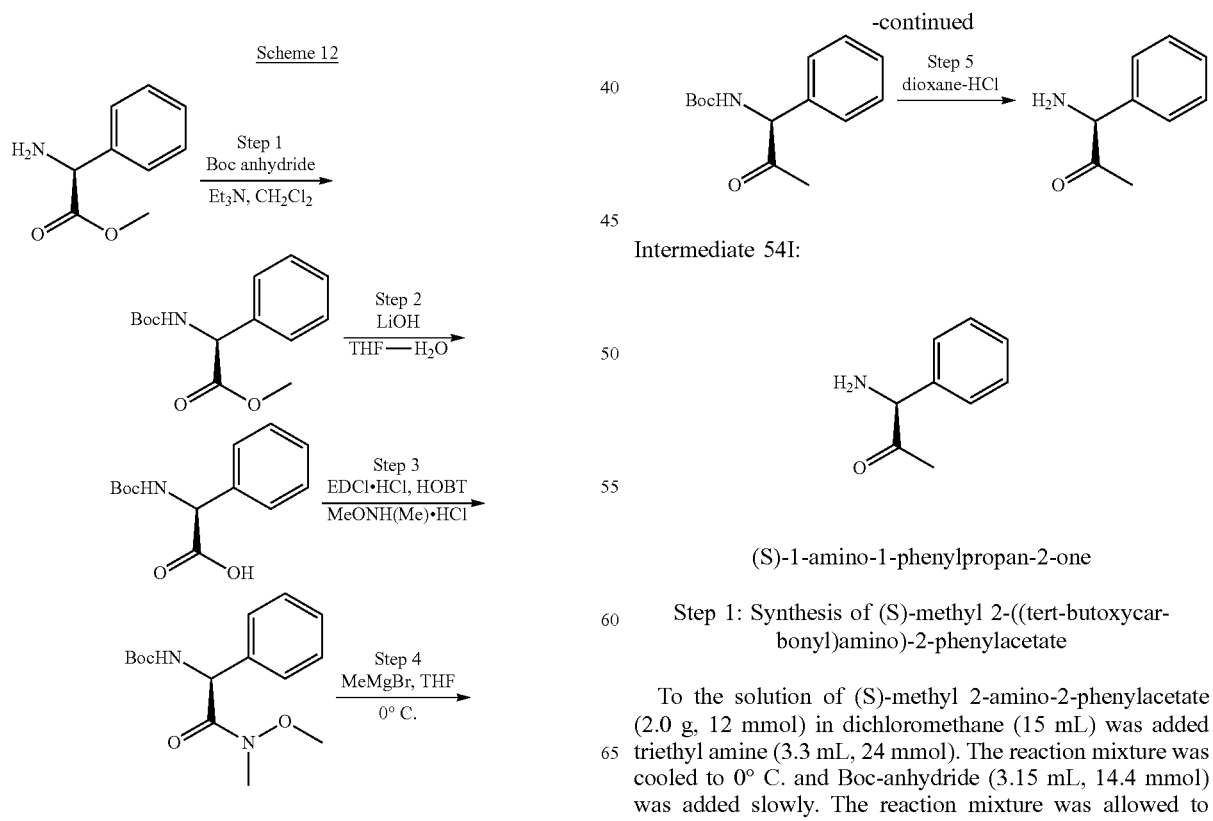

Intermediate 54I:

(S)-1-amino-1-phenylpropan-2-one

Step 1: Synthesis of (S)-methyl 2-((tert-butoxycarbonyl)amino)-2-phenylacetate

To the solution of (S)-methyl 2-amino-2-phenylacetate (2.0 g, 12 mmol) in dichloromethane (15 mL) was added triethyl amine (3.3 mL, 24 mmol). The reaction mixture was cooled to 0° C. and Boc-anhydride (3.15 mL, 14.4 mmol) was added slowly. The reaction mixture was allowed to warm up to room temperature at which it was stirred for 3 h. TLC analysis indicated complete disappearance of the starting material. The reaction mixture was bi-phased with water (15 mL) and ethyl acetate (25 mL). The aqueous layer was extracted with ethyl acetate (2×15 mL) and the combined organic layers were washed with brine (1×15 mL), dried (Na$_2$SO$_4$) and concentrated under reduced pressure to afford the crude compound which was purified by flash column chromatography to furnish the title compound. $^1$H NMR (400 MHz, CDCl$_3$) δ 7.40-7.31 (m, 5H), 5.57 (bs, 1H), 5.34 (d, 1H, J=7.4 Hz), 3.74 (s, 3H), 1.37 (s, 9H).

Step 2: Synthesis of (S)-2-((tert-butoxycarbonyl)amino)-2-phenylacetic acid

To a solution of (S)-methyl 2-((tert-butoxycarbonyl)amino)-2-phenylacetate (2.0 g, 7.5 mmol) in THF (10 mL) was added lithium hydroxide (1.57 g, 37.5 mmol) in water (5 mL). The reaction mixture was allowed to stir for 6 h. TLC analysis indicated complete disappearance of the starting material. pH of the resulting solution was brought to around 7.0 by adding citric acid. THF was concentrated under reduced pressure and the mixture was bi-phased with ethyl acetate (25 mL) and water (15 mL). The aqueous layer was extracted with ethyl acetate (2×10 mL). The combined organic layers were washed with brine (1×10 mL), dried (Na$_2$SO$_4$) and concentrated under reduced pressure to afford the title compound which was taken to the next step without further purification.

Step 3: Synthesis of (S)-tert-butyl (2-(methoxymethyl)amino)-2-oxo-1-phenylethyl)carbamate To the solution of (S)-2-((tert-butoxycarbonyl)amino)-2-phenylacetic acid (0.5 g, 1.93 mmol) in dichloromethane (6 mL) was added N,O-dimethylhydroxylamine (0.233 g, 2.38 mmol). To the resulting mixture was then added HOBT (0.082 g, 0.53 mmol), EDCI.HCl (0.457 g, 2.38 mmol) and DIPEA (0.87 mL, 4.96 mmol). The reaction mixture was stirred at ambient temperature for 3 h. TLC analysis indicated complete consumption of the starting material. The reaction mixture was bi-phased with dichloromethane (25 mL) and water (15 mL). The aqueous layer was extracted with dichloromethane (2×10 mL). The combined organic layers were washed with brine (1×10 mL), dried (Na$_2$SO$_4$) and concentrated under reduced pressure to afford the title compound. MS calc'd for C$_{15}$H$_{22}$N$_2$O$_4$ [M+H]$^+$ 295. Found: 195.2 (M+1-Boc); $^1$H NMR (400 MHz, CDCl$_3$) δ 7.41-7.24 (m, 5H), 5.80 (d, 1H, J=7.6 Hz), 5.72 (d, 1H, J=7.5 Hz), 3.47 (s, 3H), 3.19 (s, 3H), 1.43 (s, 9H).

Step 4: Synthesis of (S)-tert-butyl 2-oxo-1-phenylpropylcarbamate

To the solution of (S)-tert-butyl (2-(methoxymethyl)amino)-2-oxo-1-phenylethyl)carbamate (1.0 g, 3.39 mmol) in THF (10 mL) at 0° C. was added MeMgBr (4.27 mL, 13.5 mmol, 3M in diethylether). The reaction mixture was allowed to warm up to room temperature at which it was stirred for 2 h. TLC analysis indicated disappearance of starting material. The saturated solution of ammonium chloride (10 mL) was slowly added to the reaction mixture and extracted with dichloromethane (2×15 mL). The combined organic layers were washed with water (2×10 mL), brine (1×10 mL), dried (Na$_2$SO$_4$) and concentrated under reduced pressure to furnish the title compound which was taken up for the next step without further purification.

Step 5: Synthesis of (S)-1-amino-1-phenylpropan-2-one

To (S)-tert-butyl 2-oxo-1-phenylpropylcarbamate (0.5 g) was added solution of HCl-dioxane (5 mL) and stirred for 3 h. TLC analysis indicated disappearance of the starting material. The solvent was removed under reduced pressure to afford the crude compound which was triturated with diethyl ether to furnish the title compound. MS calc'd for C$_9$H$_{11}$NO [M+H]$^+$ 150. Found: 150; $^1$H NMR (400 MHz, CD$_3$OD) δ 7.58-7.52 (m, 3H), 7.51-7.44 (m, 2H), 5.28 (s, 1H), 2.12 (s, 3H).

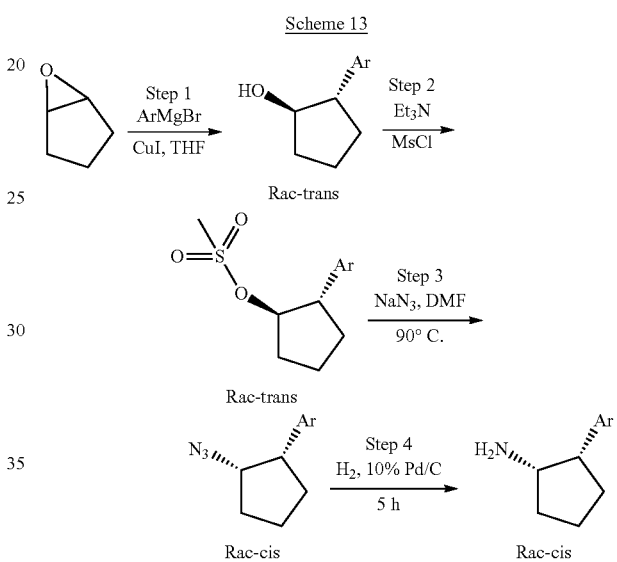

Scheme 13

Intermediate 55I:

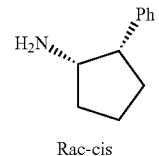

Rac-cis (Rac-cis)-2-phenylcyclopentanamine

Step 1: Synthesis of (Rac-trans)-2-phenylcyclopentanol

To a mixture of phenylmagnesium bromide (11.85 mL, 11.8 mmol, 1M in THF) and copper iodide (0.158 g, 0.83 mmol) was added drop wise a solution of cyclopentene oxide (1.0 g, 11.8 mmol) in THF. The reaction mixture was allowed to stir at room temperature for 1 h and quenched with 25% of ammonium chloride (15 mL). Ether (25 mL) was added and the organic layer was separated. The aqueous layer was extracted with ether (1×15 mL). The combined organic layers were dried (Na$_2$SO$_4$) and concentrated under reduced pressure to furnish the title compound. $^1$H NMR (400 MHz, CDCl$_3$) δ 7.38-7.20 (m, 5H), 4.17 (d, 1H, J$_1$=7.3 Hz, J$_2$=14.5 Hz), 2.94-2.85 (m, 1H), 2.21-2.08 (m, 2H), 1.94-1.62 (m, 4H).

Step 2: Synthesis of (Rac-trans)-2-phenylcyclopentyl methanesulfonate

To a solution of (Rac-trans)-2-phenylcyclopentanol (1.5 g, 9.2 mmol) in dichloromethane (10 mL) was added triethylamine (2.56 mL, 18.4 mmol) at 0° C., followed by slow addition of methanesulfonyl chloride (0.8 mL, 11.0 mmol). The reaction mixture was allowed to warm up to room temperature at which it was stirred for 2 h. TLC analysis indicated disappearance of starting material. The reaction mixture was bi-phased with water (10 mL) and dichloromethane (25 mL). The aqueous layer was extracted with dichloromethane (1×15 mL). The combined organic layers were washed with sodium bicarbonate (1×10 mL), brine (1×10 mL), dried (Na$_2$SO$_4$) and concentrated under reduced pressure to furnish the title compound. $^1$H NMR (300 MHz, CDCl$_3$) δ 7.45-7.20 (m, 5H), 5.02-4.91 (m, 1H), 3.35-3.20 (m, 1H), 2.64 (s, 3H), 2.33-2.14 (m, 2H), 2.12-1.72 (m, 4H).

Step 3: Synthesis of ((Rac-cis)-2-azidocyclopentyl)benzene

To a solution of (Rac-trans)-2-phenylcyclopentyl methanesulfonate (1.0 g, 4.16 mmol) in DMF (8 mL) was added sodium azide (1.463 g, 20.79 mmol). The reaction mixture was heated at 90° C. for 12 h. TLC analysis indicated complete consumption of the starting material. The reaction mixture was bi-phased with water (10 mL) and ethyl acetate (25 mL). The aqueous layer was extracted with ethyl acetate (2×10 mL). The combined organic layers were washed with brine (1×10 mL), dried (Na$_2$SO$_4$), and concentrated under reduced pressure to give the crude compound which was purified by flash column chromatography to furnish the title compound. $^1$H NMR (300 MHz, CDCl$_3$) δ 7.40-7.20 (m, 5H), 4.19-4.09 (m, 1H), 3.24-3.11 (m, 1H), 2.20-1.90 (m, 5H), 1.89-1.70 (m, 1H).

Step 4: Synthesis of (Rac-cis)-2-phenylcyclopentanamine

To the solution of ((Rac-cis)-2-azidocyclopentyl)benzene (0.700 g) in methanol (10 mL) was added 20% Pd/C (0.140 g). The reaction mixture was allowed to stir for 5 h under hydrogen atmosphere. The TLC analysis showed complete consumption of the starting material (Ninhydrin stain was used that gave a purple spot on drying). The reaction mixture was filtered through celite bed and washed with methanol (25 mL). The filtrate was acidified with dioxane-HCl (5 mL) and the solvent was removed under reduced pressure to furnish the title compound which was as such taken up for the next reaction.

The following intermediates were made following protocol similar to intermediate 55I using the appropriate alkylating agent in step 1

TABLE 8

| Int. # | Structure | IUPAC Name |
|---|---|---|
| 56I | 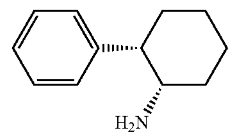 [SMILES: N[C@H]1CCCC[C@H]1c1ccccc1] | (1S,2S)-2-phenylcyclohexanamine |
| 57I | 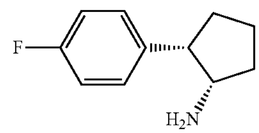 [SMILES: N[C@H]1CCC[C@H]1c1ccc(F)cc1] | (1S,2S)-2-(4-fluorophenyl)cyclopentanamine |

Scheme 14

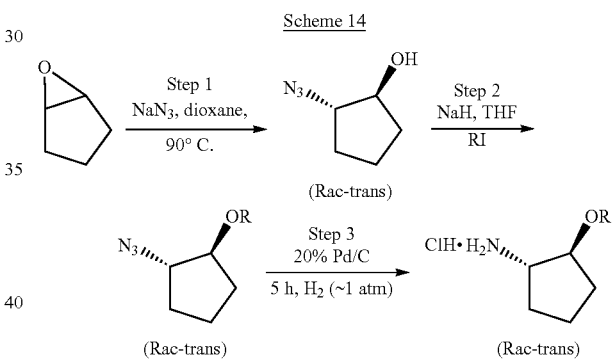

Intermediate 58I:

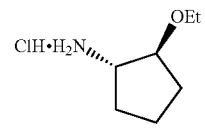

(1S,2S)-2-ethoxycyclopentanamine hydrochloride

Step-1: Synthesis of (Rac-trans)-2-azidocyclopentanol

To a solution of 6-oxabicyclo[3.1.0]hexane (1.0 g, 11.8 mmol) in dioxane (15 mL) was added a solution of NaN$_3$ (3.09 g, 47.5 mmol) in water (10 mL) and heated at 90° C. for 4 h. The reaction mixture was allowed to cool to room temperature and bi-phased with dichloromethane (20 mL) and water (10 mL). The aqueous layer was extracted with dichloromethane (1×15 mL). The combined organic layers were washed with brine (2×10 mL), dried (Na$_2$SO$_4$) and concentrated under reduced pressure at temperature (<40° C.) to furnish the title compound.

$^1$H NMR (400 MHz, CDCl$_3$) δ 4.08 (dd, 1H, J$_1$=5.2 Hz, J$_2$=11.2 Hz), 3.75-3.66 (m, 1H), 2.15-1.95 (m, 2H), 1.87-1.53 (m, 4H).

Step 2: Synthesis of (Rac-trans)-1-azido-2-ethoxycyclopentane

To the solution of (Rac-trans)-2-azidocyclopentanol (0.5 g, 3.93 mmol) in THF (5 mL) was added NaH (0.47 g, 11.8 mmol) at 0° C. followed by the addition of ethyl iodide (0.62 mL, 7.8 mmol). The reaction mixture was allowed to stir overnight at room temperature. Water (5 ml) was added and extracted with dichloromethane (2×10 mL). The combined organic layers were washed with brine (2×10 mL), dried (Na$_2$SO$_4$) and concentrated under reduced pressure at low temperature (40° C.) to furnish the title compound which was used as such for the next step without purification. $^1$H NMR (400 MHz, CDCl$_3$) δ 3.83-3.76 (m, 1H), 3.75-3.68 (m, 1H), 3.52 (q, 2H, J=6.9 Hz), 2.10-1.90 (m, 2H), 1.83-1.53 (m, 4H), 1.21 (t, 3H, J=6.9 Hz).

Step 3: Synthesis of (Rac-trans)-2-ethoxycyclopentanamine hydrochloride

To a solution of (Rac-trans)-1-azido-2-ethoxycyclopentane (0.4 g) in methanol (5 mL) was added 5% Pd/C (0.1 g) and allowed to stir for 5 h under hydrogen atmosphere. The reaction mixture was filtered through celite bed and washed with methanol and acidified with dioxane-HCl (5 mL). The solvent was removed under reduced pressure to furnish the title compound which was taken up for the next reaction without purification.

The following intermediates were made following protocol similar to intermediate 58I using the appropriate alkylating reagent:

TABLE 9

| Int. # | Structure | IUPAC Name |
|---|---|---|
| 59I | 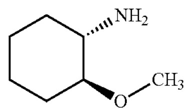 | (1S,2S)-2-methoxycyclohexanamine |
| 60I | 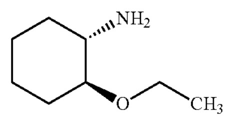 | (1S,2S)-2-ethoxycyclohexanamine |
| 61I | 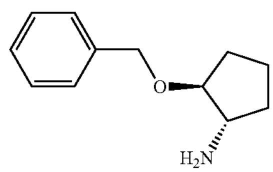 [SMILES: N[C@H]1CCC[C@@H]1OCc1ccccc1] | (1S,2S)-2-(benzyloxy)cyclopentanamine |
| 62I | 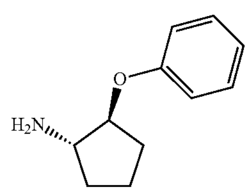 [SMILES: N[C@H]1CCC[C@@H]1Oc1ccccc1] | (1S,2S)-2-phenoxycyclopentanamine |
| 63I | 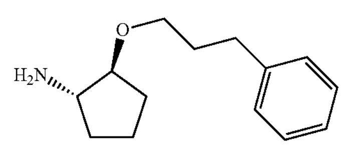 [SMILES: N[C@H]1CCC[C@@H]1OCCCc1ccccc1] | (1S,2S)-2-(3-phenylpropoxy)cyclopentanamine |
| 64I | 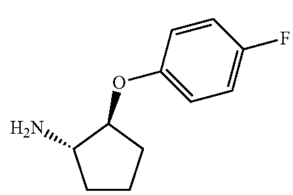 [SMILES: N[C@H]1CCC[C@@H]1Oc1ccc(F)cc1] | (1S,2S)-2-(4-fluorophenoxy)cyclopentanamine |

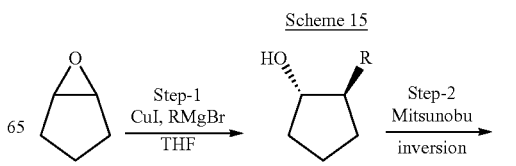

Scheme 15

-continued

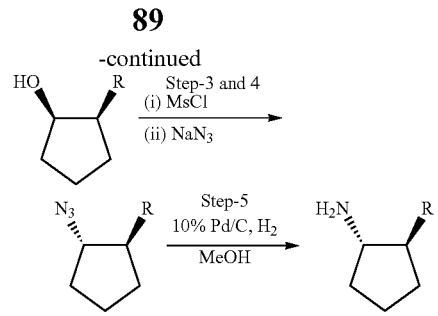

Intermediate 65I:

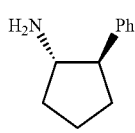

trans-2-phenylcyclopentanamine

Step 1: Synthesis of trans-2-phenylcyclopentanol

To a solution of 6-oxabicyclo[3.1.0]hexane (2.0 g, 23.8 mmol) in anhydrous THF (20 mL) was added CuI (0.46 g, 2.34 mmol) and the contents were stirred at ambient temperature. After 15 min, PhMgBr (1.0 M solution in THF, 23.8 mL, 23.8 mmol) was added at ambient temperature dropwise and the reaction mixture was allowed to stir. After 2 h, the reaction was quenched carefully with saturated aqueous NH$_4$Cl solution (5 mL) and the organic contents were extracted with EtOAc (3×25 mL) and the organic layer was dried over Na$_2$SO$_4$. The volatiles were then removed under reduced pressure and the residue thus obtained was purified by flash column chromatography using a mixture of EtOAc/hexanes afforded the title compound. $^1$H NMR (CDCl$_3$, 400 MHz): δ 7.36-7.27 (m, 5H), 4.21-4.16 (m, 1H), 2.91-2.88 (m, 1H), 2.19-2.12 (m, 2H), 1.88-1.67 (m, 5H).

Step 2: Synthesis of cis-2-phenylcyclopentanol

At 0° C., to a solution of trans-2-phenylcyclopentanol (1.3 g, 8.02 mmol) and 4-nitro benzoic acid (1.4 g, 8.02 mmol) in anhydrous THF (20 mL) was added DIPEA (1.55 g, 12.04 mmol), PPh$_3$ (3.2 g, 12.04 mmol) and DEAD (2.01 g, 12.04 mmol) and the contents were stirred at the same temperature. After 2 h, the reaction mixture was concentrated and the residue was purified by flash column chromatography gave the nitro ester (1.2 g, 3.86 mmol) which was dissolved in anhydrous MeOH (10 mL). NaOMe (0.8 g, 15.4 mmol) was added to this mixture and the contents were stirred at ambient temperature for 10 h. The reaction was carefully quenched with H$_2$O and the volatiles were removed under reduced pressure. The organic contents were then extracted with CH$_2$Cl$_2$ (2×20 mL) and the CH$_2$Cl$_2$ layer was dried over Na$_2$SO$_4$ and the solvent was removed under reduced pressure. The residue thus obtained was purified by flash column chromatography afforded the title compound. $^1$H NMR (CDCl$_3$, 400 MHz): δ 7.38-7.24 (m, 5H), 4.31-4.31 (m, 1H), 3.09-3.04 (m, 1H), 2.15-1.73 (m, 6H).

Step 3: Synthesis of trans-2-phenylcyclopentyl methanesulfonate

At 0° C., to a solution of cis-2-phenylcyclopentanol (0.4 g, 2.46 mmol) in CH$_2$Cl$_2$ (10 mL) was added Et$_3$N (0.75 g, 7.4 mmol) and MsCl (0.42 g, 3.7 mmol) and the contents were gradually allowed to warm to ambient temperature. After 2 h, the reaction was quenched with 10% NaHCO$_3$ solution and the CH$_2$Cl$_2$ layer was separated and dried over Na$_2$SO$_4$. The solvent was removed under reduced pressure afforded the title compound was pure enough and was taken directly for the azide displacement. $^1$H NMR (CDCl$_3$, 400 MHz): δ 7.34-7.25 (m, 5H), 5.15-5.14 (m, 1H), 3.23-3.18 (m, 1H), 2.24 (s, 3H), 2.22-2.18 (m, 3H), 2.17-2.11 (m, 2H), 1.83-1.81 (m, 1H).

Step 4: Synthesis of (trans-2-azidocyclopentyl)benzene

To a solution of trans-2-phenylcyclopentyl methanesulfonate (0.5 g, 2.08 mmol) in DMF (10 mL) was added NaN$_3$ (0.56 g, 8.33 mmol) and the contents were warmed to 100° C. After 3 h, the reaction mixture was diluted with EtOAc (30 mL) and the organic layer was washed with H$_2$O (2×10 mL), brine solution (1×25 mL), dried over Na$_2$SO$_4$ and the volatiles were removed under reduced pressure afforded the title compound which was directly taken to next step without further purification. Anal. Calcd. C$_{11}$H$_{13}$N$_3$[M+H] 188. Found 188.

Step 5: Synthesis of trans-2-phenylcyclopentanamine

The product (trans-2-azidocyclopentyl)benzene (from step 4) was taken up in MeOH (10 mL) and Pd—C (0.7 g) was added and the contents were stirred in the atmosphere of H$_2$ (balloon pressure) overnight. The reaction mixture was then filtered through a pad of celite. The solvent was then removed under reduced pressure afforded the title compound. Anal. Calcd. C$_{11}$H$_{15}$N [M+H]$^+$ 162. Found 162.

The following intermediates were made following protocol similar to intermediate 65I using the appropriate grignard reagent:

TABLE 10

| Int. # | Structure | IUPAC Name |
|---|---|---|
| 66I | ![NH$_2$ cyclohexyl-CH$_2$-phenyl] | (1S,2R)-2-benzylcyclohexanamine |
| 67I | ![NH$_2$ cyclohexyl-phenyl] | (1S,2R)-2-phenylcyclohexanamine |
| 68I | ![NH$_2$ cyclopentyl-(4-F-phenyl)] | (1R,2S)-2-(4-fluorophenyl)cyclopentanamine |

Intermediate 69I:

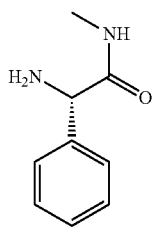

(S)-2-Amino-N-methyl-2-phenyl-acetamide

Methyl amine solution (2 mL, 40% solution in water) was added to (S)-methyl 2-amino-2-phenylacetate (0.1 g, 0.061 mmol) at 0° C. and allowed to warm up to room temperature at which it was stirred for 3 h. LCMS analysis indicated the complete consumption of the starting material. Water was removed under reduced pressure to afford the crude compound which was directly taken to next step without purification. LC MS calc'd for $C_9H_{12}N_2O$ [M+H]$^+$ 165. Found: 165.

The following intermediates were made following protocol similar to intermediate 69I using the appropriate amines:

TABLE 11

| Int. # | Structure | IUPAC Name |
|---|---|---|
| 70I | 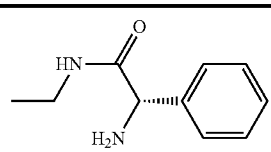 | (S)-2-amino-N-ethyl-2-phenylacetamide |
| 71I | 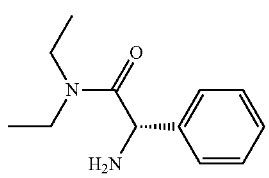 | (S)-2-amino-N,N-diethyl-2-phenylacetamide |

Scheme 16

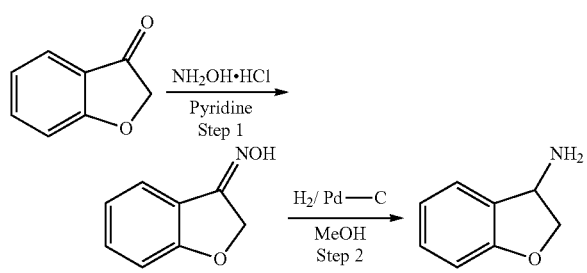

Intermediate 72I:

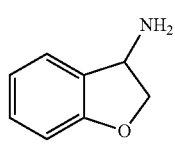

2,3-dihydrobenzofuran-3-amine

Step 1: Synthesis of benzofuran-3(2H)-one oxime

To a solution of benzofuran-3(2H)-one (1.0 g, 7.46 mmol) in pyridine (10 mL) was added NH$_2$OH.HCl (1.0 g, 14.9 mmol) and the contents were stirred at the same temperature. After 2 h (progress of the reaction was monitored by TLC), pyridine was removed under reduced pressure and the residue thus obtained was taken up in CH$_2$Cl$_2$ (50 mL). The CH$_2$Cl$_2$ layer was washed successively with H$_2$O (2×20 mL), brine (1×20 mL), dried over Na$_2$SO$_4$ and concentrated to afford the title compound. $^1$H NMR (CDCl$_3$, 400 MHz) δ 7.61 (d, J=7.7 Hz, 1H), 7.40-7.34 (m, 1H), 7.03-6.96 (m, 2H), 5.19 (s, 2H). Anal. Calcd. C$_8$H$_7$NO$_2$ 149.2. Found 150.2 (M+H).

Step 2: Synthesis of 2,3-dihydrobenzofuran-3-amine

To a solution of benzofuran-3(2H)-one oxime (1.0 g, 6.7 mmol) in MeOH (10 mL) was added 10% Pd on C (0.2 g) and the contents were stirred at ambient temperature in an atmosphere of H$_2$ (balloon pressure). After 16 h, the reaction mixture was filtered through a pad of celite and the solvent MeOH was evaporated under reduced pressure to afford the title amine. $^1$H NMR (CDCl$_3$, 400 MHz) δ 7.34-7.20 (m, 2H), 6.95-6.82 (m, 2H), 4.70-4.59 (m, 2H), 4.22-4.18 (m, 1H).

Intermediate 73I and 74I:

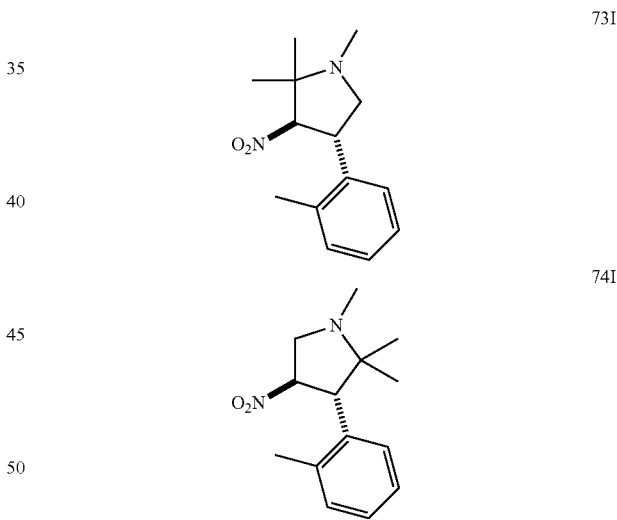

(3R,4S)-1,2,2-trimethyl-3-nitro-4-(o-tolyl)pyrrolidine (73I) and (3R,4R)-1,2,2-trimethyl-3-nitro-4-(o-tolyl)pyrrolidine (74I)

(E)-1-methyl-2-(2-nitrovinyl)benzene (1 g, 6.13 mmol), acetone (2.250 ml, 30.6 mmol), DIEA (1.606 ml, 9.19 mmol) and 2-(methylamino)acetic acid (1.092 g, 12.26 mmol) were dissolved in Toluene (20 ml) in a 50 mL round bottom flask equipped with a Dean-Stark condenser and heated to reflux overnight. The mixture was cooled to rt, diluted with 10 mL dichloromethane, filtered through celite, and the solvents were removed in vacuo. The residue was purified on silica gel 5-50% EtOAc/Hexanes. Both products contained trace impurities and were re-purified on silica gel 2-15% EtOAc/DCM to provide 73I (3R,4R)+(3S,4R)-1,2,2-trimethyl-4-nitro-3-(o-tolyl)pyrrolidine and 74I (3R,4S)+(3S,4R)-1,2,2-trimethyl-3-nitro-4-(o-tolyl)pyrrolidine. (3R,4S)-1,2,2-trimethyl-3-nitro-4-(o-tolyl)pyrrolidine 73I $^1$H NMR (600 MHz, cdcl3) δ 7.32 (d, J=7.7, 1H), 7.22-7.16 (m, 1H), 7.11 (d, J=4.1, 2H), 4.76 (d, J=7.9, 1H), 4.42 (ddd, J=5.8, 8.0, 9.3, 1H), 3.22 (t, J=9.5, 1H), 2.86 (dd, J=5.7, 9.6, 1H), 2.36 (s, 3H), 2.28 (s, 3H), 1.38 (s, 3H), 0.98 (s, 3H). and (3R,4R)-1,2,2-trimethyl-3-nitro-4-(o-tolyl)pyrrolidine 74I $^1$H NMR (500 MHz, cdcl3) δ 7.24-7.13 (m, 4H), 5.16 (td, J=4.2, 8.4, 1H), 4.16 (d, J=7.8, 1H), 3.53 (dd, J=4.0, 11.3, 1H), 3.26 (dd, J=9.2, 11.1, 1H), 2.40 (s, 3H), 2.30 (s, 3H), 1.15 (s, 3H), 0.74 (s, 3H).

Synthetic Method I

Many compounds were prepared by the reaction of an isocyanate with a pyrazolo[3,4-c]pyridin-5-amine. This method is exemplified below for the synthesis of 1-(4-fluorobenzyl)-3-(1-(4-fluorophenyl)-1H-pyrazolo[3,4-c]pyridin-5-yl)urea, and was used for the preparation of example 2-13 utilizing suitable reagents.

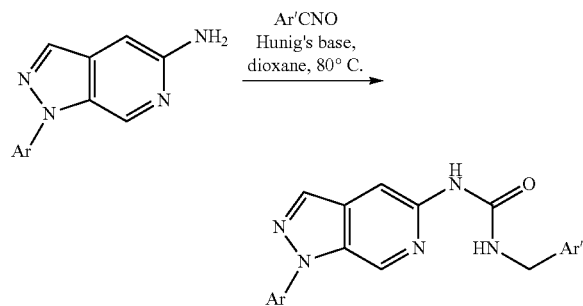

A preferred embodiment of the invention is all of the species exemplified in Examples 1-328. The ERK2 IC$_{50}$ in nanomolar (nM) for the compounds of the invention, measured according to the assay "Active human ERK2 (hERK2) Activity Assay" described below, is shown in the Example next to the structure or compound name.

Example 1

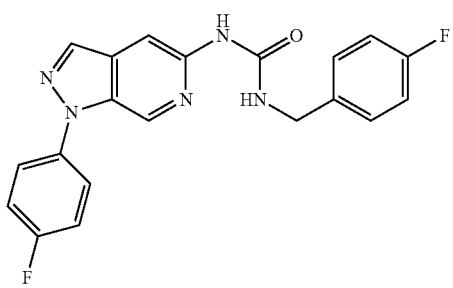 [SMILES: O=C(NCc1ccc(F)cc1)Nc1cc2cnn(-c3ccc(F)cc3)c2cn1]

1-(4-fluorobenzyl)-3-(1-(4-fluorophenyl)-1H-pyrazolo[3,4-c]pyridin-5-yl)urea (26 nM)

A solution of 1-(4-fluorophenyl)-1H-pyrazolo[3,4-c]pyridin-5-amine (12 mg, 0.053 mmol) in dioxane (0.5 mL) was treated with Hunig's base (20 μL, 0.12 mmol) and 1-fluoro-4-(isocyanatomethyl)benzene (15 mg, 0.099 mmol). The reaction mixture was warmed to 80° C., stirred for 2 hours and concentrated to dryness. The residue was dissolved in 0.5 mL of DMSO and purified by reverse phase chromatography (MeCN/water with 0.1% TFA). The LC fractions were lyophilized to provide the TFA salt of 1-(4-fluorobenzyl)-3-(1-(4-fluorophenyl)-1H-pyrazolo[3,4-c]pyridin-5-yl)urea: MS (EI) calc'd for $C_{20}H_{16}F_2N_5O$ [M+H]$^+$ 380. found 380; $^1$H NMR (600 MHz, DMSO-d$_6$) δ 9.17 (s, 1H), 8.95 (s, 1H), 8.39 (s, 1H), 8.05 (s, 1H), 7.84 (dd, J=7.4, 4.7 Hz, 2H), 7.47 (br s, 1H), 7.39 (t, J=8.5 Hz, 2H), 7.33 (t, J=6.8 Hz, 2H), 7.13 (t, J=7.6 Hz, 2H), 4.32 (d, J=5.2 Hz, 2H).

The following examples were made following protocol similar to example 1 using the appropriate reagent:

TABLE 12

| EX | Structure | IUPAC Name/ERK2 IC$_{50}$ | [M + H]+ |
|----|-----------|---------------------------|----------|
| 2 | 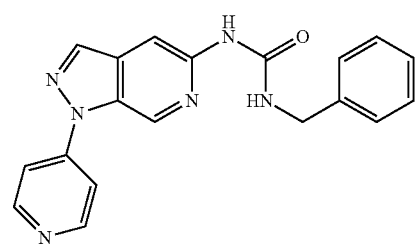 [SMILES: O=C(NCc1ccccc1)Nc1cc2cnn(-c3ccncc3)c2cn1] | 1-benzyl-3-(1-pyridin-4-yl-1H-pyrazolo[3,4-c]pyridin-5-yl)urea 2.7 nM | Calc'd 345, found 345 |
| 3 | 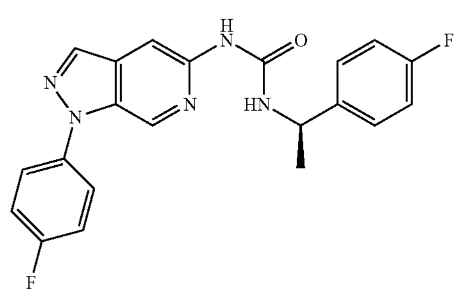 [SMILES: C[C@@H](NC(=O)Nc1cc2cnn(-c3ccc(F)cc3)c2cn1)c1ccc(F)cc1] | 1-[(1R)-1-(4-fluorophenyl)ethyl]-3-[1-(4-fluorophenyl)-1H-pyrazolo[3,4-c]pyridin-5-yl)urea 10.6 nM | Calc'd 394, found 394 |

TABLE 12-continued

| EX | Structure | IUPAC Name/ERK2 IC$_{50}$ | [M + H]+ |
|----|-----------|---------------------------|----------|
| 4 | 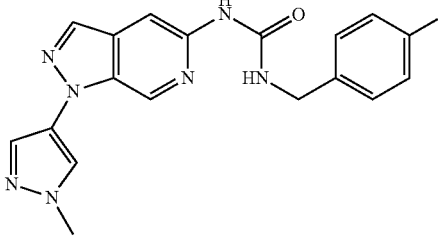 | 1-(4-fluorobenzyl)-3-[1-(1-methyl-1H-pyrazol-4-yl)-1H-pyrazolo[3,4-c]pyridin-5-yl)urea 41.3 nM | Calc'd 366, found 366 |
| 5 | 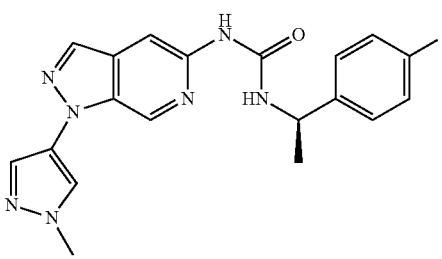 | 1-[(1R)-1-(4-fluorophenyl)ethyl]-3-[1-(1-methyl-1H-pyrazol-4-yl)-1H-pyrazolo[3,4-c]pyridin-5-yl)urea 12.2 nM | Calc'd 380, found 380 |
| 6 | 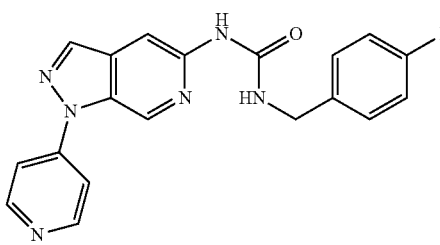 | 1-(4-fluorobenzyl)-3-(1-pyridin-4-yl-1H-pyrazolo[3,4-c]pyridin-5-yl)urea 1.8 nM | Calc'd 363, found 363 |
| 7 | 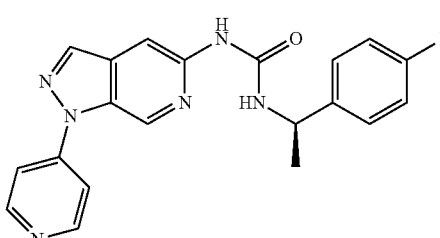 | 1-[(1R)-1-(4-fluorophenyl)ethyl]-3-(1-pyridin-4-yl-1H-pyrazolo[3,4-c]pyridin-5-yl)urea 16.2 nM | Calc'd 377, found 377 |
| 8 | 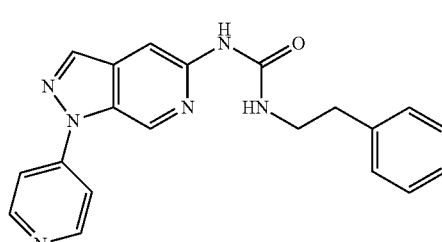 | 1-(2-phenylethyl)-3-(1-pyridin-4-yl-1H-pyrazolo[3,4-c]pyridin-5-yl)urea 16.2 nM | Calc'd 359, found 359 |
| 9 | 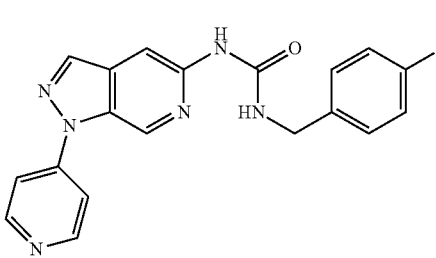 | 1-(4-methoxybenzyl)-3-(1-pyridin-4-yl-1H-pyrazolo[3,4-c]pyridin-5-yl)urea 5.3 nM | Calc'd 375, found 375 |

TABLE 12-continued

| EX | Structure | IUPAC Name/ERK2 IC$_{50}$ | [M + H]+ |
|---|---|---|---|
| 10 | 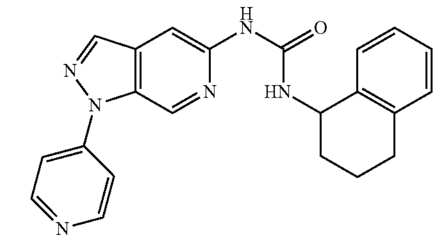 [SMILES: O=C(Nc1cc2cnn(-c3ccncc3)c2cn1)NC1CCCc2ccccc21] | 1-(1-pyridin-4-yl-1H-pyrazolo[3,4-c]pyridin-5-yl)-3-(1,2,3,4-tetrahydronaphthalen-1-yl)urea 34.7 nM | Calc'd 385, found 385 |
| 11 | 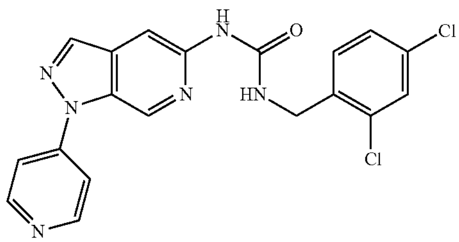 [SMILES: O=C(NCc1ccc(Cl)cc1Cl)Nc1cc2cnn(-c3ccncc3)c2cn1] | 1-(2,4-dichlorobenzyl)-3-(1-pyridin-4-yl-1H-pyrazolo[3,4-c]pyridin-5-yl)urea 26 nM | Calc'd 413, found 413 |
| 12 | 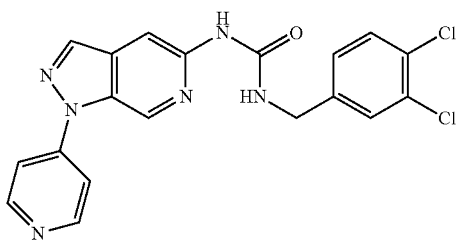 [SMILES: O=C(NCc1ccc(Cl)c(Cl)c1)Nc1cc2cnn(-c3ccncc3)c2cn1] | 1-(3,4-dichlorobenzyl)-3-(1-pyridin-4-yl-1H-pyrazolo[3,4-c]pyridin-5-yl)urea 0.9 nM | Calc'd 413, found 413 |
| 13 | 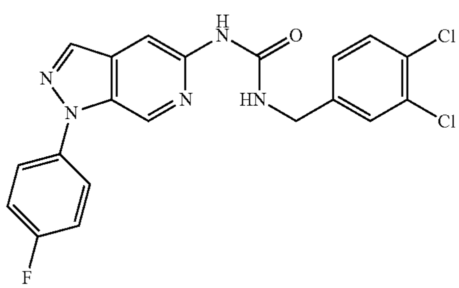 [SMILES: O=C(NCc1ccc(Cl)c(Cl)c1)Nc1cc2cnn(-c3ccc(F)cc3)c2cn1] | 1-(3,4-dichlorobenzyl)-3-[1-(4-fluorophenyl)-1H-pyrazolo[3,4-c]pyridin-5-yl]urea 19.7 nM | Calc'd 430, found 430 |

Synthetic Method II

Example 14

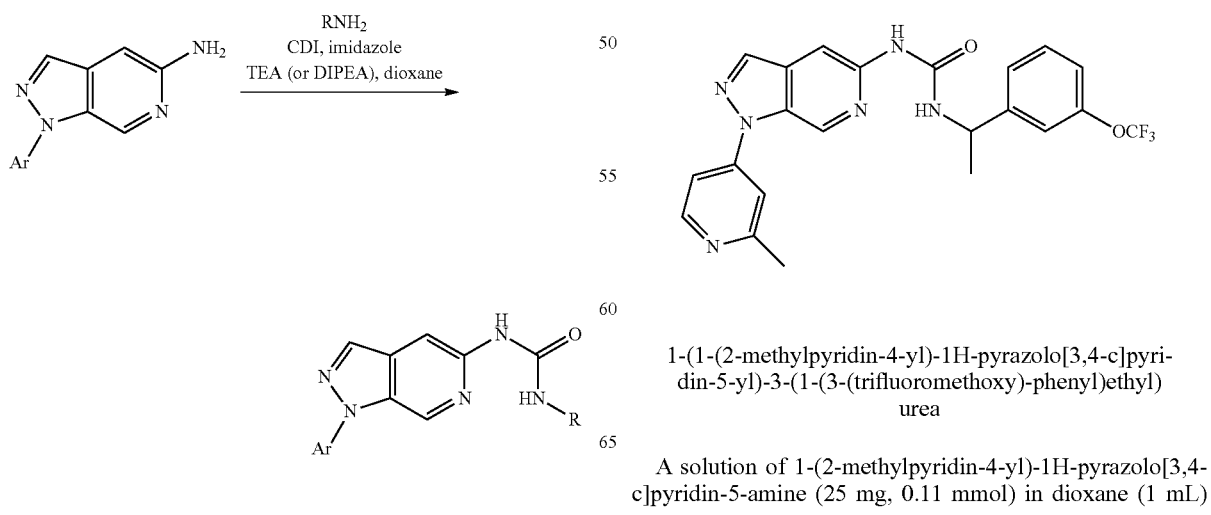

1-(1-(2-methylpyridin-4-yl)-1H-pyrazolo[3,4-c]pyridin-5-yl)-3-(1-(3-(trifluoromethoxy)-phenyl)ethyl)urea A solution of 1-(2-methylpyridin-4-yl)-1H-pyrazolo[3,4-c]pyridin-5-amine (25 mg, 0.11 mmol) in dioxane (1 mL)

was treated with imidazole (40 mg, 0.59 mmol) and carbonyl diimidazole (100 mg, 0.62 mmol). The mixture was stirred for 3 hours. An aliquot was treated with methanol, and the presence of the corresponding methyl carbamate as observed by LC/MS was used to indicate consumption of the aminopyridine. Next, 1-(3-(trifluoromethoxy)phenyl)ethanamine (110 mg, 0.54 mmol) was added followed by TEA (0.10 mL, 0.72 mmol) and the mixture stirred for 2 hours, then concentrated to dryness. The residue was dissolved in DMSO and purified by reverse phase chromatography (MeCN/water with 0.1% TFA). The LC fractions were lyophilized to provide the TFA salt of 1-(1-(2-methylpyridin-4-yl)-1H-pyrazolo[3,4-c]pyridin-5-yl)-3-(1-(3-(trifluoromethoxy)-phenyl)ethyl)urea: MS (EI) calc'd for $C_{22}H_{20}F_3N_6O_2[M+H]^+$ 457. found 457; $^1$H NMR (600 MHz, DMSO-$d_6$) δ 9.40 (s, 1H), 9.24 (s, 1H), 8.70 (d, J=6.5 Hz, 1H), 8.68 (s, 1H), 8.16 (s, 1H), 8.14 (s, 1H), 8.11 (d, J=5.6 Hz, 1H), 7.52 (d, J=6.4 Hz, 1H), 7.46 (t, J=7.9 Hz, 1H), 7.38 (d, J=7.9 Hz, 1H), 7.29 (s, 1H), 7.21 (d, J=7.6 Hz, 1H), 4.91 (dt, J=7.1 Hz, 1H), 2.70 (s, 3H), 1.40 (d, J=7.1 Hz, 3H).

Example 15

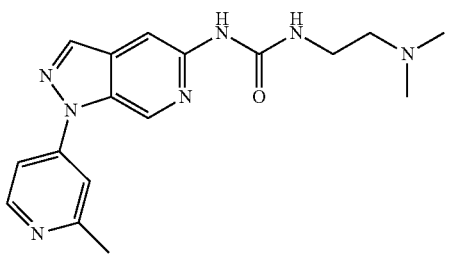 [SMILES: Cc1cc(-n2ncc3cc(NC(=O)NCCN(C)C)ncc32)ccn1]

1-(2-(dimethylamino)ethyl)-3-(1-(2-methylpyridin-4-yl)-1H-pyrazolo[3,4-c]pyridin-5-yl)urea 1430 nM To a solution of 1-(2-methylpyridin-4-yl)-1H-pyrazolo[3,4-c]pyridin-5-amine 6I (0.04 g, 0.18 mmol) in anhydrous 1,4-dioxane (2 mL) was added CDI (0.15 g, 0.9 mmol) followed by the addition of imidazole (0.062 g, 0.9 mmol) and the contents were stirred at ambient temperature. After 16 h [the completion of the reaction was confirmed by quenching small aliquot of the reaction mixture with MeOH and mass was obtained for the corresponding carbamate (M+H)=284], DIPEA (0.05 g, 0.36 mmol) and N,N-dimethyl ethylenediamine (0.016 g, 0.18 mmol) were added and the contents were stirred. After 4 h, the reaction mixture was quenched with $H_2O$ and the organic contents were extracted with EtOAc (2×15 mL), dried over $Na_2SO_4$ and concentrated. The residue thus obtained was purified by flash column chromatography afforded the title compound. $^1$H NMR (MeOD, 400 MHz) δ 9.24 (s, 1H), 8.57 (d, J=6.0 Hz, 1H), 8.39 (m, 1H), 7.87-7.80 (m, 3H), 3.73-3.70 (m, 2H), 3.51-3.49 (m, 2H), 3.05 (s, 6H), 2.36 (s, 3H). Anal. Calcd. $C_{17}H_{21}N_7O$ (M+H) 340. Found 340.

The following examples were made by using CDI coupling procedures similar to examples 14 or 15 with appropriate amines.

TABLE 13

| Ex | Structure | IUPAC Name/ERK2 IC$_{50}$ | [M + H]+ |
|---|---|---|---|
| 16. | 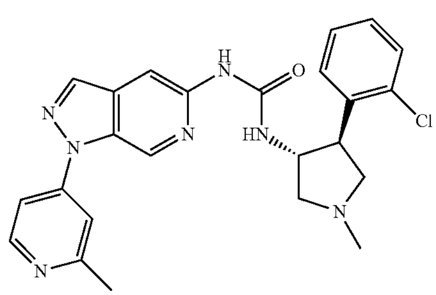 [SMILES: Cc1cc(-n2ncc3cc(NC(=O)N[C@H]4CN(C)C[C@@H]4c4ccccc4Cl)ncc32)ccn1] | 1-[(3R,4S)-4-(2-chlorophenyl)-1-methylpyrrolidin-3-yl]-3-[1-(2-methylpyridin-4-yl)-1H-pyrazolo[3,4-c]pyridin-5-yl]urea 0.9521 nM | Calc'd 462, found 462 |
| 17. | 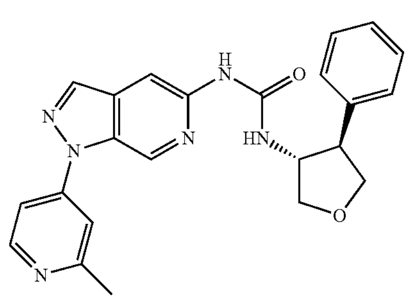 [SMILES: Cc1cc(-n2ncc3cc(NC(=O)N[C@H]4COC[C@@H]4c4ccccc4)ncc32)ccn1] | 1-[1-(2-methylpyridin-4-yl)-1H-pyrazolo[3,4-c]pyridin-5-yl]-3-[(3R,4R)-4-phenyltetrahydrofuran-3-yl]urea 1.834 nM | Calc'd 415, found 415 |

TABLE 13-continued

| Ex | Structure | IUPAC Name/ERK2 IC$_{50}$ | [M + H]+ |
|---|---|---|---|
| 18. | 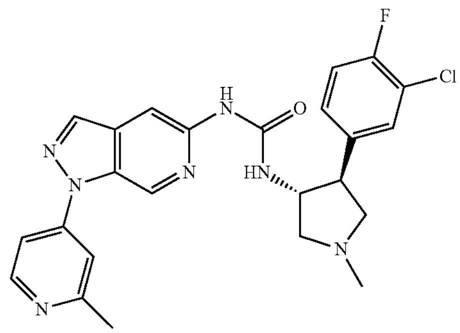 [SMILES: Cc1cc(-n2ncc3cc(NC(=O)N[C@H]4CN(C)C[C@@H]4c4ccc(F)c(Cl)c4)ncc32)ccn1] | 1-[(3R,4S)-4-(3-chloro-4-fluorophenyl)-1-methylpyrrolidin-3-yl]-3-[1-(2-methylpyridin-4-yl)-1H-pyrazolo[3,4-c]pyridin-5-yl)urea 2.143 nM | Calc'd 480, found 480 |
| 19. | 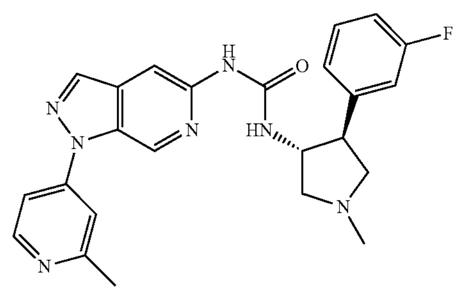 [SMILES: Cc1cc(-n2ncc3cc(NC(=O)N[C@H]4CN(C)C[C@@H]4c4cccc(F)c4)ncc32)ccn1] | 1-[(3R,4S)-4-(3-fluorophenyl)-1-methylpyrrolidin-3-yl]-3-[1-(2-methylpyridin-4-yl)-1H-pyrazolo[3,4-c]pyridin-5-yl)urea 3.067 | Calc'd 446, found 446 |
| 20. | 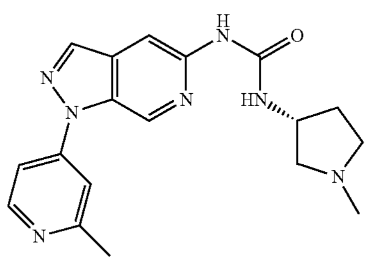 [SMILES: Cc1cc(-n2ncc3cc(NC(=O)N[C@@H]4CCN(C)C4)ncc32)ccn1] | 1-[1-(2-methylpyridin-4-yl)-1H-pyrazolo[3,4-c]pyridin-5-yl]-3-[(3R)-1-methylpyrrolidin-3-yl]urea 50.47 nM | Calc'd 352, found 352 |
| 21. | 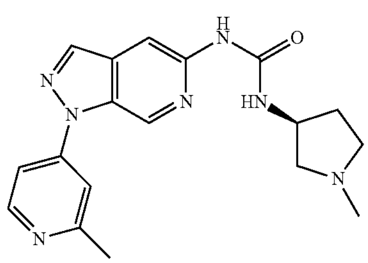 [SMILES: Cc1cc(-n2ncc3cc(NC(=O)N[C@H]4CCN(C)C4)ncc32)ccn1] | 1-[1-(2-methylpyridin-4-yl)-1H-pyrazolo[3,4-c]pyridin-5-yl]-3-[(3S)-1-methylpyrrolidin-3-yl]urea 766.7 nM | Calc'd 352, found 352 |
| 22. | 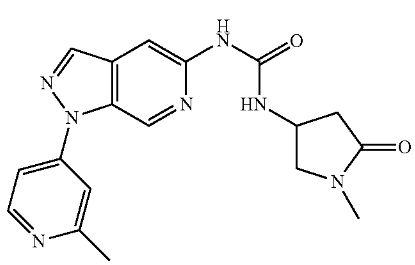 [SMILES: Cc1cc(-n2ncc3cc(NC(=O)NC4CC(=O)N(C)C4)ncc32)ccn1] | 1-(1-methyl-5-oxopyrrolidin-3-yl)-3-[1-(2-methylpyridin-4-yl)-1H-pyrazolo[3,4-c]pyridin-5-yl)urea 181 nM | Calc'd 366, found 366 |

TABLE 13-continued

| Ex | Structure | IUPAC Name/ERK2 IC$_{50}$ | [M + H]+ |
|---|---|---|---|
| 23. | 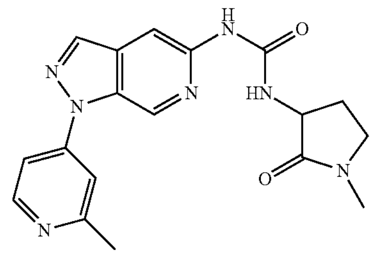 [SMILES: Cc1cc(-n2ncc3cc(NC(=O)NC4CCN(C)C4=O)ncc32)ccn1] | 1-(1-methyl-2-oxopyrrolidin-3-yl)-3-[1-(2-methylpyridin-4-yl)-1H-pyrazolo[3,4-c]pyridin-5-yl]urea 314 nM | Calc'd 366, found 366 |
| 24. | 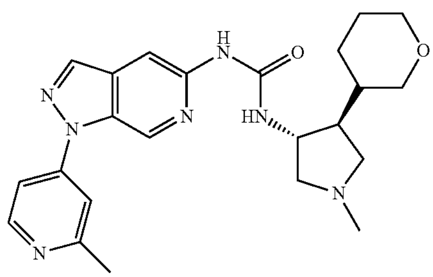 [SMILES: Cc1cc(-n2ncc3cc(NC(=O)N[C@H]4CN(C)C[C@@H]4C4CCCOC4)ncc32)ccn1] | 1-[1-(2-methylpyridin-4-yl)-1H-pyrazolo[3,4-c]pyridin-5-yl]-3-{(3R,4S)-1-methyl-4-[(3S)-tetrahydro-2H-pyran-3-yl]pyrrolidin-3-yl}urea 139.9 nM | Calc'd 436, found 436 |
| 25. | 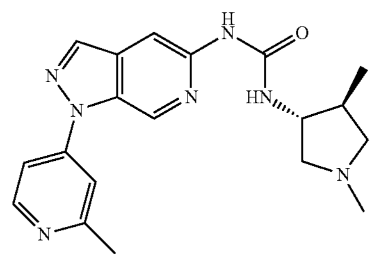 [SMILES: Cc1cc(-n2ncc3cc(NC(=O)N[C@H]4CN(C)C[C@@H]4C)ncc32)ccn1] | 1-[(3R,4S)-1,4-dimethylpyrrolidin-3-yl]-3-[1-(2-methylpyridin-4-yl)-1H-pyrazolo[3,4-c]pyridin-5-yl]urea 66.37 nM | Calc'd 366, found 366 |
| 26. | 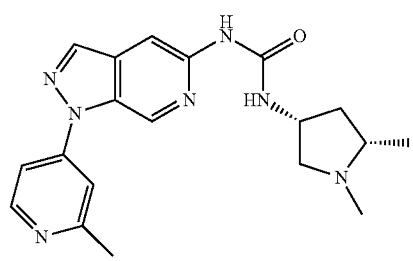 [SMILES: Cc1cc(-n2ncc3cc(NC(=O)N[C@@H]4C[C@H](C)N(C)C4)ncc32)ccn1] | 1-[(3R,5S)-1,5-dimethylpyrrolidin-3-yl]-3-[1-(2-methylpyridin-4-yl)-1H-pyrazolo[3,4-c]pyridin-5-yl]urea 274.9 nM | Calc'd 366.0, found 366 |
| 27. | 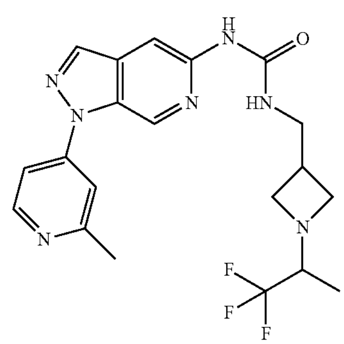 [SMILES: Cc1cc(-n2ncc3cc(NC(=O)NCC4CN(C(C)C(F)(F)F)C4)ncc32)ccn1] | 1-[1-(2-methylpyridin-4-yl)-1H-pyrazolo[3,4-c]pyridin-5-yl]-3-{[1-(2,2,2-trifluoro-1-methylethyl)azetidin-3-yl]methyl}urea 122.2 nM | Calc'd 434.0, found 434 |

TABLE 13-continued

| Ex | Structure | IUPAC Name/ERK2 IC$_{50}$ | [M + H]+ |
|---|---|---|---|
| 28. | 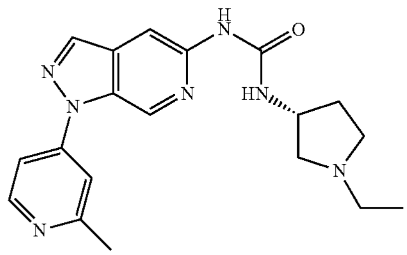 [SMILES: CCN1CC[C@@H](NC(=O)Nc2cc3cnn(-c4ccnc(C)c4)c3cn2)C1] | 1-[(3R)-1-ethylpyrrolidin-3-yl]-3-[1-(2-methylpyridin-4-yl)-1H-pyrazolo[3,4-c]pyridin-5-yl]urea 103.7 nM | Calc'd 366.0, found 366 |
| 29. | 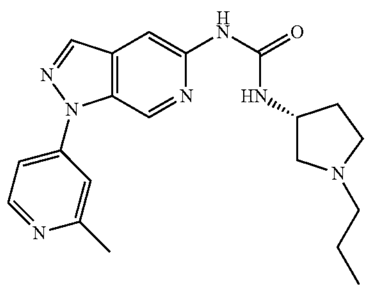 [SMILES: CCCN1CC[C@@H](NC(=O)Nc2cc3cnn(-c4ccnc(C)c4)c3cn2)C1] | 1-[1-(2-methylpyridin-4-yl)-1H-pyrazolo[3,4-c]pyridin-5-yl]-3-[(3R)-1-propylpyrrolidin-3-yl]urea 453.3 nM | Calc'd 380.0, found 380 |
| 30. | 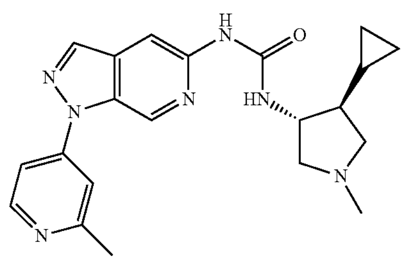 [SMILES: Cc1cc(-n2ncc3cc(NC(=O)N[C@H]4CN(C)C[C@@H]4C4CC4)ncc32)ccn1] | 1-[(3R,4S)-4-cyclopropyl-1-methylpyrrolidin-3-yl]-3-[1-(2-methylpyridin-4-yl)-1H-pyrazolo[3,4-c]pyridin-5-yl]urea 109.5 nM | Calc'd 392.0, found 392 |
| 31. | 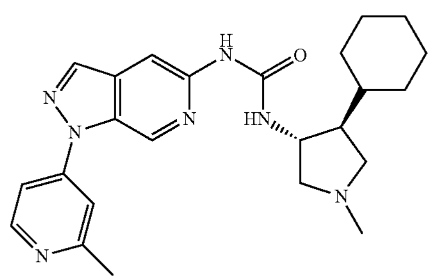 [SMILES: Cc1cc(-n2ncc3cc(NC(=O)N[C@H]4CN(C)C[C@@H]4C4CCCCC4)ncc32)ccn1] | 1-[(3R,4S)-4-cyclohexyl-1-methylpyrrolidin-3-yl]-3-[1-(2-methylpyridin-4-yl)-1H-pyrazolo[3,4-c]pyridin-5-yl]urea 35.14 nM | Calc'd 434.0, found 434 |
| 32. | 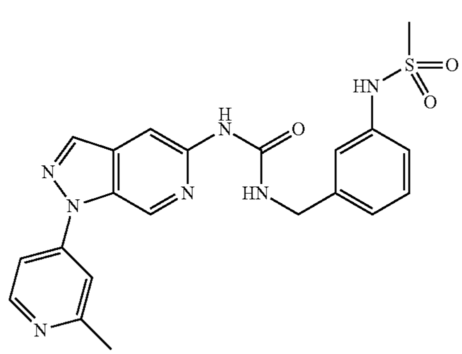 [SMILES: Cc1cc(-n2ncc3cc(NC(=O)NCc4cccc(NS(C)(=O)=O)c4)ncc32)ccn1] | N-{3-[(({[1-(2-methylpyridin-4-yl)-1H-pyrazolo[3,4-c]pyridin-5-yl]carbamoyl}amino)methyl]phenyl}methanesulfonamide 0.4419 nM | Calc'd 452.0, found 452 |

TABLE 13-continued

| Ex | Structure | IUPAC Name/ERK2 IC$_{50}$ | [M + H]+ |
|---|---|---|---|
| 33. | 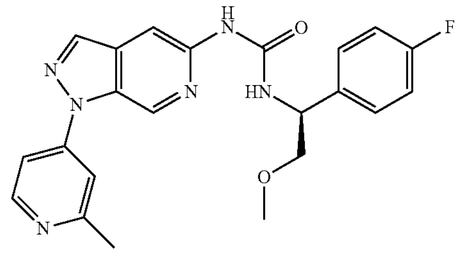 [SMILES: COC[C@@H](NC(=O)Nc1cc2cnn(-c3ccnc(C)c3)c2cn1)c1ccc(F)cc1] | 1-[(1S)-1-(4-fluorophenyl)-2-methoxyethyl]-3-[1-(2-methylpyridin-4-yl)-1H-pyrazolo[3,4-c]pyridin-5-yl]urea 590.4 nM | Calc'd 421.0, found 421 |
| 34. | 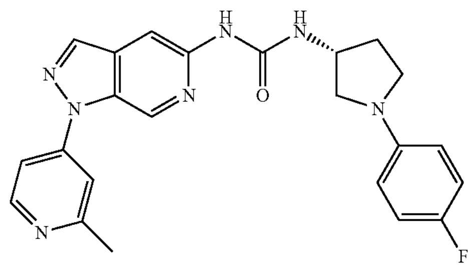 [SMILES: Cc1cc(-n2ncc3cc(NC(=O)N[C@@H]4CCN(c5ccc(F)cc5)C4)ncc32)ccn1] | 1-[(3R)-1-(4-fluorophenyl)pyrrolidin-3-yl]-3-[1-(2-methylpyridin-4-yl)-1H-pyrazolo[3,4-c]pyridin-5-yl]urea 762.4 nM | Calc'd 432, found 432 |
| 35. | 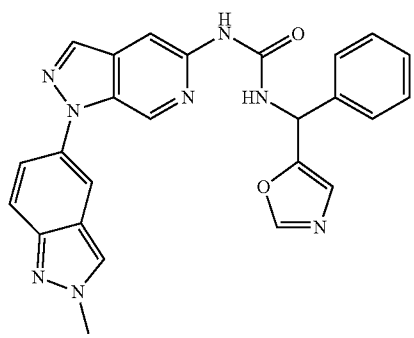 [SMILES: Cn1cc2cc(-n3ncc4cc(NC(=O)NC(c5ccccc5)c5cnco5)ncc43)ccc2n1] | 1-[1-(2-methyl-2H-indazol-5-yl)-1H-pyrazolo[3,4-c]pyridin-5-yl]-3-[1,3 oxazol-5-yl(phenyl)methyl]urea 1.562 nM | Calc'd 465, found 465 |
| 36. | 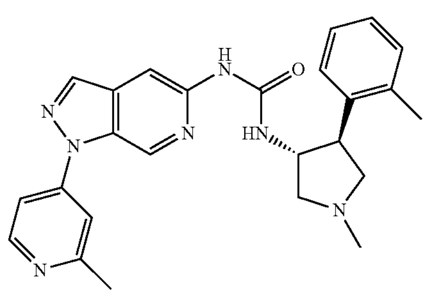 [SMILES: Cc1cc(-n2ncc3cc(NC(=O)N[C@H]4CN(C)C[C@@H]4c4ccccc4C)ncc32)ccn1] | 1-[(3R,4S) or (3S, 4R)-1-methyl-4-(2-methylphenyl)pyrrolidin-3-yl]-3-[1-(2-methylpyridin-4-yl)-1H-pyrazolo[3,4-c]pyridin-5-yl)urea 0.83 nM | Calc'd 442, found 442 |
| 37. | 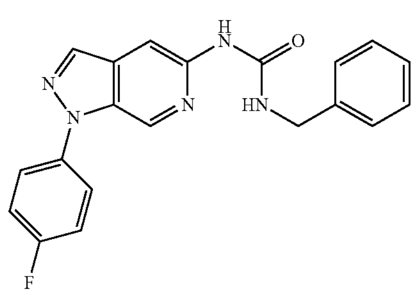 [SMILES: O=C(NCc1ccccc1)Nc1cc2cnn(-c3ccc(F)cc3)c2cn1] | 1-benzyl-3-[1-(4-fluorophenyl)-1H-pyrazolo[3,4-c]pyridin-5-yl)urea 19.8 nM | Calc'd 362, found 362 |

TABLE 13-continued

| Ex | Structure | IUPAC Name/ERK2 IC$_{50}$ | [M + H]+ |
|---|---|---|---|
| 38. | 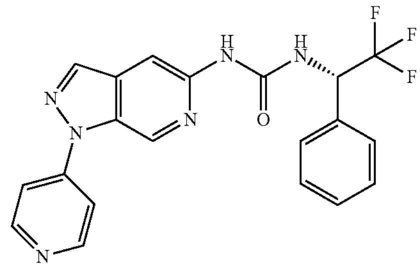 [SMILES: O=C(Nc1cc2cnn(-c3ccncc3)c2cn1)N[C@@H](c1ccccc1)C(F)(F)F] | 1-(1-pyridin-4-yl-1H-pyrazolo[3,4-c]pyridin-5-yl)-3-[(1S)-2,2,2-trifluoro-1-phenylethyl]urea 19.4 nM | Calc'd 413, found 413 |
| 39. | 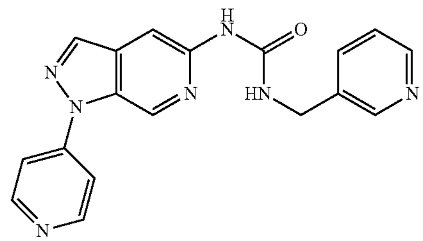 [SMILES: O=C(NCc1cccnc1)Nc1cc2cnn(-c3ccncc3)c2cn1] | 1-(pyridin-3-ylmethyl)-3-(1-pyridin-4-yl-1H-pyrazolo[3,4-c]pyridin-5-yl)urea 171 nM | Calc'd 346, found 346 |
| 40. | 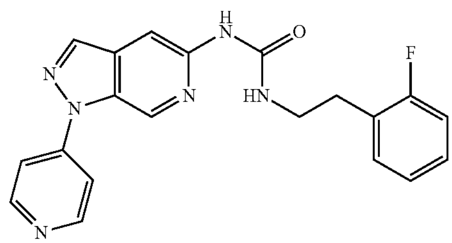 [SMILES: O=C(NCCc1ccccc1F)Nc1cc2cnn(-c3ccncc3)c2cn1] | 1-[2-(2-fluorophenyl)ethyl]-3-(1-pyridin-4-yl-1H-pyrazolo[3,4-c]pyridin-5-yl)urea 9.2 nM | Calc'd 377, found 377 |
| 41. | 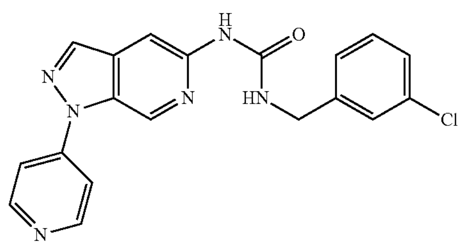 [SMILES: O=C(NCc1cccc(Cl)c1)Nc1cc2cnn(-c3ccncc3)c2cn1] | 1-(3-chlorobenzyl)-3-(1-pyridin-4-yl-1H-pyrazolo[3,4-c]pyridin-5-yl)urea 0.4987 nM | Calc'd 379, found 379 |
| 42. | 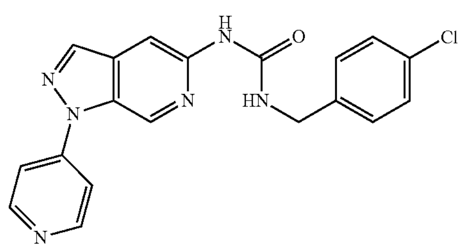 [SMILES: O=C(NCc1ccc(Cl)cc1)Nc1cc2cnn(-c3ccncc3)c2cn1] | 1-(4-chlorobenzyl)-3-(1-pyridin-4-yl-1H-pyrazolo[3,4-c]pyridin-5-yl)urea 8.031 nM | Calc'd 379, found 379 |
| 43. | 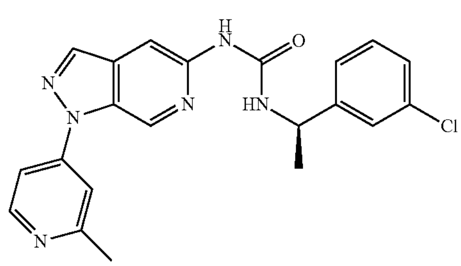 [SMILES: Cc1cc(-n2ncc3cc(NC(=O)N[C@H](C)c4cccc(Cl)c4)ncc32)ccn1] | 1-[(1R)-1-(3-chlorophenyl)ethyl]-3-[1-(2-methylpyridin-4-yl)-1H-pyrazolo[3,4-c]pyridin-5-yl]urea 0.952 nM | Calc'd 407, found 407 |

TABLE 13-continued

| Ex | Structure | IUPAC Name/ERK2 IC$_{50}$ | [M + H]+ |
| --- | --- | --- | --- |
| 44. | 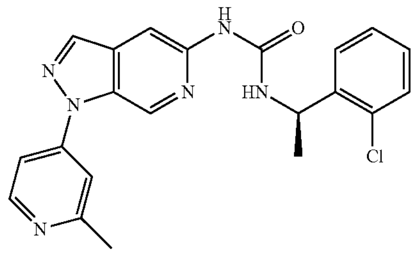 [SMILES: Cc1cc(-n2ncc3cc(NC(=O)N[C@H](C)c4ccccc4Cl)ncc32)ccn1] | 1-[(1R)-1-(2-chlorophenyl)ethyl]-3-[1-(2-methylpyridin-4-yl)-1H-pyrazolo[3,4-c]pyridin-5-yl]urea 15.64 nM | Calc'd 407, found 407 |
| 45. | 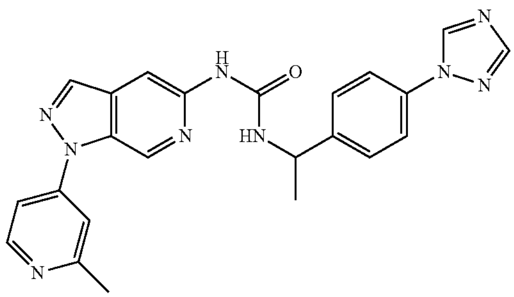 [SMILES: Cc1cc(-n2ncc3cc(NC(=O)NC(C)c4ccc(-n5cncn5)cc4)ncc32)ccn1] | 1-[1-(2-methylpyridin-4-yl)-1H-pyrazolo[3,4-c]pyridin-5-yl]-3-{1-[4-(1H-1,2,4-triazol-1-yl)phenyl]ethyl}urea 165.6 nM | Calc'd 440, found 440 |
| 46. | 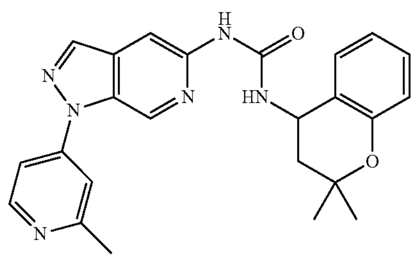 [SMILES: Cc1cc(-n2ncc3cc(NC(=O)NC4CC(C)(C)Oc5ccccc54)ncc32)ccn1] | 1-(2,2-dimethyl-3,4-dihydro-2H-chromen-4-yl)-3-[1-(2-methylpyridin-4-yl)-1H-pyrazolo[3,4-c]pyridin-5-yl]urea 173.7 nM | Calc'd 429, found 429 |
| 47. | 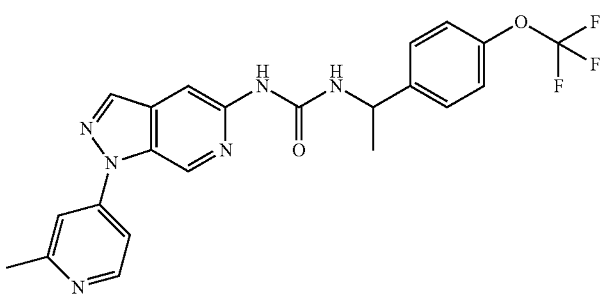 [SMILES: Cc1cc(-n2ncc3cc(NC(=O)NC(C)c4ccc(OC(F)(F)F)cc4)ncc32)ccn1] | 1-[1-(2-methylpyridin-4-yl)-1H-pyrazolo[3,4-c]pyridin-(trifluoromethoxy)phenyl]ethyl}urea 40.34 nM | Calc'd 457, found 457 |
| 48. | 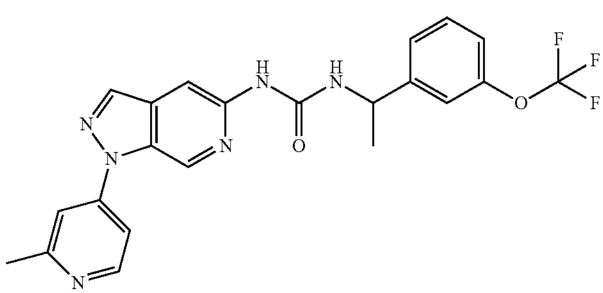 [SMILES: Cc1cc(-n2ncc3cc(NC(=O)NC(C)c4cccc(OC(F)(F)F)c4)ncc32)ccn1] | 1-[1-(2-methylpyridin-4-yl)-1H-pyrazolo[3,4-c]pyridin-5-yl]-3-{1-[3-(trifluoromethoxy)phenyl]ethyl}urea 10.73 nM | Calc'd 457, found 457 |

TABLE 13-continued

| Ex | Structure | IUPAC Name/ERK2 IC$_{50}$ | [M + H]+ |
|---|---|---|---|
| 49. | 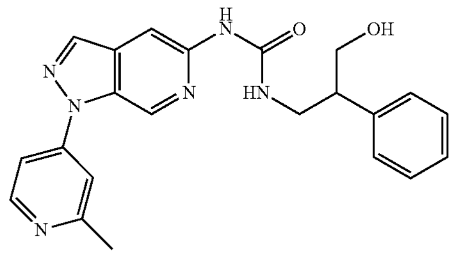 [SMILES: Cc1cc(-n2ncc3cc(NC(=O)NCC(CO)c4ccccc4)ncc32)ccn1] | 1-(3-hydroxy-2-phenylpropyl)-3-[1-(2-methylpyridin-4-yl)-1H-pyrazolo[3,4-c]pyridin-5-yl]urea 7.66 nM | Calc'd 403, found 403 |
| 50. | 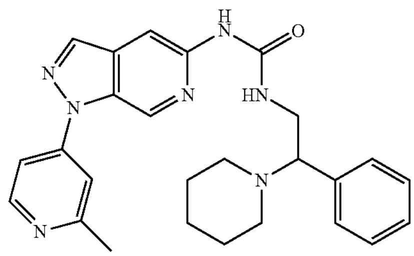 [SMILES: Cc1cc(-n2ncc3cc(NC(=O)NCC(c4ccccc4)N4CCCCC4)ncc32)ccn1] | 1-[1-(2-methylpyridin-4-yl)-1H-pyrazolo[3,4-c]pyridin-5-yl]-3-(2-phenyl-2-piperidin-1-ylethyl)urea 197.5 nM | Calc'd 456, found 456 |
| 51. | 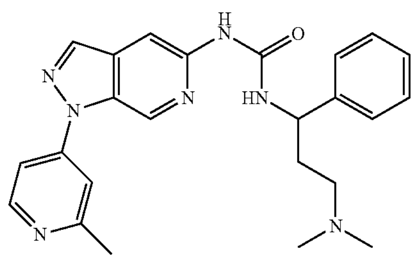 [SMILES: Cc1cc(-n2ncc3cc(NC(=O)NC(CCN(C)C)c4ccccc4)ncc32)ccn1] | 1-[3-(dimethylamino)-1-phenylpropyl]-3-[1-(2-methylpyridin-4-yl)-1H-pyrazolo[3,4-c]pyridin-5-yl)urea 2.699 nM | Calc'd 430, found 430 |
| 52. | 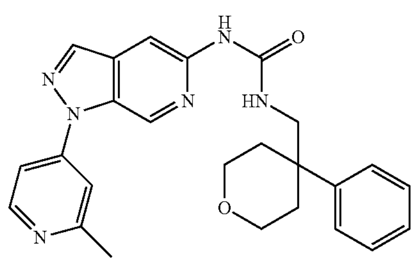 [SMILES: Cc1cc(-n2ncc3cc(NC(=O)NCC4(c5ccccc5)CCOCC4)ncc32)ccn1] | 1-[1-(2-methylpyridin-4-yl)-1H-pyrazolo[3,4-c]pyridin-5-yl]-3-[(4-phenyltetrahydro-2H-pyran-4-yl)methyl]urea 7.093 nM | Calc'd 443, found 443 |
| 53. | 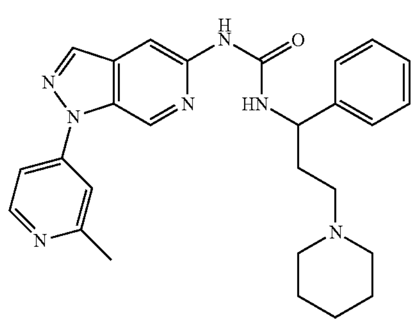 [SMILES: Cc1cc(-n2ncc3cc(NC(=O)NC(CCN4CCCCC4)c4ccccc4)ncc32)ccn1] | 1-[1-(2-methylpyridin-4-yl)-1H-pyrazolo[3,4-c]pyridin-5-yl]-3-(1-phenyl-3-piperidin-1-ylpropyl)urea 49.24 nM | Calc'd 470, found 470 |
| 54. | 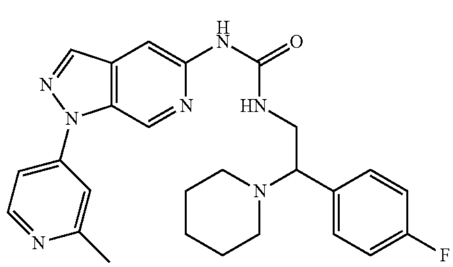 [SMILES: Cc1cc(-n2ncc3cc(NC(=O)NCC(c4ccc(F)cc4)N4CCCCC4)ncc32)ccn1] | 1-[2-(4-fluorophenyl)-2-piperidin-1-ylethyl]-3-[1-(2-methylpyridin-4-yl)-1H-pyrazolo[3,4-c]pyridin-5-yl)urea 195 nM | Calc'd 474, found 474 |

TABLE 13-continued

| Ex | Structure | IUPAC Name/ERK2 IC$_{50}$ | [M + H]+ |
|---|---|---|---|
| 55. | 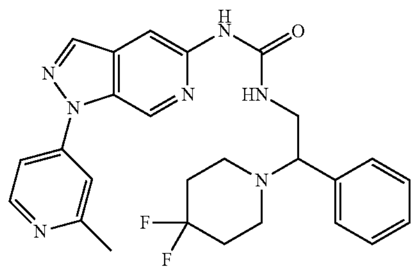 [SMILES: Cc1cc(-n2ncc3cc(NC(=O)NCC(c4ccccc4)N4CCC(F)(F)CC4)ncc32)ccn1] | 1-[2-(4,4-difluoropiperidin-1-yl)-2-phenylethyl]-3-[1-(2-methylpyridin-4-yl)-1H-pyrazolo[3,4-c]pyridin-5-yl]urea 85.07 nM | Calc'd 492, found 492 |
| 56. | 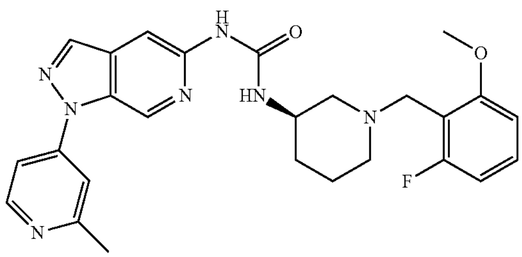 [SMILES: COc1cccc(F)c1CN1CCC[C@@H](NC(=O)Nc2cc3cnn(-c4ccnc(C)c4)c3cn2)C1] | 1-[(3R)-1-(2-fluoro-6-methoxybenzyl)piperidin-3-yl]-3-[1-(2-methylpyridin-4-yl)-1H-pyrazolo[3,4-c]pyridin-5-yl]urea 0.5239 nM | Calc'd 490, found 490 |
| 57. | 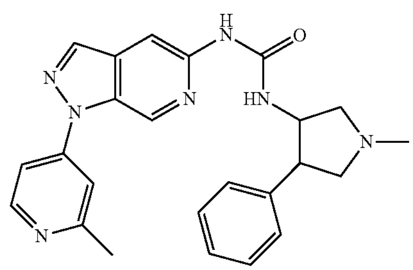 [SMILES: Cc1cc(-n2ncc3cc(NC(=O)NC4CN(C)CC4c4ccccc4)ncc32)ccn1] | 1-(1-methyl-4-phenylpyrrolidin-3-yl)-3-[1-(2-methylpyridin-4-yl)-1H-pyrazolo[3,4-c]pyridin-5-yl]urea 0.8234 nM | Calc'd 428, found 428 |
| 58. | 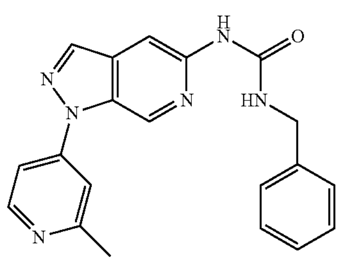 [SMILES: Cc1cc(-n2ncc3cc(NC(=O)NCc4ccccc4)ncc32)ccn1] | 1-benzyl-3-[1-(2-methylpyridin-4-yl)-1H-pyrazolo[3,4-c]pyridin-5-yl]urea 8.412 nM | Calc'd 359, found 359 |
| 59. | 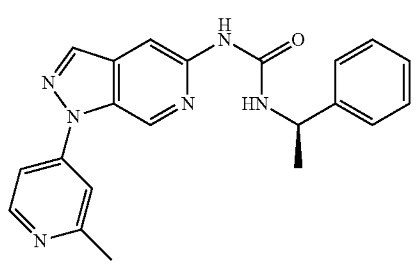 [SMILES: Cc1cc(-n2ncc3cc(NC(=O)N[C@H](C)c4ccccc4)ncc32)ccn1] | 1-[1-(2-methylpyridin-4-yl)-1H-pyrazolo[3,4-c]pyridin-5-yl]-3-[(1R)-1-phenylethyl]urea 1.008 nM | Calc'd 373, found 373 |
| 60. | 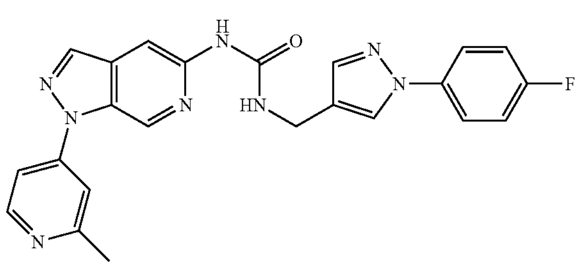 [SMILES: Cc1cc(-n2ncc3cc(NC(=O)NCc4cnn(-c5ccc(F)cc5)c4)ncc32)ccn1] | 1-{[1-(4-fluorophenyl)-1H-pyrazol-4-yl]methyl}-3-[1-(2-methylpyridin-4-yl)-1H-pyrazolo[3,4-c]pyridin-5-yl]urea 1631 nM | Calc'd 443, found 443 |

TABLE 13-continued

| Ex | Structure | IUPAC Name/ERK2 IC$_{50}$ | [M + H]+ |
|---|---|---|---|
| 61. | 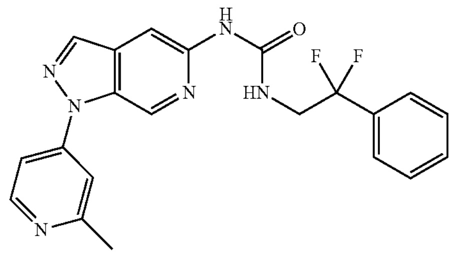 [SMILES: Cc1cc(-n2ncc3cc(NC(=O)NCC(F)(F)c4ccccc4)ncc32)ccn1] | 1-(2,2-difluoro-2-phenylethyl)-3-[1-(2-methylpyridin-4-yl)-1H-pyrazolo[3,4-c]pyridin-5-yl]urea 193 nM | Calc'd 409, found 409 |
| 62. | 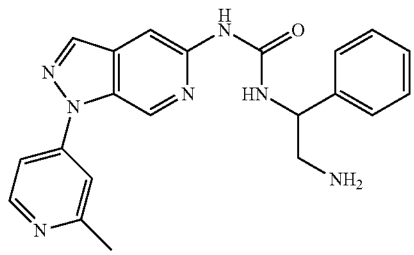 | 1-(2-amino-1-phenylethyl)-3-[1-(2-methylpyridin-4-yl)-1H-pyrazolo[3,4-c]pyridin-5-yl]urea 0.9615 nM | Calc'd 388, found 388 |
| 63. | 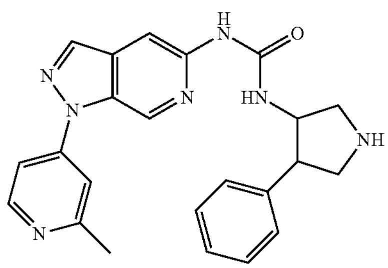 [SMILES: Cc1cc(-n2ncc3cc(NC(=O)NC4CNCC4c4ccccc4)ncc32)ccn1] | 1-[1-(2-methylpyridin-4-yl)-1H-pyrazolo[3,4-c]pyridin-5-yl]-3-(4-phenylpyrrolidin-3-yl)urea 54.4 nM | Calc'd 414, found 414 |
| 64. | 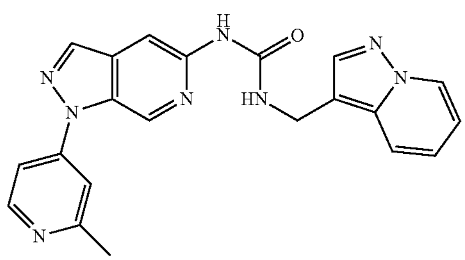 [SMILES: Cc1cc(-n2ncc3cc(NC(=O)NCc4cnn5ccccc45)ncc32)ccn1] | 1-[1-(2-methylpyridin-4-yl)-1H-pyrazolo[3,4-c]pyridin-5-yl]-3-(pyrazolo[1,5-a]pyridin-3-ylmethyl)urea 71.57 nM | Calc'd 399, found 399 |
| 65. | 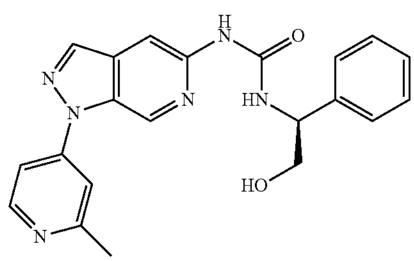 [SMILES: Cc1cc(-n2ncc3cc(NC(=O)N[C@H](CO)c4ccccc4)ncc32)ccn1] | 1-[(1S)-2-hydroxy-1-phenylethyl]-3-[1-(2-methylpyridin-4-yl)-1H-pyrazolo[3,4-c]pyridin-5-yl]urea 1.017 nM | Calc'd 389, found 389 |
| 66. | 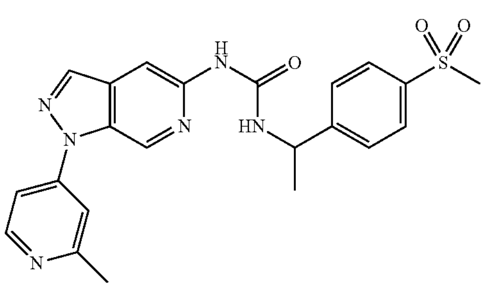 [SMILES: Cc1cc(-n2ncc3cc(NC(=O)NC(C)c4ccc(S(C)(=O)=O)cc4)ncc32)ccn1] | 1-[1-(2-methylpyridin-4-yl)-1H-pyrazolo[3,4-c]pyridin-5-yl]-3-{1-[4-(methylsulfonyl)phenyl]ethyl}urea 7.78 nM | Calc'd 451, found 451 |

TABLE 13-continued

| Ex | Structure | IUPAC Name/ERK2 IC$_{50}$ | [M + H]+ |
|---|---|---|---|
| 67. | 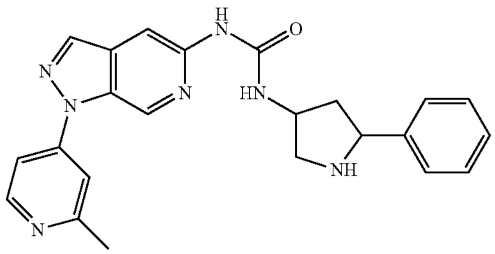 [SMILES: Cc1cc(-n2ncc3cc(NC(=O)NC4CNC(c5ccccc5)C4)ncc32)ccn1] | 1-[1-(2-methylpyridin-4-yl)-1H-pyrazolo[3,4-c]pyridin-5-yl]-3-(5-phenylpyrrolidin-3-yl)urea 200.5 nM | Calc'd 414, found 414 |
| 68. | 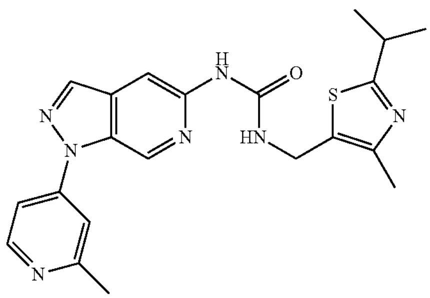 [SMILES: Cc1cc(-n2ncc3cc(NC(=O)NCc4sc(C(C)C)nc4C)ncc32)ccn1] | 1-{[4-methyl-2-(1-methylethyl)-1,3-thiazol-5-yl]methyl}-3-[1-[2-methylpyridin-4-yl)-1H-pyrazolo[3,4-c]pyridin-5-yl]urea 707.3 nM | Calc'd 422, found 422 |
| 69. | 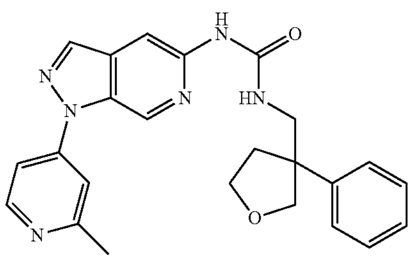 [SMILES: Cc1cc(-n2ncc3cc(NC(=O)NCC4(c5ccccc5)CCOC4)ncc32)ccn1] | 1-[1-(2-methylpyridin-4-yl)-1H-pyrazolo[3,4-c]pyridin-5-yl]-3-[(3-phenyltetrahydrofuran-3-yl)methyl]urea 17.66 nM | Calc'd 429, found 429 |
| 70. | 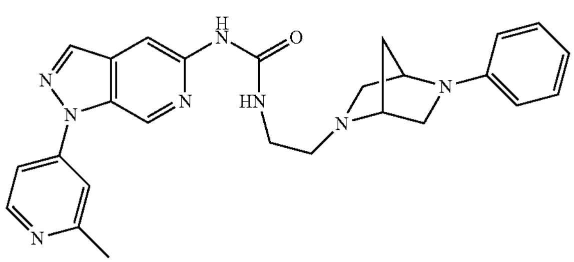 [SMILES: Cc1cc(-n2ncc3cc(NC(=O)NCCN4CC5CC4CN5c4ccccc4)ncc32)ccn1] | 1-[1-(2-methylpyridin-4-yl)-1H-pyrazolo[3,4-c]pyridin-5-yl]-3-[2-(5-phenyl-2,5-diazabicyclo[2.2.1]hept-2-yl)ethyl]urea 16.94 nM | Calc'd 469, found 469 |
| 71. | 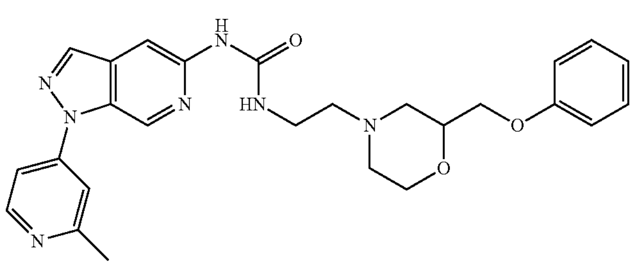 [SMILES: Cc1cc(-n2ncc3cc(NC(=O)NCCN4CCOC(COc5ccccc5)C4)ncc32)ccn1] | 1-[1-(2-methylpyridin-4-yl)-1H-pyrazolo[3,4-c]pyridin-(phenoxymethyl)morpholin-4-yl]ethyl}urea 647.7 nM | Calc'd 488, found 488 |
| 72. | 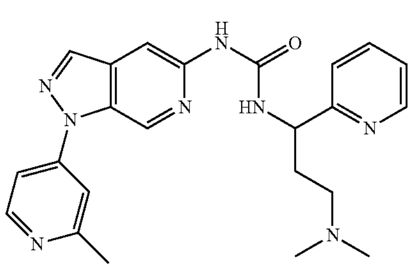 [SMILES: Cc1cc(-n2ncc3cc(NC(=O)NC(CCN(C)C)c4ccccn4)ncc32)ccn1] | 1-[3-(dimethylamino)-1-pyridin-2-ylpropyl]-3-[1-(2-methylpyridin-4-yl)-1H-pyrazolo[3,4-c]pyridin-5-yl]urea 10.19 nM | Calc'd 431, found 431 |

TABLE 13-continued

| Ex | Structure | IUPAC Name/ERK2 IC$_{50}$ | [M + H]+ |
|---|---|---|---|
| 73. | 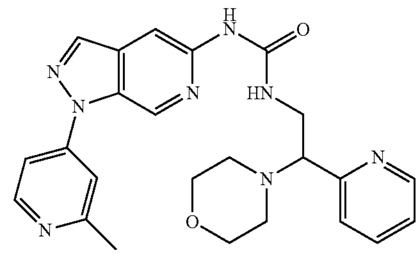 [SMILES: Cc1cc(-n2ncc3cc(NC(=O)NCC(c4ccccn4)N4CCOCC4)ncc32)ccn1] | 1-[1-(2-methylpyridin-4-yl)-1H-pyrazolo[3,4-c]pyridin-5-yl]-3-(2-morpholin-4-yl-2-pyridin-2-ylethyl)urea 242.9 nM | Calc'd 459, found |
| 74. | 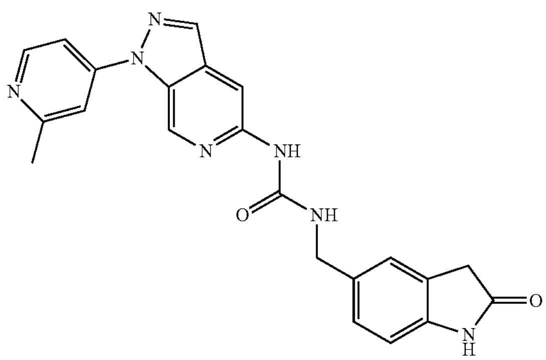 [SMILES: Cc1cc(-n2ncc3cc(NC(=O)NCc4ccc5c(c4)CC(=O)N5)ncc32)ccn1] | 1-[1-(2-methylpyridin-4-yl)-1H-pyrazolo[3,4-c]pyridin-5-yl]-3-[(2-oxo-2,3-dihydro-1H-indol-5-yl)methyl]urea 73.07 nM | Calc'd 414, found 414 |
| 75. | 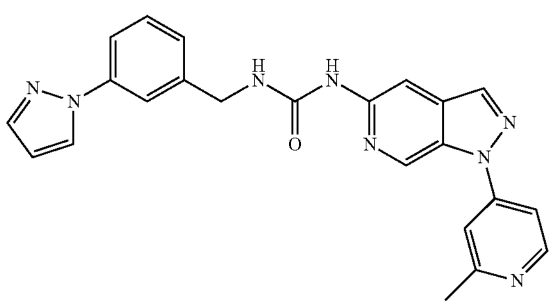 [SMILES: Cc1cc(-n2ncc3cc(NC(=O)NCc4cccc(-n5cccn5)c4)ncc32)ccn1] | 1-[1-(2-methylpyridin-4-yl)-1H-pyrazolo[3,4-c]pyridin-5-yl]-3-[3-(1H-pyrazol-1-yl)benzyl]urea 5.275 nM | Calc'd 425, found 425 |
| 76. | 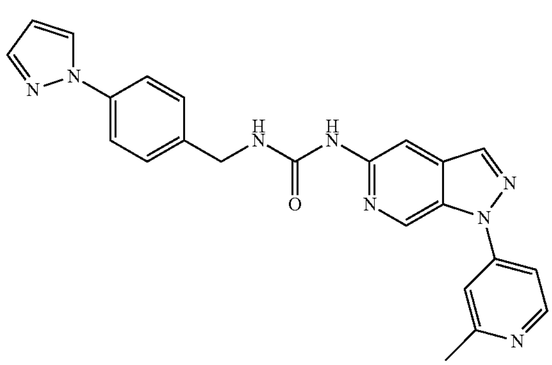 [SMILES: Cc1cc(-n2ncc3cc(NC(=O)NCc4ccc(-n5cccn5)cc4)ncc32)ccn1] | 1-[1-(2-methylpyridin-4-yl)-1H-pyrazolo[3,4-c]pyridin-5-yl]-3-[4-(1H-pyrazol-1-yl)benzyl]urea 1106 nM | Calc'd 425, found 425 |

TABLE 13-continued

| Ex | Structure | IUPAC Name/ERK2 IC$_{50}$ | [M + H]+ |
|---|---|---|---|
| 77. | 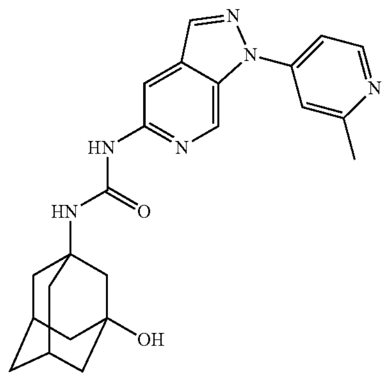 [SMILES: Cc1cc(-n2ncc3cc(NC(=O)NC45CC6CC(CC(O)(C6)C4)C5)ncc32)ccn1] | 1-(3-hydroxytricyclo[3.3.1.1~3,7~]dec-1-yl)-3-[1-(2-methylpyridin-4-yl)-1H-pyrazolo[3,4-c]pyridin-5-yl)urea 1876 nM | Calc'd 419, found 419 |
| 78. | 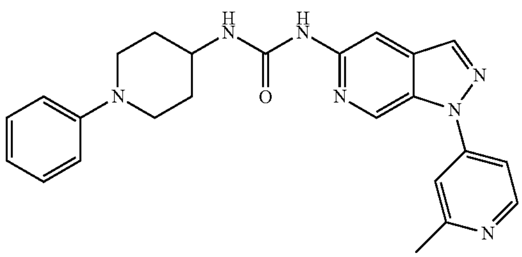 [SMILES: Cc1cc(-n2ncc3cc(NC(=O)NC4CCN(c5ccccc5)CC4)ncc32)ccn1] | 1-[1-(2-methylpyridin-4-yl)-1H-pyrazolo[3,4-c]pyridin-5-yl]-3-(1-phenylpiperidin-4-yl)urea 1741 nM | Calc'd 428, found 428 |
| 79. | 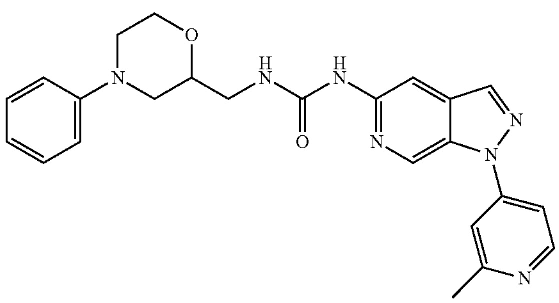 [SMILES: Cc1cc(-n2ncc3cc(NC(=O)NCC4CN(c5ccccc5)CCO4)ncc32)ccn1] | 1-[1-(2-methylpyridin-4-yl)-1H-pyrazolo[3,4-c]pyridin-5-yl]-3-[(4-phenylmorpholin-2-yl)methyl]urea 26.54 nM | Calc'd 444, found 444 |
| 80. | 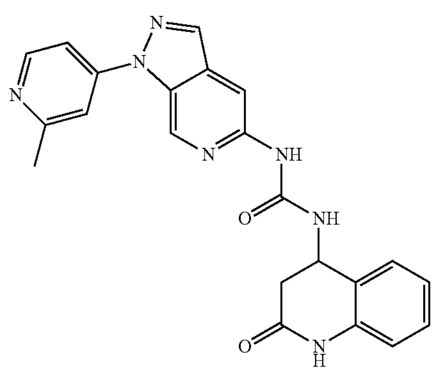 [SMILES: Cc1cc(-n2ncc3cc(NC(=O)NC4CC(=O)Nc5ccccc54)ncc32)ccn1] | 1-[1-(2-methylpyridin-4-yl)-1H-pyrazolo[3,4-c]pyridin-5-yl]-3-(2-oxo-1,2,3,4-tetrahydroquinolin-4-yl)urea 196.1 nM | Calc'd 414, found 414 |
| 81. | 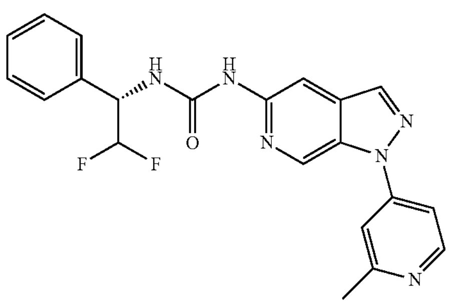 [SMILES: Cc1cc(-n2ncc3cc(NC(=O)N[C@@H](c4ccccc4)C(F)F)ncc32)ccn1] | 1-[(1S)-2,2-difluoro-1-phenylethyl]-3-[1-(2-methylpyridin-4-yl)-1H-pyrazolo[3,4-c]pyridin-5-yl)urea 914.2 nM | Calc'd 409, found 409 |

TABLE 13-continued

| Ex | Structure | IUPAC Name/ERK2 IC$_{50}$ | [M + H]+ |
|---|---|---|---|
| 82. | 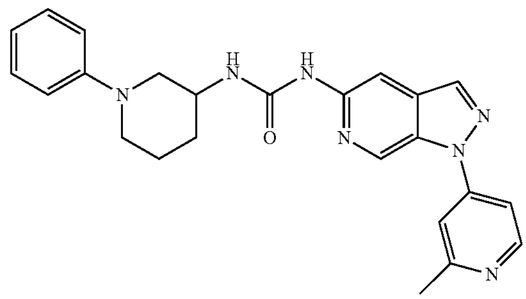 [SMILES: Cc1cc(-n2ncc3cc(NC(=O)NC4CCCN(c5ccccc5)C4)ncc32)ccn1] | 1H-pyrazolo[3,4-c]pyridin-1-[1-(2-methylpyridin-4-yl)-5-yl]-3-(1-phenylpiperidin-3-yl)urea 7.607 nM | Calc'd 428, found 428 |
| 83. | 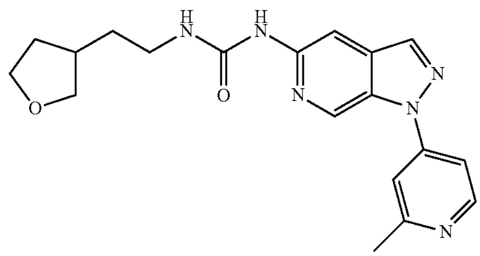 [SMILES: Cc1cc(-n2ncc3cc(NC(=O)NCCC4CCOC4)ncc32)ccn1] | 1-[1-(2-methylpyridin-4-yl)-1H-pyrazolo[3,4-c]pyridin-5-yl]-3-[2-(tetrahydrofuran-3-yl)ethyl]urea 64.67 nM | Calc'd 367, found 367 |
| 84. | 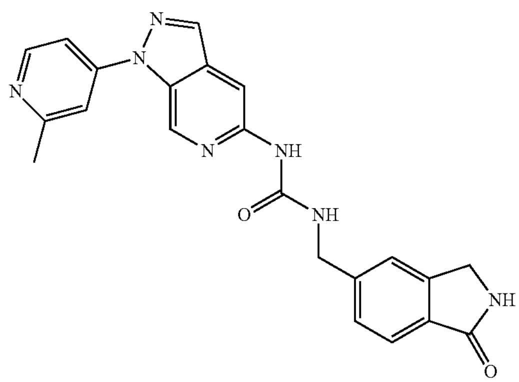 [SMILES: Cc1cc(-n2ncc3cc(NC(=O)NCc4ccc5c(c4)CNC5=O)ncc32)ccn1] | 1-[1-(2-methylpyridin-4-yl)-1H-pyrazolo[3,4-c]pyridin-5-yl]-3-[(1-oxo-2,3-dihydro-1H-isoindol-5-yl)methyl]urea 17.44 nM | Calc'd 414, found 414 |
| 85. | 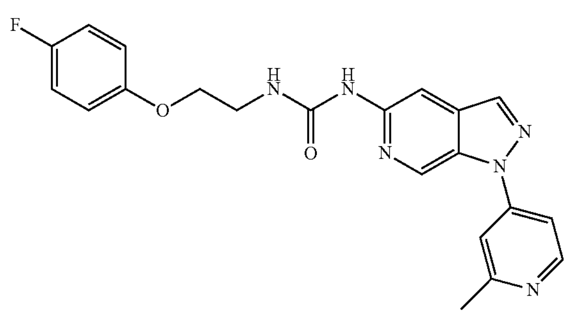 [SMILES: Cc1cc(-n2ncc3cc(NC(=O)NCCOc4ccc(F)cc4)ncc32)ccn1] | 1-[2-(4-fluorophenoxy)ethyl]-3-[1-(2-methylpyridin-4-yl)-1H-pyrazolo[3,4-c]pyridin-5-yl)urea 15.93 nM | Calc'd 407, found 407 |
| 86. | 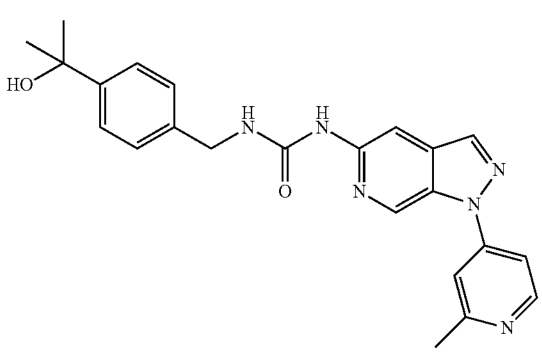 [SMILES: Cc1cc(-n2ncc3cc(NC(=O)NCc4ccc(C(C)(C)O)cc4)ncc32)ccn1] | 1-[4-(1-hydroxy-1-methylethyl)benzyl]-3-[1-(2-methylpyridin-4-yl)-1H-pyrazolo[3,4-c]pyridin-5-yl)urea 730.7 nM | Calc'd 417, found 417 |

TABLE 13-continued

| Ex | Structure | IUPAC Name/ERK2 IC$_{50}$ | [M + H]+ |
|---|---|---|---|
| 87. | 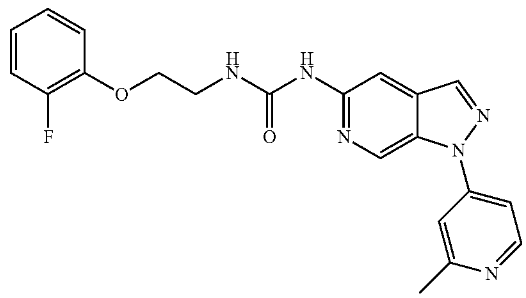 [SMILES: Cc1cc(-n2ncc3cc(NC(=O)NCCOc4ccccc4F)ncc32)ccn1] | 1-[2-(2-fluorophenoxy)ethyl]-3-[1-(2-methylpyridin-4-yl)-1H-pyrazolo[3,4-c]pyridin-5-yl)urea 6.381 nM | Calc'd 407, found 407 |
| 88. | 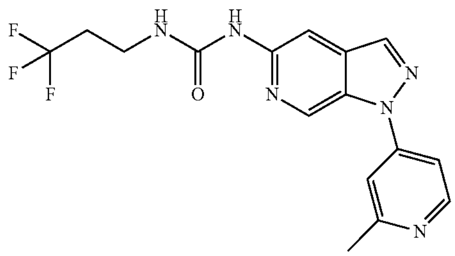 [SMILES: Cc1cc(-n2ncc3cc(NC(=O)NCCC(F)(F)F)ncc32)ccn1] | 1-[1-(2-methylpyridin-4-yl)-1H-pyrazolo[3,4-c]pyridin-5-yl]-3-(3,3,3-trifluoropropyl)urea 46.3 nM | Calc'd 365, found 365 |
| 89. | 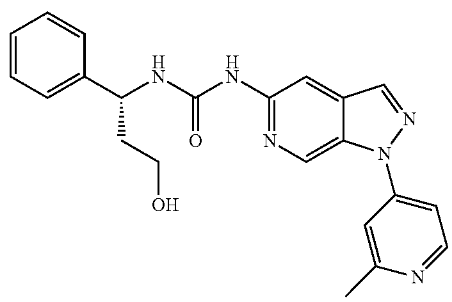 [SMILES: Cc1cc(-n2ncc3cc(NC(=O)N[C@H](CCO)c4ccccc4)ncc32)ccn1] | 1-[(1R)-3-hydroxy-1-phenylpropyl]-3-[1-(2-methylpyridin-4-yl)-1H-pyrazolo[3,4-c]pyridin-5-yl)urea 0.8211 nM | Calc'd 403, found 403 |
| 90. | 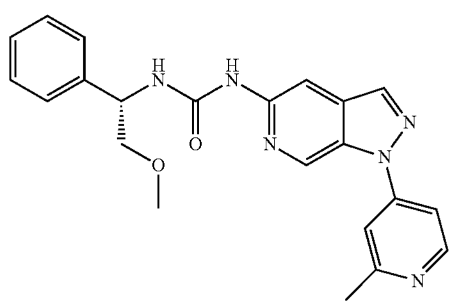 [SMILES: COC[C@@H](NC(=O)Nc1cc2cnn(-c3ccnc(C)c3)c2cn1)c1ccccc1] | 1-[(1S)-2-methoxy-1-phenylethyl]-3-[1-(2-methylpyridin-4-yl)-1H-pyrazolo[3,4-c]pyridin-5-yl)urea 0.6798 nM | Calc'd 403, found 403 |
| 91. | 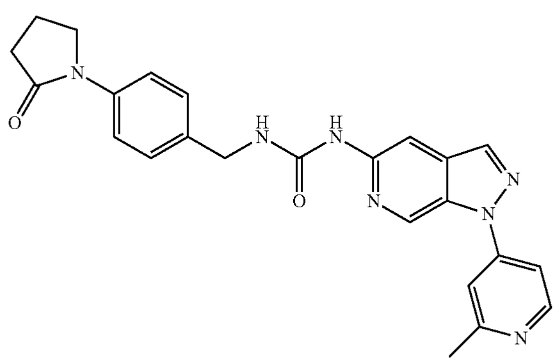 [SMILES: Cc1cc(-n2ncc3cc(NC(=O)NCc4ccc(N5CCCC5=O)cc4)ncc32)ccn1] | 1-[1-(2-methylpyridin-4-yl)-1H-pyrazolo[3,4-c]pyridin-5-yl]-3-[4-(2-oxopyrrolidin-1-yl)benzyl]urea 331.8 nM | Calc'd 442, found 442 |

TABLE 13-continued

| Ex | Structure | IUPAC Name/ERK2 IC$_{50}$ | [M + H]+ |
|---|---|---|---|
| 92. | 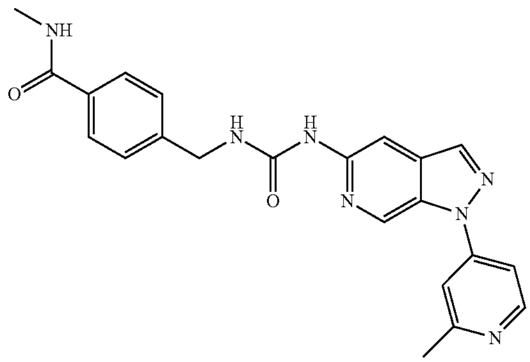 [SMILES: CNC(=O)c1ccc(CNC(=O)Nc2cc3cnn(-c4ccnc(C)c4)c3cn2)cc1] | N-methyl-4-[({[1-(2-methylpyridin-4-yl)-1H-pyrazolo[3,4-c]pyridin-5-yl]carbamoyl}amino)methyl]benzamide 800.8 nM | Calc'd 416, found 416 |
| 93. | 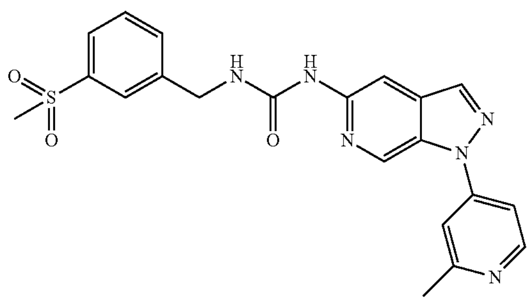 [SMILES: Cc1cc(-n2ncc3cc(NC(=O)NCc4cccc(S(C)(=O)=O)c4)ncc32)ccn1] | 1-[1-(2-methylpyridin-4-yl)-1H-pyrazolo[3,4-c]pyridin-5-yl]-3-[3-(methylsulfonyl)benzyl]urea 1.443 nM | Calc'd 437, found 437 |
| 94. | 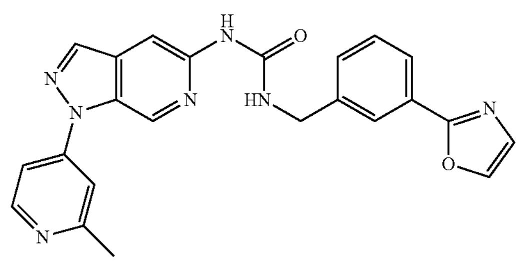 [SMILES: Cc1cc(-n2ncc3cc(NC(=O)NCc4cccc(-c5ncco5)c4)ncc32)ccn1] | 1-[1-(2-methylpyridin-4-yl)-1H-pyrazolo[3,4-c]pyridin-5-yl]-3-[3-(1,3-oxazol-2-yl)benzyl]urea 13.26 nM | Calc'd 426, found 426 |
| 95. | 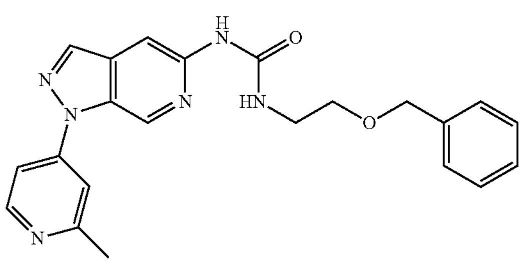 [SMILES: Cc1cc(-n2ncc3cc(NC(=O)NCCOCc4ccccc4)ncc32)ccn1] | 1-[2-(benzyloxy)ethyl]-3-[1-(2-methylpyridin-4-yl)-1H-pyrazolo[3,4-c]pyridin-5-yl]urea 5.401 nM | Calc'd 403, found 403 |
| 96. | 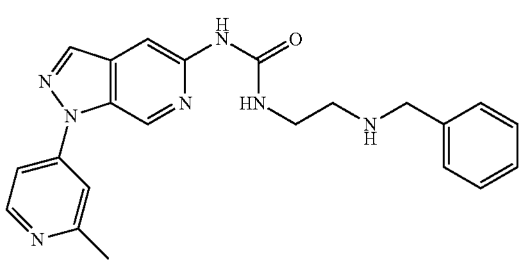 [SMILES: Cc1cc(-n2ncc3cc(NC(=O)NCCNCc4ccccc4)ncc32)ccn1] | 1-[2-(benzylamino)ethyl]-3-[1-(2-methylpyridin-4-yl)-1H-pyrazolo[3,4-c]pyridin-5-yl]urea 19.07 nM | Calc'd 402, found 402 |

TABLE 13-continued

| Ex | Structure | IUPAC Name/ERK2 IC$_{50}$ | [M + H]+ |
|---|---|---|---|
| 97. | 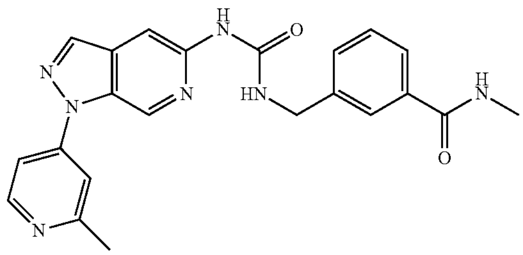 [SMILES: CNC(=O)c1cccc(CNC(=O)Nc2cc3cnn(-c4ccnc(C)c4)c3cn2)c1] | N-methyl-3-[({[1-(2-methylpyridin-4-yl)-1H-pyrazolo[3,4-c]pyridin-5-yl]carbamoyl}amino)methyl]benzamide 3.389 nM | Calc'd 416, found 416 |
| 98. | 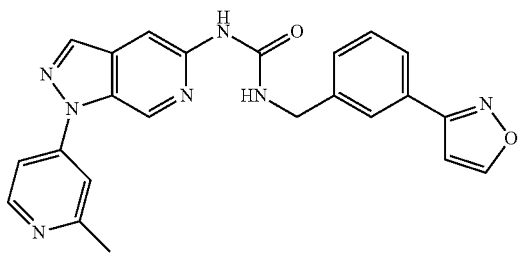 [SMILES: Cc1cc(-n2ncc3cc(NC(=O)NCc4cccc(-c5ccon5)c4)ncc32)ccn1] | 1-(3-isoxazol-3-ylbenzyl)-3-[1-(2-methylpyridin-4-yl)-1H-pyrazolo[3,4-c]pyridin-5-yl]urea 1.683 nM | Calc'd 426, found 426 |
| 99. | 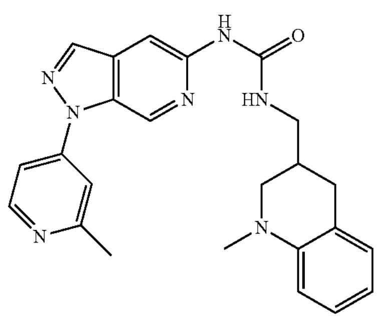 [SMILES: Cc1cc(-n2ncc3cc(NC(=O)NCC4Cc5ccccc5N(C)C4)ncc32)ccn1] | 1-[1-(2-methylpyridin-4-yl)-1H-pyrazolo[3,4-c]pyridin-5-yl]-3-[(1-methyl-1,2,3,4-tetrahydroquinolin-3-yl)methyl]urea 2.314 nM | Calc'd 428, found 428 |
| 100. | 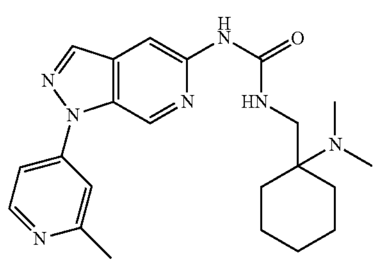 [SMILES: Cc1cc(-n2ncc3cc(NC(=O)NCC4(N(C)C)CCCCC4)ncc32)ccn1] | 1-{[1-(dimethylamino)cyclohexyl]methyl}-3-[1-(2-methylpyridin-4-yl)-1H-pyrazolo[3,4-c]pyridin-5-yl)urea 1210 nM | Calc'd 408, found 408 |
| 101. | 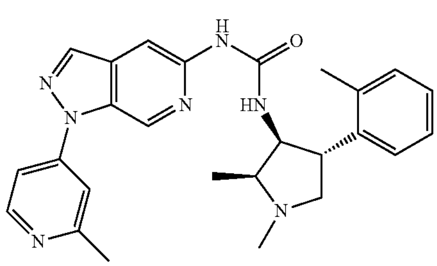 [SMILES: Cc1cc(-n2ncc3cc(NC(=O)N[C@H]4[C@H](c5ccccc5C)CN(C)[C@H]4C)ncc32)ccn1] | 1-[(2S,3S,4R)-1,2-dimethyl-4-(2-methylphenyl)-pyrrolidin-3-yl]-3-[1-(2-methylpyridin-4-yl)-1H-pyrazolo[3,4-c]pyridin-5-yl)urea 0.4999 nM | Calc'd 456, found 456 |
| 102. | 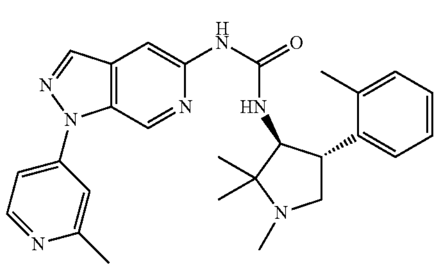 [SMILES: Cc1cc(-n2ncc3cc(NC(=O)N[C@H]4[C@H](c5ccccc5C)CN(C)C4(C)C)ncc32)ccn1] | 1-[1-(2-methylpyridin-4-yl)-1H-pyrazolo[3,4-c]pyridin-5-yl]-3-[(3S,4R)-1,2,2-trimethyl-4-(2-methylphenyl)pyrrolidin-3-yl)urea 234.6 nM | Calc'd 470, found 470 |

TABLE 13-continued

| Ex | Structure | IUPAC Name/ERK2 IC$_{50}$ | [M + H]+ |
|---|---|---|---|
| 103. | 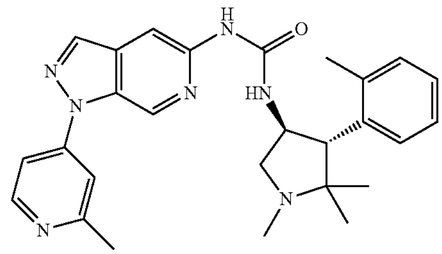 [SMILES: Cc1cc(-n2ncc3cc(NC(=O)N[C@@H]4CN(C)C(C)(C)[C@H]4c4ccccc4C)ncc32)ccn1] | 1-[1-(2-methylpyridin-4-yl)-1H-pyrazolo[3,4-c]pyridin-5-yl]-3-[(3S,4S)-1,5,5-trimethyl-4-(2-methylphenyl)pyrrolidin-3-yl]urea 1.139 nM | Calc'd 470, found 470 |
| 104. | 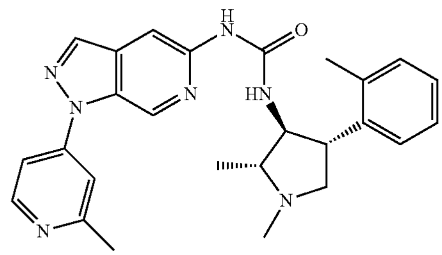 [SMILES: Cc1cc(-n2ncc3cc(NC(=O)N[C@@H]4[C@@H](C)N(C)C[C@H]4c4ccccc4C)ncc32)ccn1] | 1-[(2R,3S,4R)-1,2-dimethyl-4-(2-methyl-phenyl)pyrrolidin-3-yl]-3-[1-(2-methylpyridin-4-yl)-1H-pyrazolo[3,4-c]pyridin-5-yl]urea 35.47 nM | Calc'd 456, found 456 |
| 105. | 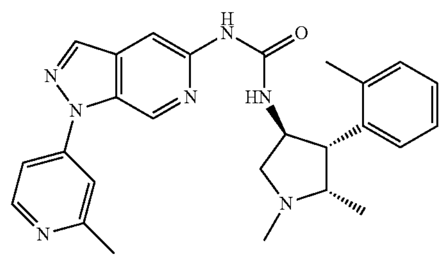 [SMILES: Cc1cc(-n2ncc3cc(NC(=O)N[C@@H]4CN(C)[C@@H](C)[C@H]4c4ccccc4C)ncc32)ccn1] | 1-[(3S,4S,5S)-1,5-dimethyl-4-(2-methylphenyl)-pyrrolidin-3-yl]-3-[1-(2-methylpyridin-4-yl)-1H-pyrazolo[3,4-c]pyridin-5-yl)urea 2.147 nM | Calc'd 456, found 456 |
| 106. | 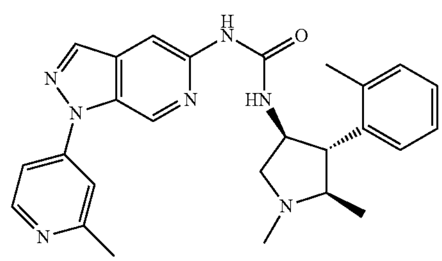 [SMILES: Cc1cc(-n2ncc3cc(NC(=O)N[C@@H]4CN(C)[C@H](C)[C@H]4c4ccccc4C)ncc32)ccn1] | 1-[(3S,4S,5R)-1,5-dimethyl-4-(2-methylphenyl)-pyrrolidin-3-yl]-3-[1-(2-methylpyridin-4-yl)-1H-pyrazolo[3,4-c]pyridin-5-yl)urea 1.521 nM | Calc'd 456, found 456 |
| 107. | 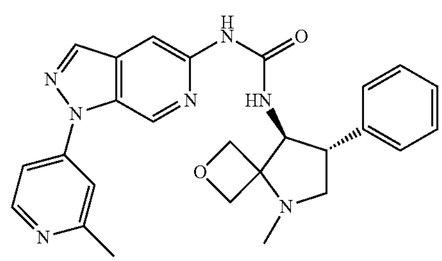 [SMILES: Cc1cc(-n2ncc3cc(NC(=O)N[C@H]4[C@H](c5ccccc5)CN(C)C45COC5)ncc32)ccn1] | 1-[(7R,8S)-5-methyl-7-phenyl-2-oxa-5-azaspiro[3.4]oct-8-yl]-3-[1-(2-methylpyridin-4-yl)-1H-pyrazolo[3,4-c]pyridin-5-yl)urea 9.035 nM | Calc'd 470, found 470 |
| 108. | 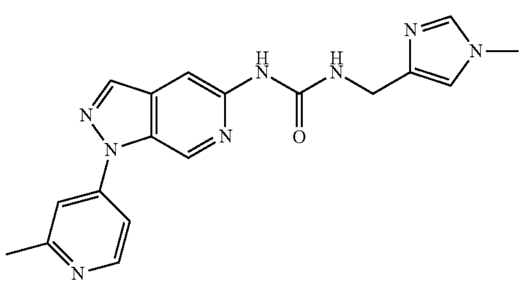 | 1-[(1-methyl-1H-imidazol-4-yl)methyl]-3-[1-(2-methylpyridin-4-yl)-1H-pyrazolo[3,4-c]pyridin-5-yl)urea 284.5 nM | Calc'd 363, found 363 |

| Ex | Structure | IUPAC Name/ERK2 IC$_{50}$ | [M + H]+ |
|---|---|---|---|
| 109. | 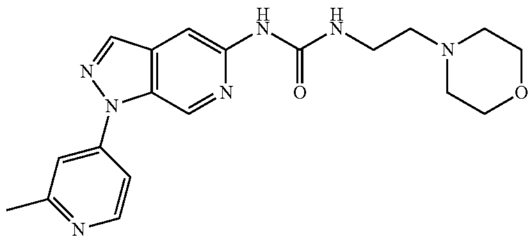 [SMILES: Cc1cc(-n2ncc3cc(NC(=O)NCCN4CCOCC4)ncc32)ccn1] | 1-[1-(2-methylpyridin-4-yl)-1H-pyrazolo[3,4-c]pyridin-5-yl]-3-(2-morpholin-4-ylethyl)urea 627.4 nM | Calc'd 382, found 382 |
| 110. | 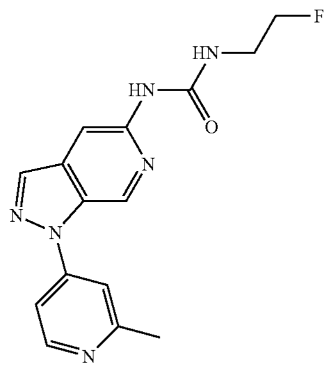 [SMILES: Cc1cc(-n2ncc3cc(NC(=O)NCCF)ncc32)ccn1] | 1-(2-fluoroethyl)-3-[1-(2-methylpyridin-4-yl)-1H-pyrazolo[3,4-c]pyridin-5-yl]urea 106.3 nM | Calc'd 315, found 315 |
| 111. | 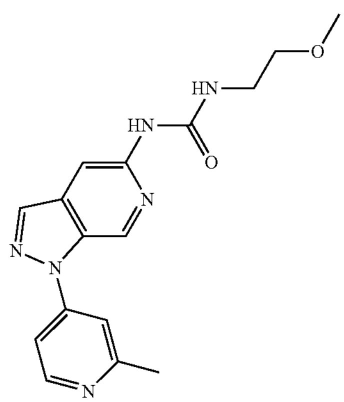 [SMILES: COCCNC(=O)Nc1cc2cnn(-c3ccnc(C)c3)c2cn1] | 1-(2-methoxyethyl)-3-[1-(2-methylpyridin-4-yl)-1H-pyrazolo[3,4-c]pyridin-5-yl)urea 81.77 nM | Calc'd 327, found 327 |
| 112. | 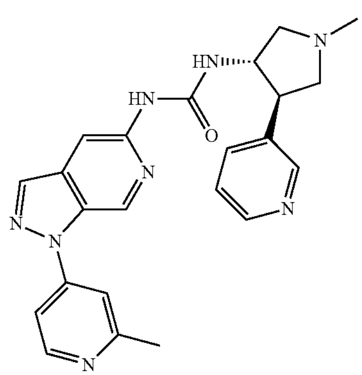 [SMILES: Cc1cc(-n2ncc3cc(NC(=O)N[C@@H]4CN(C)C[C@H]4c4cccnc4)ncc32)ccn1] | 1-[1-(2-methylpyridin-4-yl)-1H-pyrazolo[3,4-c]pyridin-5-yl]-3-[(3S,4R)-1-methyl-4-pyridin-3-ylpyrrolidin-3-yl)urea 48.7 nM | Calc'd 429, found 429 |

TABLE 13-continued

| Ex | Structure | IUPAC Name/ERK2 IC$_{50}$ | [M + H]+ |
|---|---|---|---|
| 113. | 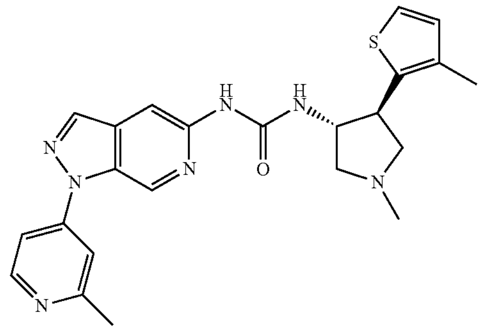 [SMILES: Cc1cc(-n2ncc3cc(NC(=O)N[C@H]4CN(C)C[C@@H]4c4sccc4C)ncc32)ccn1] | 1-[(3R,4S)-1-methyl-4-(3-methylthiophen-2-yl)pyrrolidin-3-yl]-3-[1-(2-methylpyridin-4-yl)-1H-pyrazolo[3,4-c]pyridin-5-yl]urea 7.109 nM | Calc'd 448, found 448 |
| 114. | 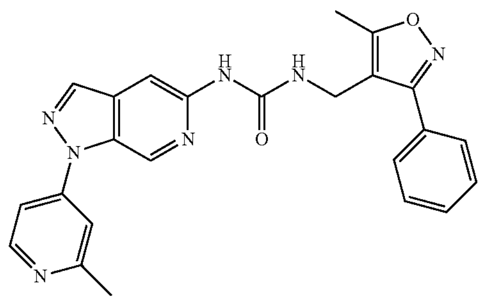 [SMILES: Cc1cc(-n2ncc3cc(NC(=O)NCc4c(-c5ccccc5)noc4C)ncc32)ccn1] | 1-[(5-methyl-3-phenyl-isoxazol-4-yl)methyl]-3-[1-(2-methylpyridin-4-yl)-1H-pyrazolo[3,4-c]pyridin-5-yl]urea 2.136 nM | Calc'd 440, found 440 |
| 115. | 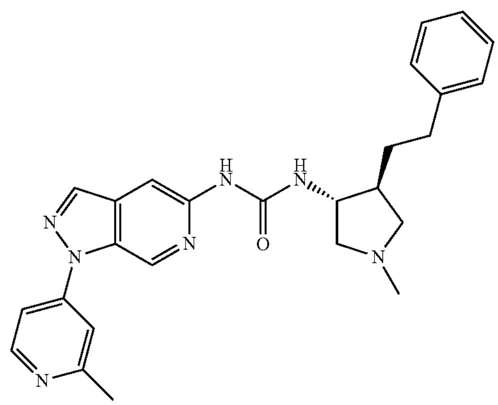 [SMILES: Cc1cc(-n2ncc3cc(NC(=O)N[C@H]4CN(C)C[C@@H]4CCc4ccccc4)ncc32)ccn1] | 1-[(3R,4S)-1-methyl-4-(2-phenylethyl)pyrrolidin-3-yl]-3-[1-(2-methylpyridin-4-yl)-1H-pyrazolo[3,4-c]-pyridin-5-yl]urea 0.6885 nM | Calc'd 456, found 456 |
| 116 | 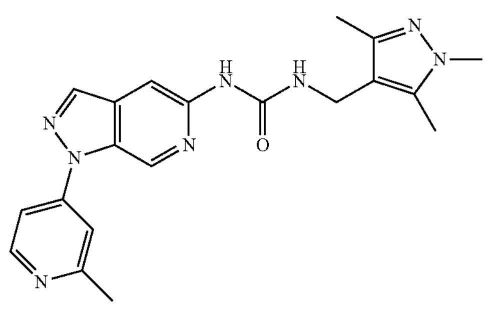 [SMILES: Cc1cc(-n2ncc3cc(NC(=O)NCc4c(C)nn(C)c4C)ncc32)ccn1] | 1-[1-(2-methylpyridin-4-yl)-1H-pyrazolo[3,4-c]pyridin-5-yl]-3-[(1,3,5-trimethyl-1H-pyrazol-4-yl)methyl]urea 27.56 nM | Calc'd 391, found 391 |
| 117. | 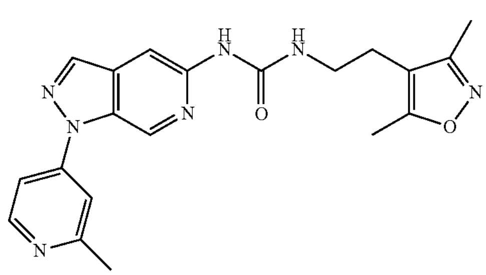 [SMILES: Cc1cc(-n2ncc3cc(NC(=O)NCCc4c(C)noc4C)ncc32)ccn1] | 1-[2-(3,5-dimethylisoxazol-4-yl)ethyl]-3-[1-(2-methylpyridin-4-yl)-1H-pyrazolo[3,4-c]pyridin-5-yl]urea 16.38 nM | Calc'd 392, found 392 |

TABLE 13-continued

| Ex | Structure | IUPAC Name/ERK2 IC$_{50}$ | [M + H]+ |
|---|---|---|---|
| 118. | 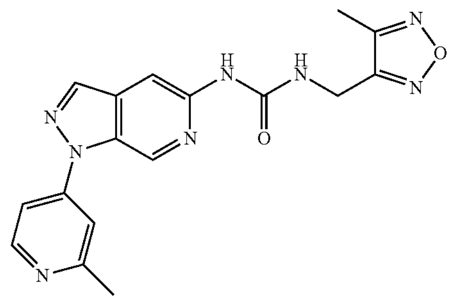 [SMILES: Cc1cc(-n2ncc3cc(NC(=O)NCc4nonc4C)ncc32)ccn1] | 1-[(4-methyl-1,2,5-oxadiazol-3-yl)methyl]-3-[1-(2-methylpyridin-4-yl)-1H-pyrazolo[3,4-c]pyridin-5-yl]urea 5.383 nM | Calc'd 365, found 365 |
| 119. | 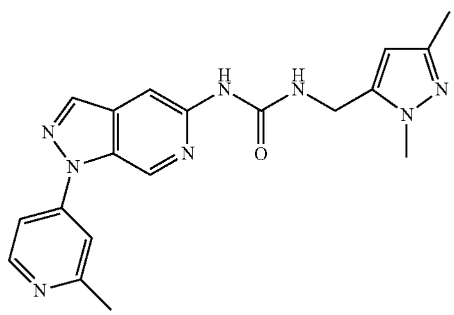 [SMILES: Cc1cc(-n2ncc3cc(NC(=O)NCc4cc(C)nn4C)ncc32)ccn1] | 1-[(1,3-dimethyl-1H-pyrazol-5-yl)methyl]-3-[1-(2-methylpyridin-4-yl)-1H-pyrazolo[3,4-c]pyridin-5-yl)urea 96.62 nM | Calc'd 377, found 377 |
| 120. | 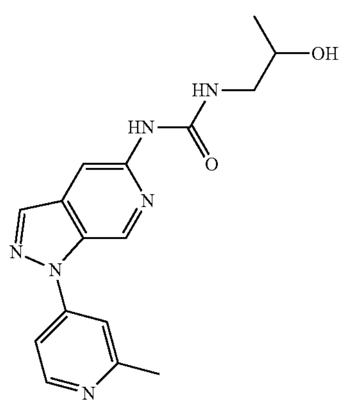 [SMILES: Cc1cc(-n2ncc3cc(NC(=O)NCC(C)O)ncc32)ccn1] | 1-(2-hydroxypropyl)-3-[1-(2-methylpyridin-4-yl)-1H-pyrazolo[3,4-c]pyridin-5-yl)urea 107.5 nM | Calc'd 327, found 327 |
| 121. | 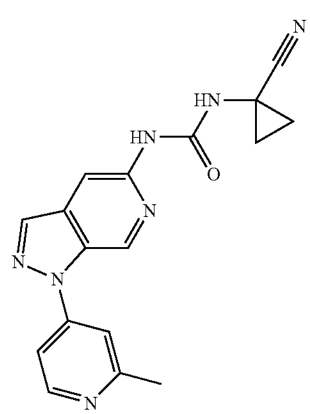 [SMILES: Cc1cc(-n2ncc3cc(NC(=O)NC4(C#N)CC4)ncc32)ccn1] | 1-(1-cyanocyclopropyl)-3-[1-(2-methylpyridin-4-yl)-1H-pyrazolo[3,4-c]pyridin-5-yl]urea 1806 nM | Calc'd 334, found 334 |

TABLE 13-continued

| Ex | Structure | IUPAC Name/ERK2 IC$_{50}$ | [M + H]+ |
|---|---|---|---|
| 122. | 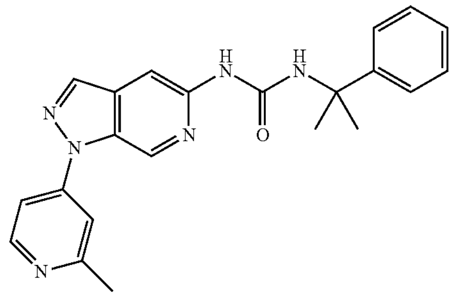 [SMILES: Cc1cc(-n2ncc3cc(NC(=O)NC(C)(C)c4ccccc4)ncc32)ccn1] | 1-(1-methyl-1-phenylethyl)-3-[1-(2-methylpyridin-4-yl)-1H-pyrazolo[3,4-c]pyridin-5-yl]urea 56.81 nM | Calc'd 387, found 387 |
| 123. | 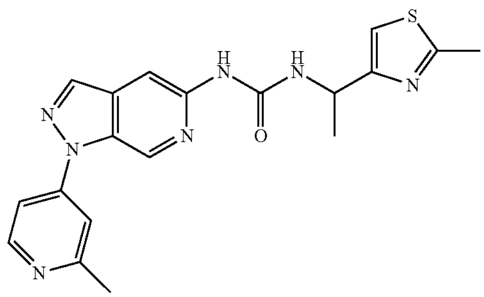 [SMILES: Cc1cc(-n2ncc3cc(NC(=O)NC(C)c4csc(C)n4)ncc32)ccn1] | 1-[1-(2-methylpyridin-4-yl)-1H-pyrazolo[3,4-c]pyridin-5-yl]-3-[1-(2-methyl-1,3-thiazol-4-yl)ethyl]urea 24.77 nM | Calc'd 394, found 394 |
| 124. | 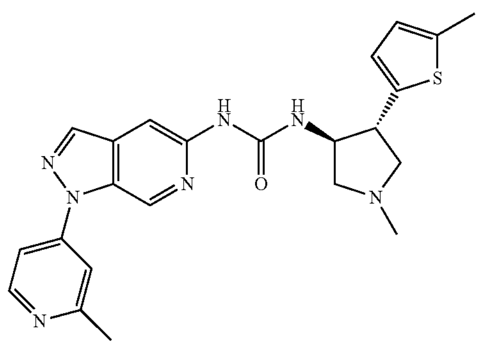 [SMILES: Cc1cc(-n2ncc3cc(NC(=O)N[C@@H]4CN(C)C[C@H]4c4ccc(C)s4)ncc32)ccn1] | 1-[(3S,4R)-1-methyl-4-(5-methylthiophen-2-yl)pyrrolidin-3-yl]-3-[1-(2-methylpyridin-4-yl)-1H-pyrazolo[3,4-c]pyridin-5-yl)urea 1.01 nM | Calc'd 448, found 448 |
| 125. | 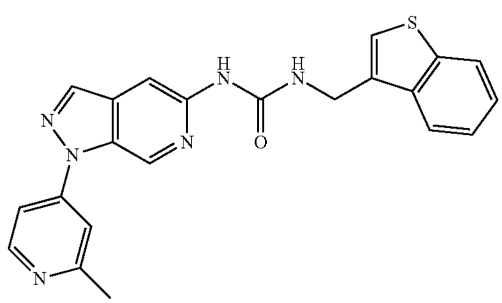 [SMILES: Cc1cc(-n2ncc3cc(NC(=O)NCc4csc5ccccc45)ncc32)ccn1] | 1-(1-benzothiophen-3-ylmethyl)-3-[1-(2-methylpyridin-4-yl)-1H-pyrazolo[3,4-c]pyridin-5-yl)urea 84.46 nM | Calc'd 415, found 415 |
| 126. | 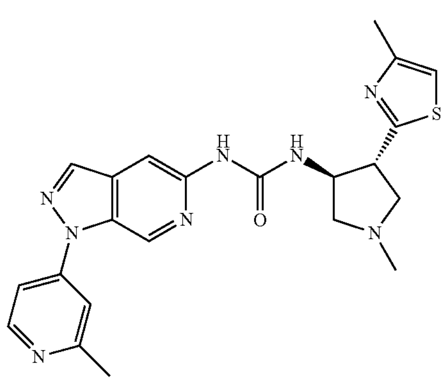 [SMILES: Cc1cc(-n2ncc3cc(NC(=O)N[C@@H]4CN(C)C[C@H]4c4nc(C)cs4)ncc32)ccn1] | 1-[(3S,4R)-1-methyl-4-(4-methyl-1,3-thiazol-2-yl)pyrrolidin-3-yl]-3-[1-(2-methylpyridin-4-yl)-1H-pyrazolo[3,4-c]pyridin-5-yl)urea 15.8 nM | Calc'd 449, found 449 |

TABLE 13-continued

| Ex | Structure | IUPAC Name/ERK2 IC$_{50}$ | [M + H]+ |
|---|---|---|---|
| 127. | 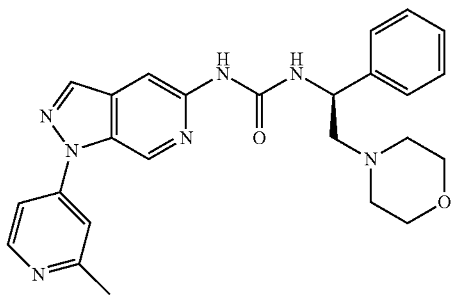 [SMILES: Cc1cc(-n2ncc3cc(NC(=O)N[C@H](CN4CCOCC4)c4ccccc4)ncc32)ccn1] | 1-[1-(2-methylpyridin-4-yl)-1H-pyrazolo[3,4-c]pyridin-5-yl]-3-[(1S)-2-morpholin-4-yl-1-phenylethyl]urea 151.8 nM | Calc'd 458, found 458 |
| 128. | 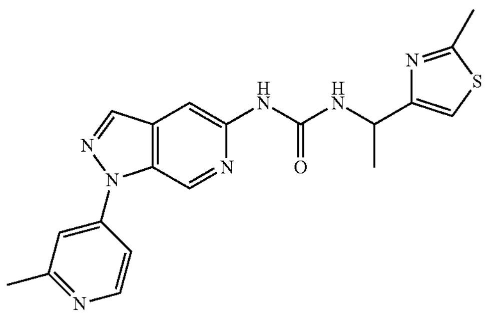 [SMILES: Cc1cc(-n2ncc3cc(NC(=O)NC(C)c4csc(C)n4)ncc32)ccn1] | 1-[1-(2-methylpyridin-4-yl)-1H-pyrazolo[3,4-c]pyridin-5-yl]-3-[1-(2-methyl-1,3-thiazol-4-yl)ethyl]urea 2030 nM | Calc'd 394, found 394 |
| 129. | 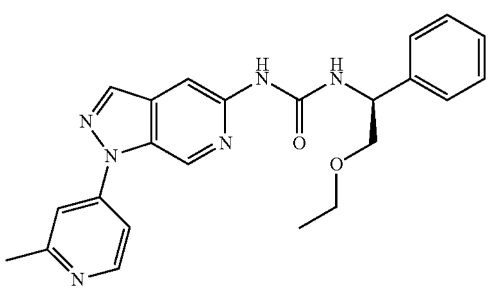 [SMILES: CCOC[C@@H](NC(=O)Nc1cc2cnn(-c3ccnc(C)c3)c2cn1)c1ccccc1] | 1-[(1S)-2-ethoxy-1-phenylethyl]-3-[1-(2-methylpyridin-4-yl)-1H-pyrazolo[3,4-c]pyridin-5-yl)urea 1.09 nM | Calc'd 417, found 417 |
| 130. | 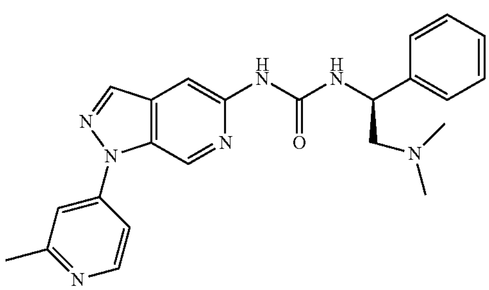 [SMILES: Cc1cc(-n2ncc3cc(NC(=O)N[C@H](CN(C)C)c4ccccc4)ncc32)ccn1] | 1-[(1S)-2-(dimethylamino)-1-phenylethyl]-3-[1-(2-methylpyridin-4-yl)-1H-pyrazolo[3,4-c]pyridin-5-yl)urea 122.6 nM | Calc'd 416, found 416 |
| 131. | 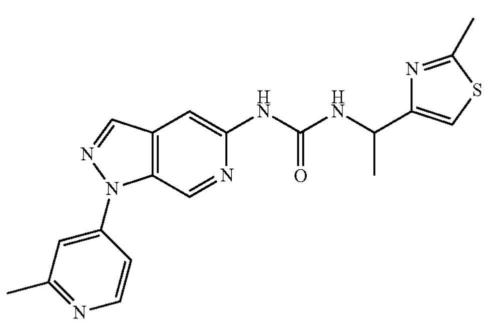 [SMILES: Cc1cc(-n2ncc3cc(NC(=O)NC(C)c4csc(C)n4)ncc32)ccn1] | 1-[1-(2-methylpyridin-4-yl)-1H-pyrazolo[3,4-c]pyridin-5-yl]-3-[1-(2-methyl-1,3-thiazol-4-yl)ethyl]urea 10.91 nM | Calc'd 394, found 394 |

TABLE 13-continued

| Ex | Structure | IUPAC Name/ERK2 IC$_{50}$ | [M + H]+ |
|---|---|---|---|
| 132. | 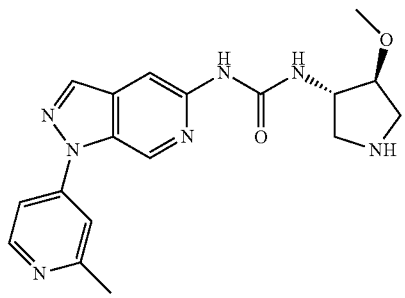 [SMILES: CO[C@H]1CNC[C@@H]1NC(=O)Nc1cc2cnn(-c3ccnc(C)c3)c2cn1] | 1-[(3S,4S)-4-methoxypyrrolidin-3-yl]-3-[1-(2-methylpyridin-4-yl)-1H-pyrazolo[3,4-c]pyridin-5-yl]urea 168.2 nM | Calc'd 368, found 368 |
| 133. | 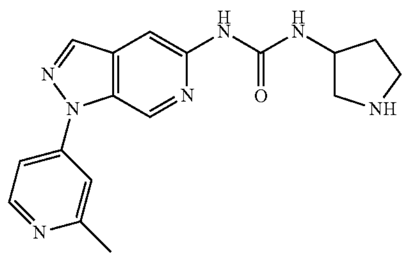 [SMILES: Cc1cc(-n2ncc3cc(NC(=O)NC4CCNC4)ncc32)ccn1] | 1-[1-(2-methylpyridin-4-yl)-1H-pyrazolo[3,4-c]pyridin-5-yl]-3-pyrrolidin-3-ylurea 455.5 nM | Calc'd 338, found 338 |
| 134. | 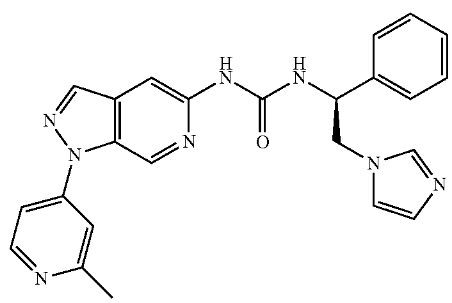 [SMILES: Cc1cc(-n2ncc3cc(NC(=O)N[C@H](Cn4ccnc4)c4ccccc4)ncc32)ccn1] | 1-[(1S)-2-(1H-imidazol-1-yl)-1-phenylethyl]-3-[1-(2-methylpyridin-4-yl)-1H-pyrazolo[3,4-c]pyridin-5-yl]urea 474.7 nM | Calc'd 439, found 439 |
| 135. | 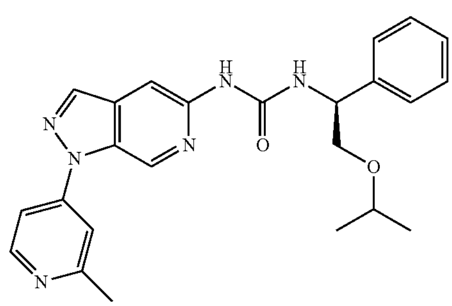 [SMILES: Cc1cc(-n2ncc3cc(NC(=O)N[C@H](COC(C)C)c4ccccc4)ncc32)ccn1] | 1-[(1S)-2-(1-methylethoxy)-1-phenylethyl]-3-[1-(2-methylpyridin-4-yl)-1H-pyrazolo[3,4-c]pyridin-5-yl]urea 0.7862 nM | Calc'd 431, found 431 |
| 136. | 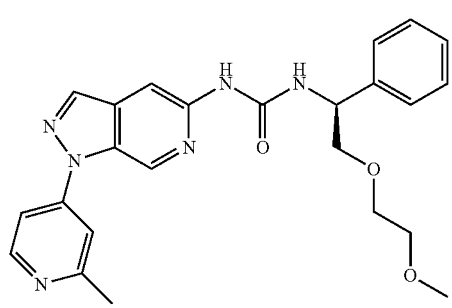 [SMILES: COCCOC[C@@H](NC(=O)Nc1cc2cnn(-c3ccnc(C)c3)c2cn1)c1ccccc1] | 1-[(1S)-2-(2-methoxyethoxy)-1-phenylethyl]-3-[1-(2-methylpyridin-4-yl)-1H-pyrazolo[3,4-c]pyridin-5-yl]urea 4.387 nM | Calc'd 447, found 447 |

TABLE 13-continued

| Ex | Structure | IUPAC Name/ERK2 IC$_{50}$ | [M + H]+ |
|---|---|---|---|
| 137. | 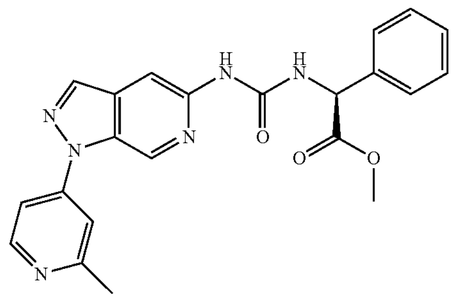 [SMILES: COC(=O)[C@@H](NC(=O)Nc1cc2cnn(-c3ccnc(C)c3)c2cn1)c1ccccc1] | methyl (2S)-({[1-(2-methylpyridin-4-yl)-1H-pyrazolo[3,4-c]pyridin-5-yl]carbamoyl}amino)(phenyl)ethanoate 857 nM | Calc'd 417, found |
| 138. | 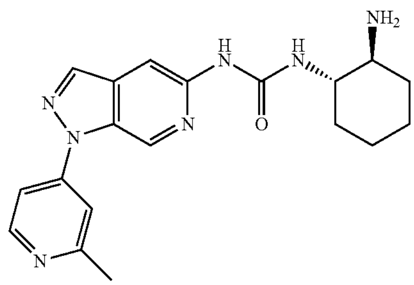 [SMILES: Cc1cc(-n2ncc3cc(NC(=O)N[C@H]4CCCC[C@@H]4N)ncc32)ccn1] | 1-[(1S,2S)-2-aminocyclohexyl]-3-[1-(2-methylpyridin-4-yl)-1H-pyrazolo[3,4-c]pyridin-5-yl]urea 395.6 nM | Calc'd 366, found 366 |
| 139. | 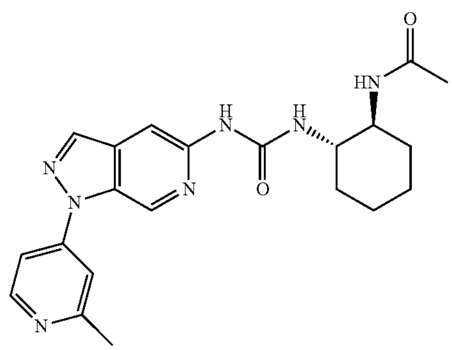 [SMILES: CC(=O)N[C@H]1CCCC[C@@H]1NC(=O)Nc1cc2cnn(-c3ccnc(C)c3)c2cn1] | N-[(1S,2S)-2-({[1-(2-methylpyridin-4-yl)-1H-pyrazolo[3,4-c]pyridin-5-yl]carbamoyl}amino)cyclohexyl]acetamide 2164 nM | Calc'd 408, found 408 |
| 140. | 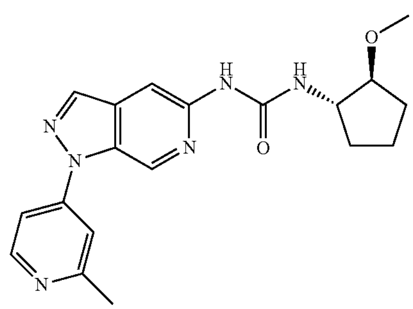 [SMILES: CO[C@H]1CCC[C@@H]1NC(=O)Nc1cc2cnn(-c3ccnc(C)c3)c2cn1] | 1-[(1S,2S)-2-methoxycyclopentyl]-3-[1-(2-methylpyridin-4-yl)-1H-pyrazolo[3,4-c]pyridin-5-yl)urea 72.14 nM | Calc'd 367, found 367 |
| 141. | 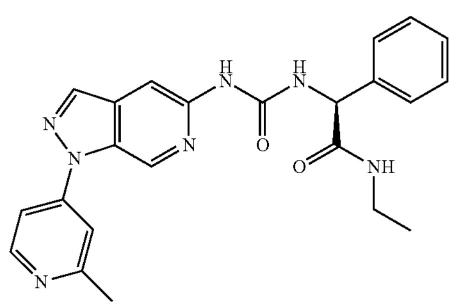 [SMILES: CCNC(=O)[C@@H](NC(=O)Nc1cc2cnn(-c3ccnc(C)c3)c2cn1)c1ccccc1] | (2S)-N-ethyl-2-({[1-(2-methylpyridin-4-yl)-1H-pyrazolo[3,4-c]pyridin-5-yl]carbamoyl}amino)-2-phenylethanamide 2.575 nM | Calc'd 430, found 430 |

TABLE 13-continued

| Ex | Structure | IUPAC Name/ERK2 IC$_{50}$ | [M + H]+ |
|---|---|---|---|
| 142. | 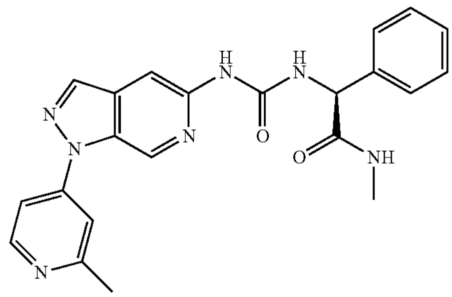 [SMILES: CNC(=O)[C@@H](NC(=O)Nc1cc2cnn(-c3ccnc(C)c3)c2cn1)c1ccccc1] | (2S)-N-methyl-2-({[1-(2-methylpyridin-4-yl)-1H-pyrazolo[3,4-c]pyridin-5-yl]carbamoyl}amino)-2-phenylethanamide 1.09 nM | Calc'd 416, found 416 |
| 143. | 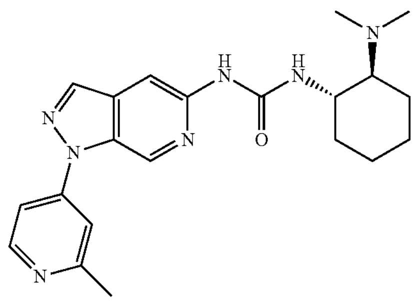 [SMILES: Cc1cc(-n2ncc3cc(NC(=O)N[C@H]4CCCC[C@@H]4N(C)C)ncc32)ccn1] | 1-[(1S,2S)-2-(dimethylamino)cyclohexyl]-3-[1-(2-methylpyridin-4-yl)-1H-pyrazolo[3,4-c]pyridin-5-yl]urea 127.3 nM | Calc'd 394, found 394 |
| 144. | 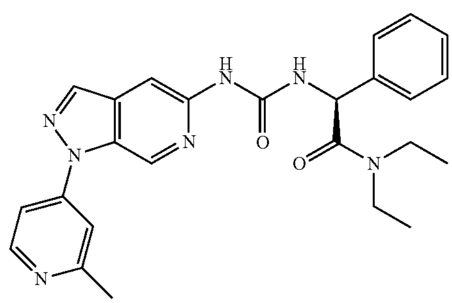 [SMILES: CCN(CC)C(=O)[C@@H](NC(=O)Nc1cc2cnn(-c3ccnc(C)c3)c2cn1)c1ccccc1] | (2S)-N,N-diethyl-2-({[1-(2-methylpyridin-4-yl)-1H-pyrazolo[3,4-c]pyridin-5-yl]carbamoyl}amino)-2-phenylethanamide 89.32 nM | Calc'd 458, found 458 |
| 145. | 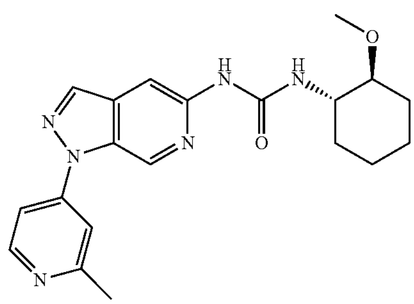 [SMILES: CO[C@H]1CCCC[C@@H]1NC(=O)Nc1cc2cnn(-c3ccnc(C)c3)c2cn1] | Racemic 1-[(1S,2S) and (1R,2R)-2-methoxycyclohexyl]-3-[1-(2-methylpyridin-4-yl)-1H-pyrazolo[3,4-c]pyridin-5-yl)urea 121.9 nM | Calc'd 381, found 381 |
| 146. | 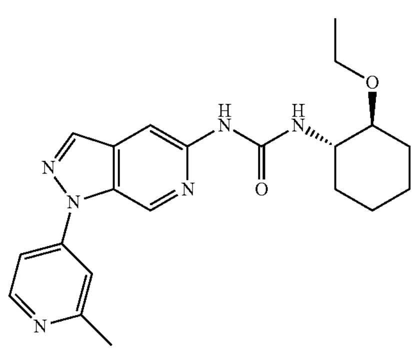 [SMILES: CCO[C@H]1CCCC[C@@H]1NC(=O)Nc1cc2cnn(-c3ccnc(C)c3)c2cn1] | Racemic 1-[(1S,2S) and (1R,2R)-2-ethoxycyclohexyl]-3-[1-(2-methylpyridin-4-yl)-1H-pyrazolo[3,4-c]pyridin-5-yl]urea 179.5 nM | Calc'd 395, found 395 |

TABLE 13-continued

| Ex | Structure | IUPAC Name/ERK2 IC$_{50}$ | [M + H]+ |
|---|---|---|---|
| 147. | 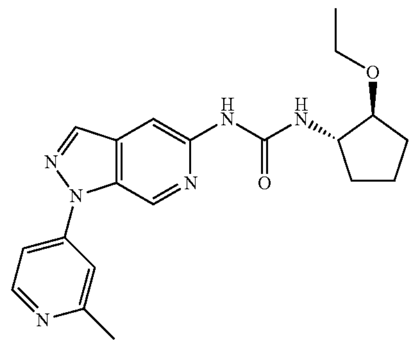 [SMILES: CCO[C@H]1CCC[C@@H]1NC(=O)Nc1cc2cnn(-c3ccnc(C)c3)c2cn1] | Racemic 1-[(1S,2S) and (1R,2R)-2-ethoxycyclopentyl]-3-[1-(2-methylpyridin-4-yl)-1H-pyrazolo[3,4-c]pyridin-5-yl]urea 33.66 nM | Calc'd 381, found 381 |
| 148. | 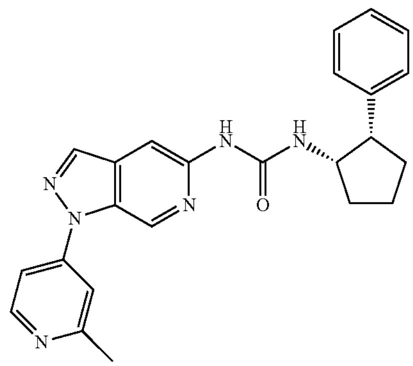 [SMILES: Cc1cc(-n2ncc3cc(NC(=O)N[C@H]4CCC[C@H]4c4ccccc4)ncc32)ccn1] | Racemic 1-[1-(2-methylpyridin-4-yl)-1H-pyrazolo[3,4-c]pyridin-5-yl]-3-[(1S,2S) and (1R, 2R)-2-phenylcyclopentyl]urea 7.928 nM | Calc'd 413, found 413 |
| 149. | 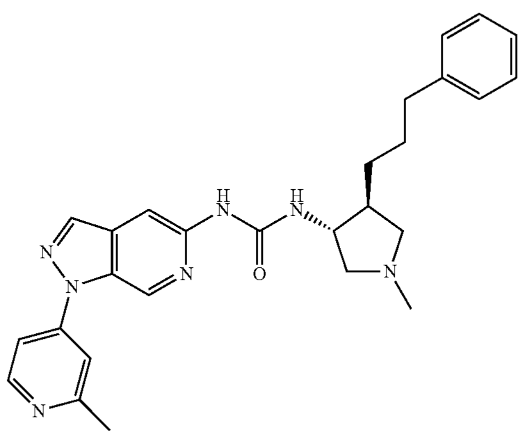 [SMILES: Cc1cc(-n2ncc3cc(NC(=O)N[C@H]4CN(C)C[C@@H]4CCCc4ccccc4)ncc32)ccn1] | 1-[(3R,4S)-1-methyl-4-(3-phenylpropyl)pyrrolidin-3-yl]-3-[1-(2-methylpyridin-4-yl)-1H-pyrazolo[3,4-c]pyridin-5-yl]urea 1.178 nM | Calc'd 470, found 470 |
| 150. | 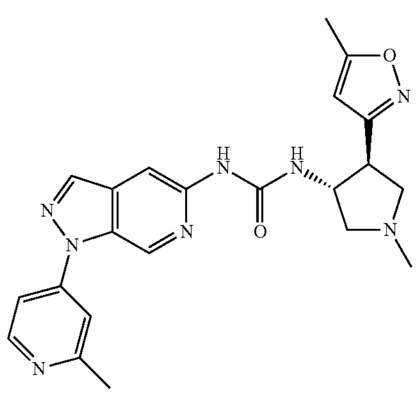 [SMILES: Cc1cc(-n2ncc3cc(NC(=O)N[C@H]4CN(C)C[C@@H]4c4cc(C)on4)ncc32)ccn1] | 1-[(3R,4S)-1-methyl-4-(5-methylisoxazol-3-yl)pyrrolidin-3-yl]-3-[1-(2-methylpyridin-4-yl)-1H-pyrazolo[3,4-c]pyridin-5-yl]urea 32.57 nM | Calc'd 433, found |

TABLE 13-continued

| Ex | Structure | IUPAC Name/ERK2 IC$_{50}$ | [M + H]+ |
|---|---|---|---|
| 151. | 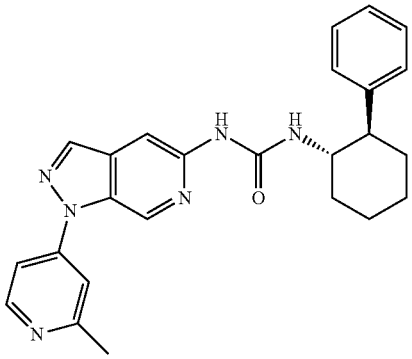 [SMILES: Cc1cc(-n2ncc3cc(NC(=O)N[C@H]4CCCC[C@@H]4c4ccccc4)ncc32)ccn1] | Racemic trans 1-[1-(2-methylpyridin-4-yl)-1H-pyrazolo[3,4-c]pyridin-5-yl]-3-[(1S,2R) and (1R,2S)-2-phenylcyclohexyl]urea 3.653 nM | Calc'd 427, found 427 |
| 152. | 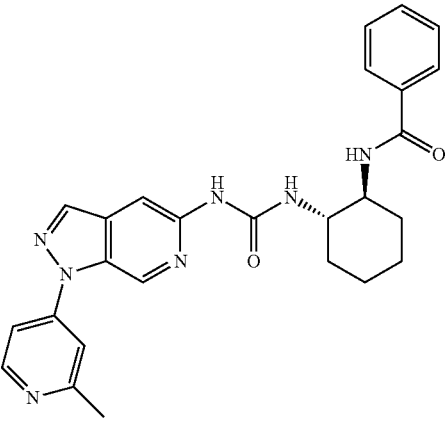 [SMILES: Cc1cc(-n2ncc3cc(NC(=O)N[C@H]4CCCC[C@@H]4NC(=O)c4ccccc4)ncc32)ccn1] | Racemic Trans N-[(1S,2S) and (1R, 2R)-2-({[1-(2-methylpyridin-4-yl)-1H-pyrazolo[3,4-c]pyridin-5-yl]carbamoyl}amino)cyclohexyl]benzamide 711.2 nM | Calc'd 470, found 470 |
| 153. | 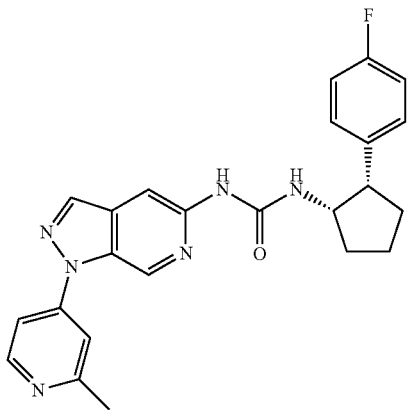 [SMILES: Cc1cc(-n2ncc3cc(NC(=O)N[C@H]4CCC[C@H]4c4ccc(F)cc4)ncc32)ccn1] | Racemic cis 1-[(1S,2S) and (1R,2R)-2-(4-fluorophenyl)cyclopentyl]-3-[1-(2-methylpyridin-4-yl)-1H-pyrazolo[3,4-c]pyridin-5-yl]urea 42.3 nM | Calc'd 431, found 431 |

TABLE 13-continued

| Ex | Structure | IUPAC Name/ERK2 IC$_{50}$ | [M + H]+ |
|---|---|---|---|
| 154. | 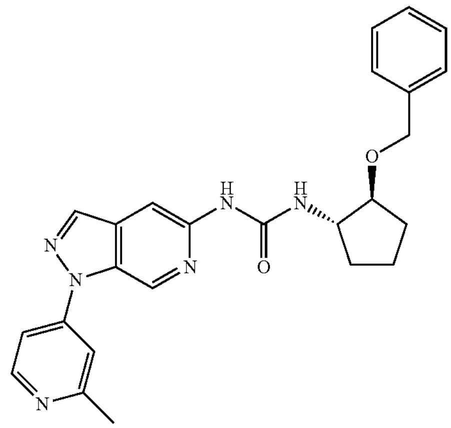 [SMILES: Cc1cc(-n2ncc3cc(NC(=O)N[C@H]4CCC[C@@H]4OCc4ccccc4)ncc32)ccn1] | 1-[(1S,2S)-2-(benzyloxy)cyclopentyl]-3-[1-(2-methylpyridin-4-yl)-1H-pyrazolo[3,4-c]pyridin-5-yl]urea 7.515 nM | Calc'd 443, found 443 |
| 155. | 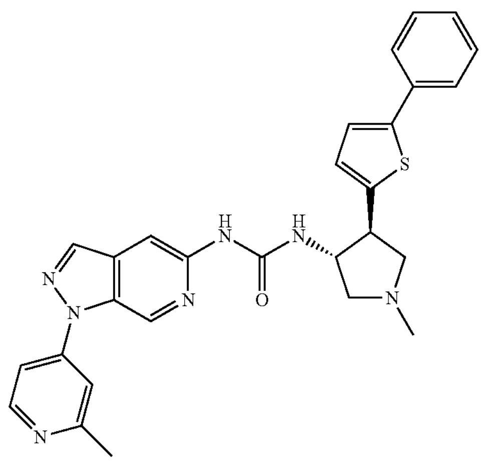 [SMILES: Cc1cc(-n2ncc3cc(NC(=O)N[C@H]4CN(C)C[C@@H]4c4ccc(-c5ccccc5)s4)ncc32)ccn1] | 1-[(3R,4S)-1-methyl-4-(5-phenylthiophen-2-yl)pyrrolidin-3-yl]-3-[1-(2-methylpyridin-4-yl)-1H-pyrazolo[3,4-c]pyridin-5-yl]urea 590.9 nM | Calc'd 510, found 510 |
| 156. | 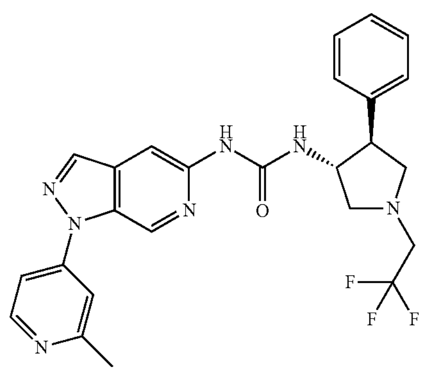 [SMILES: Cc1cc(-n2ncc3cc(NC(=O)N[C@H]4CN(CC(F)(F)F)C[C@@H]4c4ccccc4)ncc32)ccn1] | 1-[1-(2-methylpyridin-4-yl)-1H-pyrazolo[3,4-c]pyridin-5-yl]-3-[(3R,4S)-4-phenyl-1-(2,2,2-trifluoroethyl)pyrrolidin-3-yl]urea 8.854 nM | Calc'd 496, found 496 |
| 157. | 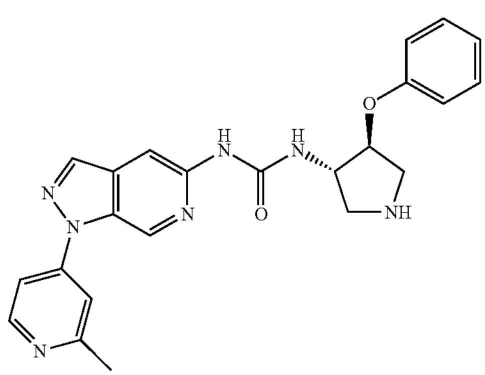 [SMILES: Cc1cc(-n2ncc3cc(NC(=O)N[C@H]4CNC[C@@H]4Oc4ccccc4)ncc32)ccn1] | 1-[1-(2-methylpyridin-4-yl)-1H-pyrazolo[3,4-c]pyridin-5-yl]-3-[(3S,4S)-4-phenoxypyrrolidin-3-yl]urea 35.29 nM | Calc'd 430, found 430 |

TABLE 13-continued

| Ex | Structure | IUPAC Name/ERK2 IC$_{50}$ | [M + H]+ |
|---|---|---|---|
| 158. | 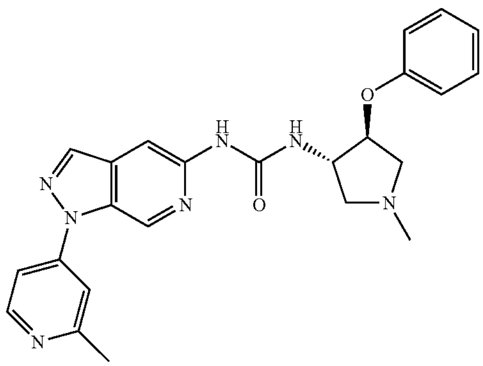 [SMILES: Cc1cc(-n2ncc3cc(NC(=O)N[C@H]4CN(C)C[C@@H]4Oc4ccccc4)ncc32)ccn1] | 1-[(3S,4S)-1-methyl-4-phenoxypyrrolidin-3-yl]-3-[1-(2-methylpyridin-4-yl)-1H-pyrazolo[3,4-c]pyridin-5-yl]urea 20.5 nM | Calc'd 444, found 444 |
| 159. | 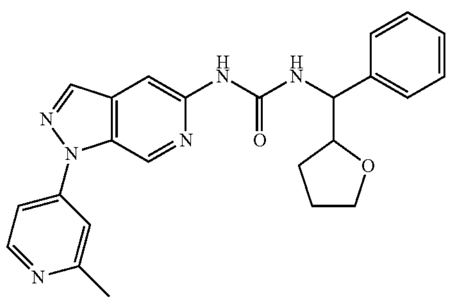 [SMILES: Cc1cc(-n2ncc3cc(NC(=O)NC(c4ccccc4)C4CCCO4)ncc32)ccn1] | 1-[1-(2-methylpyridin-4-yl)-1H-pyrazolo[3,4-c]pyridin-5-yl]-3-[phenyl(tetrahydrofuran-2-yl)methyl]urea 2.489 nM | Calc'd 429, found 429 |
| 160. | 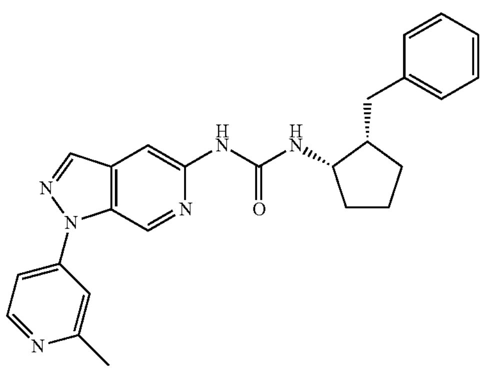 [SMILES: Cc1cc(-n2ncc3cc(NC(=O)N[C@H]4CCC[C@H]4Cc4ccccc4)ncc32)ccn1] | 1-[(1S,2S)-2-benzylcyclopentyl]-3-[1-(2-methylpyridin-4-yl)-1H-pyrazolo[3,4-c]pyridin-5-yl)urea 13.88 nM | Calc'd 427, found 427 |
| 161. | 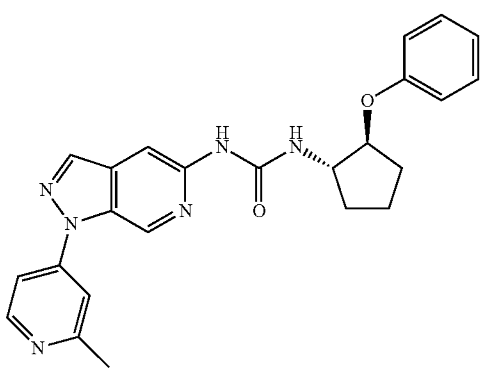 [SMILES: Cc1cc(-n2ncc3cc(NC(=O)N[C@H]4CCC[C@@H]4Oc4ccccc4)ncc32)ccn1] | 1-[1-(2-methylpyridin-4-yl)-1H-pyrazolo[3,4-c]pyridin-5-yl]-3-[(1S,2S)-2-phenoxycyclopentyl]urea 13.45 nM | Calc'd 429, found 429 |

TABLE 13-continued

| Ex | Structure | IUPAC Name/ERK2 IC$_{50}$ | [M + H]+ |
|---|---|---|---|
| 162. | 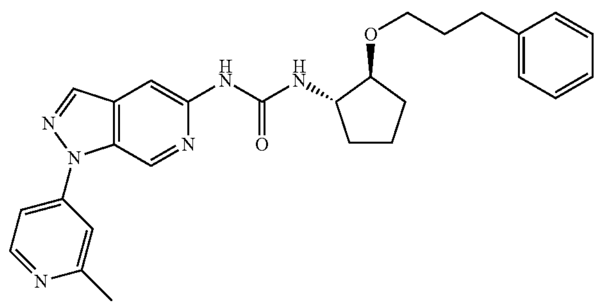 [SMILES: Cc1cc(-n2ncc3cc(NC(=O)N[C@H]4CCC[C@@H]4OCCCc4ccccc4)ncc32)ccn1] | Racemic trans 1-[1-(2-methylpyridin-4-yl)-1H-pyrazolo[3,4-c]pyridin-5-yl]-3-[(1S,2S)and (1R,2R)-2-(3-phenylpropoxy)cyclopentyl]urea 205 nM | Calc'd 471, found 471 |
| 163. | 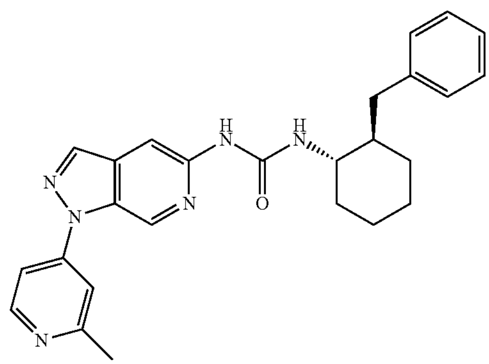 [SMILES: Cc1cc(-n2ncc3cc(NC(=O)N[C@H]4CCCC[C@@H]4Cc4ccccc4)ncc32)ccn1] | 1-[(1S,2R)-2-benzylcyclohexyl]-3-[1-(2-methylpyridin-4-yl)-1H-pyrazolo[3,4-c]pyridin-5-yl]urea 39.38 nM | Calc'd 441, found 441 |
| 164. | 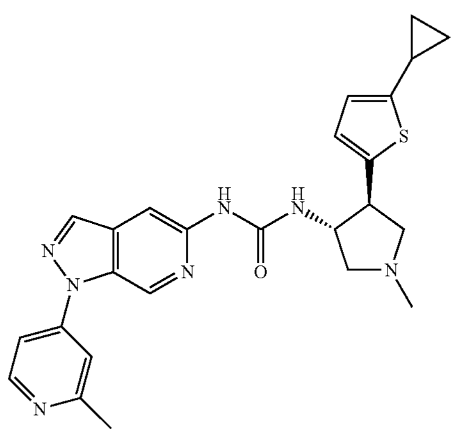 [SMILES: Cc1cc(-n2ncc3cc(NC(=O)N[C@H]4CN(C)C[C@@H]4c4ccc(C5CC5)s4)ncc32)ccn1] | 1-[(3R,4S)-4-(5-cyclopropylthiophen-2-yl)-1-methylpyrrolidin-3-yl]-3-[1-(2-methylpyridin-4-yl)-1H-pyrazolo[3,4-c]pyridin-5-yl]urea 1.13 nM | Calc'd 474, found 474 |
| 165. | 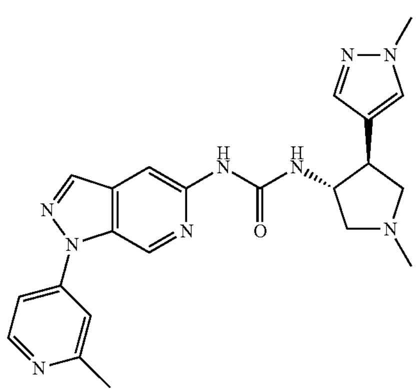 [SMILES: Cc1cc(-n2ncc3cc(NC(=O)N[C@H]4CN(C)C[C@@H]4c4cnn(C)c4)ncc32)ccn1] | 1-[(3R,4S)-1-methyl-4-(1-methyl-1H-pyrazol-4-yl)pyrrolidin-3-yl]-3-[1-(2-methylpyridin-4-yl)-1H-pyrazolo[3,4-c]pyridin-5-yl)urea 831.3 nM | Calc'd 432, found 432 |

TABLE 13-continued

| Ex | Structure | IUPAC Name/ERK2 IC$_{50}$ | [M + H]+ |
|---|---|---|---|
| 166. | 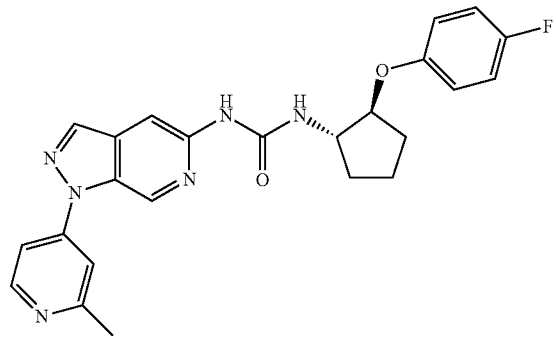 [SMILES: Cc1cc(-n2ncc3cc(NC(=O)N[C@H]4CCC[C@@H]4Oc4ccc(F)cc4)ncc32)ccn1] | Racemic trans 1-[(1S,2S) and (1R,2R)-2-(4-fluorophenoxy)cyclopentyl]-3-[1-(2-methylpyridin-4-yl)-1H-pyrazolo[3,4-c]-pyridin-5-yl)urea 66.57 nM | Calc'd 447, found 447 |
| 167. | 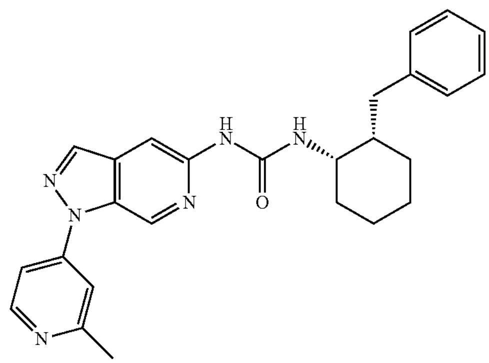 [SMILES: Cc1cc(-n2ncc3cc(NC(=O)N[C@H]4CCCC[C@H]4Cc4ccccc4)ncc32)ccn1] | Racemic cis 1-[(1S,2S) and (1R,2R)-2-benzylcyclohexyl]-3-[1-(2-methylpyridin-4-yl)-1H-pyrazolo[3,4-c]pyridin-5-yl)urea 23.15 nM | Calc'd 441, found 441 |
| 168. | 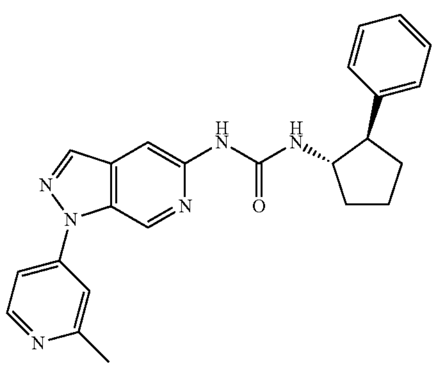 [SMILES: Cc1cc(-n2ncc3cc(NC(=O)N[C@H]4CCC[C@@H]4c4ccccc4)ncc32)ccn1] | Racemic trans 1-[1-(2-methylpyridin-4-yl)-1H-pyrazolo[3,4-c]pyridin-5-yl]-3-[(1S,2R) and (1R,2S)-2-phenylcyclopentyl]urea 7.339 nM | Calc'd 413, found 413 |
| 169. | 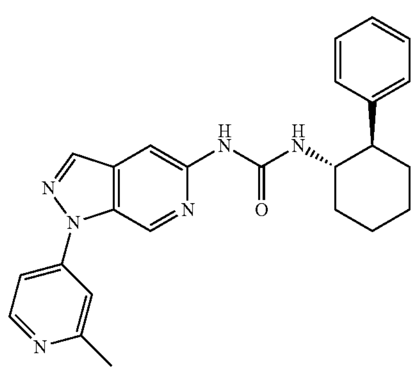 [SMILES: Cc1cc(-n2ncc3cc(NC(=O)N[C@H]4CCCC[C@@H]4c4ccccc4)ncc32)ccn1] | Racemic trans 1-[1-(2-methylpyridin-4-yl)-1H-pyrazolo[3,4-c]pyridin-5-yl]-3-[(1S,2R) and (1R,2S)-2-phenylcyclohexyl]urea 65.68 nM | Calc'd 427, found 427 |

TABLE 13-continued

| Ex | Structure | IUPAC Name/ERK2 IC$_{50}$ | [M + H]+ |
|---|---|---|---|
| 170. | 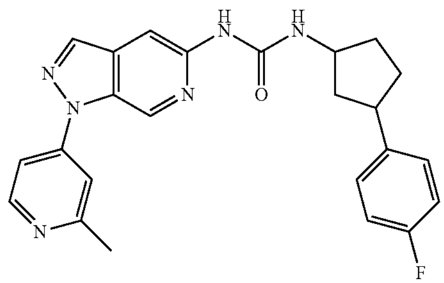 [SMILES: Cc1cc(-n2ncc3cc(NC(=O)NC4CCC(c5ccc(F)cc5)C4)ncc32)ccn1] | 1-[3-(4-fluorophenyl)cyclopentyl]-3-[1-(2-methylpyridin-4-yl)-1H-pyrazolo[3,4-c]pyridin-5-yl]urea 196.5 nM | Calc'd 431, found 431 |
| 171. | 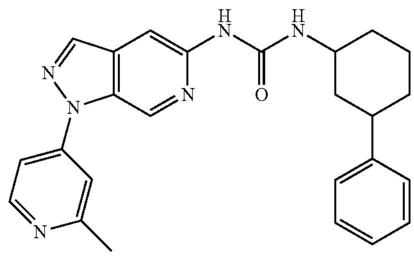 [SMILES: Cc1cc(-n2ncc3cc(NC(=O)NC4CCCC(c5ccccc5)C4)ncc32)ccn1] | 1-[1-(2-methylpyridin-4-yl)-1H-pyrazolo[3,4-c]pyridin-5-yl]-3-(3-phenylcyclohexyl)urea 2.846 nM | Calc'd 427, found 427 |
| 172. | 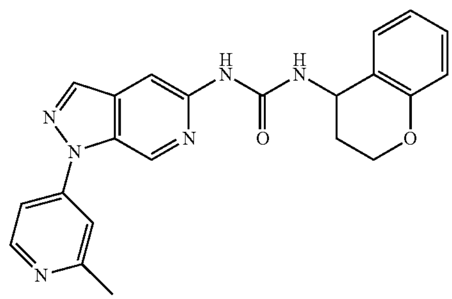 [SMILES: Cc1cc(-n2ncc3cc(NC(=O)NC4CCOc5ccccc54)ncc32)ccn1] | 1-(3,4-dihydro-2H-chromen-4-yl)-3-[1-(2-methylpyridin-4-yl)-1H-pyrazolo[3,4-c]pyridin-5-yl)urea 40.7 nM | Calc'd 401, found 401 |
| 173. | 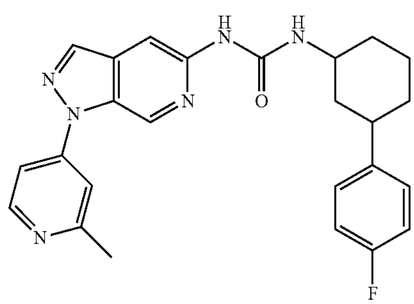 [SMILES: Cc1cc(-n2ncc3cc(NC(=O)NC4CCCC(c5ccc(F)cc5)C4)ncc32)ccn1] | 1-[3-(4-fluorophenyl)cyclohexyl]-3-[1-(2-methylpyridin-4-yl)-1H-pyrazolo[3,4-c]pyridin-5-yl]urea 11.61 nM | Calc'd 445, found 445 |
| 174. | 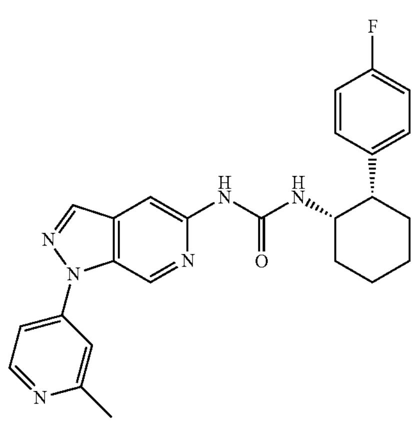 [SMILES: Cc1cc(-n2ncc3cc(NC(=O)N[C@H]4CCCC[C@H]4c4ccc(F)cc4)ncc32)ccn1] | Racemic cis 1-[(1S,2S) and (1R,2R)-2-(4-fluorophenyl)cyclohexyl]-3-[1-(2-methylpyridin-4-yl)-1H-pyrazolo[3,4-c]pyridin-5-yl]urea 19.14 nM | Calc'd 445, found 445 |

TABLE 13-continued

| Ex | Structure | IUPAC Name/ERK2 IC$_{50}$ | [M + H]+ |
|---|---|---|---|
| 175. | 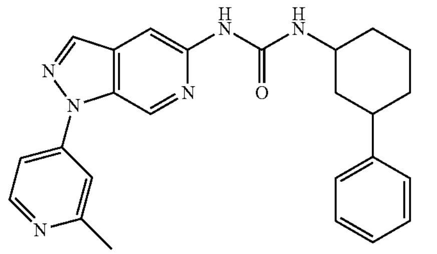 [SMILES: Cc1cc(-n2ncc3cc(NC(=O)NC4CCCC(c5ccccc5)C4)ncc32)ccn1] | 1-[1-(2-methylpyridin-4-yl)-1H-pyrazolo[3,4-c]pyridin-5-yl]-3-(3-phenylcyclohexyl)urea | Calc'd 427, found 427 |
| 176. | 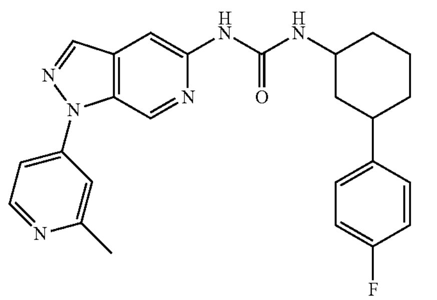 [SMILES: Cc1cc(-n2ncc3cc(NC(=O)NC4CCCC(c5ccc(F)cc5)C4)ncc32)ccn1] | 1-[3-(4-fluorophenyl)cyclohexyl]-3-[1-(2-methylpyridin-4-yl)-1H-pyrazolo[3,4-c]pyridin-5-yl]urea | Calc'd 445, found 445 |
| 177. | 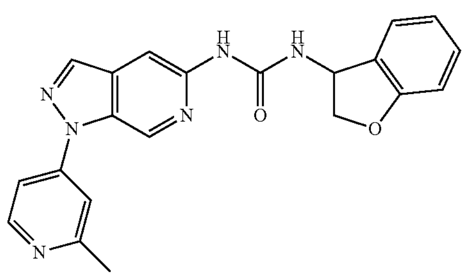 [SMILES: Cc1cc(-n2ncc3cc(NC(=O)NC4COc5ccccc54)ncc32)ccn1] | 1-(2,3-dihydro-1-benzofuran-3-yl)-3-[1-(2-methylpyridin-4-yl)-1H-pyrazolo[3,4-c]pyridin-5-yl]urea 215.3 nM | Calc'd 387, found 387 |
| 178. | 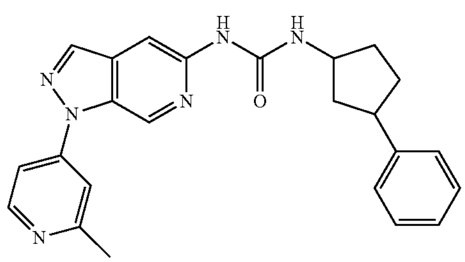 [SMILES: Cc1cc(-n2ncc3cc(NC(=O)NC4CCC(c5ccccc5)C4)ncc32)ccn1] | 1-[1-(2-methylpyridin-4-yl)-1H-pyrazolo[3,4-c]pyridin-5-yl]-3-(3-phenylcyclopentyl)urea 37.13 nM | Calc'd 413, found 413 |
| 179. | 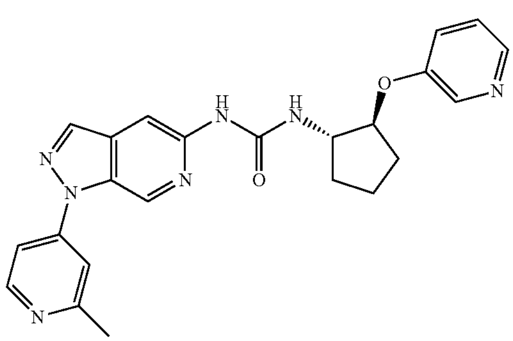 [SMILES: Cc1cc(-n2ncc3cc(NC(=O)N[C@H]4CCC[C@@H]4Oc4cccnc4)ncc32)ccn1] | 1-[1-(2-methylpyridin-4-yl)-1H-pyrazolo[3,4-c]pyridin-5-yl]-3-[(1S,2S)-2-(pyridin-3-yloxy)cyclopentyl]urea 511.2 nM | Calc'd 430, found 430 |

Chiral Separation

Example 180

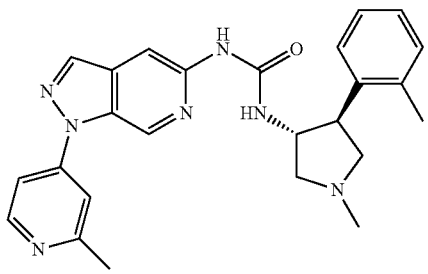 [SMILES: Cc1cc(-n2ncc3cc(NC(=O)N[C@H]4CN(C)C[C@@H]4c4ccccc4C)ncc32)ccn1]

1-[(3R,4S)-1-methyl-4-(2-methylphenyl)pyrrolidin-3-yl]-3-[1-(2-methylpyridin-4-yl)-1H-pyrazolo[3,4-c]pyridin-5-yl]urea 0.28 nM The enantiomers of 1-[(3R or 3S,4S or 4R)-1-methyl-4-(2-methylphenyl)pyrrolidin-3-yl]-3-[1-(2-methylpyridin-4-yl)-1H-pyrazolo[3,4-c]pyridin-5-yl]urea (30.2 mg, 0.045 mmol) were separated by SFC (Thar80, Column: Chiral Technology AS-H 2.1×25 cm, 5 uM, UV wavelength: 220 nM, mobile phase: 25%/75% Methanol+0.25% dimethyl ethylamine/$CO_{2(l)}$, flow rate: 70 mL/Min, 7 min run time). Elution was observed at 4.93 min. The fractions were collected and the solvent evaporated in vacuo to afford 1-[(3R,4S)-1-methyl-4-(2-methylphenyl)pyrrolidin-3-yl]-3-[1-(2-methylpyridin-4-yl)-1H-pyrazolo[3,4-c]pyridin-5-yl]urea. MS ESI calc'd. for $C_{25}H_{28}N_7O$ $[M+1]^+$ 442. found 442. $^1$H NMR (500 MHz, DMSO-$d_6$) δ $^1$H NMR (500 MHz, DMSO-$d_6$) δ 9.24 (s, 1H), 9.05 (s, 1H), 8.54 (d, J=5.6, 1H), 8.49 (s, 1H), 8.04 (s, 1H), 7.78 (d, J=2.0, 1H), 7.72 (dt, J=3.5, 7.1, 1H), 7.38 (m, 2H), 7.17 (t, J=7.4, 1H), 7.13-7.04 (m, 2H), 4.30-4.19 (m, 1H), 3.40-3.33 (m, 1H), 3.04 (t, J=8.8, 1H), 2.92 (m, 1H), 2.58 (s, 3H), 2.56-2.51 (m, 1H), 2.36 (m, 1H), 2.30 (s, 6H).

The following examples were purified using chiral separation technique similar to example 180.

TABLE 14

| Ex | Structure | IUPAC Name/ERK2 $IC_{50}$ | [M + H]+ |
|---|---|---|---|
| 181 | 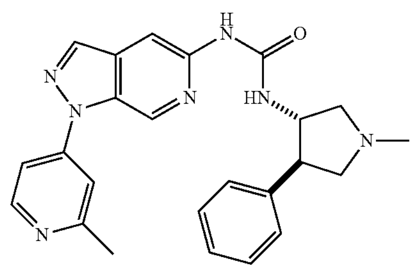 | 1-((3S,4R)1-methyl-4-phenyl-pyrrolidin-3-yl)-3-[1-(2-methyl-pyridin-4-yl)-1H-pyrazolo[3,4-c]pyridin-5-yl]urea 0.983 nM | Calc'd 428, found 428 |
| 182. | 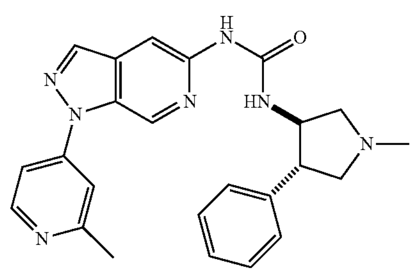 | 1-((3R,4S)1-methyl-4-phenyl-pyrrolidin-3-yl)-3-[1-(2-methyl-pyridin-4-yl)-1H-pyrazolo[3,4-c]pyridin-5-yl]urea 59.73 nM | Calc'd 428, found 428 |
| 183. | 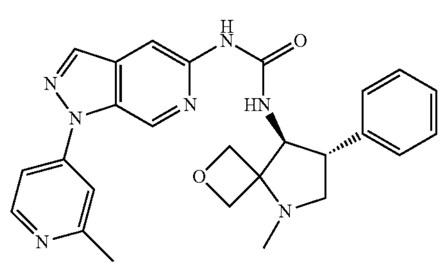 [SMILES: Cc1cc(-n2ncc3cc(NC(=O)N[C@H]4[C@H](c5ccccc5)CN(C)C45COC5)ncc32)ccn1] | 1-[(7R,8S)-5-methyl-7-phenyl-2-oxa-5-azaspiro[3.4]oct-8-yl]-3-[1-(2-methylpyridin-4-yl)-1H-pyrazolo[3,4-c]pyridin-5-yl]urea 12.16 nM | Calc'd 470, found 470 |

TABLE 14-continued

| Ex | Structure | IUPAC Name/ERK2 IC$_{50}$ | [M + H]+ |
|---|---|---|---|
| 184. | 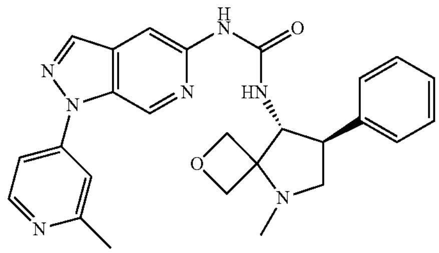 [SMILES: Cc1cc(-n2ncc3cc(NC(=O)N[C@@H]4[C@@H](c5ccccc5)CN(C)C45COC5)ncc32)ccn1] | 1-[(7S,8R)-5-methyl-7-phenyl-2-oxa-5-azaspiro[3.4]oct-8-yl]-3-[1-(2-methylpyridin-4-yl)-1H-pyrazolo[3,4-c]pyridin-5-yl]urea 873.3 nM | Calc'd 470, found 470 |
| 185. | 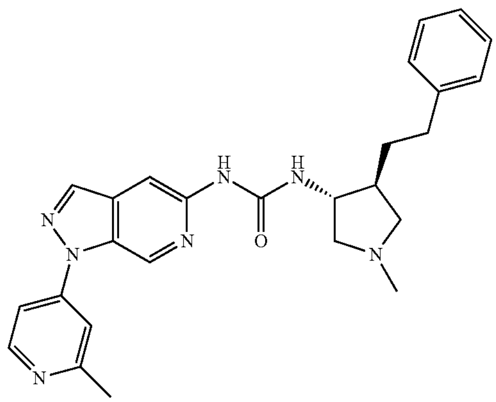 [SMILES: Cc1cc(-n2ncc3cc(NC(=O)N[C@H]4CN(C)C[C@@H]4CCc4ccccc4)ncc32)ccn1] | 1-[(3R,4S)-1-methyl-4-(2-phenylethyl)pyrrolidin-3-yl]-3-[1-(2-methylpyridin-4-yl)-1H-pyrazolo[3,4-c]pyridin-5-yl]urea 0.1822 nM | Calc'd 456, found 456 |
| 186. | 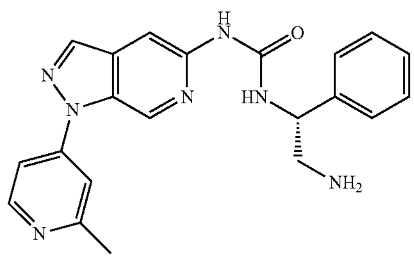 [SMILES: Cc1cc(-n2ncc3cc(NC(=O)N[C@@H](CN)c4ccccc4)ncc32)ccn1] | 1-[(1R)-2-amino-1-phenylethyl]-3-[1-(2-methylpyridin-4-yl)-1H-pyrazolo[3,4-c]pyridin-5-yl]urea 42.54 nM | Calc'd 388, found 388 |
| 187. | 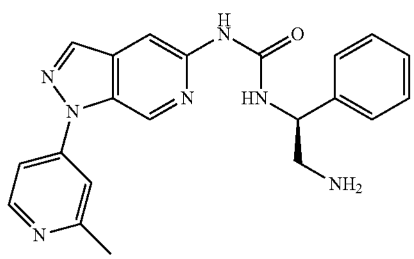 [SMILES: Cc1cc(-n2ncc3cc(NC(=O)N[C@H](CN)c4ccccc4)ncc32)ccn1] | 1-[(1S)-2-amino-1-phenylethyl]-3-[1-(2-methylpyridin-4-yl)-1H-pyrazolo[3,4-c]pyridin-5-yl]urea 0.6854 nM | Calc'd 388, found 388 |
| 188. | 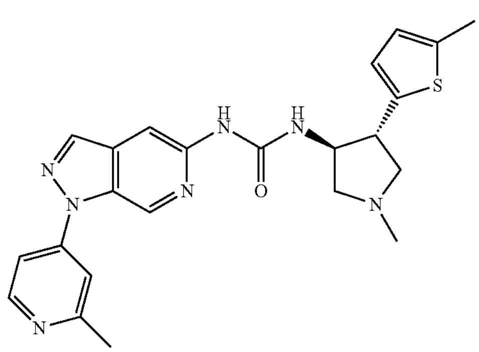 [SMILES: Cc1cc(-n2ncc3cc(NC(=O)N[C@@H]4CN(C)C[C@H]4c4ccc(C)s4)ncc32)ccn1] | 1-[(3S,4R)-1-methyl-4-(5-methylthiophen-2-yl)pyrrolidin-3-yl]-3-[1-(2-methylpyridin-4-yl)-1H-pyrazolo[3,4-c]pyridin-5-yl]urea 70.1 nM | Calc'd 448, found 448 |

TABLE 14-continued

| Ex | Structure | IUPAC Name/ERK2 IC$_{50}$ | [M + H]+ |
|---|---|---|---|
| 189. | 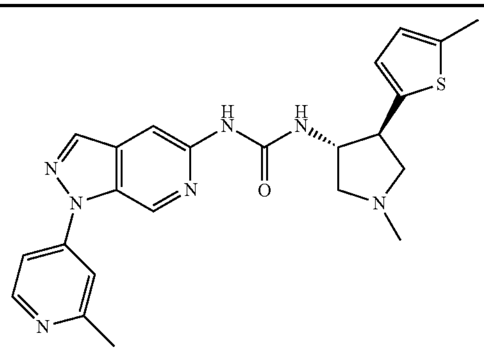 | 1-[(3R,4S)-1-methyl-4-(5-methylthiophen-2-yl)pyrrolidin-3-yl]-3-[1-(2-methylpyridin-4-yl)-1H-pyrazolo[3,4-c]pyridin-5-yl]urea 0.254 nM | Calc'd 448, found 448 |

The following examples were made by using procedures similar to example 14 and 15 followed by chiral purification as exemplified by example 180.

TABLE 15

| EX | Structure | IUPAC Name/ERK2 IC$_{50}$ | [M + H]+ |
|---|---|---|---|
| 190. | 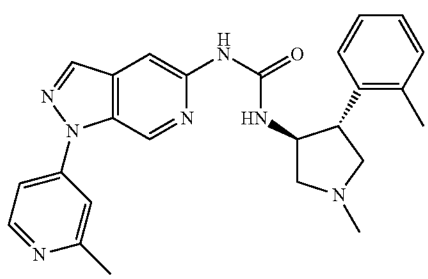 [SMILES: Cc1cc(-n2ncc3cc(NC(=O)N[C@@H]4CN(C)C[C@H]4c4ccccc4C)ncc32)ccn1] | 1-[(3S,4R)-1-methyl-4-(2-methylphenyl)pyrrolidin-3-yl]-3-[1-(2-methylpyridin-4-yl)-1H-pyrazolo[3,4-c]pyridin-5-yl]urea 11.7 nM | Calc'd 442, found 442 |
| 191. | 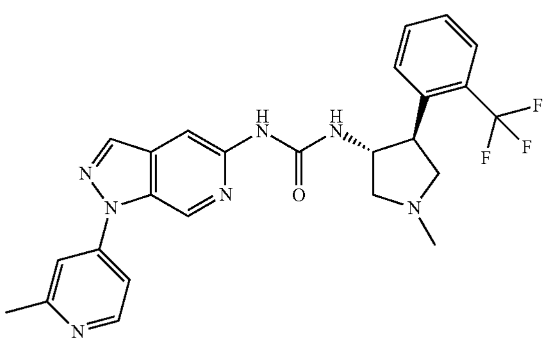 [SMILES: Cc1cc(-n2ncc3cc(NC(=O)N[C@H]4CN(C)C[C@@H]4c4ccccc4C(F)(F)F)ncc32)ccn1] | 1-[1-(2-methylpyridin-4-yl)-1H-pyrazolo[3,4-c]pyridin-5-yl]-3-{(3R,4S)-1-methyl-4-[2-(trifluoromethyl)-phenyl]pyrrolidin-3-yl}urea 0.5091 nM | Calc'd 496, found 496 |
| 192. | 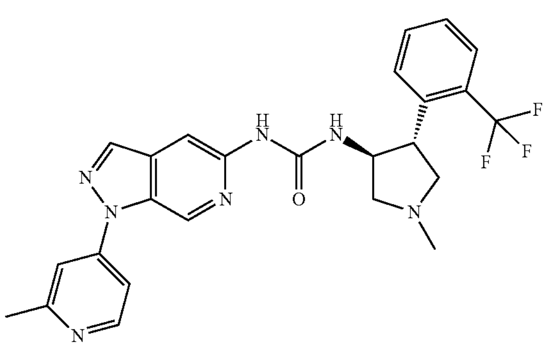 [SMILES: Cc1cc(-n2ncc3cc(NC(=O)N[C@@H]4CN(C)C[C@H]4c4ccccc4C(F)(F)F)ncc32)ccn1] | 1-[1-(2-methylpyridin-4-yl)-1H-pyrazolo[3,4-c]pyridin-5-yl]-3-{(3S,4R)-1-methyl-4-[2-(trifluoromethyl)-phenyl]pyrrolidin-3-yl}urea 235.3 nM | Calc'd 496, found 496 |

TABLE 15-continued

| EX | Structure | IUPAC Name/ERK2 IC$_{50}$ | [M + H]+ |
|---|---|---|---|
| 193. | 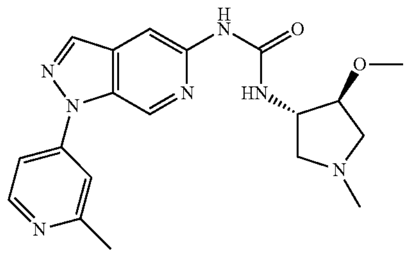 [SMILES: CO[C@H]1CN(C)C[C@@H]1NC(=O)Nc1cc2cnn(-c3ccnc(C)c3)c2cn1] | 1-[(3S,4S)-4-methoxy-1-methylpyrrolidin-3-yl]-3-[1-(2-methylpyridin-4-yl)-1H-pyrazolo[3,4-c]pyridin-5-yl]urea 2531 nM | Calc'd 382, found 382 |
| 194. | 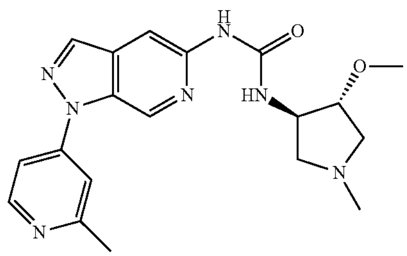 [SMILES: CO[C@@H]1CN(C)C[C@H]1NC(=O)Nc1cc2cnn(-c3ccnc(C)c3)c2cn1] | 1-[(3R,4R)-4-methoxy-1-methylpyrrolidin-3-yl]-3-[1-(2-methylpyridin-4-yl)-1H-pyrazolo[3,4-c]pyridin-5-yl]urea 47.66 nM | Calc'd 382, found 382 |
| 195. | 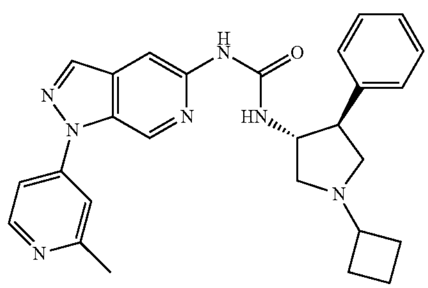 [SMILES: Cc1cc(-n2ncc3cc(NC(=O)N[C@H]4CN(C5CCC5)C[C@@H]4c4ccccc4)ncc32)ccn1] | 1-[(3R,4S)-1-cyclobutyl-4-phenylpyrrolidin-3-yl]-3-[1-(2-methylpyridin-4-yl)-1H-pyrazolo[3,4-c]pyridin-5-yl]urea 3.598 nM | Calc'd 468, found 468 |
| 196. | 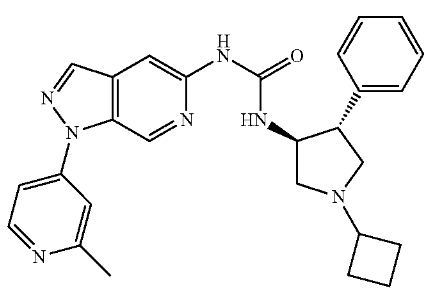 [SMILES: Cc1cc(-n2ncc3cc(NC(=O)N[C@@H]4CN(C5CCC5)C[C@H]4c4ccccc4)ncc32)ccn1] | 1-[(3S,4R)-1-cyclobutyl-4-phenylpyrrolidin-3-yl]-3-[1-(2-methylpyridin-4-yl)-1H-pyrazolo[3,4-c]pyridin-5-yl]urea 354.1 nM | Calc'd 468, found 468 |
| 197. | 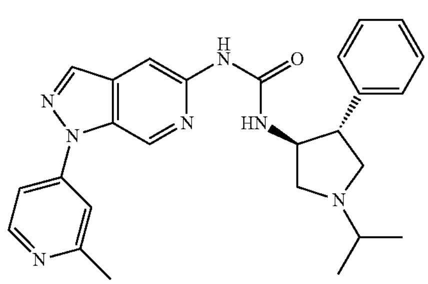 [SMILES: Cc1cc(-n2ncc3cc(NC(=O)N[C@@H]4CN(C(C)C)C[C@H]4c4ccccc4)ncc32)ccn1] | 1-[(3S,4R)-1-(1-methylethyl)-4-phenylpyrrolidin-3-yl]-3-[1-(2-methylpyridin-4-yl)-1H-pyrazolo[3,4-c]-pyridin-5-yl]urea 60.76 nM | Calc'd 456, found 456 |

TABLE 15-continued

| EX | Structure | IUPAC Name/ERK2 IC$_{50}$ | [M + H]+ |
|---|---|---|---|
| 198. | 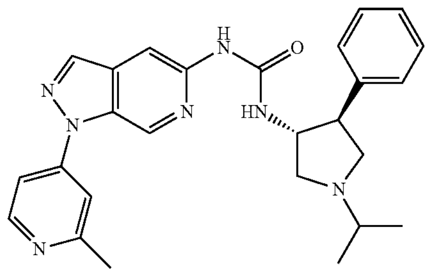 [SMILES: Cc1cc(-n2ncc3cc(NC(=O)N[C@H]4CN(C(C)C)C[C@@H]4c4ccccc4)ncc32)ccn1] | 1-[(3R,4S)-1-(1-methylethyl)-4-phenylpyrrolidin-3-yl]-3-[1-(2-methylpyridin-4-yl)-1H-pyrazolo[3,4-c]pyridin-5-yl]urea 2.637 nM | Calc'd 456, found 456 |
| 199. | 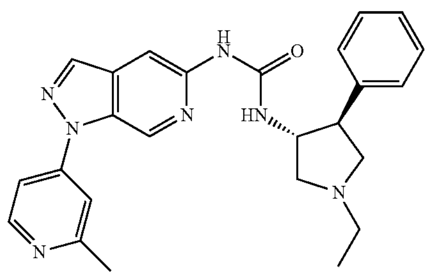 [SMILES: CCN1C[C@H](NC(=O)Nc2cc3cnn(-c4ccnc(C)c4)c3cn2)[C@@H](c2ccccc2)C1] | 1-[(3R,4S)-1-ethyl-4-phenylpyrrolidin-3-yl]-3-[1-(2-methylpyridin-4-yl)-1H-pyrazolo[3,4-c]pyridin-5-yl]urea 0.7184 nM | Calc'd 442, found 442 |
| 200. | 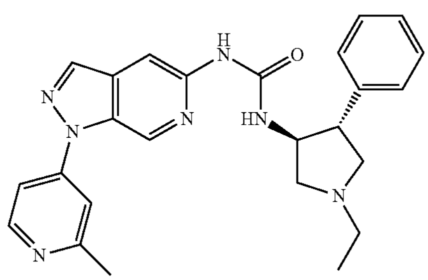 [SMILES: CCN1C[C@@H](NC(=O)Nc2cc3cnn(-c4ccnc(C)c4)c3cn2)[C@H](c2ccccc2)C1] | 1-[(3S,4R)-1-ethyl-4-phenylpyrrolidin-3-yl]-3-[1-(2-methylpyridin-4-yl)-1H-pyrazolo[3,4-c]pyridin-5-yl]urea 20.64 nM | Calc'd 442, found 442 |
| 201. | 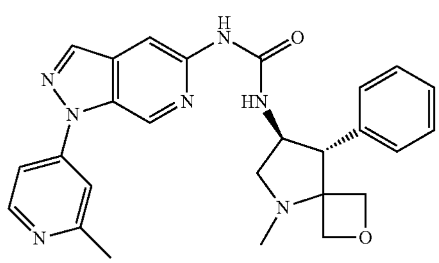 [SMILES: Cc1cc(-n2ncc3cc(NC(=O)N[C@@H]4CN(C)C5(COC5)[C@H]4c4ccccc4)ncc32)ccn1] | 1-[(7S,8S)-5-methyl-8-phenyl-2-oxa-5-azaspiro[3.4]oct-7-yl]-3-[1-(2-methylpyridin-4-yl)-1H-pyrazolo[3,4-c]pyridin-5-yl]urea 0.6889 nM | Calc'd 470, found 470 |
| 202. | 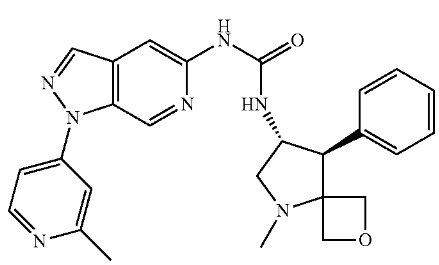 [SMILES: Cc1cc(-n2ncc3cc(NC(=O)N[C@H]4CN(C)C5(COC5)[C@@H]4c4ccccc4)ncc32)ccn1] | 1-[(7R,8R)-5-methyl-8-phenyl-2-oxa-5-azaspiro[3.4]oct-7-yl]-3-[1-(2-methylpyridin-4-yl)-1H-pyrazolo[3,4-c]pyridin-5-yl]urea 300.1 nM | Calc'd 470, found 470 |

TABLE 15-continued

| EX | Structure | IUPAC Name/ERK2 IC$_{50}$ | [M + H]+ |
|---|---|---|---|
| 203. | 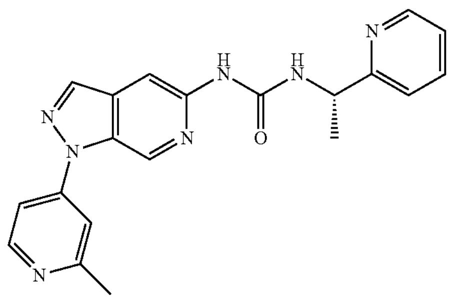 [SMILES: Cc1cc(-n2ncc3cc(NC(=O)N[C@@H](C)c4ccccn4)ncc32)ccn1] | 1-[1-(2-methylpyridin-4-yl)-1H-pyrazolo[3,4-c]pyridin-5-yl]-3-[(1S)-1-pyridin-2-ylethyl]urea 1185 nM | Calc'd 374, found 374 |
| 204. | 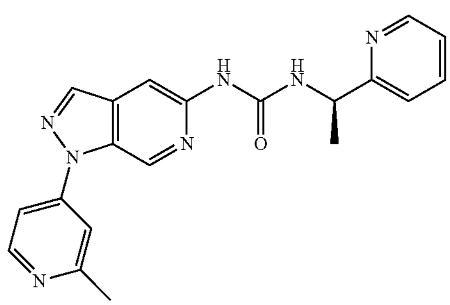 [SMILES: Cc1cc(-n2ncc3cc(NC(=O)N[C@H](C)c4ccccn4)ncc32)ccn1] | 1-[1-(2-methylpyridin-4-yl)-1H-pyrazolo[3,4-c]pyridin-5-yl]-3-[(1R)-1-pyridin-2-ylethyl]urea 7.843 nM | Calc'd 374, found 374 |

Synthetic Method III

Many compounds were prepared by the palladium(0)-mediated coupling reaction of a primary urea with a 5-chloro-pyrazolo[3,4-c]pyridine, which in turn was prepared by copper(I)-mediated N-arylation of 5-chloro-1H-pyrazolo[3,4-c]pyridine. The primary urea was prepared by the reaction of an amine with potassium cyanate and HCl. This method is exemplified below for the synthesis of (R)-1-(1-(3-chloro-4-fluorophenyl)ethyl)-3-(1-(1-methyl-1H-pyrazol-4-yl)-1H-pyrazolo[3,4-c]pyridin-5-yl)urea, and was used for the preparation of 208-225 utilizing suitable reagents.

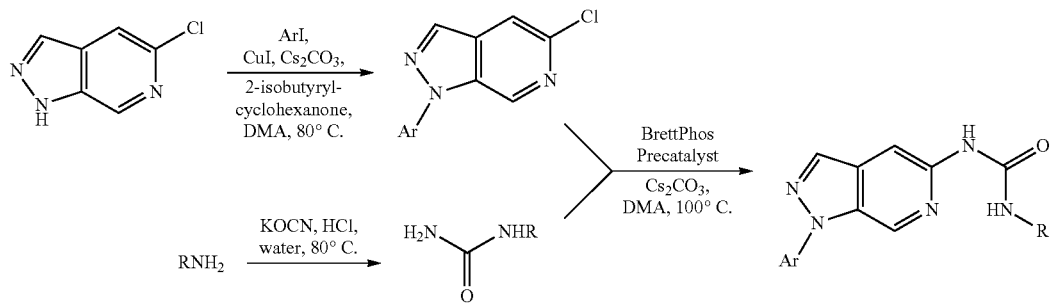

Example 205

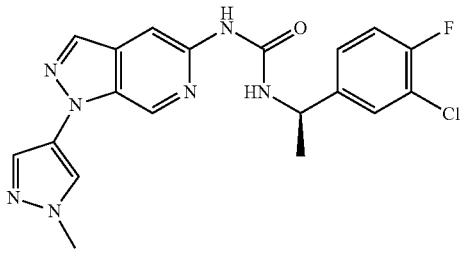 [SMILES: C[C@@H](NC(=O)Nc1cc2cnn(-c3cnn(C)c3)c2cn1)c1ccc(F)c(Cl)c1]

R)-1-(1-(3-chloro-4-fluorophenyl)ethyl)-3-(1-(1-methyl-1H-pyrazol-4-yl)-1H-pyrazolo[3,4-c]pyridin-5-yl)urea 12.09 nM Step 1: 5-Chloro-1-(1-methyl-1H-pyrazol-4-yl)-1H-pyrazolo[3,4-c]pyridine A suspension of 5-chloro-1H-pyrazolo[3,4-c]pyridine (300 mg, 1.95 mmol), 4-iodo-1-methylpyrazole (600 mg, 2.88 mmol), 2-isobutyrylcyclohexanone (130 mg, 0.773 mmol), copper(I) iodide (75 mg, 0.39 mmol) and cesium carbonate (1.5 g, 4.60 mmol) in 5 mL of DMA was deoxygenated by bubbling nitrogen for 15 min. Next, the reaction mixture was warmed to 100° C. and stirred overnight. The reaction mixture was then cooled and diluted with DCM, washed with 1 N aqueous NaOH and water, dried ($Na_2SO_4$) and concentrated to dryness. The solid residue was suspended in ether and filtered to collect the desired intermediate, 5-chloro-1-(1-methyl-1H-pyrazol-4-yl)-1H-pyrazolo[3,4-c]pyridine: MS (EI) calc'd for $C_{10}H_9ClN_5$ [M+H]$^+$ 234. found 234; $^1$H NMR (600 MHz, DMSO-$d_6$) δ 9.02 (s, 1H), 8.41 (s, 1H), 8.38 (s, 1H), 7.97 (s, 1H), 7.96 (s, 1H), 3.91 (s, 3H).

Step 2: (R)-1-(1-(3-Chloro-4-fluorophenyl)ethyl)urea

A mixture of (R)-1-(3-chloro-4-fluorophenyl)ethanamine (200 mg, 1.15 mmol) in 2 N aqueous HCl (1 mL) was treated with KOCN (500 mg, 6.16 mmol) and the mixture was then stirred at 80° C. for 1 hour. Upon cooling to room temperature, a precipitate had formed. The reaction mixture was taken-up in 5:1 DCM/MeOH and washed with 1 N aqueous NaOH, dried ($Na_2SO_4$) and concentrated to provide (R)-1-(1-(3-chloro-4-fluorophenyl)ethyl)urea: $^1$H NMR (600 MHz, DMSO-$d_6$) δ 7.42 (dd, J=7.0, 2.0 Hz, 1H), 7.31 (t, J=8.8 Hz, 1H), 7.24 (m, 1H), 6.46 (d, J=8.2 Hz, 1H), 5.43 (s, 2H), 4.64 (dt, J=7.3 Hz, 1H), 1.25 (d, J=7.0 Hz, 3H).

Step 3: (R)-1-(1-(3-Chloro-4-fluorophenyl)ethyl)-3-(1-(1-methyl-1H-pyrazol-4-yl)-1H-pyrazolo[3,4-c]pyridin-5-yl)urea A suspension of 5-chloro-1-(1-methyl-1H-pyrazol-4-yl)-1H-pyrazolo[3,4-c]pyridine (30 mg, 0.13 mmol), (R)-1-(1-(3-chloro-4-fluorophenyl)ethyl)urea (33 mg, 1.2 mmol), $Cs_2CO_3$ (100 mg, 0.31 mmol) and chloro[2-(dicyclohexylphosphino)-3,6-dimethoxy-2'-4'-6'-tri-i-propyl-1,1'-biphenyl][2-(2-aminoethyl)phenyl]palladium(II) (15 mg, 0.019 mmol) in DMA (1 mL) was deoxygenated by bubbling nitrogen for 10 min and heated with stirring to 100° C. overnight. The cooled reaction mixture was filtered and purified by reverse phase chromatography (MeCN/water with 0.1% TFA). The LC fractions were lyophilized to provide the TFA salt of (R)-1-(1-(3-chloro-4-fluorophenyl)ethyl)-3-(1-(1-methyl-1H-pyrazol-4-yl)-1H-pyrazolo[3,4-c]pyridin-5-yl)urea: MS (EI) calc'd for $C_{19}H_{18}ClFN_7O$ [M+H]$^+$ 414. found 414; $^1$H NMR (600 MHz, DMSO-$d_6$) □ 8.98 (s, 1H), 8.89 (s, 1H), 8.36 (s, 1H), 8.26 (s, 1H), 7.97 (s, 1H), 7.93 (s, 1H), 7.51 (d, J=7.0 Hz, 1H), 7.47 (br s, 1H), 7.33-7.36 (m, 2H), 4.84 (dt, J=7.0 Hz, 1H), 3.89 (s, 3H), 1.37 (d, J=7.0 Hz, 3H).

The following examples were made by using procedures similar to example 205 with appropriate aryl halide and amines.

TABLE 16

| Ex. | Structure | IUPAC Name/ERK2 IC$_{50}$ | [M + H]+ |
|---|---|---|---|
| 206. | 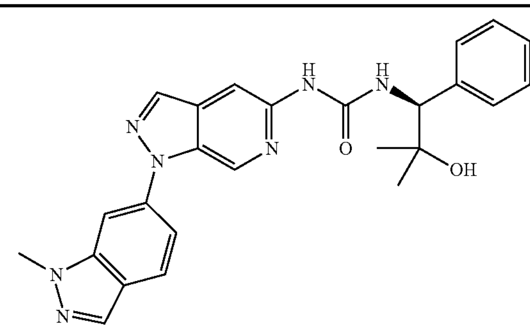 | 1-[(1S)-2-hydroxy-2-methyl-1-phenylpropyl]-3-[1-(1-methyl-1H-indazol-6-yl)-1H-pyrazolo[3,4-c]pyridin-5-yl]urea 0.9895 nM | Calc'd 456, found 456 |

| Ex. | Structure | IUPAC Name/ERK2 IC$_{50}$ | [M + H]+ |
|---|---|---|---|
| 207. | 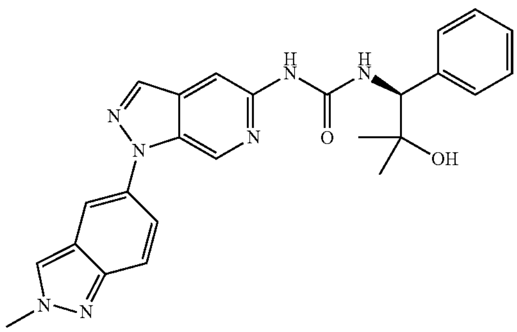 [SMILES: Cn1cc2cc(-n3ncc4cc(NC(=O)N[C@@H](c5ccccc5)C(C)(C)O)ncc43)ccc2n1] | 1-[(1S)-2-hydroxy-2-methyl-1-phenylpropyl]-3-[1-(2-methyl-2H-indazol-5-yl)-1H-pyrazolo[3,4-c]pyridin-5-yl]urea 0.3301 nM | Calc'd 456, found 456 |
| 208. | 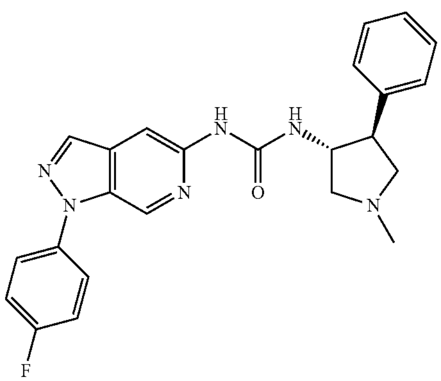 [SMILES: CN1C[C@H](NC(=O)Nc2cc3cnn(-c4ccc(F)cc4)c3cn2)[C@@H](c2ccccc2)C1] | 1-[1-(4-fluorophenyl)-1H-pyrazolo[3,4-c]pyridin-5-yl]-3-[(3R,4S)-1-methyl-4-phenylpyrrolidin-3-yl]urea 0.5791 nM | Calc'd 431, found 431 |
| 209. | 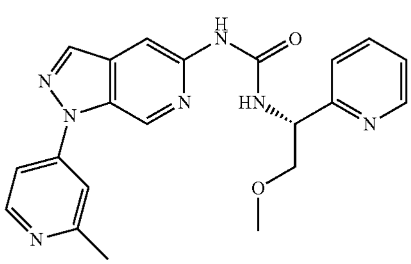 [SMILES: COC[C@H](NC(=O)Nc1cc2cnn(-c3ccnc(C)c3)c2cn1)c1ccccn1] | 1-[(1R)-2-methoxy-1-pyridin-2-ylethyl]-3-[1-(2-methylpyridin-4-yl)-1H-pyrazolo[3,4-c]pyridin-5-yl]urea 24.51 nM | Calc'd 404, found 404 |
| 210. | 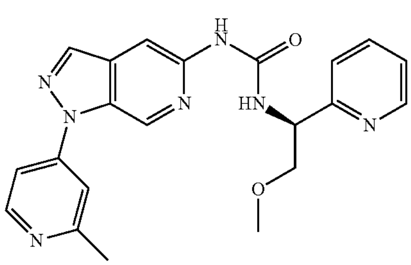 [SMILES: COC[C@@H](NC(=O)Nc1cc2cnn(-c3ccnc(C)c3)c2cn1)c1ccccn1] | 1-[(1S)-2-methoxy-1-pyridin-2-ylethyl]-3-[1-(2-methylpyridin-4-yl)-1H-pyrazolo[3,4-c]pyridin-5-yl]urea 745.3 nM | Calc'd 404, found 404 |

TABLE 16-continued

| Ex. | Structure | IUPAC Name/ERK2 IC$_{50}$ | [M + H]+ |
|---|---|---|---|
| 211. | 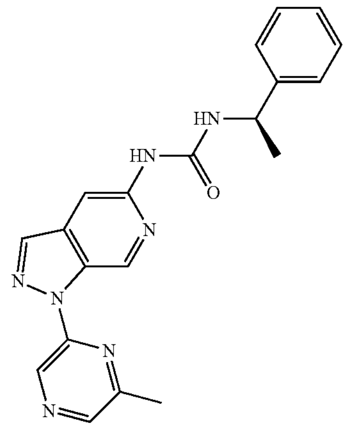 [SMILES: Cc1cncc(-n2ncc3cc(NC(=O)N[C@H](C)c4ccccc4)ncc32)n1] | 1-[1-(6-methylpyrazin-2-yl)-1H-pyrazolo[3,4-c]pyridin-5-yl]-3-[(1R)-1-phenylethyl]urea 549.3 nM | Calc'd 374, found 374 |
| 212. | 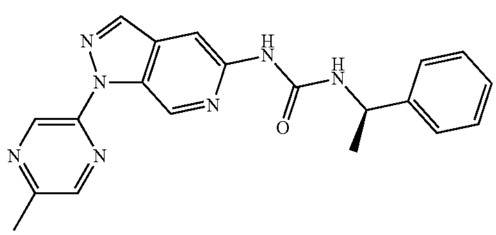 [SMILES: Cc1cnc(-n2ncc3cc(NC(=O)N[C@H](C)c4ccccc4)ncc32)cn1] | 1-[1-(5-methylpyrazin-2-yl)-1H-pyrazolo[3,4-c]pyridin-5-yl]-3-[(1R)-1-phenylethyl]urea 521.2 nM | Calc'd 374, found 374 |
| 213. | 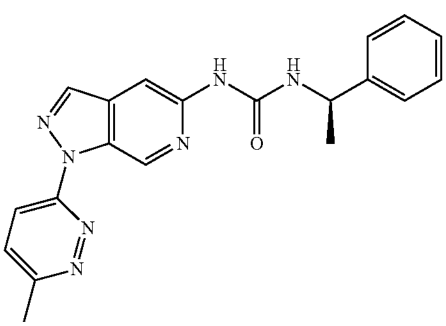 [SMILES: Cc1ccc(-n2ncc3cc(NC(=O)N[C@H](C)c4ccccc4)ncc32)nn1] | 1-[1-(6-methylpyridazin-3-yl)-1H-pyrazolo[3,4-c]pyridin-5-yl]-3-[(1R)-1-phenylethyl]urea 208.4 nM | Calc'd 374, found 374 |
| 214. | 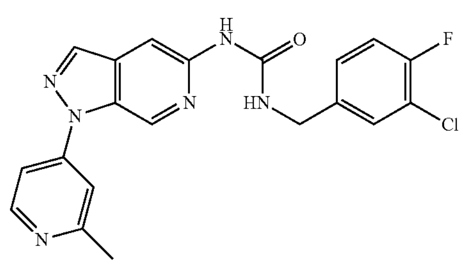 [SMILES: Cc1cc(-n2ncc3cc(NC(=O)NCc4ccc(F)c(Cl)c4)ncc32)ccn1] | 1-(3-chloro-4-fluorobenzyl)-3-[1-(2-methylpyridin-4-yl)-1H-pyrazolo[3,4-c]pyridin-5-yl]urea 4.051 nM | Calc'd 411, found 411 |
| 215. | 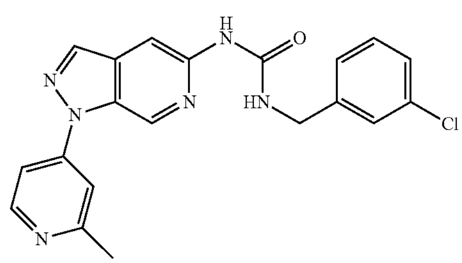 [SMILES: Cc1cc(-n2ncc3cc(NC(=O)NCc4cccc(Cl)c4)ncc32)ccn1] | 1-(3-chlorobenzyl)-3-[1-(2-methylpyridin-4-yl)-1H-pyrazolo[3,4-c]pyridin-5-yl]urea 5.035 nM | Calc'd 393, found 393 |

TABLE 16-continued

| Ex. | Structure | IUPAC Name/ERK2 IC$_{50}$ | [M + H]+ |
|---|---|---|---|
| 216. | 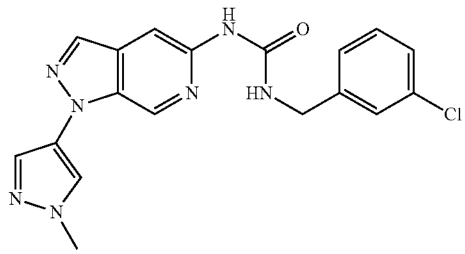 [SMILES: Cn1cc(-n2ncc3cc(NC(=O)NCc4cccc(Cl)c4)ncc32)cn1] | 1-(3-chlorobenzyl)-3-[1-(1-methyl-1H-pyrazol-4-yl)-1H-pyrazolo[3,4-c]pyridin-5-yl]urea 15.72 nM | Calc'd 382, found 382 |
| 217. | 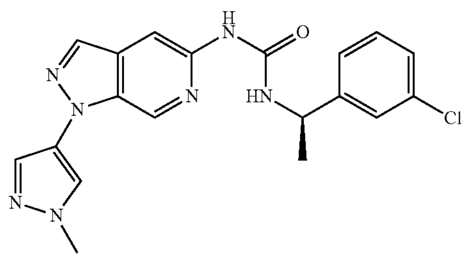 [SMILES: C[C@@H](NC(=O)Nc1cc2cnn(-c3cnn(C)c3)c2cn1)c1cccc(Cl)c1] | 1-[(1R)-1-(3-chlorophenyl)ethyl]-3-[1-(1-methyl-1H-pyrazol-4-yl)-1H-pyrazolo[3,4-c]pyridin-5-yl]urea 5.45 nM | Calc'd 396, found 396 |
| 218. | 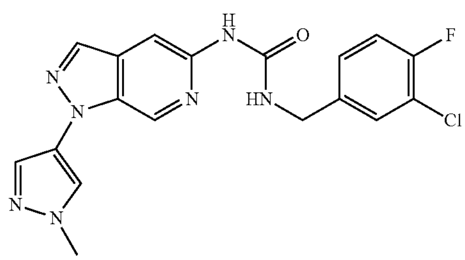 [SMILES: Cn1cc(-n2ncc3cc(NC(=O)NCc4ccc(F)c(Cl)c4)ncc32)cn1] | 1-(3-chloro-4-fluorobenzyl)-3-[1-(1-methyl-1H-pyrazol-4-yl)-1H-pyrazolo[3,4-c]pyridin-5-yl]urea 20.84 nM | Calc'd 400, found 400 |
| 219. | 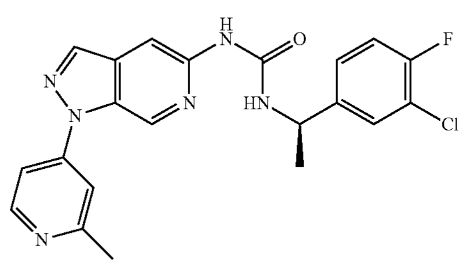 | 1-[(1R)-1-(3-chloro-4-fluorophenyl)ethyl]-3-[1-(2-methylpyridin-4-yl)-1H-pyrazolo[3,4-c]pyridin-5-yl]urea 2.854 nM | Calc'd 425, found 425 |
| 220. | 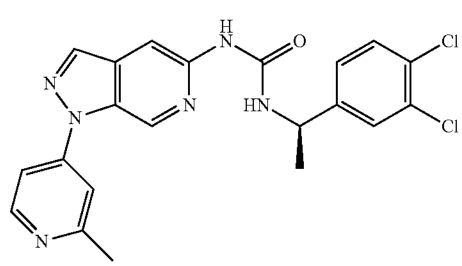 [SMILES: Cc1cc(-n2ncc3cc(NC(=O)N[C@H](C)c4ccc(F)c(Cl)c4)ncc32)ccn1] | 1-[(1R)-1-(3,4-dichlorophenyl)ethyl]-3-[1-(2-methylpyridin-4-yl)-1H-pyrazolo[3,4-c]pyridin-5-yl]urea 3.326 nM | Calc'd 441, found 441 |

The following examples were made by using procedures similar to example 205 with appropriate aryl halide and amines followed by chiral separation similar to example 180.

TABLE 17

| Ex | Structure | IUPAC Name/ERK2 IC$_{50}$ | [M + H]+ |
|---|---|---|---|
| 221. | 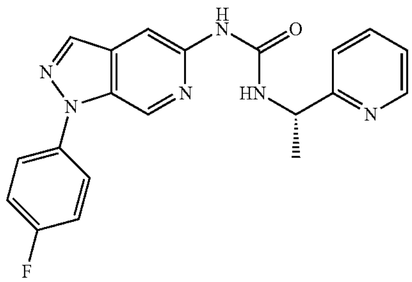 [SMILES: C[C@H](NC(=O)Nc1cc2cnn(-c3ccc(F)cc3)c2cn1)c1ccccn1] | 1-[1-(4-fluorophenyl)-1H-pyrazolo[3,4-c]pyridin-5-yl]-3-[(1S)-1-pyridin-2-ylethyl]urea 1790 nM | Calc'd 377, found 377 |
| 222. | 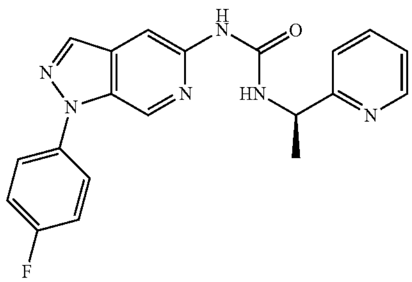 [SMILES: C[C@@H](NC(=O)Nc1cc2cnn(-c3ccc(F)cc3)c2cn1)c1ccccn1] | 1-[1-(4-fluorophenyl)-1H-pyrazolo[3,4-c]pyridin-5-yl]-3-[(1R)-1-pyridin-2-ylethyl]urea 7.533 nM | Calc'd 377, found 377 |

Synthetic Method IV

Another synthetic method involves the palladium(0)-mediated coupling reaction of a primary urea with a 5-bromo-pyrazolo[3,4-c]pyridine, followed by N-arylation. This method is exemplified below for the synthesis of (R)-1-(1-(4-fluorophenyl)ethyl)-3-(1-(2-methylpyridin-4-yl)-1H-pyrazolo[3,4-c]pyridin-5-yl)urea.

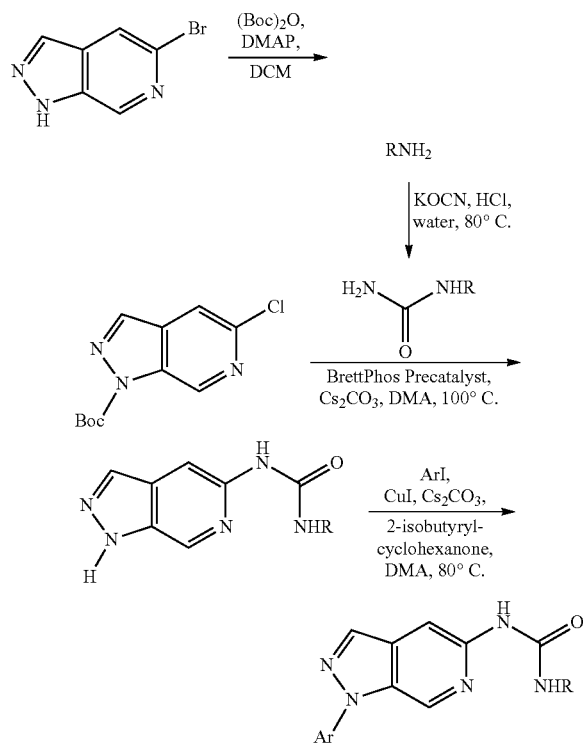

Example 223

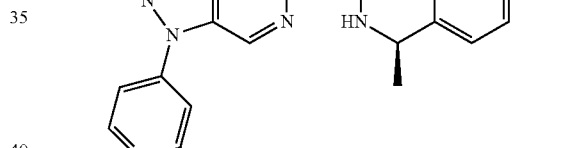

(R)-1-(1-(4-fluorophenyl)ethyl)-3-(1-(2-methylpyridin-4-yl)-1H-pyrazolo[3,4-c]pyridin-5-yl)urea 2.284 nM Step 1: tert-Butyl 5-bromo-1H-pyrazolo[3,4-c]pyridine-1-carboxylate A suspension of 5-bromo-1H-pyrazolo[3,4-c]pyridine (760 mg, 3.80 mmol) in DCM (10 mL) was treated with DMAP (50 mg, 0.41 mmol) and Boc$_2$O (1.00 g, 4.58 mmol). After stirring for 20 min, a homogeneous solution had formed. The reaction was stirred another 12 hours, after which it was washed with 1 N aqueous HCl, water, dried (Na$_2$SO$_4$) and concentrated to dryness, providing tert-butyl 5-bromo-1H-pyrazolo[3,4-c]pyridine-1-carboxylate: MS (EI) calc'd for C$_{11}$H$_{13}$BrN$_3$O$_2$[M+H]$^+$ 298 and 300. found 298 and 300; $^1$H NMR (600 MHz, CDCl$_3$) δ 9.30 (s, 1H), 8.16 (s, 1H), 7.83 (s, 1H), 1.71 (s, 9H).

Step 2: (R)-1-(1-(4-Fluorophenyl)ethyl)urea

A mixture of (R)-1-(4-fluorophenyl)ethanamine (5.15 g, 37.0 mmol) in 2 N aqueous HCl (40 mL) was treated with KOCN (15.0 g, 185 mmol). The mixture was then stirred at 80° C. for 3 hours. Upon cooling to room temperature, a precipitate had formed which was collected by filtration and washed with water. The solid was partitioned between water and EtOAc, and the aqueous phase extracted once more with EtOAc. The combined organic extract was dried ($Na_2SO_4$), filtered and concentrated, providing (R)-1-(1-(4-fluorophenyl)ethyl)urea as a solid: MS (EI) calc'd for $C_9H_{12}FN_2O$ [M+H]$^+$ 183. found 183; $^1$H NMR (600 MHz, DMSO-$d_6$) δ 7.29 (m, 2H), 7.11 (m, 2H), 6.40 (d, J=8.0 Hz, 1H), 5.40 (s, 2H), 4.67 (dt, J=7.3 Hz, 1H), 1.27 (d, J=7.1 Hz, 3H).

Step 3: (R)-1-(1-(4-Fluorophenyl)ethyl)-3-(1H-pyrazolo[3,4-c]pyridin-5-yl)urea

A suspension of tert-butyl 5-bromo-1H-pyrazolo[3,4-c]pyridine-1-carboxylate (150 mg, 0.500 mmol), (R)-1-(1-(4-fluorophenyl)ethyl)urea (100 mg, 0.549 mmol), chloro[2-(dicyclohexylphosphino)-3,6-dimethoxy-2'-4'-6'-tri-i-propyl-1,1'-biphenyl][2-(2-aminoethyl)phenyl]palladium (II) (40 mg, 0.050 mmol) and $Cs_2O_3$ (300 mg, 0.921 mmol) in DMA (3 mL) was deoxygenated by bubbling nitrogen for 10 min and heated with stirring to 100° C. for 8 hours. The cooled reaction mixture was filtered and purified by reverse phase chromatography (MeCN/water with 0.1% TFA). The LC fractions were lyophilized to provide the TFA salt of (R)-1-(1-(4-fluorophenyl)ethyl)-3-(1H-pyrazolo[3,4-c]pyridin-5-yl)urea: MS (EI) calc'd for $C_{15}H_{15}FN_5O$ [M+H]$^+$ 300. found 300.

Step 4: (R)-1-(1-(4-Fluorophenyl)ethyl)-3-(1-(2-methylpyridin-4-yl)-1H-pyrazolo[3,4-c]pyridin-5-yl)urea A suspension of (R)-1-(1-(4-fluorophenyl)ethyl)-3-(1H-pyrazolo[3,4-c]pyridin-5-yl)urea (40 mg, 0.13 mmol), 4-iodo-2-methylpyridine (40 mg, 0.18 mmol), 2-isobutyrylcyclohexanone (20 mg, 0.12 mmol), copper(I) iodide (10 mg, 0.053 mmol) and cesium carbonate (100 mg, 0.31 mmol) in 1 mL of DMA was deoxygenated by bubbling nitrogen for 15 min. Next, the reaction mixture was warmed to 100° C. and stirred overnight. The reaction mixture was then cooled and diluted with 4:1 DCM/MeOH, washed with 1 N aqueous NaOH and water, dried ($Na_2SO_4$) and concentrated to dryness. The residue was purified by reverse phase chromatography (MeCN/water with 0.1% TFA), and the LC fractions were lyophilized to provide the TFA salt of (R)-1-(1-(4-fluorophenyl)ethyl)-3-(1-(2-methylpyridin-4-yl)-1H-pyrazolo[3,4-c]pyridin-5-yl)urea: MS (EI) calc'd for $C_{21}H_{20}FN_6O$ [M+H]$^+$ 391. found 391; $^1$H NMR (600 MHz, DMSO-$d_6$) δ 9.42 (s, 1H), 9.23 (s, 1H), 8.73 (m, 2H), 8.23 (s, 1H), 8.19 (d, J=6.2 Hz, 1H), 8.16 (s, 1H), 7.48 (br d, J=6.8 Hz, 1H), 7.36 (dd, J=8.5, 5.9 Hz, 2H), 7.14 (t, J=8.0 Hz, 2H), 4.86 (dt, J=7.3 Hz, 1H), 2.73 (s, 3H), 1.38 (d, J=7.0 Hz, 3H).

Synthetic Method V

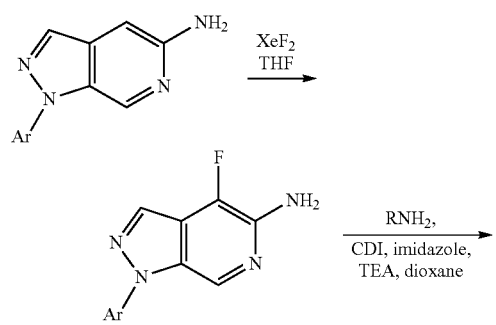

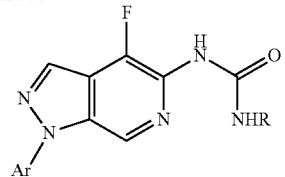

Intermediate 1-(aryl)-1H-pyrazolo[3,4-c]pyridin-5-amine was converted to the 4-fluoro analog by treatment with xenon difluoride, and the resulting aminopyrazolopyridine converted to the final urea by the reaction with CDI and imidazole. This method was used for the preparation of (R)-1-(4-Fluoro-1-(2-methylpyridin-4-yl)-1H-pyrazolo[3,4-c]pyridin-5-yl)-3-(1-phenylethyl)urea.

Example 224

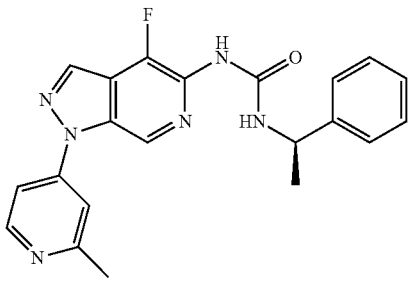 [SMILES: Cc1cc(-n2ncc3c(F)c(NC(=O)N[C@H](C)c4ccccc4)ncc32)ccn1]

(R)-1-(4-Fluoro-1-(2-methylpyridin-4-yl)-1H-pyrazolo[3,4-c]pyridin-5-yl)-3-(1-phenylethyl)urea. 8.264 nM Step 1: 4-Fluoro-1-(2-methylpyridin-4-yl)-1H-pyrazolo[3,4-c]pyridin-5-amine A suspension of 1-(2-methylpyridin-4-yl)-1H-pyrazolo[3,4-c]pyridin-5-amine (75 mg, 0.33 mmol) in 1 mL of THF was treated with xenon difluoride (85 mg, 0.50 mmol) and stirred for 5 hours. The reaction mixture was diluted with DCM and washed with 1 N aqueous NaOH, water, dried ($Na_2SO_4$), and concentrated. The residue was then dissolved in DMSO and purified by reverse phase chromatography. The fractions were taken-up in DCM and washed with 1 N aqueous NaOH, water, dried ($Na_2SO_4$) and concentrated, providing 4-fluoro-1-(2-methylpyridin-4-yl)-1H-pyrazolo[3,4-c]pyridin-5-amine: MS (EI) calc'd for $C_{12}H_{11}FN_5$ [M+H]$^+$ 244. found 244; $^1$H NMR (600 MHz, DMSO-$d_6$) δ 8.90 (s, 1H), 8.51 (d, J=5.6 Hz, 1H), 8.48 (s, 1H), 7.71 (d, J=2.0 Hz, 1H), 7.66 (dd, J=5.5, 2.3 Hz, 1H), 5.96 (s, 2H), 2.54 (s, 3H).

Step 2: (R)-1-(4-Fluoro-1-(2-methylpyridin-4-yl)-1H-pyrazolo[3,4-c]pyridin-5-yl)-3-(1-phenylethyl)urea A solution of 4-fluoro-1-(2-methylpyridin-4-yl)-1H-pyrazolo[3,4-c]pyridin-5-amine (10 mg, 0.041 mmol) in dioxane (1 mL) was treated with imidazole (15 mg, 0.22 mmol) and CDI (30 mg, 0.19 mmol), then stirred overnight. To this reaction mixture, (R)-1-phenylethanamine (10 mg, 0.083 mmol) and Hunig's base (0.050 mL, 0.29 mmol) were added and the reaction stirred for 5 hours. The mixture was concentrated, redissolved in DMSO and purified by reverse phase chromatography. Lyophilization of the LC fraction gave the TFA salt of (R)-1-(4-fluoro-1-(2-methylpyridin-4-yl)-1H-pyrazolo[3,4-c]pyridin-5-yl)-3-(1-phenylethyl)urea: MS (EI) calc'd for $C_{21}H_{20}FN_6O$ [M+H]$^+$ 391. found 391; $^1$H NMR (600 MHz, DMSO-d$_6$) δ 9.29 (s, 1H), 8.96 (s, 1H), 8.88 (s, 1H), 8.71 (d, J=6.2 Hz, 1H), 8.12 (s, 1H), 8.07 (d, J=5.0 Hz, 1H), 7.99 (d, J=7.3 Hz, 1H), 7.30-7.35 (m, 4H), 7.21 (m, 1H), 4.90 (dt, J=7.3 Hz, 1H), 2.69 (s, 3H), 1.41 (d, J=7.0 Hz, 3H).

Synthetic Method VI

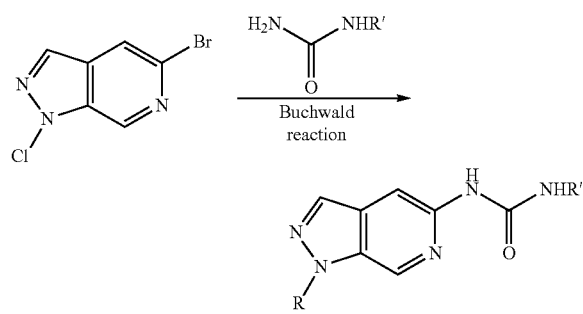

Example 225

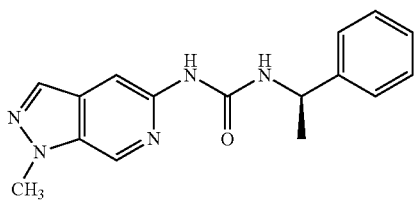 [SMILES: C[C@@H](NC(=O)Nc1cc2cnn(C)c2cn1)c1ccccc1]

(R)-1-(1-methyl-1H-pyrazolo[3,4-c]pyridin-5-yl)-3-(1-phenylethyl)urea 920.2 nM

To a solution of 5-chloro-1-methyl-1H-pyrazolo[3,4-c]pyridine Intermediate 8I (0.05 g, 0.3 mmol) and (R)-1-(1-phenylethyl)urea (0.054 g, 0.328 mmol) in anhydrous THF (3 mL) was added chloro(1-di-t-Butylphosphino-2',4',6'-triisopropyl-1,1'-biphenyl)[2-(2-aminoethyl)phenyl] palladium(II) (0.025 g, 0.036 mmol), t-BuOK (1 M solution in THF, 0.6 mL, 0.6 mmol) and the contents heated to reflux. After 16 h, the reaction mixture was brought to ambient temperature, filtered through a pad of celite, solvents was removed under reduced pressure and the residue thus obtained was purified by flash column chromatography afforded the title compound. $^1$H NMR (MeOD, 400 MHz) δ 8.79 (s, 1H), 8.00 (s, 1H), 7.63 (s, 1H), 7.43-7.23 (m, 5H), 5.04-5.02 (m, 1H), 4.16 (s, 3H), 1.33 (d, J=5.5 Hz, 3H). Anal. Calcd. $C_{16}H_{17}N_5O$ (M+H) 296.36. Found 296.4.

Example 226

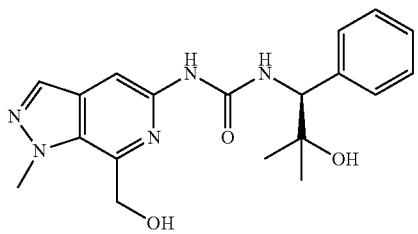 [SMILES: Cn1ncc2cc(NC(=O)N[C@@H](c3ccccc3)C(C)(C)O)nc(CO)c21]

1-[7-(hydroxymethyl)-1-methyl-1H-pyrazolo[3,4-c]pyridin-5-yl]-3-[(1S)-2-hydroxy-2-methyl-1-phenyl-propyl]urea 69.29 nM (5-Chloro-1-methyl-1H-pyrazolo[3,4-c]pyridin-7-yl) methanol (47.9 mg, 0.242 mmol), (S)-1-(2-hydroxy-2-methyl-1-phenylpropyl)urea (76 mg, 0.364 mmol), Brettphos palladacycle (19.36 mg, 0.024 mmol), cesium carbonate (205 mg, 0.630 mmol), and 2-(dicyclohexylphosphino)3,6-dimethoxy-2',4',6'-triisopropyl-1,1'-biphenyl (13.01 mg, 0.024 mmol) were dissolved in Dioxane (1.0 mL) and purged under argon for five minutes. The reaction mixture was heated to 90° C. and stirred for 6 hrs. The reaction mixture was filtered through Celite rinsing with methanol and concentrated in vacuo. The reaction mixture was diluted with DMSO (2 mL), filtered, and purified by mass-triggered reverse-phase HPLC. Fractions containing pure compound were concentrated in vacuo to afford the TFA salt of (S)-1-(2-hydroxy-2-methyl-1-phenylpropyl)-3-(7-(hydroxymethyl)-1-methyl-1H-pyrazolo[3,4-c]pyridin-5-yl)urea. MS ESI calc'd. for $C_{19}H_{24}N_5O_3$ [M+1]$^+$ 370. found 370. $^1$H NMR (500 MHz, DMSO-d$_6$) δ 9.24 (s, 1H), 8.02 (s, 1H), 7.64 (s, 1H), 7.32 (d, J=7.2 Hz, 2H), 7.29-7.22 (m, 2H), 7.19 (t, J=7.2 Hz, 1H), 4.97 (s, 2H), 4.60-4.56 (m, 1H), 4.27 (s, 3H), 1.17 (s, 3H), 0.99 (s, 3H).

Example 227

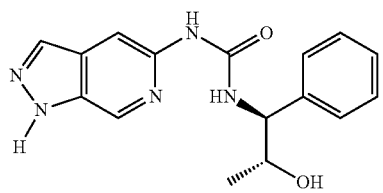 [SMILES: C[C@@H](O)[C@@H](NC(=O)Nc1cc2cn[nH]c2cn1)c1ccccc1]

1-((1S,2R)-2-Hydroxy-1-phenylpropyl)-3-(1H-pyrazolo[3,4-c]pyridin-5-yl)urea 133.5 nM 5-Chloro-1H-pyrazolo[3,4-c]pyridine (100 mg, 0.651 mmol), 1-((1S,2R)-2-hydroxy-1-phenylpropyl)urea (190 mg, 0.977 mmol), Brettphos palladacycle (41.6 mg, 0.052 mmol), and potassium tert-butoxide (1.954 mL, 1.954 mmol) were dissolved in THF (1 mL) and purged under argon for five minutes. The reaction mixture was heated to 80° C. and stirred for 4 hours. The reaction mixture was filtered through Celite rinsing with methanol and concentrated in vacuo. The reaction mixture was diluted with DMSO (2 mL), filtered, and purified by mass-triggered reverse-phase HPLC. Fractions containing pure compound were concentrated in vacuo. The residue was dissolved in methanol and filtered through a PS—HCO₃ cartridge, eluting with MeOH and DCM.

Diluted with a small amount of DCM and methanol. Purification by flash chromatography (Biotage, 2-20% CH₂Cl₂/MeOH) gave 1-((1S,2R)-2-hydroxy-1-phenylpropyl)-3-(1H-pyrazolo[3,4-c]pyridin-5-yl)urea. MS ESI calc'd. for $C_{16}H_{18}N_5O_2$ [M+1]⁺ 312. found 312. ¹H NMR (500 MHz, DMSO-d₆) δ 13.34 (s, 1H), 9.01 (s, 1H), 8.70 (s, 1H), 8.05 (s, 1H), 7.87 (s, 1H), 7.31-7.28 (m, 4H), 7.22-7.18 (m, 1H), 4.86 (d, J=5.0 Hz, 1H), 4.70 (dd, J=4.5 Hz, 8.6 Hz, 1H), 3.91 (dd, J=4.9 Hz, 11.2 Hz, 1H), 0.94 (d, J=6.4 Hz, 3H).

The following examples were made using Buchwald coupling procedures similar to example 225-227 with the appropriate urea.

TABLE 18

| EX. | Structure | IUPAC Name/ERK2 IC₅₀ | M + H]+ |
|---|---|---|---|
| 228. | 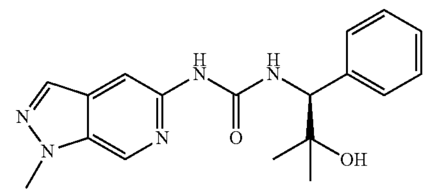 [SMILES: Cn1ncc2cc(NC(=O)N[C@@H](c3ccccc3)C(C)(C)O)ncc21] | 1-[(1S)-2-hydroxy-2-methyl-1-phenylpropyl]-3-(1-methyl-1H-pyrazolo[3,4-c]pyridin-5-yl)urea 36.87 nM | Calc'd 340, found 340 |
| 229. | 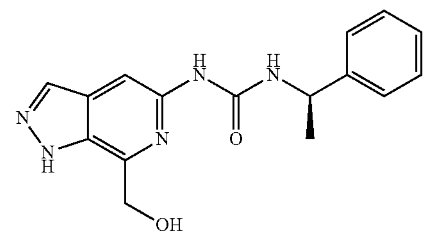 [SMILES: C[C@@H](NC(=O)Nc1cc2cn[nH]c2c(CO)n1)c1ccccc1] | (R)-1-(7-(hydroxymethyl)-1H-pyrazolo[3,4-c]pyridin-5-yl)-3-(1-phenylethyl)urea 40.95 nM | Calc'd 312 found 312 |
| 230. | 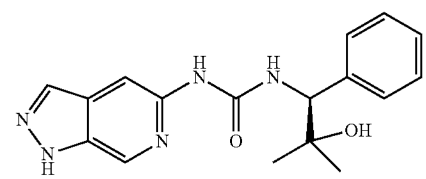 [SMILES: CC(C)(O)[C@@H](NC(=O)Nc1cc2cn[nH]c2cn1)c1ccccc1] | (S)-1-(2-hydroxy-2-methyl-1-phenylpropyl)-3-(1H-pyrazolo[3,4-c]pyridin-5-yl)urea (TFA salt) 69.95 nM | Calc'd 326 Found 326 |
| 231. | 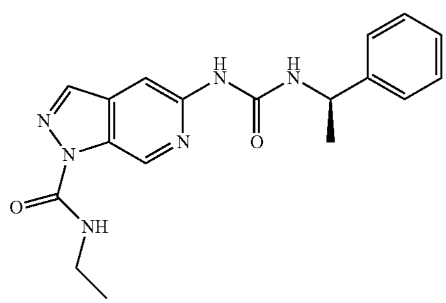 [SMILES: CCNC(=O)n1ncc2cc(NC(=O)N[C@H](C)c3ccccc3)ncc21] | N-ethyl-5-({[(1R)-1-phenylethyl]carbamoyl}amino)-1H-pyrazolo[3,4-c]pyridine-1-carboxamide 64.07 nM | Calc'd 353, found 353 |
| 232. | 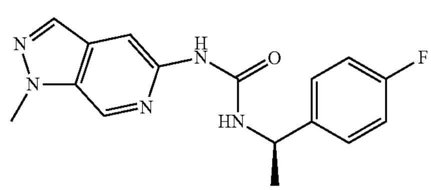 [SMILES: C[C@@H](NC(=O)Nc1cc2cnn(C)c2cn1)c1ccc(F)cc1] | 1-[(1R)-1-(4-fluorophenyl)ethyl]-3-(1-methyl-1H-pyrazolo[3,4-c]pyridin-5-yl)urea 579.3 nM | Calc'd 314.0, found |
| 233. | 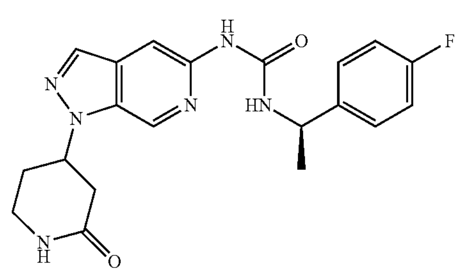 [SMILES: C[C@@H](NC(=O)Nc1cc2cnn(C3CCNC(=O)C3)c2cn1)c1ccc(F)cc1] | 1-[(1R)-1-(4-fluorophenyl)ethyl]-3-[1-(2-oxopiperidin-4-yl)-1H-pyrazolo[3,4-c]pyridin-5-yl]urea 1225 nM | Calc'd 397, found 397 |

TABLE 18-continued

| EX. | Structure | IUPAC Name/ERK2 IC$_{50}$ | M + H]+ |
|---|---|---|---|
| 234. | 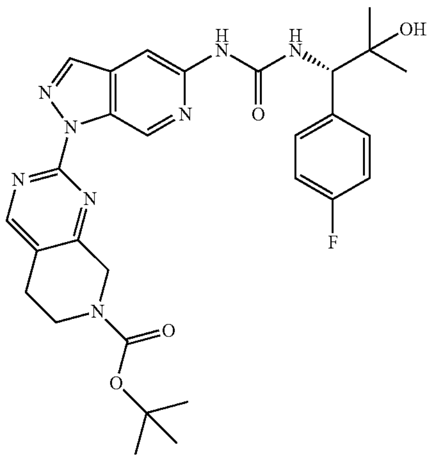 [SMILES: CC(C)(C)OC(=O)N1CCc2cnc(-n3ncc4cc(NC(=O)N[C@@H](c5ccc(F)cc5)C(C)(C)O)ncc43)nc2C1] | tert-butyl 2-[5-({[(1S)-1-(4-fluorophenyl)-2-hydroxy-2-methylpropyl]carbamoyl}amino)-1H-pyrazolo[3,4-c]pyridin-1-yl]-5,8-dihydropyrido[3,4-d]pyrimidine-7(6H)-carboxylate 1810 nM | Calc'd 577, found 577 |
| 235. | 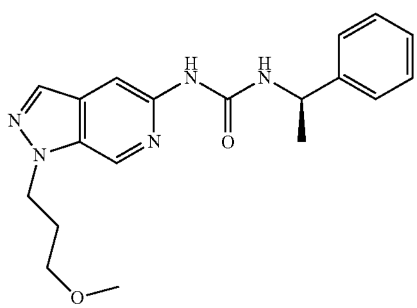 [SMILES: COCCCn1ncc2cc(NC(=O)N[C@H](C)c3ccccc3)ncc21] | 1-[1-(3-methoxypropyl)-1H-pyrazolo[3,4-c]pyridin-5-yl]-3-[(1R)-1-phenylethyl]urea 1519 nM | Calc'd 354, found 354 |
| 236. | 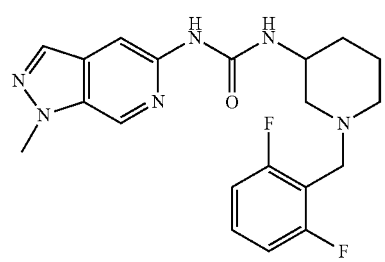 [SMILES: Cn1ncc2cc(NC(=O)NC3CCCN(Cc4c(F)cccc4F)C3)ncc21] | 1-[1-(2,6-difluorobenzyl)piperidin-3-yl]-3-(1-methyl-1H-pyrazolo[3,4-c]pyridin-5-yl)urea 531.2 nM | Calc'd 401, found 401 |
| 237. | 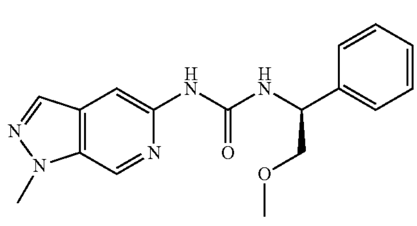 [SMILES: COC[C@@H](NC(=O)Nc1cc2cnn(C)c2cn1)c1ccccc1] | 1-[(1S)-2-methoxy-1-phenylethyl]-3-(1-methyl-1H-pyrazolo[3,4-c]pyridin-5-yl)urea 882.1 nM | Calc'd 326, found 326 |

TABLE 18-continued

| EX. | Structure | IUPAC Name/ERK2 IC$_{50}$ | M + H]+ |
|---|---|---|---|
| 238. | 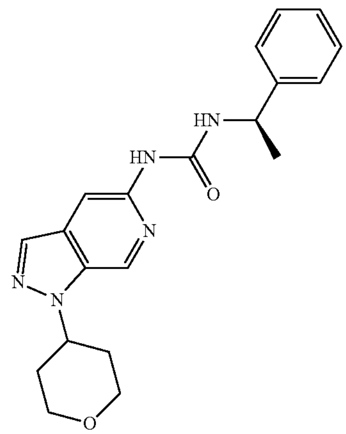 [SMILES: C[C@@H](NC(=O)Nc1cc2cnn(C3CCOCC3)c2cn1)c1ccccc1] | 1-[(1R)-1-phenylethyl]-3-[1-(tetrahydro-2H-pyran-4-yl)-1H-pyrazolo[3,4-c]pyridin-5-yl]urea 147.1 nM | Calc'd 366, found 366 |
| 239. | 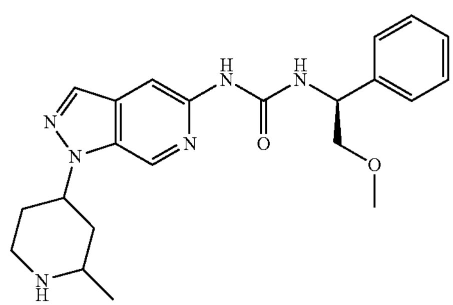 [SMILES: COC[C@@H](NC(=O)Nc1cc2cnn(C3CCNC(C)C3)c2cn1)c1ccccc1] | 1-[(1S)-2-methoxy-1-phenylethyl]-3-[1-(2-methylpiperidin-4-yl)-1H-pyrazolo[3,4-c]pyridin-5-yl]urea 2177 nM | Calc'd 409, found 409 |
| 240. | 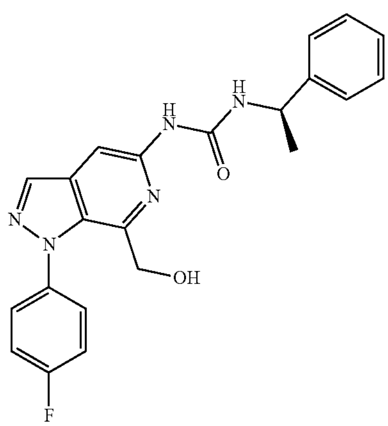 [SMILES: C[C@@H](NC(=O)Nc1cc2cnn(-c3ccc(F)cc3)c2c(CO)n1)c1ccccc1] | 1-[1-(4-fluorophenyl)-7-(hydroxymethyl)-1H-pyrazolo[3,4-c]pyridin-5-yl]-3-[(1R)-1-phenylethyl]urea 40.09 nM | Calc'd 406, found 406 |
| 241. | 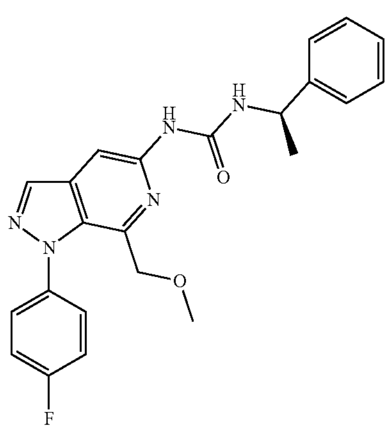 [SMILES: COCc1nc(NC(=O)N[C@H](C)c2ccccc2)cc2cnn(-c3ccc(F)cc3)c12] | 1-[1-(4-fluorophenyl)-7-(methoxymethyl)-1H-pyrazolo[3,4-c]pyridin-5-yl]-3-[(1R)-1-phenylethyl]urea 55.94 nM | Calc'd 420, found 420 |

TABLE 18-continued

| EX. | Structure | IUPAC Name/ERK2 IC$_{50}$ | M + H]+ |
|---|---|---|---|
| 242. | 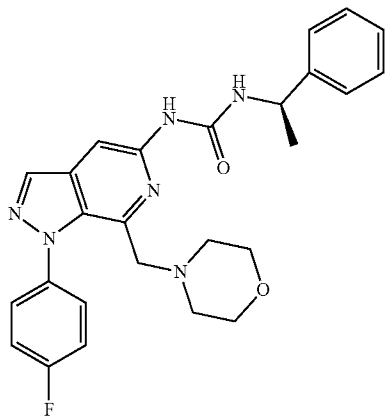 [SMILES: C[C@@H](NC(=O)Nc1cc2cnn(-c3ccc(F)cc3)c2c(CN2CCOCC2)n1)c1ccccc1] | 1-[1-(4-fluorophenyl)-7-(morpholin-4-ylmethyl)-1H-pyrazolo[3,4-c]pyridin-5-yl]-3-[(1R)-1-phenylethyl]urea 2241 nM | Calc'd 475, found 475 |
| 243. | 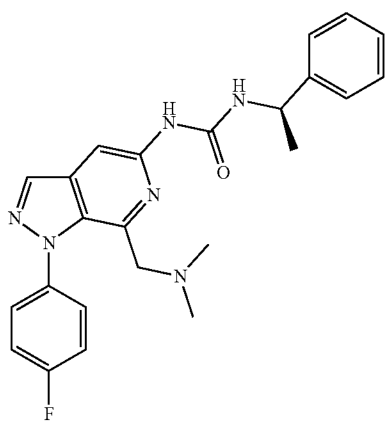 [SMILES: C[C@@H](NC(=O)Nc1cc2cnn(-c3ccc(F)cc3)c2c(CN(C)C)n1)c1ccccc1] | 1-{7-[(dimethylamino)methyl]-1-(4-fluorophenyl)-1H-pyrazolo[3,4-c]pyridin-5-yl}-3-[(1R)-1-phenylethyl]urea 1577 nM | Calc'd 433, found 433 |
| 244. | 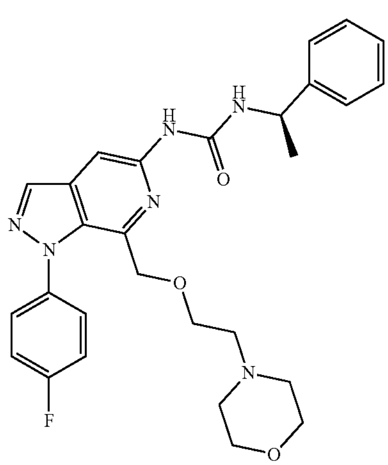 [SMILES: C[C@@H](NC(=O)Nc1cc2cnn(-c3ccc(F)cc3)c2c(COCCN2CCOCC2)n1)c1ccccc1] | 1-{1-(4-fluorophenyl)-7-[(2-morpholin-4-ylethoxy)methyl]-1H-pyrazolo[3,4-c]pyridin-5-yl}-3-[(1R)-1-phenylethyl]urea 188.2 nM | Calc'd 519, found 519 |

TABLE 18-continued

| EX. | Structure | IUPAC Name/ERK2 IC$_{50}$ | M + H]+ |
|---|---|---|---|
| 245. | 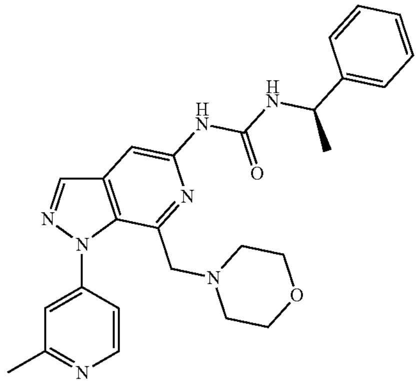 [SMILES: Cc1cc(-n2ncc3cc(NC(=O)N[C@H](C)c4ccccc4)nc(CN4CCOCC4)c32)ccn1] | 1-[1-(2-methylpyridin-4-yl)-7-(morpholin-4-ylmethyl)-1H-pyrazolo[3,4-c]pyridin-5-yl]-3-[(1R)-1-phenylethyl]urea 831.5 nM | Calc'd 472, found 472 |
| 246. | 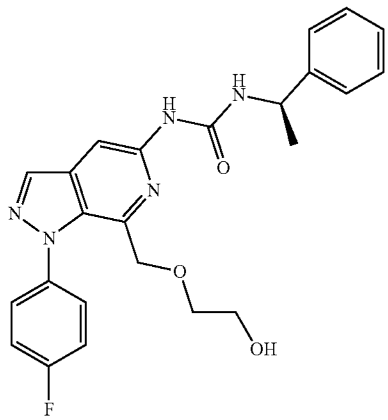 [SMILES: C[C@@H](NC(=O)Nc1cc2cnn(-c3ccc(F)cc3)c2c(COCCO)n1)c1ccccc1] | 1-{1-(4-fluorophenyl)-7-[(2-hydroxyethoxy)methyl]-1H-pyrazolo[3,4-c]pyridin-5-yl}-3-[(1R)-1-phenylethyl]urea 52.2 nM | Calc'd 450, found 450 |
| 247. | 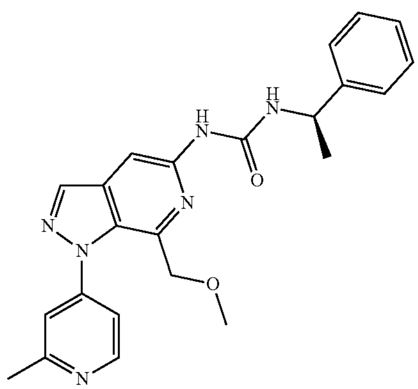 [SMILES: COCc1nc(NC(=O)N[C@H](C)c2ccccc2)cc2cnn(-c3ccnc(C)c3)c12] | 1-[7-(methoxymethyl)-1-(2-methylpyridin-4-yl)-1H-pyrazolo[3,4-c]pyridin-5-yl]-3-[(1R)-1-phenylethyl]urea 11.08 nM | Calc'd 417, found 417 |
| 248. | 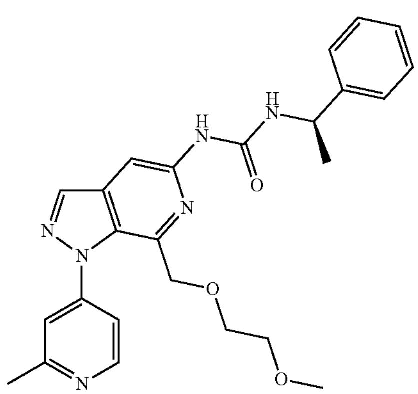 [SMILES: COCCOCc1nc(NC(=O)N[C@H](C)c2ccccc2)cc2cnn(-c3ccnc(C)c3)c12] | 1-{7-[(2-methoxyethoxy)methyl]-1-(2-methylpyridin-4-yl)-1H-pyrazolo[3,4-c]pyridin-5-yl}-3-[(1R)-1-phenylethyl]urea 11.39 nM | Calc'd 461, found 461 |

TABLE 18-continued

| EX. | Structure | IUPAC Name/ERK2 IC$_{50}$ | M + H]+ |
| --- | --- | --- | --- |
| 249. | 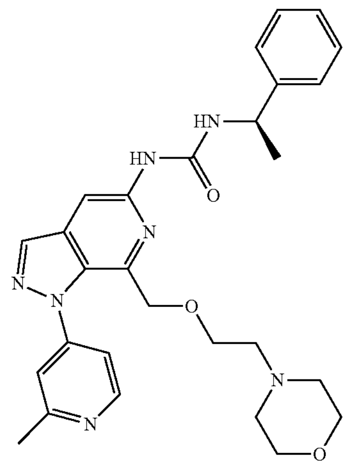 [SMILES: Cc1cc(-n2ncc3cc(NC(=O)N[C@H](C)c4ccccc4)nc(COCCN4CCOCC4)c32)ccn1] | 1-{1-(2-methylpyridin-4-yl)-7-[(2-morpholin-4-ylethoxy)methyl]-1H-pyrazolo[3,4-c]pyridin-5-yl}-3-[(1R)-1-phenylethyl]urea 127.1 nM | Calc'd 516, found 516 |
| 250. | 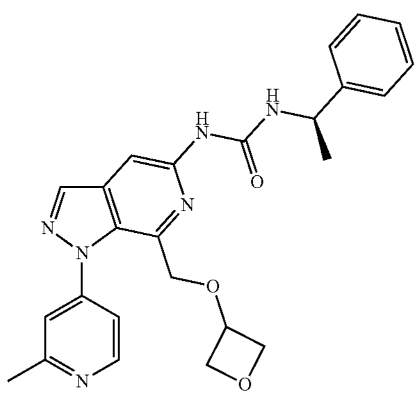 [SMILES: Cc1cc(-n2ncc3cc(NC(=O)N[C@H](C)c4ccccc4)nc(COC4COC4)c32)ccn1] | 1-{1-(2-methylpyridin-4-yl)-7-[(oxetan-3-yloxy)methyl]-1H-pyrazolo[3,4-c]pyridin-5-yl}-3-[(1R)-1-phenylethyl]urea 25.04 nM | Calc'd 459, found 459 |
| 251. | 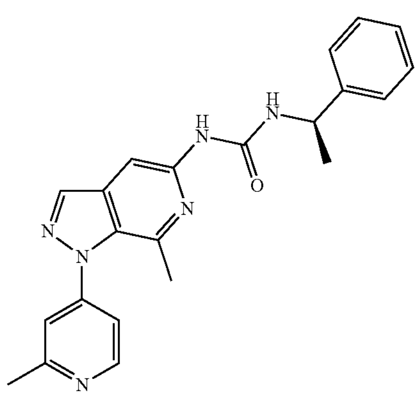 [SMILES: Cc1cc(-n2ncc3cc(NC(=O)N[C@H](C)c4ccccc4)nc(C)c32)ccn1] | 1-[7-methyl-1-(2-methylpyridin-4-yl)-1H-pyrazolo[3,4-c]pyridin-5-yl]-3-[(1R)-1-phenylethyl]urea 2.806 nM | Calc'd 387, found 387 |

TABLE 18-continued

| EX. | Structure | IUPAC Name/ERK2 IC$_{50}$ | M + H]+ |
|---|---|---|---|
| 252. | 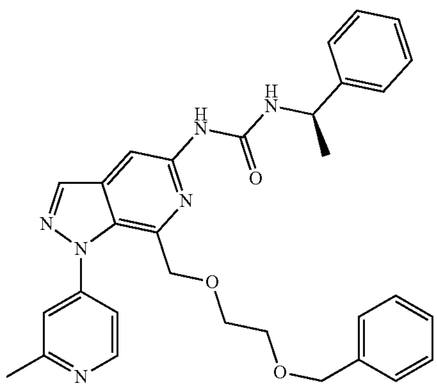 [SMILES: Cc1cc(-n2ncc3cc(NC(=O)N[C@H](C)c4ccccc4)nc(COCCOCc4ccccc4)c32)ccn1] | 1-[7-{[2-(benzyloxy)ethoxy]methyl}-1-(2-methylpyridin-4-yl)-1H-pyrazolo[3,4-c]pyridin-5-yl]-3-[(1R)-1-phenylethyl]urea 25.27 nM | Calc'd 537, found 537 |
| 253. | 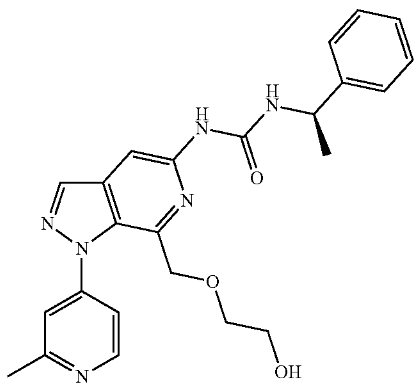 [SMILES: Cc1cc(-n2ncc3cc(NC(=O)N[C@H](C)c4ccccc4)nc(COCCO)c32)ccn1] | 1-{7-[(2-hydroxyethoxy)methyl]-1-(2-methylpyridin-4-yl)-1H-pyrazolo[3,4-c]pyridin-5-yl}-3-[(1R)-1-phenylethyl]urea 23.41 nM | Calc'd 447, found 447 |
| 254. | 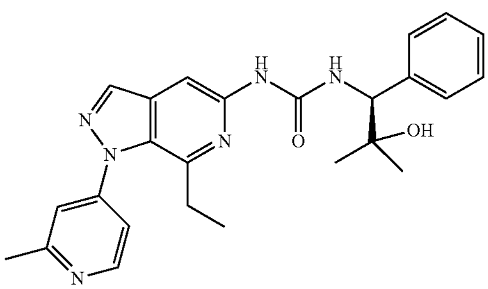 [SMILES: CCc1nc(NC(=O)N[C@@H](c2ccccc2)C(C)(C)O)cc2cnn(-c3ccnc(C)c3)c12] | 1-[7-(hydroxymethyl)-1-(2-methylpyridin-4-yl)-1H-pyrazolo[3,4-c]pyridin-5-yl]-3-[(1S)-2-hydroxy-2-methyl-1-phenylpropyl]urea 4.295 nM | Calc'd 447, found 447 |
| 255. | 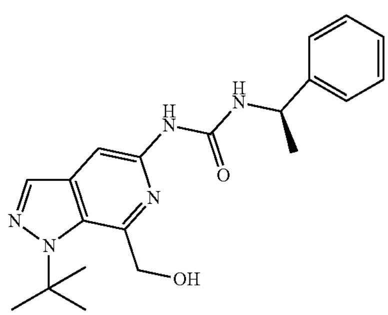 [SMILES: C[C@@H](NC(=O)Nc1cc2cnn(C(C)(C)C)c2c(CO)n1)c1ccccc1] | 1-[1-tert-butyl-7-(hydroxymethyl)-1H-pyrazolo[3,4-c]pyridin-5-yl]-3-[(1R)-1-phenylethyl]urea 1259 nM | Calc'd 368, found 368 |
| 256. | 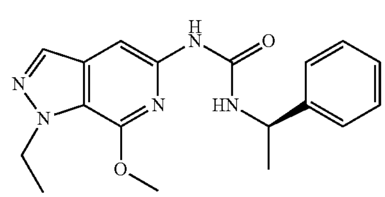 [SMILES: CCn1ncc2cc(NC(=O)N[C@H](C)c3ccccc3)nc(OC)c21] | 1-(1-ethyl-7-methoxy-1H-pyrazolo[3,4-c]pyridin-5-yl)-3-[(1R)-1-phenylethyl]urea 100.2 nM | Calc'd 340, found 340 |

TABLE 18-continued

| EX. | Structure | IUPAC Name/ERK2 IC$_{50}$ | M + H]+ |
|---|---|---|---|
| 257. | 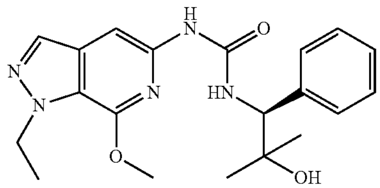 [SMILES: CCn1ncc2cc(NC(=O)N[C@@H](c3ccccc3)C(C)(C)O)nc(OC)c21] | 1-(1-ethyl-7-methoxy-1H-pyrazolo[3,4-c]pyridin-5-yl)-3-[(1S)-2-hydroxy-2-methyl-1-phenylpropyl]urea 44.94 nM | Calc'd 384, found 384 |
| 258. | 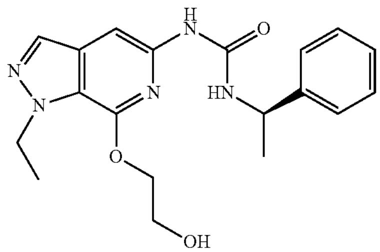 [SMILES: CCn1ncc2cc(NC(=O)N[C@H](C)c3ccccc3)nc(OCCO)c21] | 1-[1-ethyl-7-(2-hydroxyethoxy)-1H-pyrazolo[3,4-c]pyridin-5-yl]-3-[(1R)-1-phenylethyl]urea 35.27 nM | Calc'd 370, found 370 |

Synthetic Method VII

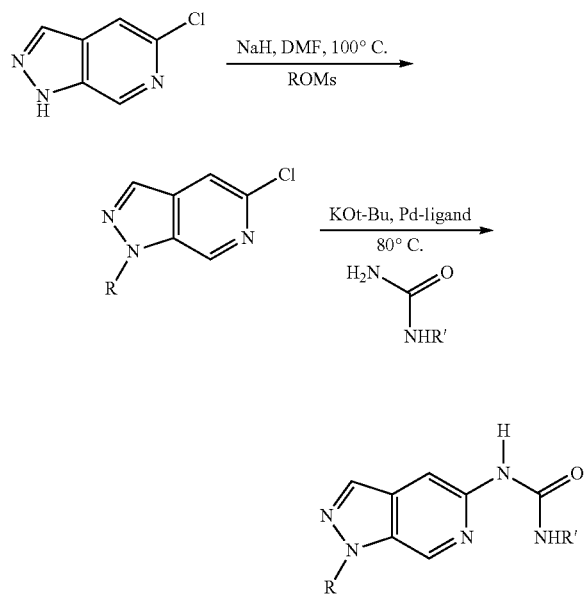

Example 259

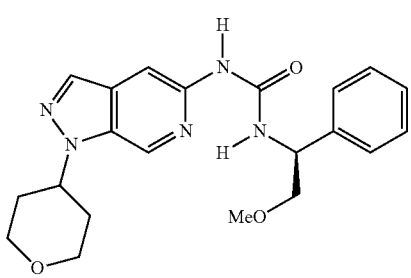 [SMILES: COC[C@@H](NC(=O)Nc1cc2cnn(C3CCOCC3)c2cn1)c1ccccc1]

(S)-1-(2-methoxy-1-phenylethyl)-3-(1-(tetrahydro-2H-pyran-4-yl)-1H-pyrazolo[3,4-c]pyridin-5-yl)urea 196.4 nM Step 1: Synthesis of 5-chloro-1-(tetrahydro-2H-pyran-4-yl)-1H-pyrazolo[3,4-c]pyridine To the solution of 5-chloro-1H-pyrazolo[3,4-c]pyridine (0.300 g, 1.95 mmol) in DMF (5 mL) at 0° C. was added NaH (0.234 g, 5.86 mmol, 60% dispersion in oil). After stirring for 5 min. tetrahydro-2H-pyran-4-yl methanesulfonate (0.632 g, 3.5 mmol) was added and the reaction mixture was heated at 100° C. for 5 h. TLC analysis indicated complete consumption of starting material and formation of 2 new spots. The reaction mixture was quenched by slow addition of ice-cold water (3 mL). The residue was bi-phased with water (15 mL) and ethyl acetate (25 mL). The aqueous layer was extracted with ethyl acetate (2×10 mL). The combined organic layers were washed with brine (1×15 mL), dried (anh. Na$_2$SO$_4$) and concentrated under reduced pressure to furnish the title compound (0.230 g.).

In step-1, the non-polar spot amongst the two new spots in the TLC, was the required regio-isomer (5). Both the regio-isomers obtained during N-alkylation were purified by flash column chromatography and the structure was confirmed by NMR and NOE experiments. MS (EI) calc'd for C$_{11}$H$_{12}$N$_3$OCl [M+H]$^+$ Expected: 238. Found: 238; $^1$H NMR (400 MHz, CDCl$_3$) δ 9.06 (s, 1H), 8.15 (s, 1H), 7.79 (s, 1H), 4.90-4.78 (m, 1H), 4.24 (dd, 2H, J$_1$=3.6 Hz, J$_2$=11.2 Hz), 3.76-3.64 (m, 2H), 2.52-2.37 (m, 2H), 2.06 (dd, 2H, J$_1$=2.4 Hz, J$_2$=12.8 Hz).

Step 2: Synthesis of (S)-1-(2-methoxy-1-phenylethyl)-3-(1-(tetrahydro-2H-pyran-4-yl)-1H-pyrazolo[3,4-c]pyridin-5-yl)urea To a solution of 5-chloro-1-(tetrahydro-2H-pyran-4-yl)-1H-pyrazolo[3,4-c]pyridine (0.060 g, 0.252 mmol) and (S)-1-(2-methoxy-1-phenylethyl)urea (0.0489 g, 0.252 mmol) in THF was purged nitrogen for 10 min. and t-BuX-phos palladium catalyst (0.0207 g, 0.0302 mmol) and potassium tert-butoxide (0.54 mL, 0.547 mmol). The reaction mixture was heated at 80° C. for 2 h. The starting material was completely consumed as revealed by the TLC. The reaction mixture was filtered through celite bed and washed with ethyl acetate. The filtrate was concentrated under reduced pressure and purified by preparative HPLC to furnish the title compound. MS (EI) calc'd for $C_{21}H_{25}N_5O_3$ [M+H]$^+$ 396. Found: 396; $^1$H NMR (400 MHz, CD$_3$OD) δ 8.91 (bs, 1H), 8.03 (s, 1H), 7.62 (bs, 1H), 7.40 (d, 2H, J=7.60 Hz), 7.37-7.30 (m, 2H), 7.30-7.21 (m, 1H), 5.09 (t, 1H, J=5.3 Hz), 5.00-4.90 (m, 1H), 4.12 (dd, 2H, J$_1$=3.8 Hz, J$_2$=11.6 Hz), 3.75-3.62 (m, 4H), 3.39 (s, 3H), 2.40-2.21 (m, 2H), 2.06-1.97 (m, 2H).

The following examples were made by using procedures similar to example 259 with appropriate reagent.

-continued

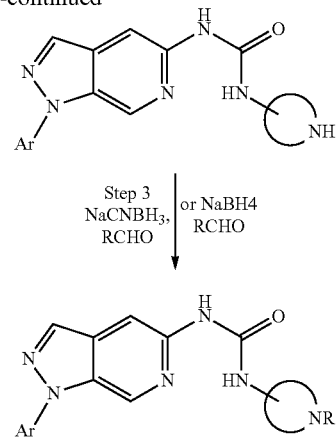

TABLE 19

| EX | Structure | IUPAC Name/ERK2 IC$_{50}$ | [M + H]+ |
|---|---|---|---|
| 260. | 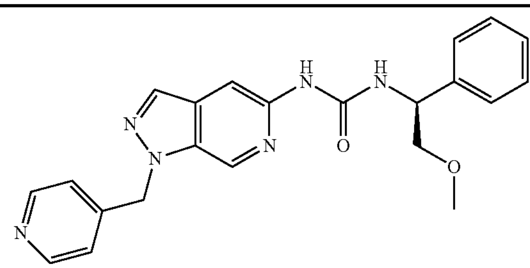 | 1-[(1S)-2-methoxy-1-phenylethyl]-3-[1-(pyridin-4-ylmethyl)-1H-pyrazolo[3,4-c]pyridin-5-yl]urea 30.9 nM | Calc'd 403, found 403 |
| 261. | 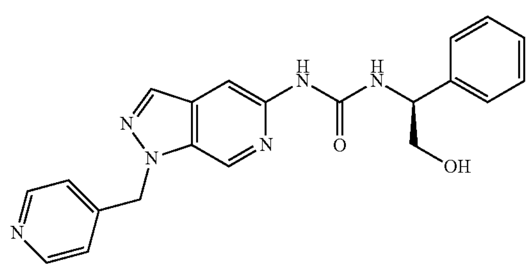 [SMILES: O=C(Nc1cc2cnn(Cc3ccncc3)c2cn1)N[C@H](CO)c1ccccc1] | 1-[(1S)-2-hydroxy-1-phenylethyl]-3-[1-(pyridin-4-ylmethyl)-1H-pyrazolo[3,4-c]pyridin-5-yl]urea 2427 nM | Calc'd 389, found 389 |

Synthetic Method VIII

Example 262

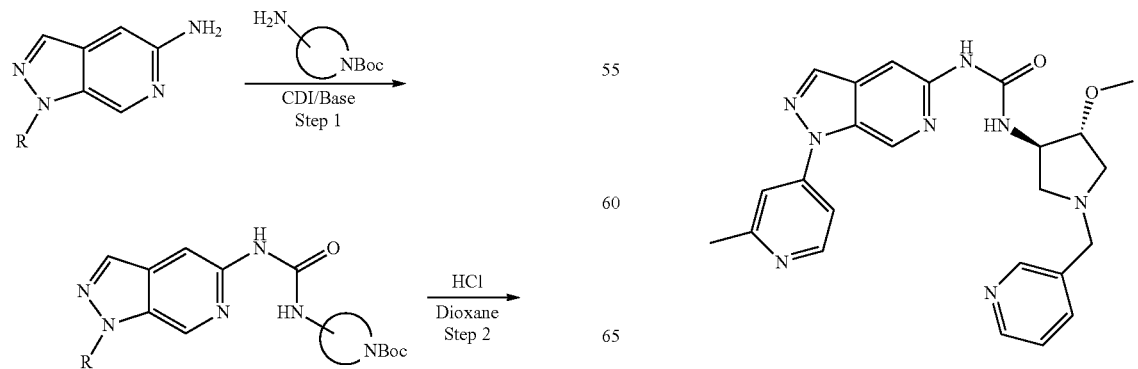

1-((3R,4R)-4-methoxy-1-(pyridin-3-ylmethyl)pyrrolidin-3-yl)-3-(1-(2-methylpyridin-4-yl)-1H-pyrazolo[3,4-c]pyridin-5-yl)urea 253 nM Step 1: Synthesis of trans-tert-butyl 3-methoxy-4-(3-(1-(2-methylpyridin-4-yl)-1H-pyrazolo[3,4-c]pyridin-5-yl)ureido)pyrrolidine-1-carboxylate To a solution of 1-(2-methylpyridin-4-yl)-1H-pyrazolo[3,4-c]pyridin-5-amine 5 (0.15 g, 0.66 mmol) in anhydrous 1,4-dioxane (5 mL) was added CDI (0.54 g, 3.3 mmol) followed by the addition of imidazole (0.23 g, 3.0 mmol) and the contents were stirred at ambient temperature. After 16 h [the completion of the reaction was confirmed by quenching small aliquot of the reaction mixture with MeOH and mass was obtained for the corresponding carbamate (M+H)=284], DIPEA (0.25 g, 2.0 mmol) and trans-tert-butyl 3-amino-4-methoxypyrrolidine-1-carboxylate (0.3 g, 1.3 mmol) were added and the contents were stirred at ambient temperature. After 4 h, the reaction mixture was quenched with H$_2$O and the organic contents were extracted with EtOAc (3×25 mL), dried over Na$_2$SO$_4$ and concentrated. The residue thus obtained was purified by preparative HPLC afforded the title compound. Anal. Calcd. C$_{23}$H$_{29}$N$_7$O$_4$ [M+H] 469. Found 469.

Step 2: Synthesis of 1-(trans-4-methoxypyrrolidin-3-yl)-3-(1-(2-methylpyridin-4-yl)-1H-pyrazolo[3,4-c]pyridin-5-yl)urea To a solution of trans-tert-butyl 3-methoxy-4-(3-(1-(2-methylpyridin-4-yl)-1H-pyrazolo[3,4-c]pyridin-5-yl)ureido)pyrrolidine-1-carboxylate (0.12 g, 0.25 mmol) in anhydrous CH$_2$Cl$_2$ (5 mL) was added HCl in Dioxane (2 mL) and the contents were stirred at ambient temperature for 2 h. The volatiles were then evaporated under reduced pressure and the residue thus obtained was triturated with Et$_2$O (3×5 mL) afforded the title compound as its hydrochloride salt. Anal. Calcd. C$_{18}$H$_{21}$N$_7$O$_2$ [M+H] 369. Found 369; $^1$H NMR (CD$_3$OD, 400 MHz): δ 9.58 (s, 1H), 8.80-8.76 (m, 2H), 8.44-8.42 (m, 2H), 8.01 (s, 1H), 4.52-4.51 (m, 1H), 4.20-4.19 (m, 1H), 3.75-3.62 (m, 2H), 3.55-3.48 (m, 5H), 2.92 (s, 3H).

Step 3: Synthesis of 1-(trans-4-methoxy-1-(pyridin-3-ylmethyl)pyrrolidin-3-yl)-3-(1-(2-methylpyridin-4-yl)-1H-pyrazolo[3,4-c]pyridin-5-yl)urea Nicotinaldehyde (0.01 g, 0.009 mmol) was added to a solution of 1-(trans-4-methoxypyrrolidin-3-yl)-3-(1-(2-methylpyridin-4-yl)-1H-pyrazolo[3,4-c]pyridin-5-yl)urea (0.03 g, 0.08 mmol) hydrochloride salt in anhydrous 1,2-dimethoxy ethane (3 mL) and the contents were stirred at ambient temperature for 30 min followed by the addition of sodium triacetoxy borohydride (0.02 g, 0.09 mmol). The reaction mixture was stirred additionally for about 1 h and the reaction was quenched with H$_2$O (5 mL) and the organic contents were extracted with EtOAc. The EtOAc layer was dried over anhydrous Na$_2$SO$_4$ and concentrated under reduced pressure. The product this obtained was triturated with Et$_2$O (3×5 mL) afforded the title compound. Anal. Calcd. C$_{24}$H$_{26}$N$_8$O$_2$ [M+H] 459. Found 459; $^1$H NMR (CD$_3$OD, 400 MHz): δ 9.19 (s, 1H), 8.57 (d, J=5.7 Hz, 1H), 8.38 (s, 1H), 7.86 (s, 1H), 7.82 (m, 3H), 7.39-7.34 (m, 1H), 7.04-6.9 (m, 2H), 4.22 (m, 1H), 3.85 (s, 2H), 3.70 (bs, 1H), 3.5 (s, 3H), 3.16-3.12 (m, 1H), 2.97-2.93 (m, 1H), 2.68 (s, 3H), 2.68-2.60 (m, 1H), 2.53-2.50 (m, 1H).

Example 263

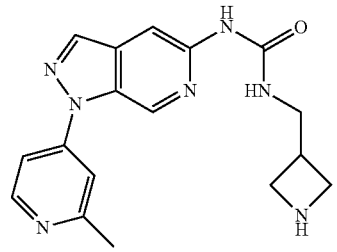 [SMILES: Cc1cc(-n2ncc3cc(NC(=O)NCC4CNC4)ncc32)ccn1]

1-(azetidin-3-ylmethyl)-3-(1-(2-methylpyridin-4-yl)-1H-pyrazolo[3,4-c]pyridin-5-yl)urea 102 nM Step 1: tert-butyl 3-((3-(1-(2-methylpyridin-4-yl)-1H-pyrazolo[3,4-c]pyridin-5-yl)ureido)methyl)azetidine-1-carboxylate tert-butyl 3-((3-(1-(2-methylpyridin-4-yl)-1H-pyrazolo[3,4-c]pyridin-5-yl)ureido)methyl)azetidine-1-carboxylate was prepared using the same procedure as demonstrated for example 14 using CDI coupling synthetic method II. MS ESI calc'd. For C$_{22}$H$_{28}$N$_7$O$_3$ [M+1]$^+$ 438. found 438.

Step 2: 1-(azetidin-3-ylmethyl)-3-(1-(2-methylpyridin-4-yl)-1H-pyrazolo[3,4-c]pyridin-5-yl)urea tert-butyl 3-((3-(1-(2-methylpyridin-4-yl)-1H-pyrazolo[3,4-c]pyridin-5-yl)ureido)methyl)azetidine-1-carboxylate (48 mg, 0.11 mmol) was taken up in 4N HCl in 1,4-Dioxane (0.50 ml) and the reaction mixture was allowed to stir at 50° C. for 2 hrs. LCMS showed that Boc group deprotection was complete. The reaction mixture was concentrated in vacuo. The residual oil was diluted with DMSO (2 ml) and was purified by reverse-phase mass-triggered preparative HPLC. The fractions containing product were concentrated down to give 1-(azetidin-3-ylmethyl)-3-(1-(2-methylpyridin-4-yl)-1H-pyrazolo[3,4-c]pyridin-5-yl)urea as the trifluoroacetic acid salt. MS ESI calc'd. For C$_{17}$H$_{20}$N$_7$O [M+1]$^+$ 338. found 338. $^1$H NMR (500 MHz, DMSO-d$_6$) δ 9.44 (s, 1H), 9.40 (s, 1H) 8.6 (m, 2H), 8.62 (br s, 1H), 8.51 (br s, 1H), 8.25-8.20 (m, 2H), 7.24 (m, 1H), 3.95 (m, 2H), 3.75 (m, 2H), 3.37 (t, J=6.24, 2H), 2.96 (m, 1H), 2.75 (s, 3H).

Example 264

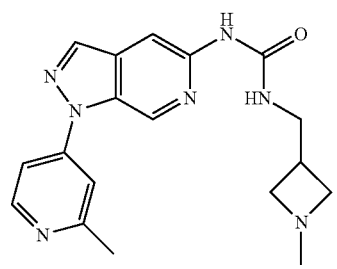 [SMILES: Cc1cc(-n2ncc3cc(NC(=O)NCC4CN(C)C4)ncc32)ccn1]

1-((1-methylazetidin-3-yl)methyl)-3-(1-(2-methyl-pyridin-4-yl)-1H-pyrazolo[3,4-c]pyridin-5-yl)urea
69.96 nM 1-(azetidin-3-ylmethyl)-3-(1-(2-methylpyridin-4-yl)-1H-pyrazolo[3,4-c]pyridin-5-yl)urea (Example 263) was taken up in MeOH (2 ml) formaldehyde (10.16 µl, 0.136 mmol) was added followed by sodium borohydride (5.53 mg, 0.146 mmol). The reaction was allowed to stir at rt for 1 hour. The reaction mixture was then concentrated in vacuo. The residual oil was resuspended in EtOAc and water. The products were extracted into EtOAc (3×). The combined organics were washed with brine and dried over MgSO$_4$ and concentrated in vacuo. The oil was taken up in DMSO and MeOH (3.5 ml total) and purified by reverse phase preparative HPLC. The returned fractions were dried down to give 1-((1-methylazetidin-3-yl)methyl)-3-(1-(2-methylpyridin-4-yl)-1H-pyrazolo[3,4-c]pyridin-5-yl)urea as the trifluoroacetic acid salt. MS ESI calc'd. for C$_{18}$H$_{22}$N$_7$O [M+1]$^+$ 352. found 352. $^1$H NMR (500 MHz, DMSO-d$_6$) δ 9.44 (s, 1H), 9.40 (s, 1H) 8.6 (m, 2H), 8.62 (br s, 1H), 8.51 (br s, 1H), 8.25-8.20 (m, 2H), 3.95 (m, 2H), 3.75 (m, 2H), 3.37 (t, J=6.24, 2H), 2.96 (m, 1H), 2.75 (s, 3H), 2.52 (s, 3H).

The following compounds were made by similar procedure as described in example 264.

TABLE 20

| Ex. | Structure | IUPAC Name/ERK2 IC$_{50}$ | [M + H]+ |
|---|---|---|---|
| 265. | 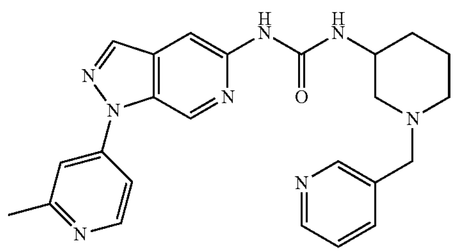 [SMILES: Cc1cc(-n2ncc3cc(NC(=O)NC4CCCN(Cc5cccnc5)C4)ncc32)ccn1] | 1-[1-(2-methylpyridin-4-yl)-1H-pyrazolo[3,4-c]pyridin-5-yl]-3-[1-pyridin-3-ylmethyl)-piperidin-3-yl]urea 115.4 nM | Calc'd 443, found 443 |
| 266. | 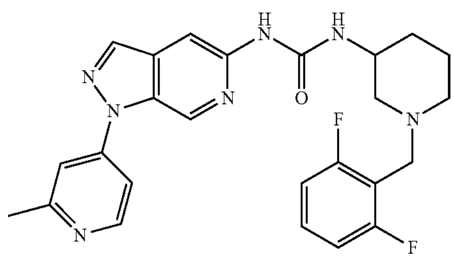 [SMILES: Cc1cc(-n2ncc3cc(NC(=O)NC4CCCN(Cc5c(F)cccc5F)C4)ncc32)ccn1] | 1-[1-(2,6-difluorobenzyl)piperidin-3-yl]-3-[1-(2-methylpyridin-4-yl)-1H-pyrazolo[3,4-c]pyridin-5-yl]urea 2.778 nM | Calc'd 478, found 478 |
| 267. | 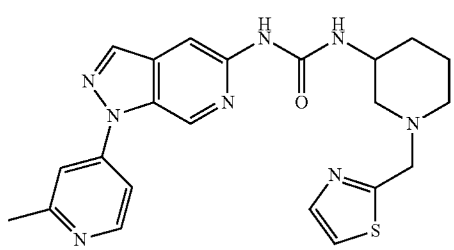 [SMILES: Cc1cc(-n2ncc3cc(NC(=O)NC4CCCN(Cc5nccs5)C4)ncc32)ccn1] | 1-[1-(2-methylpyridin-4-yl)-1H-pyrazolo[3,4-c]pyridin-5-yl]-3-[1-(1,3-thiazol-2-ylmethyl)piperidin-3-yl]urea 22.19 nM | Calc'd 449, found 449 |
| 268. | 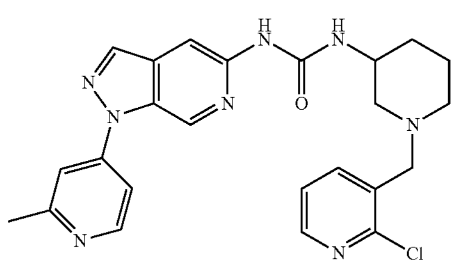 [SMILES: Cc1cc(-n2ncc3cc(NC(=O)NC4CCCN(Cc5cccnc5Cl)C4)ncc32)ccn1] | 1-{1-[(2-chloropyridin-3-yl)methyl]piperidin-3-yl}-3-[1-(2-methylpyridin-4-yl)-1H-pyrazolo[3,4-c]pyridin-5-yl]urea 18.63 nM | Calc'd 477, found 477 |

| Ex. | Structure | IUPAC Name/ERK2 IC$_{50}$ | [M + H]+ |
|---|---|---|---|
| 269. | 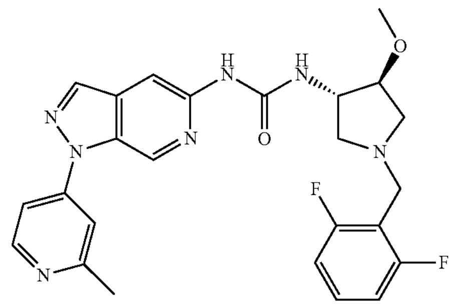 [SMILES: CO[C@H]1CN(Cc2c(F)cccc2F)C[C@@H]1NC(=O)Nc1cc2cnn(-c3ccnc(C)c3)c2cn1] | 1-[(3S,4S)-1-(2,6-difluorobenzyl)-4-methoxypyrrolidin-3-yl]-3-[1-(2-methylpyridin-4-yl)-1H-pyrazolo[3,4-c]pyridin-5-yl]urea 5.389 nM | Calc'd 494, found 494 |
| 270. | 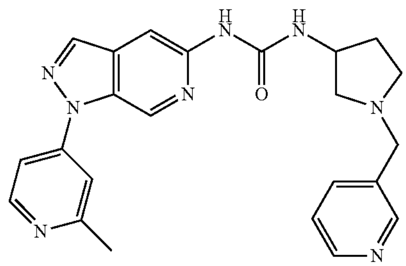 [SMILES: Cc1cc(-n2ncc3cc(NC(=O)NC4CCN(Cc5cccnc5)C4)ncc32)ccn1] | 1-[1-(2-methylpyridin-4-yl)-1H-pyrazolo[3,4-c]pyridin-5-yl]-3-[1-(pyridin-3-ylmethyl)-pyrrolidin-3-yl]urea 45.31 nM | Calc'd 429, found 429 |
| 271. | 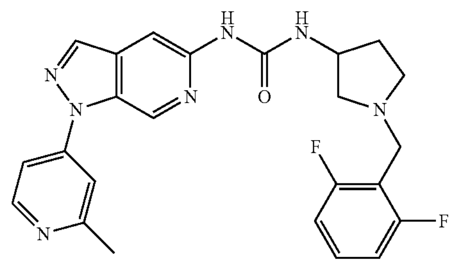 [SMILES: Cc1cc(-n2ncc3cc(NC(=O)NC4CCN(Cc5c(F)cccc5F)C4)ncc32)ccn1] | 1-[1-(2,6-difluorobenzyl)pyrrolidin-3-yl]-3-[1-(2-methylpyridin-4-yl)-1H-pyrazolo[3,4-c]pyridin-5-yl]urea 0.9968 nM | Calc'd 464, found 464 |
| 272. | 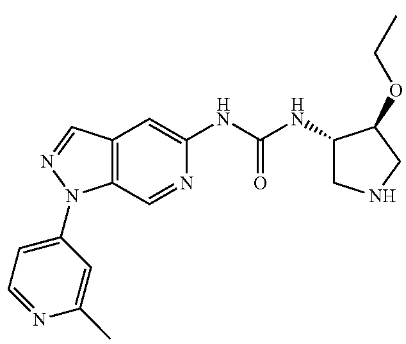 [SMILES: CCO[C@H]1CNC[C@@H]1NC(=O)Nc1cc2cnn(-c3ccnc(C)c3)c2cn1] | 1-[(3S,4S)-4-ethoxypyrrolidin-3-yl]-3-[1-(2-methylpyridin-4-yl)-1H-pyrazolo[3,4-c]pyridin-5-yl]urea 39.85 nM | Calc'd 382, found 382 |
| 273. | 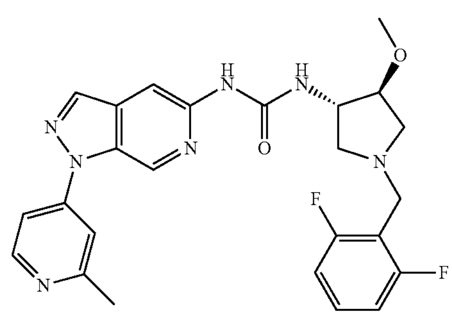 [SMILES: CO[C@H]1CN(Cc2c(F)cccc2F)C[C@@H]1NC(=O)Nc1cc2cnn(-c3ccnc(C)c3)c2cn1] | 1-[(3S,4S) or (3R, 4R)-1-(2,6-difluorobenzyl)-4-methoxypyrrolidin-3-yl]-3-[1-(2-methylpyridin-4-yl)-1H-pyrazolo[3,4-c]pyridin-5-yl]urea 2057 nM | Calc'd 494, found 494 |

TABLE 20-continued

| Ex. | Structure | IUPAC Name/ERK2 IC$_{50}$ | [M + H]+ |
|---|---|---|---|
| 274. | 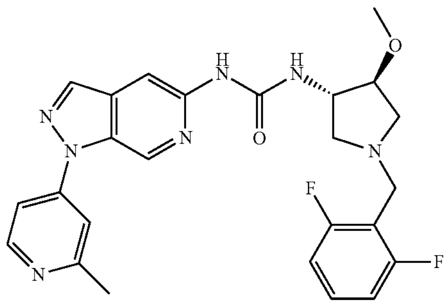 [SMILES: CO[C@H]1CN(Cc2c(F)cccc2F)C[C@@H]1NC(=O)Nc1cc2cnn(-c3ccnc(C)c3)c2cn1] | 1-[(3R,4R) or (3S, 4S)-1-(2,6-difluorobenzyl)-4-methoxypyrrolidin-3-yl]-3-[1-(2-methylpyridin-4-yl)-1H-pyrazolo[3,4-c]pyridin-5-yl]urea 3.537 nM | Calc'd 494, found 494 |
| 275. | 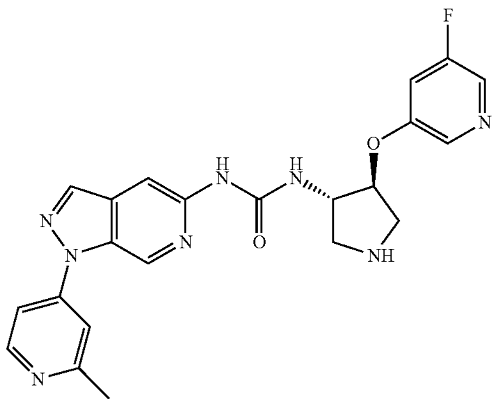 [SMILES: Cc1cc(-n2ncc3cc(NC(=O)N[C@H]4CNC[C@@H]4Oc4cncc(F)c4)ncc32)ccn1] | 1-{(3S,4S)-4-[(5-fluoropyridin-3-yl)oxy]pyrrolidin-3-yl}-3-[1-(2-methylpyridin-4-yl)-1H-pyrazolo[3,4-c]pyridin-5-yl]urea 326.7 nM | Calc'd 449, found 449 |
| 276. | 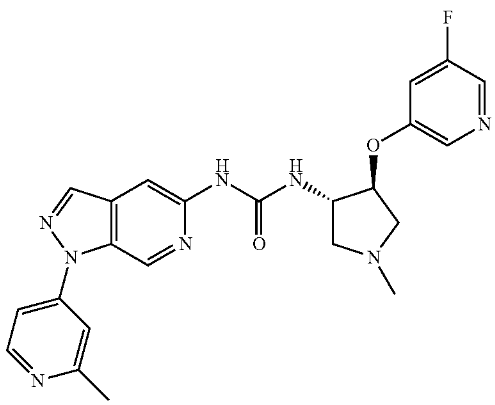 [SMILES: Cc1cc(-n2ncc3cc(NC(=O)N[C@H]4CN(C)C[C@@H]4Oc4cncc(F)c4)ncc32)ccn1] | 1-{(3S,4S)-4-[(5-fluoropyridin-3-yl)oxy]-1-methylpyrrolidin-3-yl}-3-[1-(2-methylpyridin-4-yl)-1H-pyrazolo[3,4-c]pyridin-5-yl]urea 242.4 nM | Calc'd 463, found 463 |
| 277. | 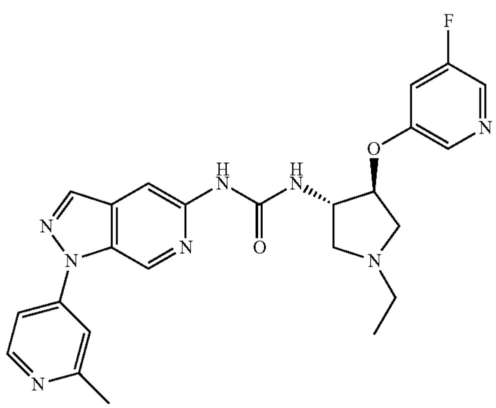 [SMILES: CCN1C[C@H](NC(=O)Nc2cc3cnn(-c4ccnc(C)c4)c3cn2)[C@@H](Oc2cncc(F)c2)C1] | 1-{(3S,4S)-1-ethyl-4-[(5-fluoropyridin-3-yl)oxy]pyrrolidin-3-yl}-3-[1-(2-methylpyridin-4-yl)-1H-pyrazolo[3,4-c]pyridin-5-yl]urea 593.9 nM | Calc'd 477, found 477 |

TABLE 20-continued

| Ex. | Structure | IUPAC Name/ERK2 IC$_{50}$ | [M + H]+ |
|---|---|---|---|
| 278. | 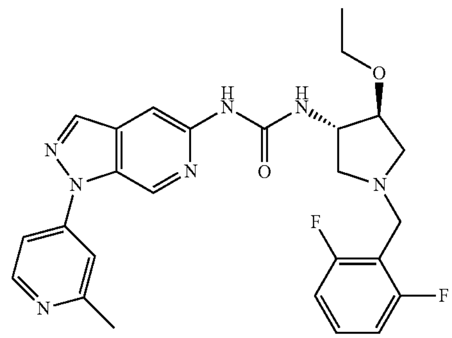 [SMILES: CCO[C@H]1CN(Cc2c(F)cccc2F)C[C@@H]1NC(=O)Nc1cc2cnn(-c3ccnc(C)c3)c2cn1] | 1-[(3S,4S)-1-(2,6-difluorobenzyl)-4-ethoxypyrrolidin-3-yl]-3-[1-(2-methylpyridin-4-yl)-1H-pyrazolo[3,4-c]pyridin-5-yl]urea 45.28 nM | Calc'd 508, found 508 |
| 279. | 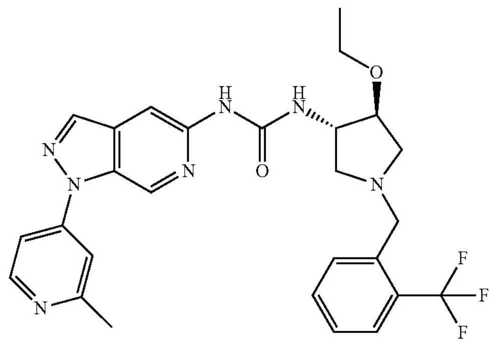 [SMILES: CCO[C@H]1CN(Cc2ccccc2C(F)(F)F)C[C@@H]1NC(=O)Nc1cc2cnn(-c3ccnc(C)c3)c2cn1] | 1-{(3S,4S)-4-ethoxy-1-[2-(trifluoromethyl)benzyl]pyrrolidin-3-yl}-3-[1-(2-methylpyridin-4-yl)-1H-pyrazolo[3,4-c]pyridin-5-yl]urea 1751 nM | Calc'd 540, found 540 |
| 280. | 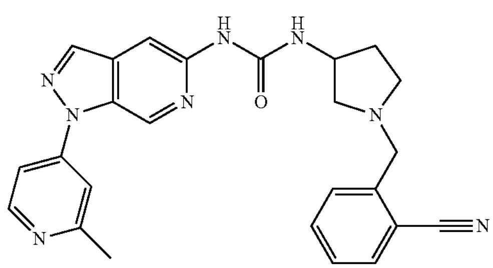 [SMILES: Cc1cc(-n2ncc3cc(NC(=O)NC4CCN(Cc5ccccc5C#N)C4)ncc32)ccn1] | 1-[1-(2-cyanobenzyl)pyrrolidin-3-yl]-3-[1-(2-methylpyridin-4-yl)-1H-pyrazolo[3,4-c]pyridin-5-yl]urea 4.354 nM | Calc'd 453, found 453 |
| 281. | 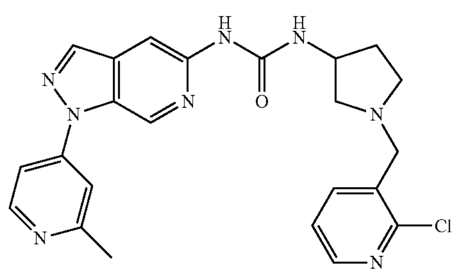 [SMILES: Cc1cc(-n2ncc3cc(NC(=O)NC4CCN(Cc5cccnc5Cl)C4)ncc32)ccn1] | 1-{1-[(2-chloropyridin-3-yl)methyl]pyrrolidin-3-yl}-3-[1-(2-methylpyridin-4-yl)-1H-pyrazolo[3,4-c]pyridin-5-yl]urea 2.84 nM | Calc'd 463, found 463 |
| 282. | 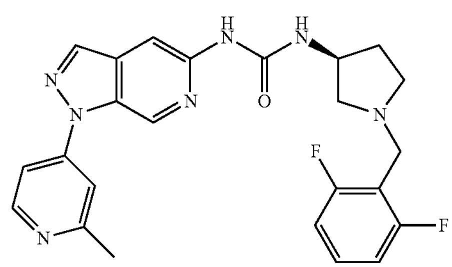 [SMILES: Cc1cc(-n2ncc3cc(NC(=O)N[C@H]4CCN(Cc5c(F)cccc5F)C4)ncc32)ccn1] | 1-[(3S)-1-(2,6-difluorobenzyl)pyrrolidin-3-yl]-3-[1-(2-methylpyridin-4-yl)-1H-pyrazolo[3,4-c]pyridin-5-yl]urea 169.3 nM | Calc'd 464, found 464 |

TABLE 20-continued

| Ex. | Structure | IUPAC Name/ERK2 IC$_{50}$ | [M + H]+ |
|---|---|---|---|
| 283. | 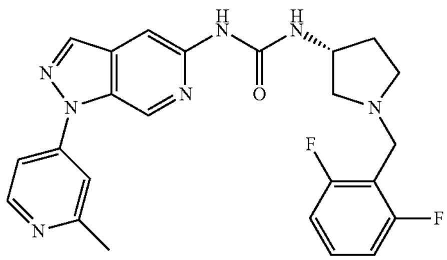 [SMILES: Cc1cc(-n2ncc3cc(NC(=O)N[C@@H]4CCN(Cc5c(F)cccc5F)C4)ncc32)ccn1] | 1-[(3R)-1-(2,6-difluorobenzyl)pyrrolidin-3-yl]-3-[1-(2-methylpyridin-4-yl)-1H-pyrazolo[3,4-c]pyridin-5-yl]urea 0.3228 nM | Calc'd 464, found 464 |
| 284. | 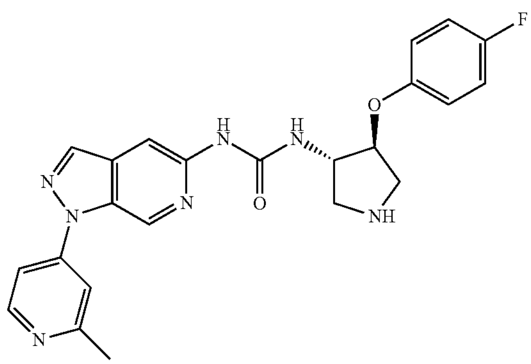 [SMILES: Cc1cc(-n2ncc3cc(NC(=O)N[C@H]4CNC[C@@H]4Oc4ccc(F)cc4)ncc32)ccn1] | 1-[(3S,4S)-4-(4-fluorophenoxy)pyrrolidin-3-yl]-3-[1-(2-methylpyridin-4-yl)-1H-pyrazolo[3,4-c]pyridin-5-yl]urea 24.13 nM | Calc'd 448, found 448 |
| 285. | 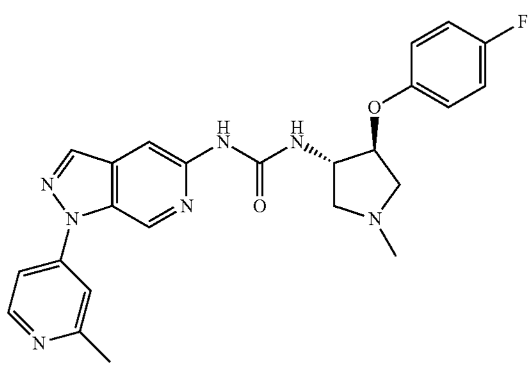 [SMILES: Cc1cc(-n2ncc3cc(NC(=O)N[C@H]4CN(C)C[C@@H]4Oc4ccc(F)cc4)ncc32)ccn1] | 1-[(3S,4S)-4-(4-fluorophenoxy)-1-methylpyrrolidin-3-yl]-3-[1-(2-methylpyridin-4-yl)-1H-pyrazolo[3,4-c]pyridin-5-yl]urea 16.43 nM | Calc'd 462, found 462 |
| 286. | 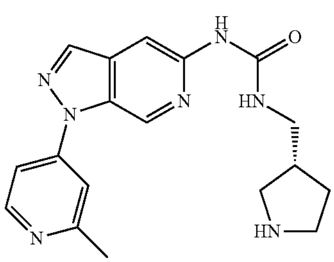 [SMILES: Cc1cc(-n2ncc3cc(NC(=O)NC[C@@H]4CCNC4)ncc32)ccn1] | 1-[1-(2-methylpyridin-4-yl)-1H-pyrazolo[3,4-c]pyridin-5-yl]-3-[(3R)-pyrrolidin-3-ylmethyl]urea 23.35 nM | Calc'd 352, found 352 |
| 287. | 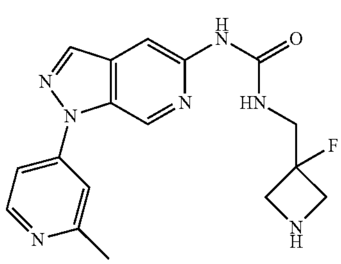 [SMILES: Cc1cc(-n2ncc3cc(NC(=O)NCC4(F)CNC4)ncc32)ccn1] | 1-[(3-fluoroazetidin-3-yl)methyl]-3-[1-(2-methylpyridin-4-yl)-1H-pyrazolo[3,4-c]pyridin-5-yl]urea 43.19 nM | Calc'd 356, found 356 |

TABLE 20-continued

| Ex. | Structure | IUPAC Name/ERK2 IC$_{50}$ | [M + H]+ |
|---|---|---|---|
| 288. | 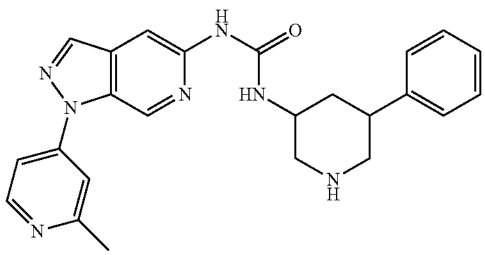 [SMILES: Cc1cc(-n2ncc3cc(NC(=O)NC4CNCC(c5ccccc5)C4)ncc32)ccn1] | 1-[1-(2-methylpyridin-4-yl)-1H-pyrazolo[3,4-c]pyridin-5-yl]-3-(5-phenylpiperidin-3-yl)urea 10.53 nM | Calc'd 428, found 428 |
| 289. | 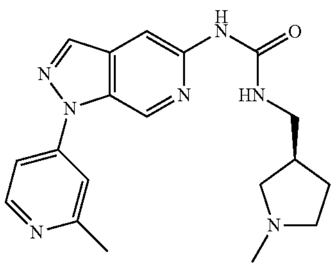 [SMILES: Cc1cc(-n2ncc3cc(NC(=O)NC[C@H]4CCN(C)C4)ncc32)ccn1] | 1-[1-(2-methylpyridin-4-yl)-1H-pyrazolo[3,4-c]pyridin-5-yl]-3-{[(3R)-1-methylpyrrolidin-3-yl]methyl}urea 36.62 nM | Calc'd 366.0, found 366 |
| 290. | 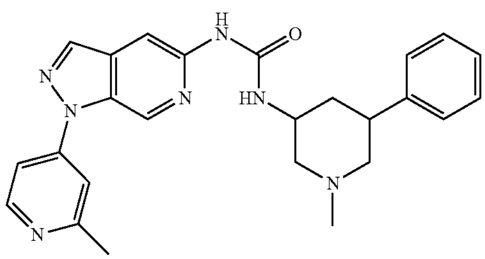 [SMILES: Cc1cc(-n2ncc3cc(NC(=O)NC4CC(c5ccccc5)CN(C)C4)ncc32)ccn1] | 1-(1-methyl-5-phenylpiperidin-3-yl)-3-[1-(2-methylpyridin-4-yl)-1H-pyrazolo[3,4-c]pyridin-5-yl]urea 17.83 nM | Calc'd 442.0, found 442 |
| 291. | 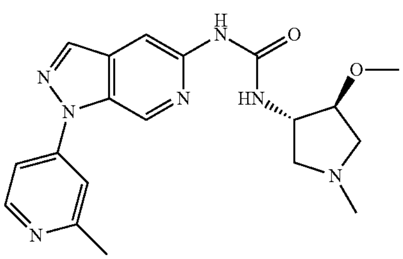 [SMILES: CO[C@H]1CN(C)C[C@@H]1NC(=O)Nc1cc2cnn(-c3ccnc(C)c3)c2cn1] | 1-[(3S,4S)-4-methoxy-1-methylpyrrolidin-3-yl]-3-[1-(2-methylpyridin-4-yl)-1H-pyrazolo[3,4-c]pyridin-5-yl]urea 46.38 nM | Calc'd 382.0, found 382 |

Synthetic Method IX

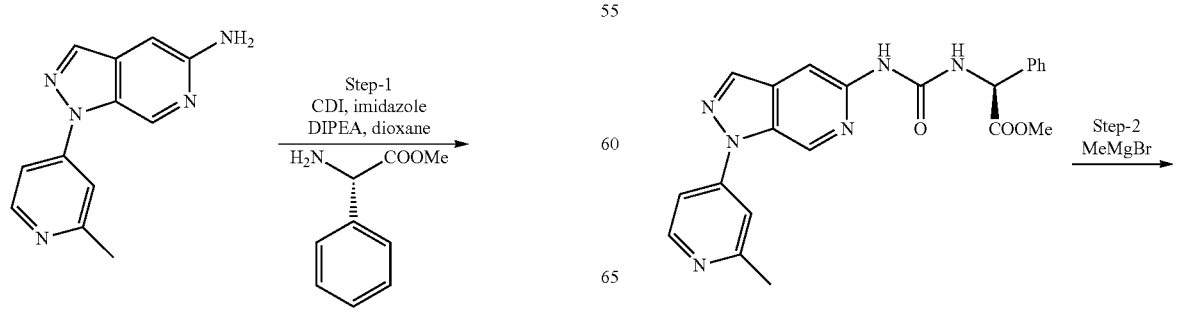

225
-continued

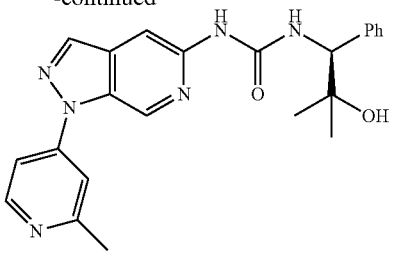

Example 292

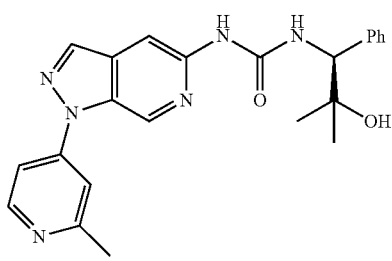 [SMILES: Cc1cc(-n2ncc3cc(NC(=O)N[C@@H](c4ccccc4)C(C)(C)O)ncc32)ccn1]

(S)-1-(2-methyl-2-hydroxy-1-phenylpropyl)-3-(1-(2-methylpyridin-4-yl)-1H-pyrazolo[3,4-c]pyridin-5-yl)urea 0.558 nM Step-1: Synthesis of (S)-methyl 2-(3-(1-(2-methyl-pyridin-4-yl)-1H-pyrazolo[3,4-c]pyridin-5-yl)ureido)-2-phenylacetate To a solution of 1-(2-methylpyridin-4-yl)-1H-pyrazolo[3,4-c]pyridin-5-amine (0.1 g, 0.44 mmol) in dioxane (4 mL) at 0° C. was added imidazole (0.15 g, 2.22 mmol) and N,N-carbonyl imidazole (0.36 g, 2.20 mmol) and the reaction mixture was stirred for 16 h at room temperature [the completion of the reaction was confirmed by quenching small aliquot of the reaction mixture with MeOH and mass was obtained for the corresponding carbamate [M+H]=284]. In a separate reaction flask was taken (S)-methyl 2-amino-2-phenylacetate (0.11 g, 0.67 mmol) in dioxane (2 mL) and

226

DIPEA (0.113 g, 0.88 mmol) was added. To this reaction mixture was added solution of carbamate of 1-(2-methyl-pyridin-4-yl)-1H-pyrazolo[3,4-c]pyridin-5-amine and the reaction mixture was stirred for 6 h at room temperature. LCMS analysis indicated the complete consumption of the starting material. The reaction mixture was bi-phased with ethyl acetate and water. The aqueous layer was extracted with ethyl acetate (2×5 mL) and the combined organic layers were washed with brine (1×10 mL), dried ($Na_2SO_4$) and concentrated under reduced pressure to afford the crude compound which was purified by flash column chromatography to furnish the title compound. MS (EI) calc'd for $C_{22}H_{20}N_6O_3$ [M+H]$^+$ 417. Found: 417; $^1$H NMR (400 MHz, DMSO-d6) δ 9.46 (d, 2H, J=12.3 Hz), 8.76-8.71 (m, 2H), 8.20 (bs, 2H), 8.15 (d, 1H, J=6.2 Hz), 7.98 (bs, 1H), 7.48-7.33 (m, 5H), 5.44 (d, 1H, J=7.1 Hz), 3.67 (s, 3H), 2.75 (s, 3H).

Step-2: Synthesis of (S)-1-(2-hydroxy-2-methyl-1-phenylpropyl)-3-(1-(2-methylpyridin-4-yl)-1H-pyrazolo[3,4-c]pyridin-5-yl)urea To a solution of (S)-methyl 2-(3-(1-(2-methylpyridin-4-yl)-1H-pyrazolo[3,4-c]pyridin-5-yl)ureido)-2-phenylacetate (0.03 g, 0.072 mmol) in THF (1 mL) at 0° C. was added methyl magnesium bromide (0.1 mL, 0.14 mmol, 1.4 M in THF) and stirred for 3 h at room temperature. TLC analysis indicated complete consumption of the starting material. The reaction mixture was bi-phased with $NH_4Cl$ solution and ethyl acetate. The aqueous layer was extracted with ethyl acetate (2×5 mL) and the combined organic layers were washed with brine (1×10 mL), dried ($Na_2SO_4$) and concentrated under reduced pressure to afford the crude compound which was purified by prep HPLC to furnish the title compound. MS calc'd for $C_{23}H_{24}N_6O_2$ [M+H]$^+$ 417. Found: 417; $^1$H NMR (400 MHz, $CD_3OD$) δ 9.47 (s, 1H), 8.71 (d, 1H, J=6.7 Hz), 8.62 (s, 1H), 8.41 (bs, 2H), 7.58 (s, 1H), 7.43 (d, 2H, J=7.5 Hz), 7.38-7.23 (m, 3H), 4.79 (s, 1H), 2.88 (s, 3H), 1.36 (s, 3H), 1.17 (s, 3H).

The following examples were made by using procedures similar to example 292 with appropriate reagent.

TABLE 21

| Ex. | Structure | IUPAC Name/ERK2 IC$_{50}$ | [M + H]+ |
|---|---|---|---|
| 293. | 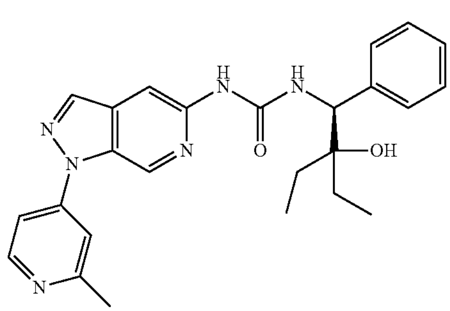 [SMILES: CCC(O)(CC)[C@@H](NC(=O)Nc1cc2cnn(-c3ccnc(C)c3)c2cn1)c1ccccc1] | 1-[(1S)-2-ethyl-2-hydroxy-1-phenylbutyl]-3-[1-(2-methylpyridin-4-yl)-1H-pyrazolo[3,4-c]pyridin-5-yl]urea 2.656 nM | Calc'd 445, found 445 |

TABLE 21-continued
| Ex. | Structure | IUPAC Name/ERK2 IC$_{50}$ | [M + H]+ |
|---|---|---|---|
| 294. | 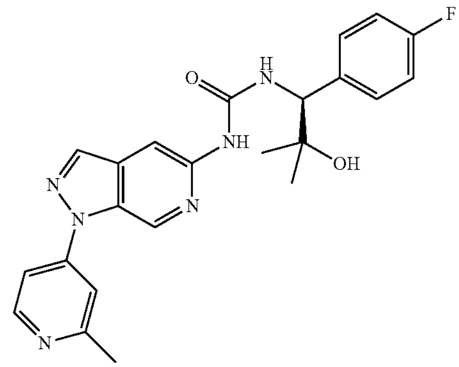 [SMILES: Cc1cc(-n2ncc3cc(NC(=O)N[C@@H](c4ccc(F)cc4)C(C)(C)O)ncc32)ccn1] | 1-[(1S)-1-(4-fluorophenyl)-2-hydroxy-2-methylpropyl]-3-[1-(2-methylpyridin-4-yl)-1H-pyrazolo[3,4-c]pyridin-5-yl]urea 1.081 nM | Calc'd 435, found 435 |
| 295. | 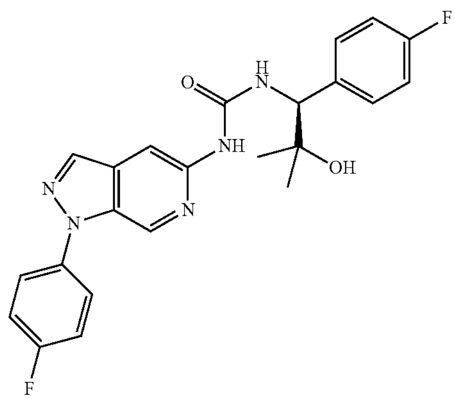 [SMILES: CC(C)(O)[C@@H](NC(=O)Nc1cc2cnn(-c3ccc(F)cc3)c2cn1)c1ccc(F)cc1] | 1-[(1S)-1-(4-fluorophenyl)-2-hydroxy-2-methylpropyl]-3-[1-(4-fluorophenyl)-1H-pyrazolo[3,4-c]pyridin-5-yl]urea 1.287 nM | Calc'd 438, found 438 |
| 296. | 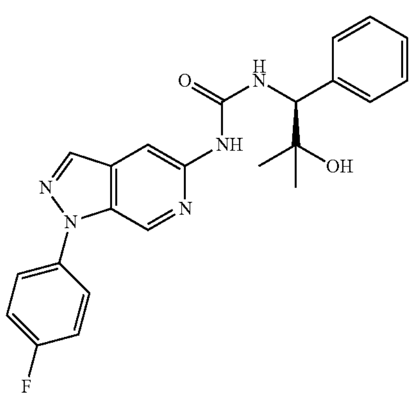 [SMILES: CC(C)(O)[C@@H](NC(=O)Nc1cc2cnn(-c3ccc(F)cc3)c2cn1)c1ccccc1] | 1-[1-(4-fluorophenyl)-1H-pyrazolo[3,4-c]pyridin-5-yl]-3-[(1S)-2-hydroxy-2-methyl-1-phenylpropyl]urea 0.8123 nM | Calc'd 420, found 420 |
Synthetic Method X
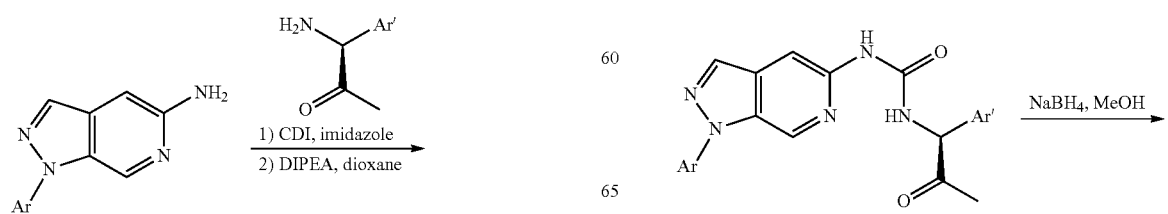

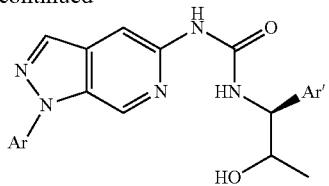

Example 297

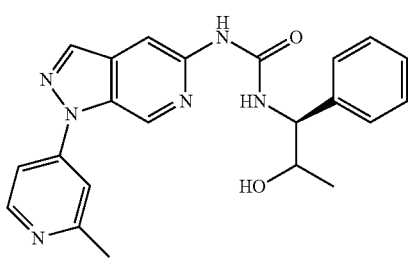 [SMILES: Cc1cc(-n2ncc3cc(NC(=O)N[C@@H](c4ccccc4)C(C)O)ncc32)ccn1]

(S)-1-(2-hydroxy-1-phenylpropyl)-3-(1-(2-methyl-pyridin-4-yl)-1H-pyrazolo[3,4-c]pyridin-5-yl)urea
1.062 nM Step 1: Synthesis of (S)-1-(1-(2-methylpyridin-4-yl)-1H-pyrazolo[3,4-c]pyridin-5-yl)-3-(2-oxo-1-phenylpropyl)urea To a solution of 1-(2-methylpyridin-4-yl)-1H-pyrazolo[3,4-c]pyridin-5-amine (0.05 g, 0.22 mmol) in dioxane (4 mL) at 0° C. was added imidazole (0.074 g, 1.11 mmol) and N,N'-carbonyl imidazole (0.179 g, 1.10 mmol) and stirred for 12 h at room temperature [the completion of the reaction was confirmed by quenching a small aliquot of the reaction mixture with MeOH and mass was obtained for the corresponding carbamate (M+H)=284]. In a separate reaction flask was taken (S)-1-amino-1-phenylpropan-2-one (0.271 g, 1.36 mmol) in dioxane (2 mL) and DIPEA (0.4 mL, 2.14 mmol) was added. To the reaction mixture was added solution of 1-(2-methylpyridin-4-yl)-1H-pyrazolo[3,4-c]pyridin-5-amine carbamate and the reaction mixture was stirred for 3 h at room temperature. LCMS analysis indicated the complete consumption of the starting material. The reaction mixture was bi-phased with ethyl acetate and water. The aqueous layer was extracted with ethyl acetate (2×5 mL) and the combined organic layers were washed with brine (1×10 mL), dried ($Na_2SO_4$) and concentrated under reduced pressure to afford the crude compound which was purified by flash column chromatography to furnish the title compound. MS calc'd for $C_{22}H_{20}N_6O_2$ [M+H]$^+$ 401. found: 401.

Step 2: Synthesis of (S)-1-(2-hydroxy-1-phenylpropyl)-3-(1-(2-methylpyridin-4-yl)-1H-pyrazolo[3,4-c]pyridin-5-yl)urea To a solution of (S)-1-(1-(2-methylpyridin-4-yl)-1H-pyrazolo[3,4-c]pyridin-5-yl)-3-(2-oxo-1-phenylpropyl)urea (0.23 g, 0.574 mmol) in methanol (5 mL) at 0° C. was added sodium borohydride (0.043 g, 1.15 mmol) portion wise. The reaction mixture was allowed to warm up to room temperature at which it was stirred for 3 h. TLC analysis indicated disappearance of the starting material. The solvent was removed under reduced pressure and the residue was bi-phased with water (10 mL) and dichloromethane (15 mL). The aqueous layer was extracted with dichloromethane (1×15 mL) and the combined organic layers were washed with water (1×10 mL), brine (1×10 mL), dried ($Na_2SO_4$) and concentrated under reduced pressure to furnish the title compound. MS calc'd for $C_{22}H_{22}N_6O_2$ [M+H]$^+$ 403. Found: 403; $^1$H NMR (400 MHz, $CD_3OD$) δ 9.44 (s, 1H), 8.69 (d, 1H, J=7.4 Hz), 8.60 (s, 1H), 8.40-8.30 (m, 2H), 7.90-7.82 (m, 1H), 7.44-7.32 (m, 4H), 7.31-7.23 (m, 1H), 4.91-4.80 (m, 1H), 4.20-4.10 (m, 1H), 2.86 (s, 3H), 1.14 (d, 3H, J=6.4 Hz).

Synthetic Method XI

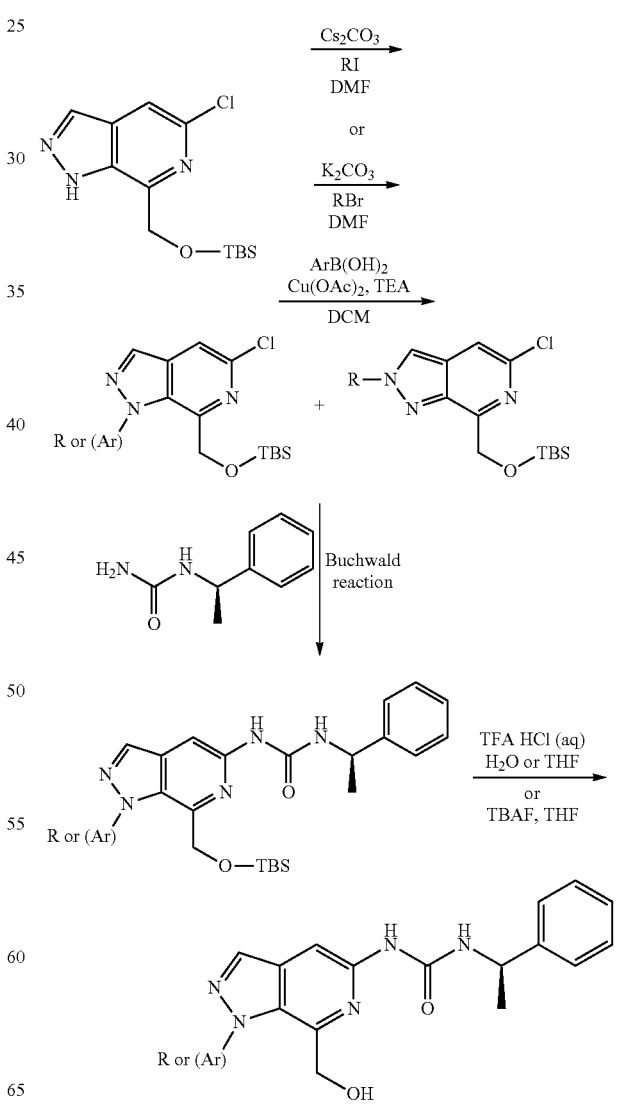

Example 298

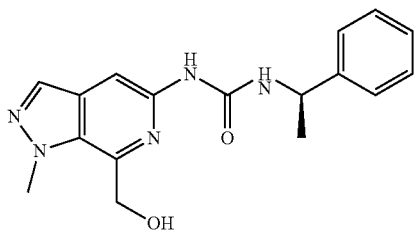 [SMILES: C[C@@H](NC(=O)Nc1cc2cnn(C)c2c(CO)n1)c1ccccc1]

(R)-1-(7-(Hydroxymethyl)-1-methyl-1H-pyrazolo[3,4-c]pyridin-5-yl)-3-(1-phenylethyl)urea 60.36 nM

Step 1: 7-(((tert-Butyldimethylsilyl)oxy)methyl)-5-chloro-1-methyl-1H-pyrazolo[3,4-c]pyridine 7-(((tert-Butyldimethylsilyl)oxy)methyl)-5-chloro-1H-pyrazolo[3,4-c]pyridine (243.7 mg, 0.818 mmol) and cesium carbonate (533 mg, 1.636 mmol) were dissolved in DMF (4 mL) and stirred for 10 min. Methyl iodide (0.061 mL, 0.982 mmol) was then added and stirred at RT overnight. Ethyl acetate was added and the organic layer was washed with brine, dried over sodium sulfate, filtered, and concentrated in vacuo while loading onto silica gel. Purification by flash chromatography (Biotage, 5-40% EtOAc/isohexane) gave 7-(((tert-butyldimethylsilyl)oxy)methyl)-5-chloro-1-methyl-1H-pyrazolo[3,4-c]pyridine (116 mg, 0.372 mmol) and 7-(((tert-butyldimethylsilyl)oxy)methyl)-5-chloro-2-methyl-2H-pyrazolo[3,4-c]pyridine. MS ESI calc'd. for $C_{14}H_{23}ClN_3OSi$ $[M+1]^+$ 312. found 312.

Step 2: (R)-1-(7-(((tert-Butyldimethylsilyl)oxy)methyl)-1-methyl-1H-pyrazolo[3,4-c]pyridin-5-yl)-3-(1-phenylethyl)urea 7-(((tert-Butyldimethylsilyl)oxy)methyl)-5-chloro-1-methyl-1H-pyrazolo[3,4-c]pyridine (116 mg, 0.372 mmol), (R)-1-(1-phenylethyl)urea (92 mg, 0.558 mmol), Brettphos palladacycle (29.7 mg, 0.037 mmol), cesium carbonate (315 mg, 0.967 mmol), and 2-(dicyclohexylphosphino)3,6-dimethoxy-2',4',6'-triisopropyl-1,1'-biphenyl (19.96 mg, 0.037 mmol) were dissolved in Dioxane (1.5 mL) and purged under argon for five minutes. The reaction mixture was heated to 90° C. and stirred for 6 hrs. Additional (R)-1-(1-phenylethyl)urea (46 mg, 0.279 mmol), cesium carbonate (157.5 mg, 0.483 mmol), and Brettphos palladacycle (14.85 mg, 0.0185 mmol) was added. The reaction mixture was degassed and stirred at 90° C. for 1.5 hours. The reaction mixture was filtered through Celite and rinsed with methanol. The filtrate was concentrated in vacuo while loading onto silica gel. Purification by flash chromatography (Biotage, 7-60% EtOAc/isohexane) gave (R)-1-(7-(((tert-Butyldimethylsilyl)oxy)methyl)-1-methyl-1H-pyrazolo[3,4-c]pyridin-5-yl)-3-(1-phenylethyl)urea. MS ESI calc'd. for $C_{23}H_{34}N_5O_2Si$ $[M+1]^+$ 440. found 440.

Step 4: (R)-1-(7-(Hydroxymethyl)-1-methyl-1H-pyrazolo[3,4-c]pyridin-5-yl)-3-(1-phenylethyl)urea (R)-1-(7-(((tert-Butyldimethylsilyl)oxy)methyl)-1-methyl-1H-pyrazolo[3,4-c]pyridin-5-yl)-3-(1-phenylethyl)urea (63.4 mg, 0.144 mmol) was dissolved in TFA (1.0 mL) and water (0.5 mL) and stirred at rt for 3 hours. Ethyl acetate was added and the organic layer washed with sat. sodium bicarbonate (×2), dried over sodium sulfate, filtered, and concentrated in vacuo while loading onto silica gel. Purification by flash chromatography (Biotage, 0-10% $CH_2Cl_2$/MeOH) gave (R)-1-(7-(hydroxymethyl)-1-methyl-1H-pyrazolo[3,4-c]pyridin-5-yl)-3-(1-phenylethyl)urea. MS ESI calc'd. for $C_{17}H_{20}N_5O_2$ $[M+1]^+$ 326. found 326. $^1$H NMR (500 MHz, DMSO-$d_6$) δ 8.88 (s, 1H), 7.99 (s, 1H), 7.72 (s, 1H), 7.36-7.29 (m, 4H), 7.22 (t, J=5.9 Hz, 1H), 5.70-5.59 (m, 1H), 4.93-4.80 (m, 2H), 4.26 (s, 3H), 1.39 (d, J=6.9 Hz, 3H).

Example 299

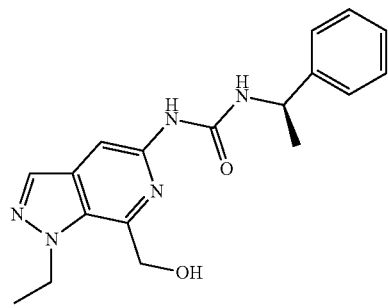 [SMILES: CCn1ncc2cc(NC(=O)N[C@H](C)c3ccccc3)nc(CO)c21]

1-[1-Ethyl-7-(hydroxymethyl)-1H-pyrazolo[3,4-c]pyridin-5-yl]-3-[(1R)-1-phenylethyl]urea 18.15 nM

Step 1: 7-[[(tert-Butyldimethylsilyl)oxy]methyl]-5-chloro-1-ethyl-1H-pyrazolo[3,4-c]pyridine To a solution of 7-[[(tert-butyldimethylsilyl)oxy]methyl]-5-chloro-1H-pyrazolo[3,4-c]pyridine (250 mg, 0.84 mmol) in N,N-dimethylformamide (5 mL) was added $K_2CO_3$ (174 mg, 1.25 mmol) and bromoethane (458 mg, 4.20 mmol). The resulting mixture was warmed to 80° C. and stirred for 2 h. Then the reaction mixture was concentrated under vacuum. The residue was diluted with EtOAc and washed with saturated. NaHCO$_3$, then dried (Na$_2$SO$_4$) and concentrated to afford 150 mg of a mixture of 7-[[(tert-butyldimethylsilyl)oxy]methyl]-5-chloro-1-ethyl-1H-pyrazolo[3,4-c]pyridine and 7-[[(tert-butyldimethylsilyl)oxy]methyl]-5-chloro-2-ethyl-2H-pyrazolo[3,4-c]pyridine, which was used in the next step without further purification: MS (EI) calc'd for $C_{15}H_{25}ClN_3OSi[M+H]^+$ 326. found 326.

Step 2: 1-[1-Ethyl-7-[[(tert-butyldimethylsilyl)oxy]methyl]-1H-pyrazolo[3,4-c]pyridin-5-yl]-3-[(1R)-1-phenylethyl]urea 1-[1-ethyl-7-[[(tert-butyldimethylsilyl)oxy]methyl]-1H-pyrazolo[3,4-c]pyridin-5-yl]-3-[(1R)-1-phenylethyl]urea was synthesized in one step from 7-[[(tert-butyldimethylsilyl)oxy]methyl]-5-chloro-1-ethyl-1H-pyrazolo[3,4-c]pyridine and (1R)-1-phenylethyl]urea as described in example 229: MS (EI) calc'd for $C_{24}H_{36}N_5O_2Si$ $[M+H]^+$ 454. found 454.

Step 3: 1-[1-Ethyl-7-(hydroxymethyl)-1H-pyrazolo[3,4-c]pyridin-5-yl]-3-[(1R)-1-phenylethyl]urea 1-[1-ethyl-7-[[(tert-butyldimethylsilyl)oxy]methyl]-1H-pyrazolo[3,4-c]pyridin-5-yl]-3-[(1R)-1-phenylethyl]urea (100 mg, 0.22 mmol) was dissolved in THF and 4 N HCl (1:3 by volume) (20 mL) and stirred for 2 h at 25° C. The resulting solution was concentrated under vacuum. The residue was diluted with saturated NaHCO$_3$, extracted with DCM, washed with brine, dried (Na$_2$SO$_4$) and concentrated under vacuum. The crude product was purified by Prep-HPLC with conditions: Column, XBridge Prep Shield RP18, 5 μm, 19×150 mm; Mobile phase, H$_2$O (0.05% TFA)/CH$_3$CN (30%-55% in 8 min); Detector, 254 nm and 220 nm. The desired fraction afforded 1-[1-ethyl-7-(hydroxymethyl)-1H-pyrazolo[3,4-c]pyridin-5-yl]-3-[(1R)-1-phenylethyl] ureas: MS (EI) calc'd for C$_{18}$H$_{22}$N$_5$O$_2$ [M+H]$^+$ 340. found 340; $^1$H NMR (300 MHz, DMSO-d$_6$): δ 8.96 (br s, 1H), 8.08 (s, 1H), 7.80 (br s, 1H), 7.73 (s, 1H), 7.35-7.30 (m, 4H), 7.27-7.21 (m, 1H), 4.90-4.82 (m, 3H), 4.63 (q, J=7.2 Hz, 2H), 1.41-1.39 (m, 6H).

Example 300

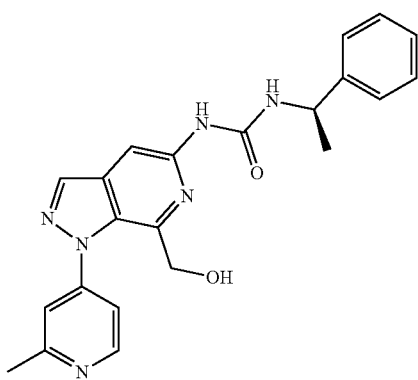 [SMILES: Cc1cc(-n2ncc3cc(NC(=O)N[C@H](C)c4ccccc4)nc(CO)c32)ccn1]

1-[7-(Hydroxymethyl)-1-(2-methylpyridin-4-yl)-1H-pyrazolo[3,4-c]pyridin-5-yl]-3-[(1R)-1-phenylethyl] urea 10.29 nM Step 1: 7-((tert-Butyldimethylsilyloxy)methyl)-5-chloro-1-(2-methylpyridin-4-yl)-1H-pyrazolo[3,4-c]pyridine A solution of 7-[[(tert-butyldimethylsilyl)oxy]methyl]-5-chloro-1H-pyrazolo[3,4-c]pyridine (2 g, 6.71 mmol) in DCM (50 mL) was treated with (2-methylpyridin-4-yl) boronic acid (1.84 g, 13.44 mmol), Cu(OAc)$_2$ (3.6 g, 20.00 mmol) and TEA (2.04 g, 20.16 mmol). The resulting mixture was stirred for 24 h at 25° C. and then quenched by the addition of saturated NH$_4$Cl. The mixture was extracted with DCM, washed with brine, then dried (Na$_2$SO$_4$), filtered and concentrated. The crude product was purified by chromatography on SiO$_2$, eluted with DCM/MeOH (50:1) to afford of 7-((tert-butyldimethylsilyloxy)methyl)-5-chloro-1-(2-methylpyridin-4-yl)-1H-pyrazolo[3,4-c]pyridine. MS (EI) calc'd for C$_{19}$H$_{26}$ClN$_4$OSi [M+H]$^+$ 389. found 389.

Step 2: 1-[7-((tert-butyldimethylsilyloxy)methyl)-1-(2-methylpyridin-4-yl)-1H-pyrazolo[3,4-c]pyridin-5-yl]-3-[(1R)-1-phenylethyl]urea 1-[7-((tert-butyldimethylsilyloxy)methyl)-1-(2-methylpyridin-4-yl)-1H-pyrazolo[3,4-c]pyridin-5-yl]-3-[(1R)-1-phenylethyl]urea was synthesized using Buchwald coupling similar to example 229 from 7-((tert-butyldimethylsilyloxy)methyl)-5-chloro-1-(2-methylpyridin-4-yl)-1H-pyrazolo[3,4-c]pyridine and (1R)-1-phenylethyl]urea: MS (EI) calc'd for C$_{28}$H$_{37}$N$_6$O$_2$Si [M+H]$^+$ 517. found 517.

Step 3: 1-[7-(hydroxymethyl)-1-(2-methylpyridin-4-yl)-1H-pyrazolo[3,4-c]pyridin-5-yl]-3-[(1R)-1-phenylethyl]urea A solution of 1-[7-((tert-butyldimethylsilyloxy)methyl)-1-(2-methylpyridin-4-yl)-1H-pyrazolo[3,4-c]pyridin-5-yl]-3-[(1R)-1-phenylethyl]urea (80 mg, 0.15 mmol) in THF (3 mL) was treated with TBAF (1 M in THF) (0.3 mL). The resulting solution was stirred for 1 h at 25° C. and then concentrated under reduced pressure. The crude product was purified by Prep-HPLC with conditions: Column, XBridge Prep Shield RP18, 5 μm, 19×150 mm; Mobile phase, H$_2$O (10 mM NH$_4$HCO$_3$)/CH$_3$CN (25%~32% in 6 min); Detector, 254 nm and 220 nm. The desired fraction afforded 8.2 mg (13%) of 1-[7-(hydroxymethyl)-1-(2-methylpyridin-4-yl)-1H-pyrazolo[3,4-c]pyridin-5-yl]-3-[(1R)-1-phenylethyl]urea: MS (EI) calc'd for C$_{22}$H$_{23}$N$_6$O$_2$ [M+H]$^+$ 403. found 403; $^1$H NMR (300 MHz, CD$_3$OD): δ 8.58 (d, J=5.4 Hz, 1H), 8.34 (s, 1H), 7.60 (s, 2H), 7.52 (d, J=5.4 Hz, 1H), 7.42 (d, J=7.5 Hz, 2H), 7.34 (t, J=7.5 Hz, 2H), 7.21 (t, J=7.2 Hz, 1H), 5.01 (q, J=6.9 Hz, 1H), 4.74 (s, 2H), 2.66 (s, 3H), 1.54 (d, J=6.9 Hz, 3H).

The following examples were made following protocol similar to examples 300 using the appropriate reagent.

TABLE 22

| EX | Structure | IUPAC Name/ERK2 IC$_{50}$ | [M + H]+ |
|---|---|---|---|
| 301. | 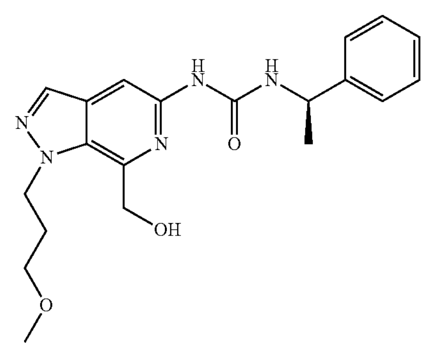 [SMILES: COCCCn1ncc2cc(NC(=O)N[C@H](C)c3ccccc3)nc(CO)c21] | 1-[7-(hydroxymethyl)-1-(3-methoxypropyl)-1H-pyrazolo[3,4-c]pyridin-5-yl]-3-[(1R)-1-phenylethyl]urea 77.97 nM | Calc'd 384, found 384 |

TABLE 22-continued

| EX | Structure | IUPAC Name/ERK2 IC$_{50}$ | [M + H]+ |
|---|---|---|---|
| 302. | 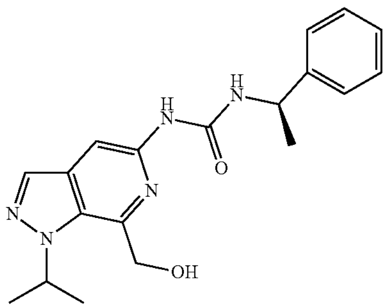 [SMILES: CC(C)n1ncc2cc(NC(=O)N[C@H](C)c3ccccc3)nc(CO)c21] | 1-[7-(hydroxymethyl)-1-(1-methylethyl)-1H-pyrazolo[3,4-c]pyridin-5-yl]-3-[(1R)-1-phenylethyl]urea 62.16 nM | Calc'd 354, found 354 |
| 303. | 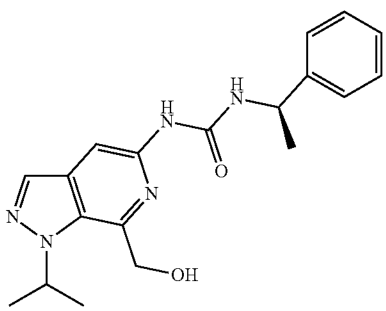 [SMILES: CC(C)n1ncc2cc(NC(=O)N[C@H](C)c3ccccc3)nc(CO)c21] | 1-[1-(cyclopentylmethyl)-7-(hydroxymethyl)-1H-pyrazolo[3,4-c]pyridin-5-yl]-3-[(1R)-1-phenylethyl]urea 294.2 nM | Calc'd 394, found 394 |
| 304. | 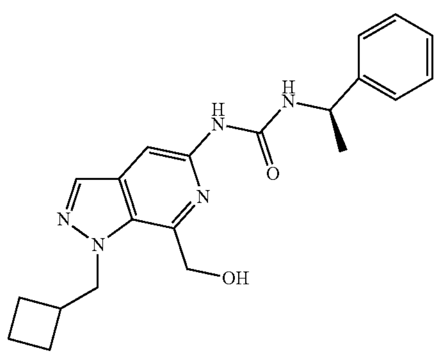 [SMILES: C[C@@H](NC(=O)Nc1cc2cnn(CC3CCC3)c2c(CO)n1)c1ccccc1] | 1-[1-(cyclobutylmethyl)-7-(hydroxymethyl)-1H-pyrazolo[3,4-c]pyridin-5-yl]-3-[(1R)-1-phenylethyl]urea 230.4 nM | Calc'd 380, found 380 |
| 305. | 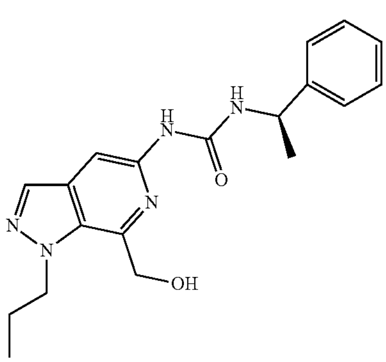 [SMILES: CCCn1ncc2cc(NC(=O)N[C@H](C)c3ccccc3)nc(CO)c21] | 1-[7-(hydroxymethyl)-1-propyl-1H-pyrazolo[3,4-c]pyridin-5-yl]-3-[(1R)-1-phenylethyl]urea 43.67 nM | Calc'd 354, found 354 |

TABLE 22-continued

| EX | Structure | IUPAC Name/ERK2 IC$_{50}$ | [M + H]+ |
|---|---|---|---|
| 306. | 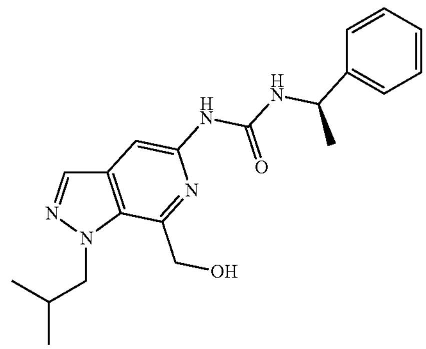 [SMILES: CC(C)Cn1ncc2cc(NC(=O)N[C@H](C)c3ccccc3)nc(CO)c21] | 1-[7-(hydroxymethyl)-1-(2-methylpropyl)-1H-pyrazolo[3,4-c]pyridin-5-yl]-3-[(1R)-1-phenylethyl]urea 178.2 nM | Calc'd 368, found 368 |
| 307. | 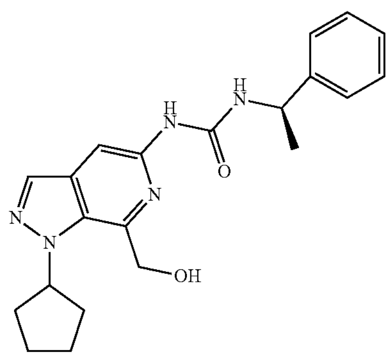 [SMILES: C[C@@H](NC(=O)Nc1cc2cnn(C3CCCC3)c2c(CO)n1)c1ccccc1] | 1-[1-cyclopentyl-7-(hydroxymethyl)-1H-pyrazolo[3,4-c]pyridin-5-yl]-3-[(1R)-1-phenylethyl]urea 125.4 nM | Calc'd 380, found 380 |
| 308. | 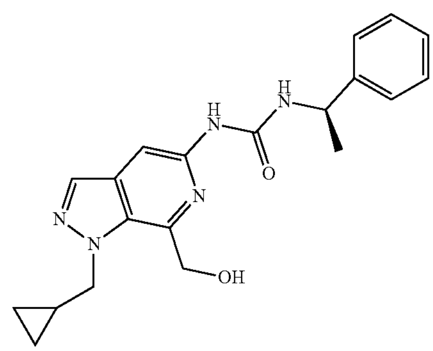 [SMILES: C[C@@H](NC(=O)Nc1cc2cnn(CC3CC3)c2c(CO)n1)c1ccccc1] | 1-[1-(cyclopropylmethyl)-7-(hydroxymethyl)-1H-pyrazolo[3,4-c]pyridin-5-yl]-3-[(1R)-1-phenylethyl]urea 79.5 nM | Calc'd 366, found 366 |
| 309. | 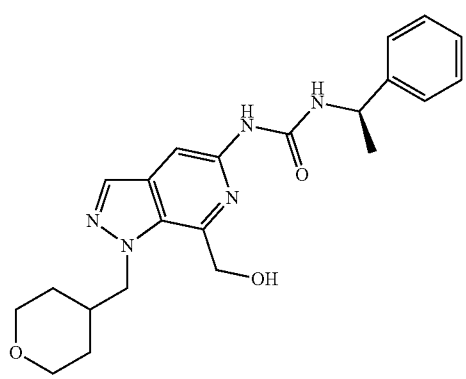 [SMILES: C[C@@H](NC(=O)Nc1cc2cnn(CC3CCOCC3)c2c(CO)n1)c1ccccc1] | 1-[7-(hydroxymethyl)-1-(tetrahydro-2H-pyran-4-ylmethyl)-1H-pyrazolo[3,4-c]pyridin-5-yl]-3-[(1R)-1-phenylethyl]urea 284.5 nM | Calc'd 410, found 410 |

TABLE 22-continued

| EX | Structure | IUPAC Name/ERK2 IC$_{50}$ | [M + H]+ |
|---|---|---|---|
| 310. | 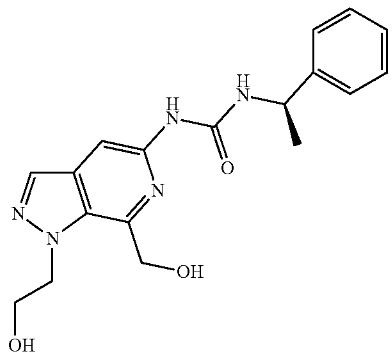 [SMILES: C[C@@H](NC(=O)Nc1cc2cnn(CCO)c2c(CO)n1)c1ccccc1] | 1-[1-(2-hydroxyethyl)-7-(hydroxymethyl)-1H-pyrazolo[3,4-c]pyridin-5-yl]-3-[(1R)-1-phenylethyl]urea 159.5 nM | Calc'd 356, found 356 |
| 311. | 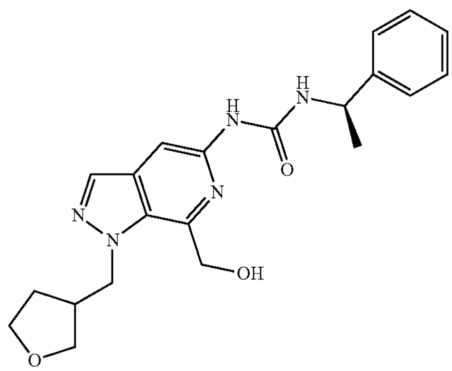 [SMILES: C[C@@H](NC(=O)Nc1cc2cnn(CC3CCOC3)c2c(CO)n1)c1ccccc1] | 1-[7-(hydroxymethyl)-1-(tetrahydrofuran-3-ylmethyl)-1H-pyrazolo[3,4-c]pyridin-5-yl]-3-[(1R)-1-phenylethyl]urea 157.6 nM | Calc'd 396, found 396 |
| 312. | 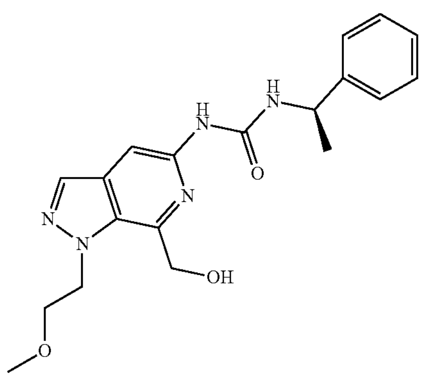 [SMILES: COCCn1ncc2cc(NC(=O)N[C@H](C)c3ccccc3)nc(CO)c21] | 1-[7-(hydroxymethyl)-1-(2-methoxyethyl)-1H-pyrazolo[3,4-c]pyridin-5-yl]-3-[(1R)-1-phenylethyl]urea 296 nM | Calc'd 370, found 370 |
| 313. | 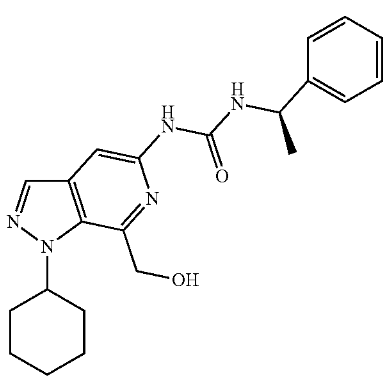 [SMILES: C[C@@H](NC(=O)Nc1cc2cnn(C3CCCCC3)c2c(CO)n1)c1ccccc1] | 1-[1-cyclohexyl-7-(hydroxymethyl)-1H-pyrazolo[3,4-c]pyridin-5-yl]-3-[(1R)-1-phenylethyl]urea 49.15 nM | Calc'd 394, found 394 |

TABLE 22-continued

| EX | Structure | IUPAC Name/ERK2 IC$_{50}$ | [M + H]+ |
|---|---|---|---|
| 314. | 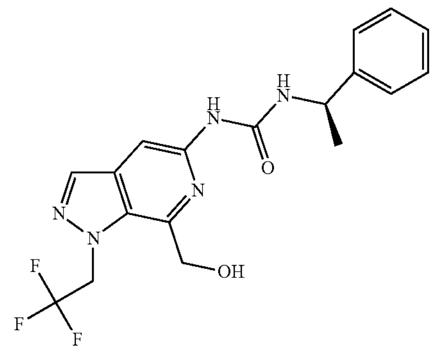 [SMILES: C[C@@H](NC(=O)Nc1cc2cnn(CC(F)(F)F)c2c(CO)n1)c1ccccc1] | 1-[7-(hydroxymethyl)-1-(2,2,2-trifluoroethyl)-1H-pyrazolo[3,4-c]pyridin-5-yl]-3-[(1R)-1-phenylethyl]urea 175.3 nM | Calc'd 394, found 394 |
| 315. | 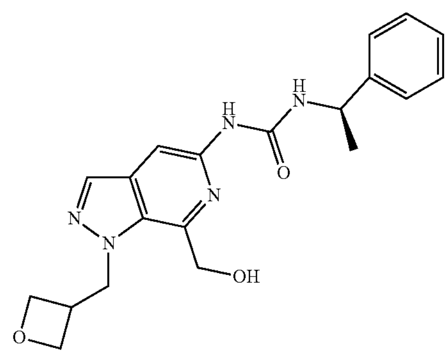 [SMILES: C[C@@H](NC(=O)Nc1cc2cnn(CC3COC3)c2c(CO)n1)c1ccccc1] | 1-[7-(hydroxymethyl)-1-(oxetan-3-ylmethyl)-1H-pyrazolo[3,4-c]pyridin-5-yl]-3-[(1R)-1-phenylethyl]urea 143.2 nM | Calc'd 382, found 382 |
| 316. | 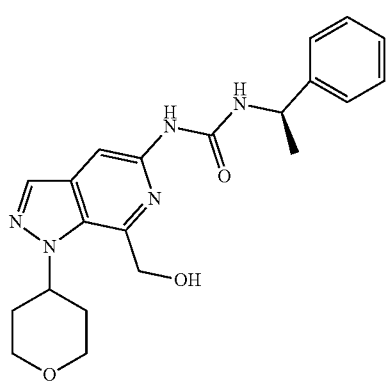 [SMILES: C[C@@H](NC(=O)Nc1cc2cnn(C3CCOCC3)c2c(CO)n1)c1ccccc1] | 1-[7-(hydroxymethyl)-1-(tetrahydro-2H-pyran-4-yl)-1H-pyrazolo[3,4-c]pyridin-5-yl]-3-[(1R)-1-phenylethyl]urea 235.5 nM | Calc'd 396, found 396 |

Example 317

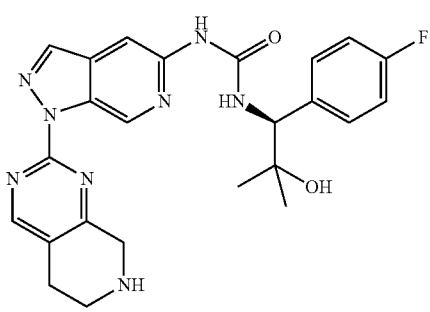 [SMILES: CC(C)(O)[C@@H](NC(=O)Nc1cc2cnn(-c3ncc4c(n3)CNCC4)c2cn1)c1ccc(F)cc1]

1-[(1S)-1-(4-fluorophenyl)-2-hydroxy-2-methylpropyl]-3-[1-(5,6,7,8-tetrahydropyrido[3,4-d]pyrimidin-2-yl)-1H-pyrazolo[3,4-c]pyridin-5-yl]urea 326.8 nM (S)-tert-butyl 2-(5-(3-(1-(4-fluorophenyl)-2-hydroxy-2-methylpropyl)ureido)-1H-pyrazolo[3,4-c]pyridin-1-yl)-5,6-dihydropyrido[3,4-d]pyrimidine-7(8H)-carboxylate (5 mg, 8.67 mol) and hydrogen chloride 1N in diethyl either (0.087 ml, 0.087 mmol) and Dioxane (1 ml) were added to a reaction tube. It was stirred at rt for overnight. The solvent was removed and the product was dried under vacuum to afford 1-[(1S)-1-(4-fluorophenyl)-2-hydroxy-2-methylpropyl]-3-[1-(5,6,7,8-tetrahydropyrido[3,4-d]pyrimidin-2-yl)-1H-pyrazolo[3,4-c]pyridin-5-yl]urea. LCMS calc'd for $C_{24}H_{25}FN_8O_2$ [M+H]$^+$ 477 found 477; 1H NMR (CDCl$_3$), 8.1-8.8 (m, 3H), 7.2 (m, 4H), 6.9 (s, 1H), 5.6 (b, 2H) 5.2 (b, 1H), 4.7 (s, 1H), 3.6 (m, 5H), 2.0 (b, 2H), 1.24 (s, 6H)

Synthetic Method XII

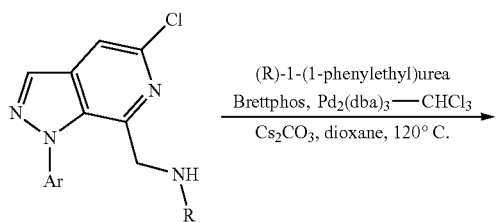

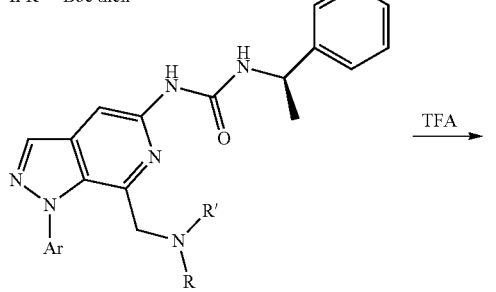

R' = Boc or R

If R' = Boc then

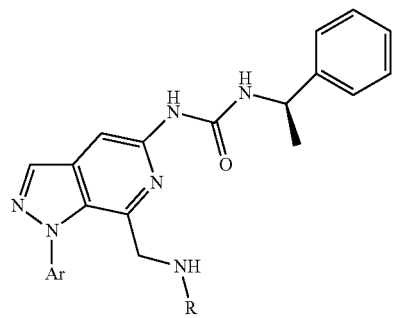

Example 318

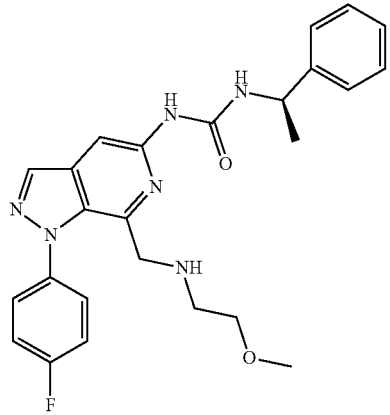 [SMILES: COCCNCc1nc(NC(=O)N[C@H](C)c2ccccc2)cc2cnn(-c3ccc(F)cc3)c12]

1-[1-(4-Fluorophenyl)-7-{[(2-methoxyethyl)amino]methyl}-1H-pyrazolo[3,4-c]pyridin-5-yl]-3-[(1R)-1-phenylethyl]urea 140.7 nM Step 1: tert-Butyl N-[[1-(4-fluorophenyl)-5-([[(1R)-1-phenylethyl]carbamoyl]amino)-1H-pyrazolo[3,4-c]pyridin-7-yl]methyl]-N-(2-methoxyethyl)carbamate tert-Butyl N-[[1-(4-fluorophenyl)-5-([[(1R)-1-phenylethyl]carbamoyl]amino)-1H-pyrazolo[3,4-c]pyridin-7-yl]methyl]-N-(2-methoxyethyl)carbamate was synthesized in one step from tert-butyl N-[[5-chloro-1-(4-fluorophenyl)-1H-pyrazolo[3,4-c]pyridin-7-yl]methyl]-N-(2-methoxyethyl)carbamate as described in example 226 procedure: MS (EI) calc'd for $C_{30}H_{36}FN_6O_4[M+H]^+$ 563. found 563.

Step 2: 1-[1-(4-Fluorophenyl)-7-{[(2-methoxyethyl)amino]methyl)}-1H-pyrazolo[3,4-c]pyridin-5-yl]-3-[(1R)-1-phenylethyl]urea Tert-butyl N-[[1-(4-fluorophenyl)-5-([[(1R)-1-phenylethyl]carbamoyl]amino)-1H-pyrazolo[3,4-c]pyridin-7-yl]methyl]-N-(2-methoxyethyl)carbamate (200 mg, 0.36 mmol, 1.00 equiv) was dissolved with trifluoroacetic acid (3 mL)/DCM (5 mL) and stirred for 2 h at 25° C. Then the resulting solution was concentrated under reduced pressure. The crude product was purified by Prep-HPLC with conditions: Column, XBridge Prep Shield RP18, 5 μm, 19×150 mm; Mobile phase, $H_2O$ (10 mM $NH_4HCO_3$)/$CH_3CN$ (25%~35% in 6 min); Detector, 254 nm and 220 nm. The desired fraction afforded 77 mg of 1-[1-(4-fluorophenyl)-7-{[(2-methoxyethyl)amino]methyl}-1H-pyrazolo[3,4-c]pyridin-5-yl]-3-[(1R)-1-phenylethyl]urea as an off-white solid: MS (EI) calc'd for $C_{25}H_{28}FN_6O_2[M+H]^+$ 463. found 463; $^1H$ NMR (300 MHz, DMSO-$d_6$): δ 8.92 (s, 1H), 8.29 (s, 1H), 7.81 (s, 1H), 7.72 (br s, 1H), 7.64-7.60 (m, 2H), 7.39-7.27 (m, 7H), 7.22-7.17 (m, 1H), 4.80 (q, J=6.9 Hz, 1H), 3.60 (s, 2H), 3.28 (s, 2H), 3.19 (t, J=5.4 Hz, 2H), 3.09 (s, 3H), 1.37 (d, J=6.9 Hz, 3H).

The following examples were made by using similar procedure as described in example 318.

TABLE 23

| EX | Structure | IUPAC Name/ERK2 IC$_{50}$ | [M + H]+ |
|---|---|---|---|
| 319. | 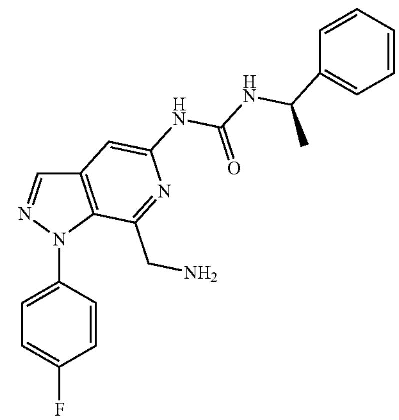 | 1-[7-(aminomethyl)-1-(4-fluorophenyl)-1H-pyrazolo[3,4-c]pyridin-5-yl]-3-[(1R)-1-phenylethyl]urea 515.5 nM | Calc'd 405, found 405 |
| 320. | 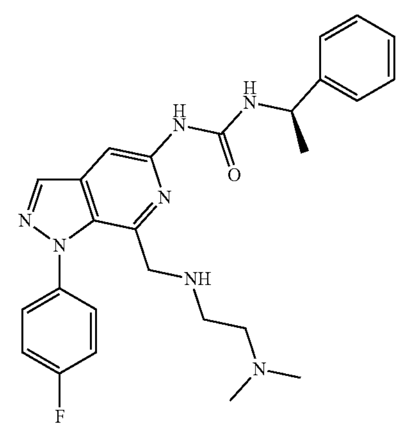 [SMILES: C[C@@H](NC(=O)Nc1cc2cnn(-c3ccc(F)cc3)c2c(CNCCN(C)C)n1)c1ccccc1] | 1-[7-({[2-(dimethylamino)ethyl]amino}methyl)-1-(4-fluorophenyl)-1H-pyrazolo[3,4-c]pyridin-5-yl]-3-[(1R)-1-phenylethyl]urea 1240 nM | Calc'd 476, found 476 |
| 321. | 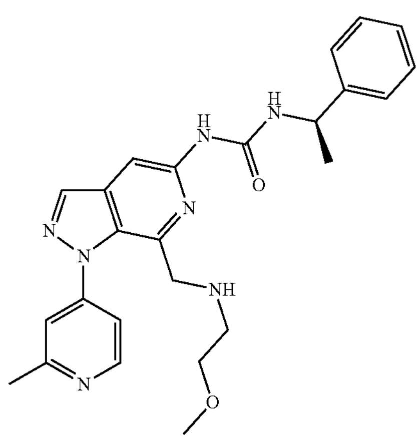 [SMILES: COCCNCc1nc(NC(=O)N[C@H](C)c2ccccc2)cc2cnn(-c3ccnc(C)c3)c12] | 1-[7-{[(2-methoxyethyl)amino]methyl}-1-(2-methylpyridin-4-yl)-1H-pyrazolo[3,4-c]pyridin-5-yl]-3-[(1R)-1-phenylethyl]urea 103.2 nM | Calc'd 460, found 460 |

| EX | Structure | IUPAC Name/ERK2 IC$_{50}$ | [M + H]+ |
|---|---|---|---|
| 322. | 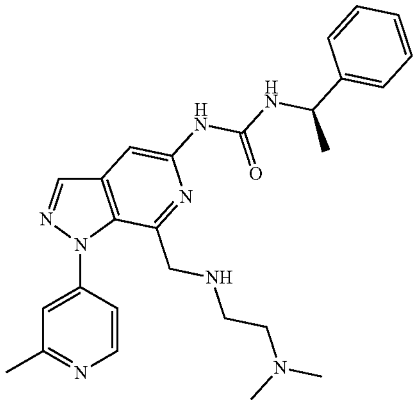 [SMILES: Cc1cc(-n2ncc3cc(NC(=O)N[C@H](C)c4ccccc4)nc(CNCCN(C)C)c32)ccn1] | 1-[7-({[2-(dimethylamino)ethyl]amino}methyl)-1-(2-methylpyridin-4-yl)-1H-pyrazolo[3,4-c]pyridin-5-yl]-3-[(1R)-1-phenylethyl]urea 86.61 nM | Calc'd 473, found 473 |

Example 323

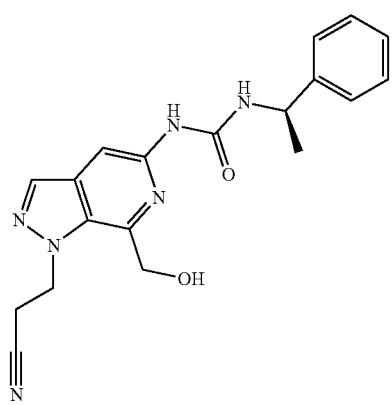 [SMILES: C[C@@H](NC(=O)Nc1cc2cnn(CCC#N)c2c(CO)n1)c1ccccc1]

1-[1-(2-Cyanoethyl)-7-(hydroxymethyl)-1H-pyrazolo[3,4-c]pyridin-5-yl]-3-[(R)-1-phenylethyl]urea 110.5 nM To a solution of 3-[7-(hydroxymethyl)-1H-pyrazolo[3,4-c]pyridin-5-yl]-1-[(1R)-1-phenylethyl]urea (30 mg, 0.10 mmol) in N,N-dimethylformamide (2 mL) was added 3-bromopropanenitrile (15.6 mg, 0.12 mmol) and potassium carbonate (40 mg, 0.29 mmol). The resulting solution was stirred for 1 h at 90° C. under microwave irradiation. The resulting solution was concentrated under vacuum. The residue was diluted with EtOAc, washed with brine, then dried (Na$_2$SO$_4$) and concentrated under vacuum. The crude product was purified by Prep-HPLC with conditions: Column, XBridge Prep Shield RP18, 5 μm, 19×150 mm; Mobile phase, H$_2$O (0.05% NH$_4$HCO$_3$)/CH$_3$CN (15%~55% in 10 min); Detector, 254 nm and 220 nm. The desired fraction afforded 6 mg of 1-[1-(2-cyanoethyl)-7-(hydroxymethyl)-1H-pyrazolo[3,4-c]pyridin-5-yl]-3-[(1R)-1-phenylethyl]urea. MS (EI) calc'd for C$_{19}$H$_{21}$N$_6$O$_2$ [M+H]$^+$ 365. found 365. $^1$H NMR (400 MHz, DMSO-d$_6$) δ 8.97 (s, 1H), 8.20 (s, 1H), 7.82 (s, 1H), 7.73 (br s, 1H), 7.38-7.36 (t, J=2.6 Hz, 4H), 7.25-7.27 (q, J=2.8 Hz, 1H), 5.86 (s, 1H), 4.94-4.88 (m, 5H), 3.17 (t, J=6.4 Hz, 2H), 1.43 (d, J=6.8 Hz, 3H).

Synthetic Method 20

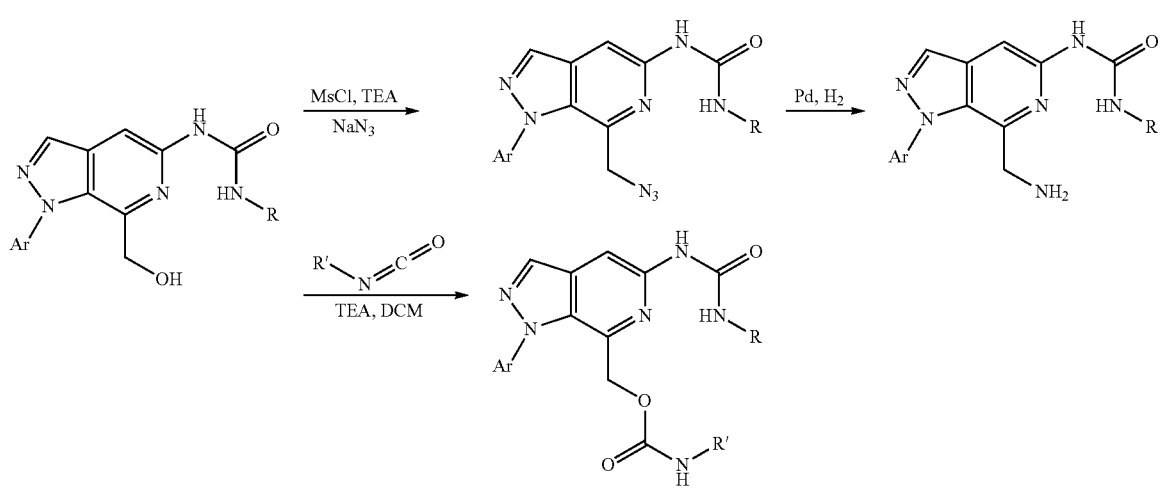

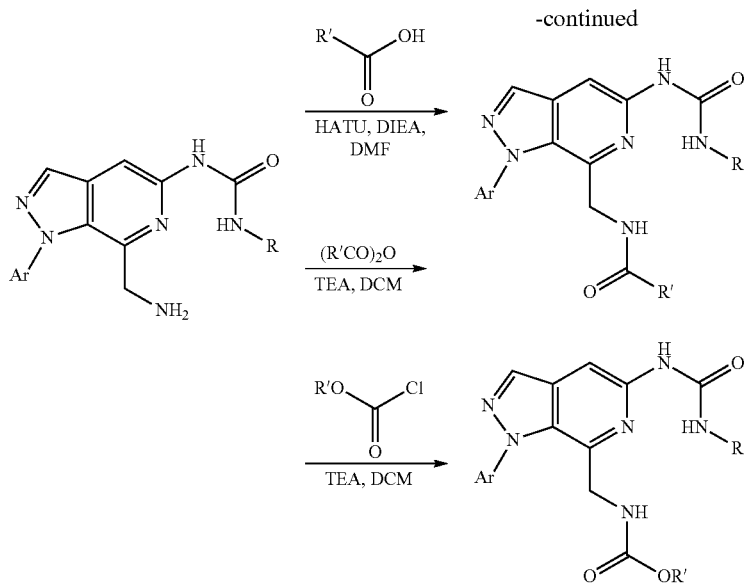

Example 324

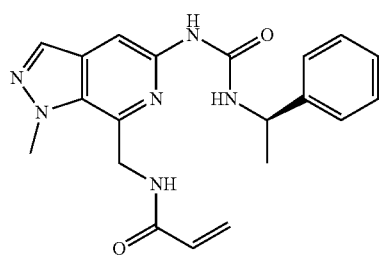 [SMILES: C=CC(=O)NCc1nc(NC(=O)N[C@H](C)c2ccccc2)cc2cnn(C)c12]

N-{[1-Methyl-5-({[(1R)-1-phenylethyl]carbamoyl}amino)-1H-pyrazolo[3,4-c]pyridin-7-yl]methyl}prop-2-enamide 432.4 nM Step 1: (R)-1-(7-(Azidomethyl)-1-methyl-1H-pyrazolo[3,4-c]pyridin-5-yl)-3-(1-phenylethyl)urea To a solution of (R)-1-(7-(hydroxymethyl)-1-methyl-1H-pyrazolo[3,4-c]pyridin-5-yl)-3-(1-phenylethyl)urea (900 mg, 2.07 mmol) in THF (10 ml) was added methanesulfonyl chloride (238 mg, 2.07 mmol) at 0° C. in 5 min. The resulting solution was stirred at 25° C. for 2 h and then quenched by the addition of water (10 mL). The mixture was extracted with EtOAc, washed with brine, dried ($Na_2SO_4$), filtered and concentrated under reduced pressure to give (R)-(1-methyl-5-(3-(1-phenylethyl)ureido)-1H-pyrazolo[3,4-c]pyridin-7-yl)methyl methanesulfonate (688 mg) as a solid, which was dissolved in N,N-dimethylacetamide (10 ml). Then sodium azide (135 mg, 2.07 mmol) was added and the resulting solution was stirred at 25° C. for 12 h. The mixture was diluted with water, extracted with EtOAc, washed with brine, dried ($Na_2SO_4$), filtered and concentrated under reduced pressure to give (R)-1-(7-(azidomethyl)-1-methyl-1H-pyrazolo[3,4-c]pyridin-5-yl)-3-(1-phenylethyl)urea (410 mg), which was used in the next step directly without further purification. MS (EI) calc'd for $C_{17}H_{19}N_8O$ $[M+H]^+$ 351. found 351.

Step 2: (S)-1-(2-Amino-1-phenylethyl)-3-(1-methyl-1H-pyrazolo[3,4-c]pyridin-5-yl)urea A mixture of (R)-1-(7-(azidomethyl)-1-methyl-1H-pyrazolo[3,4-c]pyridin-5-yl)-3-(1-phenylethyl)urea (500 mg, 1.17 mmol) and Pd/C (623 mg, 0.58 mmol) (10%, dry) in MeOH (10 ml) was deoxygenated by bubbling hydrogen for 5 min. Then the reaction mixture was stirred for 2 h at 25° C. under an atmosphere of hydrogen (3-4 atm). The resulting mixture was filtered. The filtrate was concentrated under vacuum. The residue was purified by chromatography on $SiO_2$, eluted with DCM/MeOH (15/1) to give (R)-1-(7-(aminomethyl)-1-methyl-1H-pyrazolo[3,4-c]pyridin-5-yl)-3-(1-phenylethyl)urea: MS (EI) calc'd for $C_{17}H_{21}N_6O$ $[M+H]^+$ 325. found 325.

Step 3: N-{[1-Methyl-5-({[(1R)-1-phenylethyl]carbamoyl}amino)-1H-pyrazolo[3,4-c]pyridin-7-yl]methyl}prop-2-enamide HATU (527 mg, 1.38 mmol) was added to a stirred mixture of acrylic acid (100 mg, 1.38 mmol) in DMF (10 ml), and then (R)-1-(7-(aminomethyl)-1-methyl-1H-pyrazolo[3,4-c]pyridin-5-yl)-3-(1-phenylethyl)urea (300 mg, 0.93 mmol), DIEA (0.48 ml, 2.76 mmol) were added. The reaction mixture was stirred at 25° C. for 3 h. The resulting mixture was diluted with water, extracted with EtOAc, washed with brine, dried ($Na_2SO_4$), filtered and concentrated under reduced pressure. The residue was purified by Prep-TLC (petroleum ether/EtOAc=1/5) to give N-{[1-methyl-5-({[(1R)-1-phenylethyl]carbamoyl}amino)-1H-pyrazolo[3,4-c]pyridin-7-yl]methyl}prop-2-enamide. MS (EI) calc'd for $C_{20}H_{23}N_6O_2$ $[M+H]^+$ 379. found 379. $^1$H NMR (400 MHz, DMSO-$d_6$): δ 8.84 (s, 1H), 8.66 (d, J=4.8 Hz, 1H), 8.03 (s, 1H), 7.78 (s, 1H), 7.68 (br s, 1H), 7.34-7.31 (m, 4H), 7.25-7.22 (m, 1H), 6.31-6.17 (m, 2H), 5.64-5.61 (m, 1H), 4.90-4.85 (m, 3H), 4.22 (s, 3H), 1.41 (d, J=7.2 Hz, 3H).

Example 325

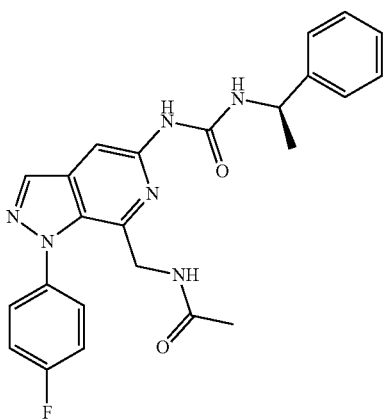 [SMILES: CC(=O)NCc1nc(NC(=O)N[C@H](C)c2ccccc2)cc2cnn(-c3ccc(F)cc3)c12]

N-{[1-(4-Fluorophenyl)-5-({[(1R)-1-phenylethyl]carbamoyl}amino)-1H-pyrazolo[3,4-c]pyridin-7-yl]methyl)}acetamide 289.3 nM To a solution of 3-[7-(aminomethyl)-1-(4-fluorophenyl)-1H-pyrazolo[3,4-c]pyridin-5-yl]-1-[(1R)-1-phenylethyl]urea (27 mg, 0.07 mmol) in DCM (0.5 mL) was added triethylamine (20.3 mg, 0.20 mmol) and acetic anhydride (8.2 mg, 0.08 mmol). The resulting solution was stirred for 2 h at 20° C. Then the mixture was quenched by the addition of MeOH and concentrated under reduced pressure. The crude product was purified by Prep-HPLC with conditions: Column, XBridge Prep Shield RP18, 5 μm, 19×150 mm; Mobile phase, H$_2$O (0.05% NH$_4$HCO$_3$)/CH$_3$CN (44%~57% in 8 min); Detector, 254 nm and 220 nm. The desired fraction afforded of N-{[1-(4-fluorophenyl)-5-({[(1R)-1-phenylethyl]carbamoyl}amino)-1H-pyrazolo[3,4-c]pyridin-7-yl]methyl}acetamide. MS (EI) calc'd for C$_{24}$H$_{24}$FN$_6$O$_2$ [M+H]$^+$ 447. found 447. $^1$H NMR (300 MHz, DMSO-d$_6$): δ 8.90 (s, 1H), 8.30 (s, 1H), 7.97 (t, J=4.8 Hz, 1H), 7.84 (s, 1H), 7.63-7.59 (m, 3H), 7.39-7.27 (m, 6H), 7.22-7.18 (m, 1H), 4.83 (t, J=7.2 Hz, 1H), 4.07 (d, J=4.8 Hz, 2H), 1.67 (s, 3H), 1.37 (d, J=6.9 Hz, 3H).

Example 326

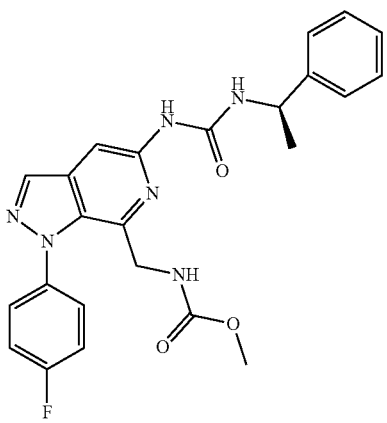 [SMILES: COC(=O)NCc1nc(NC(=O)N[C@H](C)c2ccccc2)cc2cnn(-c3ccc(F)cc3)c12]

Methyl {[1-(4-fluorophenyl)-5-({[(1R)-1-phenylethyl]carbamoyl}amino)-1H-pyrazolo[3,4-c]pyridin-7-yl]methyl}carbamate 17.65 nM To a solution of 1-[7-(aminomethyl)-1-(4-fluorophenyl)-1H-pyrazolo[3,4-c]pyridin-5-yl]-3-[(1R)-1-phenylethyl]urea (42 mg, 0.10 mmol) in DCM (2 mL, 31.46 mmol) under nitrogen was added TEA (15 mg, 0.15 mmol) and methyl chloroformate (12 mg, 0.13 mmol). The resulting solution was stirred for 2 h at 20° C. and then concentrated under vacuum. The crude product was purified by Prep-HPLC with conditions: Column, XBridge Prep Shield RP18, 5 μm, 19×150 mm; Mobile phase, H$_2$O (0.05% TFA)/CH$_3$CN (30%~50% in 10 min); Detector, 254 nm and 220 nm. The desired fraction afforded methyl {[1-(4-fluorophenyl)-5-({[(1R)-1-phenylethyl]carbamoyl}amino)-1H-pyrazolo[3,4-c]pyridin-7-yl]methyl}carbamate. MS (EI) calc'd for C$_{24}$H$_{24}$FN$_6$O$_3$[M+H]$^+$ 463. found 463. $^1$H NMR (300 MHz, CD$_3$OD): δ 8.17 (s, 1H), 7.62-7.51 (m, 3H), 7.34-7.27 (m, 6H), 7.25-7.15 (m, 1H), 4.98 (q, J=6.9 Hz, 1H), 4.18 (dd, J=16.2, 5.1 Hz, 2H), 3.46 (s, 3H), 1.50 (d, J=6.9 Hz, 3H).

Example 327

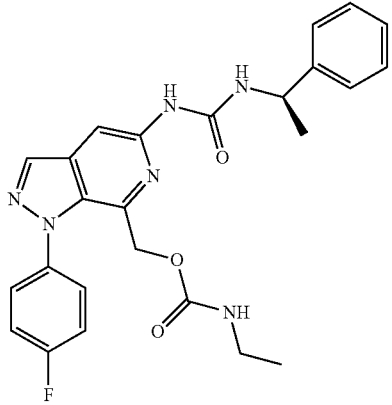 [SMILES: CCNC(=O)OCc1nc(NC(=O)N[C@H](C)c2ccccc2)cc2cnn(-c3ccc(F)cc3)c12]

[1-(4-Fluorophenyl)-5-({[(1R)-1-phenylethyl]carbamoyl}amino)-1H-pyrazolo[3,4-c]pyridin-7-yl]methyl ethylcarbamate 116.4 nM To a solution of 1-[7-(hydroxymethyl)-1-(4-fluorophenyl)-1H-pyrazolo[3,4-c]pyridin-5-yl]-3-[(1R)-1-phenylethyl]urea (70 mg, 0.17 mmol) in DCM (3 mL) was added isocyanatomethane (30 mg, 0.53 mmol) and TEA (52 mg, 0.51 mmol). The resulting mixture was stirred for 3 h at 25° C. and then concentrated under reduced pressure. The crude product was purified by Prep-HPLC with conditions: Column, XBridge Prep Shield RP18, 5 μm, 19×150 mm; Mobile phase, H$_2$O (10 mM NH$_4$HCO$_3$)/CH$_3$CN (25%~32% in 6 min); Detector, 254 nm and 220 nm. The desired fraction afforded 16.7 mg of [1-(4-fluorophenyl)-5-({[(1R)-1-phenylethyl]carbamoyl}amino)-1H-pyrazolo[3,4-c]pyridin-7-yl] methyl ethylcarbamate. MS (EI) calc'd for C$_{25}$H$_{26}$FN$_6$O$_3$ [M+H]$^+$ 477. found 477. $^1$H NMR (300 MHz, CDCl$_3$): δ 8.17 (s, 1H), 7.50 (t, J=6.9 Hz, 2H), 7.42 (d, J=8.7 Hz, 2H), 7.33 (t, J=7.4 Hz, 3H), 7.27-7.22 (m, 3H), 5.15 (t, J=6.9 Hz, 1H), 5.00 (s, 2H), 3.02-3.08 (m, 2H), 1.59 (d, J=6.9 Hz, 3H), 0.94 (t, J=6.9 Hz, 3H).

Synthetic Method

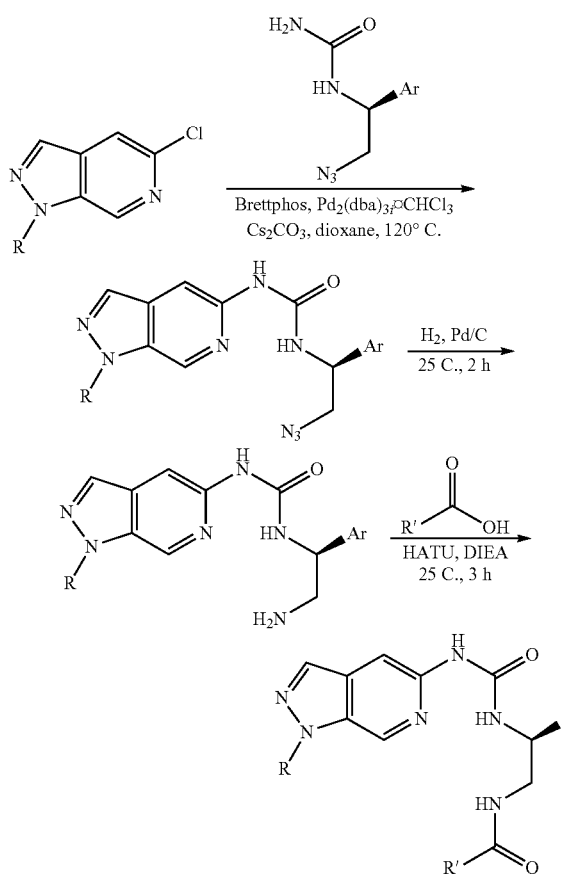

Example 328

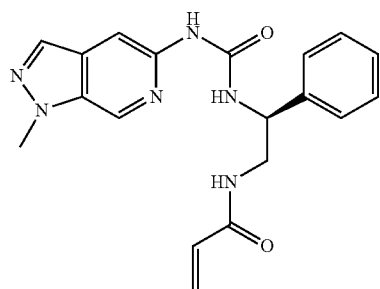 [SMILES: C=CC(=O)NC[C@@H](NC(=O)Nc1cc2cnn(C)c2cn1)c1ccccc1]

N-[(2S)-2-{[(1-Methyl-1H-pyrazolo[3,4-c]pyridin-5-yl)carbamoyl]amino}-2-phenylethyl]prop-2-enamide
796.2 nM

Step 1: (S)-1-(2-azido-1-phenylethyl)-3-(1-methyl-1H-pyrazolo[3,4-c]pyridin-5-yl)urea This compound was synthesized by the same method as described in example 229 Buchwald coupling except 5-chloro-1-methyl-1H-pyrazolo[3,4-c]pyridine and (S)-1-(2-azido-1-phenylethyl)urea were used: MS (EI) calc'd for $C_{16}H_{17}N_8O$ [M+H]$^+$ 337. found 337.

Step 2: (S)-1-(2-amino-1-phenylethyl)-3-(1-methyl-1H-pyrazolo[3,4-c]pyridin-5-yl)urea A mixture of (S)-1-(2-azido-1-phenylethyl)-3-(1-methyl-1H-pyrazolo[3,4-c]pyridin-5-yl)urea (620 mg, 1.60 mmol) and Pd/C (80 mg, 0.75 mmol) in MeOH (10 ml) was deoxygenated by bubbling hydrogen for 5 min. Then the reaction mixture was stirred for 2 h at 25° C. under an atmosphere of hydrogen (3~4 atm). The resulting mixture was filtered. The filtrate was concentrated under vacuum to give (S)-1-(2-amino-1-phenylethyl)-3-(1-methyl-1H-pyrazolo[3,4-c]pyridin-5-yl)urea. MS (EI) calc'd for $C_{16}H_{19}N_6O$ [M+H]$^+$ 311. found 311.

Step 3: N-[(2S)-2-{[(1-methyl-1H-pyrazolo[3,4-c]pyridin-5-yl)carbamoyl]amino}-2-phenylethyl]prop-2-enamide Into a mixture of HATU (680 mg, 1.79 mmol) and acrylic acid (90 mg, 1.25 mmol) in DMF (10 ml) were added (S)-1-(2-amino-1-phenylethyl)-3-(1-methyl-1H-pyrazolo[3,4-c]pyridin-5-yl)urea (530 mg, 1.30 mmol) and DIEA (0.622 ml, 3.56 mmol). After stirring for 3 h at 25° C., the reaction mixture was diluted with water, extracted with EtOAc, washed with brine, dried (Na$_2$SO$_4$), and filtered. The filtrate was concentrated under reduced pressure. The residue was purified by Prep-TLC (DCM/MeOH=10:1). The crude product was recrystallized with EtOAc/MeOH (1:1) to give N-[(2S)-2-{[(1-methyl-1H-pyrazolo[3,4-c]pyridin-5-yl)carbamoyl]amino}-2-phenylethyl]prop-2-enamide. MS (EI) calc'd for $C_{19}H_{21}N_6O_2$ [M+H]$^+$ 365. found 365. $^1$H NMR (400 MHz, DMSO-d$_6$): δ 9.00 (s, 1H), 8.84 (s, 1H), 8.28 (t, J=5.6 Hz, 1H), 8.03 (s, 1H), 7.86 (s, 1H), 7.70 (br s, 1H), 7.39-7.25 (m, 5H), 6.27-6.20 (m, 1H), 6.08 (d, J=16.8 Hz, 1H), 5.57 (d, J=10.4 Hz, 1H), 4.95 (q, J=6.8 Hz, 1H), 4.10 (s, 3H), 3.50-3.42 (m, 2H).

Synthetic Method 21

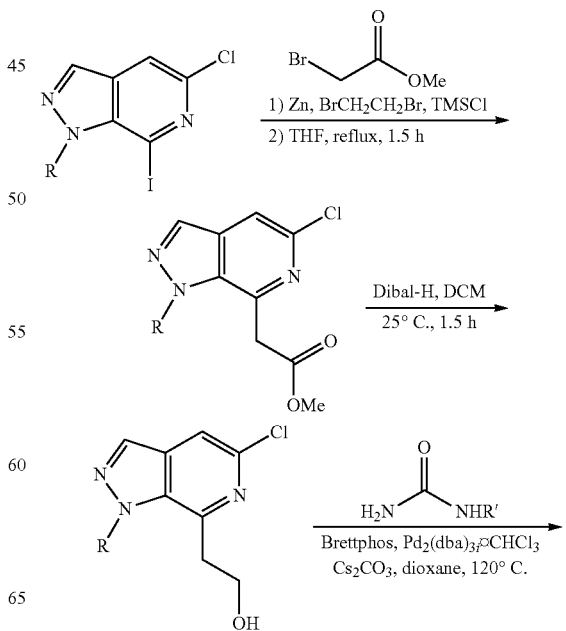

-continued

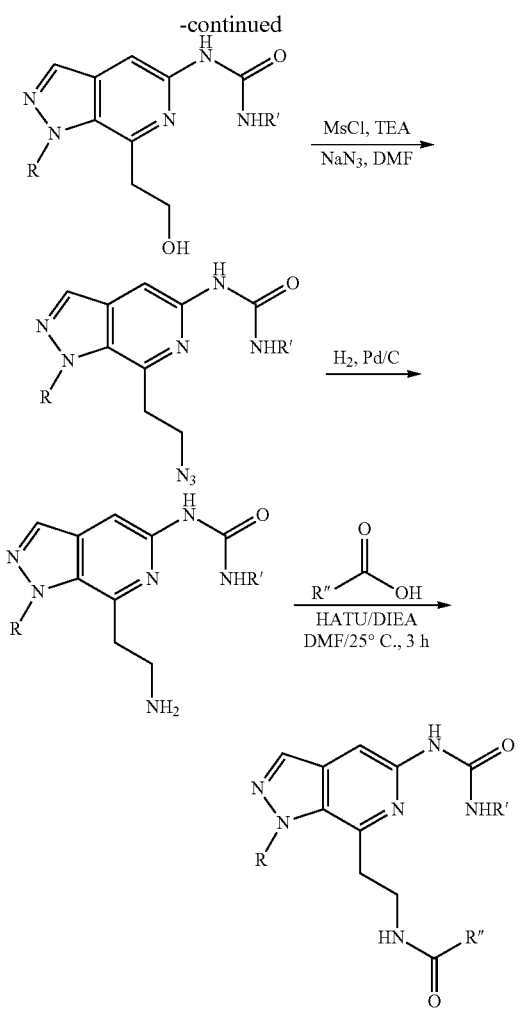

Example 329

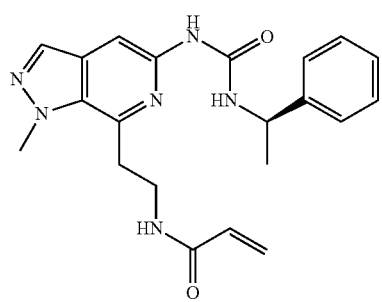 [SMILES: C=CC(=O)NCCc1nc(NC(=O)N[C@H](C)c2ccccc2)cc2cnn(C)c12]

N-{2-[1-Methyl-5-({[(1R)-1-phenylethyl]
carbamoyl}amino)-1H-pyrazolo[3,4-c]pyridin-7-yl]
ethyl}prop-2-enamide 562.9 nM

Step 1: 2-(5-Chloro-1-methyl-1H-pyrazolo[3,4-c]pyridin-7-yl)acetate

To a suspension of Zn (5.0 g, 76 mmol) powder in dry THF (20 ml) under nitrogen was added 1,2-dibromoethane (0.70 g, 3.73 mmol) at room temperature. The reaction mixture was stirred at 65° C. for 1 h and then cooled down to room temperature. TMS-Cl (0.47 ml, 3.68 mmol) was added and the resulting suspension was stirred at room temperature for 15 min. Then the mixture was heated to 45° C. and a solution of methyl 2-bromoacetate (5.0 g, 32.7 mmol) in dry THF (10 mL) was added at such a rate that reflux was maintained. Upon completion of the addition, the reaction mixture was stirred at 45° C. for an additional 30 min and allowed to cool down to room temperature. The resulting mixture was filtered and 20 mL of the filtrate was added dropwise to a stirred mixture of 5-chloro-7-iodo-1-methyl-1H-pyrazolo[3,4-c]pyridine (2.0 g, 5.79 mmol) and Pd(Ph$_3$P)$_4$ (0.4 g, 0.346 mmol) in dry THF (30 ml) under nitrogen at room temperature. The reaction mixture was stirred under reflux for 1.5 h and then quenched by saturated NH$_4$Cl, extracted with EtOAc, washed with brine, dried (Na$_2$SO$_4$), filtered and concentrated under reduced pressure. The residue was purified by chromatography on SiO$_2$, eluted with petroleum ether/EtOAc (1:1) to give methyl 2-(5-chloro-1-methyl-1H-pyrazolo[3,4-c]pyridin-7-yl)acetate. MS (EI) calc'd for $C_{10}H_{11}ClN_5O_2$ [M+H]$^+$ 240. found 240.

Step 2: 2-(5-Chloro-1-methyl-1H-pyrazolo[3,4-c]pyridin-7-yl)ethanol

DIBAL-H (10 ml, 10.00 mmol) was added to a stirred, cooled (0° C.) mixture of methyl 2-(5-chloro-1-methyl-1H-pyrazolo[3,4-c]pyridin-7-yl)acetate (1.1 g, 3.26 mmol) in dry DCM (30 ml) under nitrogen, and then the reaction mixture was stirred at 25° C. for 1.5 h. The reaction mixture was then quenched by saturated seignette salt and diluted with EtOAc. The organic layer was separated, washed with brine, dried (Na$_2$SO$_4$), filtered and concentrated under reduced pressure. The residue was purified by chromatography on SiO$_2$, eluted with petroleum ether/EtOAc (1:4) to give 2-(5-chloro-1-methyl-1H-pyrazolo[3,4-c]pyridin-7-yl)ethanol. MS (EI) calc'd for $C_9H_{11}ClN_3O$ [M+H]$^+$ 212. found 212.

Step 3: N-{2-[1-Methyl-5-({[(R)-1-phenylethyl]carbamoyl}amino)-1H-pyrazolo[3,4-c]pyridin-7-yl]ethyl}prop-2-enamide This compound was synthesized by the same method as described in example 335 step 3 except 2-(5-chloro-1-methyl-1H-pyrazolo[3,4-c]pyridin-7-yl)ethanol was used: MS (EI) calc'd for $C_{21}H_{25}N_6O_2$ [M+H]$^+$ 393. found 393. $^1$H NMR (300 MHz, DMSO-d$_6$): δ 8.88 (s, 1H), 8.32 (t, J=5.2 Hz, 1H), 7.98 (s, 1H), 7.73-7.67 (m, 2H), 7.35-7.31 (m, 4H), 7.27-7.20 (m, 1H), 6.26-6.06 (m, 2H), 5.59 (dd, J=7.2, 2.7 Hz, 1H), 4.93-4.83 (m, 1H), 4.26 (s, 3H), 3.63-3.57 (m, 2H), 3.40-3.35 (m, 2H), 1.42 (d, J=6.9 Hz, 3H).

Active Human ERK2 (hERK2) Activity Assay:

Activated ERK2 activity was determined in an IMAP-FP assay (Molecular Devices). Using this assay format, the potency (IC$_{50}$) of each compound was determined from a 10 point (1:3 serial dilution, 3 μM starting compound concentration) titration curve using the following outlined procedure. To each well of a black Corning 384-well plate (Corning Catalog #3575), 7.5 nL of compound (3333 fold dilution in final assay volume of 25 μL) was dispensed, followed by the addition of 15 μL of kinase buffer (tween containing kinase buffer, Molecular Devices) containing 0.0364 ng/mL (0.833 nM) of phosphorylated active hERK2 enzyme. Following a 15 minute compound & enzyme incubation, each reaction was initiated by the addition of 10 μL kinase buffer containing 2.45 μM ERK2 IMAP substrate peptides and 75 µM ATP. The final reaction in each well of 25 µL consists of 0.5 nM hERK2, 900 nM unlabeled peptide, 80 nM labeled-peptide, and 30 µM ATP. Phosphorylation reactions were allowed to proceed for 60 minutes and were immediately quenched by the addition of 60 µL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer). The ERK2 $IC_{50}$ in nanomolar (nM) for the compounds of the invention is shown in the Example next to the structure.

While the present invention has been described in conjunction with the specific examples set forth above, many alternatives, modifications and variations thereof will be apparent to those of ordinary skill in the art. All such alternatives, modifications and variations are intended to fall within the spirit and scope of the present invention.

What is claimed is:
1. A compound of formula I

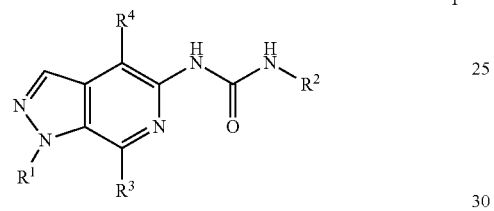

I or a pharmaceutically acceptable salt thereof, wherein $R^1$ is
1) a $C_{4-8}$ monocyclic or bicyclic carbocycle, wherein the monocyclic carbocyle is saturated or unsaturated, and wherein the bicyclic carbocyle comprises 2 fused rings which are independently saturated or unsaturated, wherein the monocyclic or bicyclic carbocycle is unsubstituted or monosubstituted with halogen,
2) a 5-10 membered monocyclic or bicyclic heterocycle having 1-3 heteroatoms independently selected from N, S and O, wherein the monocyclic heterocycle is saturated or unsaturated, and wherein the bicyclic heterocycle comprises 2 fused rings which are independently saturated or unsaturated, wherein the monocyclic or bicyclic heterocycle is unsubstituted or substituted with $C_{1-4}$alkyl, =O, or $C(O)OC(C_{1-4}$alkyl$)_3$,
3) —$CH_2R^5$, wherein $R^5$ is H, $C_{1-4}$alkyl, pyridine, $C_{3-5}$cycloalkyl, —$CH_2OH$, $CH_2OCH_3$, $CF_3$, $CH_2CN$, $CH_2CH_2OC_{1-4}$alkyl, $CH(C_{1-4}$alkyl$)_2$, or a 4-6 membered unsubstituted monocyclic saturated heterocycle having 1 O atom,
4) hydrogen,
5) $C(O)R^6$, wherein $R^6$ is —$NHC_{1-4}$alkyl,
6) —$CHR^7R^8$, wherein $R^7$ and $R^8$ are independently $C_{1-4}$alkyl, or
7) $C_{1-4}$alkyl;

$R^2$ is
1) $CH_2R^9$, where $R^9$ is
a) unsubstituted phenyl or phenyl substituted one, two or three times independently selected from
1) halogen, 2) —$OC_{1-4}$alkyl, 3) 5-membered saturated or unsaturated heterocycle which is unsubstituted or substituted with =O having 1 or 2 heteroatoms selected from O and N,

4)

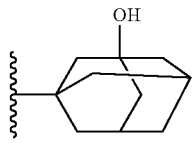 [SMILES: *C12CC3CC(C1)CC(O)(C3)C2]

5) —$SO_2C_{1-4}$alkyl, 6) —$C(O)NHC_{1-4}$alkyl, 7) —$C(C_{1-4}$alkyl$)_2OH$, or
8) —$NHSO_2C_{1-4}$alkyl,
b) —$CH_2R^{13}$ wherein $R^{13}$ is
1) $C_6H_5$, 2) $N(C_{1-4}$alkyl$)_2$, 3) $C_6H_4F$, 4) halogen, 5) —$OC_{1-4}$alkyl, 6) $CF_3$, 7) O—$C_6H_4F$, 8) $OCH_2C_6H_5$, 9) $NHCH_2C_6H_5$, 10) 6-membered saturated heterocycle which is unsubstituted or substituted with —$CH_2OC_6H_5$ having 1 or 2 heteroatoms selected from O and N, 11) 5-membered saturated heterocycle which is unsubstituted having 1 heteroatom which is O, 12) 5-membered unsaturated heterocycle which is unsubstituted or mono- or di-substituted with $C_{1-4}$alkyl having 1 or 2 heteroatoms independently selected from N and O, or
12)

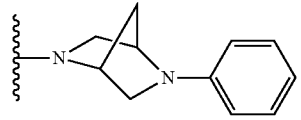

c) $C_{3-6}$cycloalkyl unsubstituted or substituted with —$N(C_{1-4}$alkyl$)_2$,
d) 10-membered bicyclic carbocycle comprising two fused rings, wherein one ring is unsaturated,
e) —$CHR^{19}R^{10}$, wherein $R^{19}$ and $R^{10}$ are independently selected from
1) pyridine, 2) 6-membered saturated heterocycle, having 1 or 2 heteroatoms selected from O and N, which is unsubstituted or substituted with one or two F, 3) —$CH_2OH$, 4) phenyl, 5) piperidine, 6) $C_6H_4F$, 7) $CH_3$, 8) OH, or 9) $C_6H_4CF_3$,
f) a 4-10 membered monocyclic or bicyclic heterocycle having
1-3 heteroatoms independently selected from N, S and O, wherein the monocyclic heterocycle is saturated or unsaturated, and wherein the bicyclic heterocycle is saturated or unsaturated, wherein the monocyclic or bicyclic heterocycle is unsubstituted or independently mono-, di- or tri-substituted with —$CHCF_3CH_3$, $C_6H_4F$, $C_6H_4FCl$, $CH_2CF_3$, $C_{1-4}$alkyl, =O, $C_6H_5$, or halogen,
g) $CF_2C_6H_5$
h)

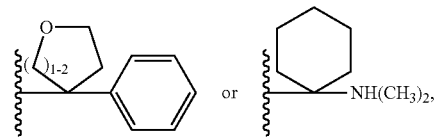

2) —CHR$^{11}$R$^{12}$, where R$^{11}$ and R$^{12}$ are independently selected from
   a) C$_{1-4}$alkyl, b) —OC$_{1-4}$alkyl, c) CF$_3$,
   d) C$_6$H$_4$R$^{12'}$ where R$^{12'}$ is halogen, —OCF$_3$, —SO$_2$C$_{1-4}$alkyl, H, or a 5-membered unsaturated unsubstituted heterocycle or heterocycle substituted with C$_{1-4}$alkyl having 2 or 3 heteroatoms selected from O, N and S,
   e) CH$_2$CH$_2$N(C$_{1-4}$alkyl)$_2$,
   f) CH$_2$CH$_2$R$^{12''}$ where R$^{12''}$ is a 6-membered saturated or unsaturated heterocycle which heterocycle is unsubstituted or mono- or di- substituted with halogen,
   g) CH$_2$NH$_2$, h) CH$_2$OH, i) C$_6$H$_5$SO$_2$C$_{1-4}$alkyl, j) CHF$_2$, k) CH$_2$CH$_2$OH,
   l) CH$_2$OC$_{1-4}$alkyl, m) —OC$_{1-4}$alkyl, n) —CH$_2$N(CH$_3$)$_2$,
   o) —CH$_2$R$^{12'''}$ where R$^{12'''}$ is a
      1) 5-membered unsaturated unsubstituted heterocycle having 2 N atoms, 2) —OC$_{1-4}$ alkyl, 3) N(C$_{1-4}$alkyl)$_2$, 4) —CH$_2$OCH$_2$CH$_2$OC$_{1-4}$alkyl, 5) C(O)OC$_{1-4}$alkyl, 6) NH$_2$, 7) NHC(O)CH=CH$_2$, 8) C(C$_{1-4}$alkyl)$_2$OH,
      9) OH, 10) a 6-membered saturated heterocycle having 2 heteroatoms independently selected from N and O,
   p) C(O)NHC$_{1-4}$alkyl, q) C(O)N(C$_{1-4}$alkyl)$_2$, r) C$_6$H$_3$FCl,
   s) C(C$_{1-4}$alkyl)$_2$OH, t) C$_6$H$_3$Cl$_2$, u) C(C$_{1-4}$alkyl)$_2$OH, v) CH(C$_{1-4}$alkyl)OH, w) C(C$_{1-4}$alkyl)$_3$, x) —C(C$_{1-4}$alkyl)$_2$OH,
   y) a 5-membered unsaturated or saturated heterocycle having one or two heteroatoms independently selected from N, O and S atoms, which heterocycle is unsubstituted or substituted with C$_{1-4}$alkyl,
   z) a 6-membered unsaturated heterocycle having one heteroatom which is N, which heterocycle is unsubstituted, or
   aa) C(O)OCH$_3$,
3) a C$_{4-10}$ monocyclic or bicyclic saturated or unsaturated carbocycle, wherein the bicyclic carbocyle comprises 2 fused rings, wherein the monocyclic or bicyclic carbocycle is unsubstituted or monosubstituted with
   a) NH$_2$, b) NHC(O)C$_{1-4}$alkyl, c) —OC$_{1-4}$alkyl, d) —N(C$_{1-4}$alkyl)$_2$,
   e) —OC$_{1-4}$alkyl, f) C$_6$H$_5$, g) NHC(O)C$_6$H$_5$, h) C$_6$H$_4$F, i) —OCH$_2$C$_6$H$_5$, j) —CH$_2$C$_6$H$_5$,
   k) —OC$_6$H$_5$, l) —OCH$_2$CH$_2$CH$_2$C$_6$H$_5$, m) —OC$_6$H$_4$F, or n) —O-pyridine,
4) a 5-10 membered monocyclic or bicyclic saturated or unsaturated heterocycle having 1-3 heteroatoms independently selected from N and O, wherein the monocyclic or bicyclic heterocycle is unsubstituted or independently mono-, di-, tri- or tetra-substituted with
   a) C$_6$H$_4$Cl, b) C$_{1-4}$alkyl, c) =O, d) C$_6$H$_5$, e) C$_{3-6}$cycloalkyl, f) C$_6$H$_4$F,
   g) CH$_2$C$_6$H$_3$(OC$_{1-4}$alkyl)(F), h) C$_6$H$_4$(C$_{1-4}$alkyl), i) CH$_2$CH$_2$C$_6$H$_5$,
   j) CH$_2$CH$_2$CH$_2$C$_6$H$_5$, k) OC$_{1-4}$alkyl, l) —OC$_6$H$_5$, m) CH$_2$C$_6$H$_3$F$_2$,
   n) CH$_2$C$_6$H$_4$CF$_3$, o) CH$_2$C$_6$H$_4$CN, p) OC$_6$H$_4$F, q) —OC$_{1-4}$alkyl,
   r) a 5-6-membered heterocycle saturated or unsaturated, unsubstituted or substituted with C$_{1-4}$alkyl, C$_6$H$_5$ or C$_{3-6}$cycloalkyl, having 1 or 2 heteroatoms independently selected from O, N and S,
   s) —CH$_2$—R$^{2'}$, wherein R$^{2'}$ is a 5-6-membered unsaturated heterocycle, unsubstituted or substituted with halogen, having 1 or 2 heteroatoms independently selected from N and S, or
   t) —O—R$^{2''}$, wherein R$^{2''}$ is a 6-membered unsaturated heterocycle, unsubstituted or mono- or di- substituted with halogen, having 1 N heteroatom,
5) —CR$^{13}$R$^{14}$R$^{15}$ where R$^{13}$ and R$^{14}$ are independently C$_{1-4}$alkyl or together with the carbon atom to which they are attached form cyclopropyl, and R$^{15}$ is CN or C$_6$H$_5$,
6)

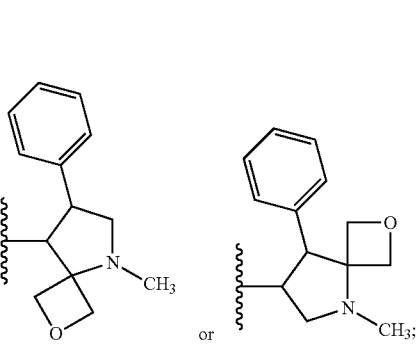 [SMILES: *C1C(c2ccccc2)CN(C)C12COC2 ; *C1CN(C)C2(COC2)C1c1ccccc1]

R$^3$ is hydrogen, —OC$_{1-4}$alkyl, —OC$_{1-4}$alkyl-OH, or —CH$_2$R$^{3'}$, wherein R$^{3'}$ is
   1) —OC$_{1-4}$alkyl, 2) 6-membered saturated unsubstituted heterocycle having 1 or 2 heteroatoms independently selected from N and O, 3) —NHC$_{1-4}$alkyl,
   4) —OC$_{1-4}$alkyleneR$^{3''}$ where R$^{3''}$ is a 4-6-membered saturated unsubstituted heterocycle having 1 or 2 heteroatoms selected from N and O,
   5) —OC$_{1-4}$alkylene-OH, 6) —OC$_{1-4}$alkylene-OCH$_3$, 7) hydrogen,
   8) —OC$_{1-4}$alkylene-OCH$_2$C$_6$H$_5$, 9) —OH, 10) —NHC$_{1-4}$alkyleneOC$_{1-4}$alkyl,
   11) NH$_2$, 12) —NHC$_{1-4}$alkyleneN(C$_{1-4}$alkyl)$_2$, 13) —NHC(O)CH=CH$_2$,
   14) —NHC(O)C$_{1-4}$alkyl, 15) —NHC(O)OC$_{1-4}$alkyl, 16) —OC(O)NHC$_{1-4}$alkyl, 17) —CH$_2$NHC(O)CH=CH$_2$, 18) N(C$_{1-4}$alkyl)$_2$, or
   19)

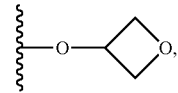 [SMILES: *OC1COC1]

and
R$^4$ is hydrogen or halogen.
2. A compound of claim 1, or a pharmaceutically acceptable salt thereof, wherein
R$^1$ is
   1) a C$_{4-8}$ monocyclic or bicyclic carbocycle, wherein the monocyclic carbocycle is saturated or unsaturated, and wherein the bicyclic carbocycle comprises 2 fused rings which are independently saturated or unsaturated, wherein the monocyclic or bicyclic carbocycle is unsubstituted or monosubstituted with F,
   2) a 5-10 membered monocyclic or bicyclic heterocycle having 1-3 heteroatoms independently selected from N, S and O, wherein the monocyclic heterocycle is saturated or unsaturated, and wherein the bicyclic heterocycle comprises 2 fused rings which are independently saturated or unsaturated, wherein the monocyclic or bicyclic heterocycle is unsubstituted or substituted with $CH_3$, =O, or $C(O)OC(CH_3)_3$,
3) —$CH_2R^5$, wherein $R^5$ is H, $CH_3$, pyridine, cyclopentyl, cyclobutyl, $CH_2CH_3$, cyclopropyl, —$CH_2OH$, $CH_2OCH_3$, $CF_3$, $CH_2CN$, $CH_2CH_2OCH_3$, $CH(CH_3)_2$, or a 4-6 membered unsubstituted monocyclic saturated heterocycle having 1 O atom,
4) hydrogen,
5) $C(O)R^6$, wherein $R^6$ is —$NHCH_2CH_3$,
6) —$CHR^7R^8$, wherein $R^7$ and $R^8$ are independently $CH_3$, or
7) $C_{1-4}$alkyl;

$R^2$ is
1) $CH_2R^9$, where $R^9$ is
    a) unsubstituted phenyl or phenyl substituted one, two or three times independently selected from
        1) F, 2) —$OCH_3$ 3) Cl, 4) 5-membered saturated or unsaturated heterocycle which is unsubstituted or substituted with =O having 1 or 2 heteroatoms selected from O and N,
        5)

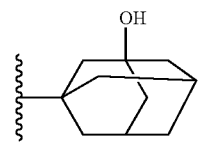 [SMILES: *C12CC3CC(C1)CC(O)(C3)C2]

6) —$SO_2CH_3$, 7) —$C(O)NHCH_3$, 8) —$C(CH_3)_2OH$, or 9) —$NHSO_2CH_3$,
    b) —$CH_2R^{13}$ wherein $R^{13}$ is
        1) $C_6H_5$, 2) $N(CH_3)_2$, 3) $C_6H_4F$, 4) F, 5) —$OCH_3$, 6) $CF_3$, 7) O—$C_6H_4F$, 8) $OCH_2C_6H_5$, 9) $NHCH_2C_6H_5$, 10) 6-membered saturated heterocycle which is unsubstituted or substituted with —$CH_2OC_6H_5$ having 1 or 2 heteroatoms selected from O and N, 11) 5-membered saturated heterocycle which is unsubstituted having 1 heteroatom which is O, 12) 5-membered unsaturated heterocycle which is unsubstituted or mono- or di-substituted with $CH_3$ having 1 or 2 heteroatoms independently selected from N and O, or
        13)

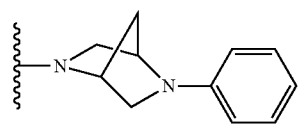 [SMILES: *N1CC2CC1CN2c1ccccc1]

c) cyclohexyl unsubstituted or substituted with —$N(CH_3)_2$,
    d) 10-membered bicyclic carbocycle comprising two fused rings, wherein one ring is unsaturated,
    e) —$CHR^{19}R^{10}$, wherein $R^{19}$ and $R^{10}$ are independently selected from
        1) pyridine, 2) 6-membered saturated heterocycle which is unsubstituted having 1 or 2 heteroatoms selected from O and N, which is unsubstituted or substituted with one or two F, 3) —$CH_2OH$, 4) phenyl, 5) piperidine, 6) $C_6H_4F$, 7) $CH_3$, 8) OH, or 9) $C_6H_4CF_3$,
    f) a 4-10 membered monocyclic or bicyclic heterocycle having
        1-3 heteroatoms independently selected from N, S and O, wherein the monocyclic heterocycle is saturated or unsaturated, and wherein the bicyclic heterocycle is saturated or unsaturated, wherein the monocyclic or bicyclic heterocycle is unsubstituted or independently mono-, di- or tri-substituted with —$CHCF_3CH_3$, $C_6H_4F$, $C_6H_3FCl$, $CH_2CF_3$, $CH_2CH_2CH_3$, $CH(CH_3)_2$, =O, $C_6H_5$, $CH_3$, or F,
    g) $CF_2C_6H_5$ or
    h)

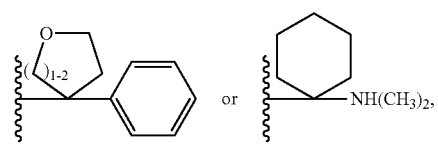

2) —$CHR^{11}R^{12}$, where $R^{11}$ and $R^{12}$ are independently selected from
    a) —$CH_3$, b) —$OCH_3$, c) $CF_3$,
    d) $C_6H_5R^{12'}$ where $R^{12'}$ is F, Cl, —$OCF_3$, —$SO_2CH_3$, H, or a 5-membered unsaturated unsubstituted heterocycle or heterocycle substituted with $CH_3$ having 2 or 3 heteroatoms selected from O, N and S,
    e) $CH_2CH_2N(CH_3)_2$,
    f) $CH_2CH_2R^{12''}$ where $R^{12''}$ is a 6-membered saturated or unsaturated heterocycle which heterocycle is unsubstituted or mono- or di- substituted with F,
    g) $CH_2NH_2$, h) $CH_2OH$, i) $C_6H_5SO_2CH_3$, j) $CHF_2$, k) $CH_2CH_2OH$,
    l) $CH_2OCH_3$, m) —$OCH_2CH_3$, n) —$CH_2N(CH_3)_2$,
    o) —$CH_2R^{12'''}$ where $R^{12'''}$ is a
        1) 5-membered unsaturated unsubstituted heterocycle having 2 N atoms, 2) —$OCH_2CH_3$, 3) $N(CH_3)_2$, 4) —$OCH(CH_3)_2$, 5) —$CH_2OCH_2CH_2OCH_3$, 6) $C(O)OCH_3$, 7) $NH_2$, 8) $NHC(O)CH=CH_2$, 9) $C(CH_2CH_3)_2OH$, 10) OH, 11) 6-membered saturated heterocycle having 2 heteroatoms independently selected from N and O,
    p) $C(O)NHCH_2CH_3$, q) $C(O)NHCH_3$, r) $C(O)N(CH_2CH_3)_2$, s) $C_6H_3FCl$,
    t) $C(CH_3)_2OH$, u) $C_6H_3Cl_2$, v) $C(CH_3)_2OH$, w) $CH(CH_3)OH$, x) $C(CH_3)_3$, y) —$C(CH_2CH_3)_2OH$,
    z) a 5-membered unsaturated or saturated heterocycle having one or two heteroatoms independently selected from N, O and S atoms, which heterocycle is unsubstituted or substituted with $CH_3$,
    aa) a 6-membered unsaturated heterocycle having one heteroatom which is N, which heterocycle is unsubstituted, or
    bb) $C(O)OCH_3$,
3) a $C_{4-10}$ monocyclic or bicyclic saturated or unsaturated carbocycle, wherein the bicyclic carbocycle comprises 2 fused rings, wherein the monocyclic or bicyclic carbocycle is unsubstituted or monosubstituted with
  a) $NH_2$, b) $NHC(O)CH_3$, c) $—OCH_3$, d) $—N(CH_3)_2$, e) $—OCH_2CH_3$, f) $C_6H_5$, g) $NHC(O)C_6H_5$, h) $C_6H_4F$, i) $—OCH_2C_6H_5$, j) $—CH_2C_6H_5$, k) $—OC_6H_5$,
  l) $—OCH_2CH_2CH_2C_6H_5$, m) $—OC_6H_4F$, or n) —O-pyridine,
4) a 5-10 membered monocyclic or bicyclic saturated or unsaturated heterocycle having 1-3 heteroatoms independently selected from N and O, wherein the monocyclic or bicyclic heterocycle is unsubstituted or independently mono-, di-, tri- or tetra-substituted with
  a) $C_6H_4Cl$, b) $CH_3$, c) =O, d) $C_6H_5$, e) $CH_2CH_3$, f) $CH_2CH_2CH_3$,
  g) cyclopropyl, h) cyclohexyl, i) $C_6H_4F$, j) $CH_2C_6H_3(OCH_3)(F)$,
  k) $C_6H_4(CH_3)$, l) $CH_2CH_2C_6H_5$, m) $CH_2CH_2CH_2C_6H_5$, n) $OCH_3$,
  o) $—OC_6H_5$, p) cyclobutyl, q) $CH(CH_3)_2$, r) $CH_2C_6H_3F_2$, s) $CH_2C_6H_4CF_3$,
  t) $CH_2C_6H_4CN$, u) $OC_6H_4F$, v) $—OCH_2CH_3$,
  w) a 5-6-membered heterocycle saturated or unsaturated, unsubstituted or substituted with $CH_3$, $C_6H_5$ or cyclopropyl, having 1 or 2 heteroatoms independently selected from O, N and S,
  x) $—CH_2—R^{2'}$, wherein $R^{2'}$ is a 5-6-membered unsaturated heterocycle, unsubstituted or substituted with Cl, having 1 or 2 heteroatoms independently selected from N and S, or
  y) $—O—R^{2''}$, wherein $R^{2''}$ is a 6-membered unsaturated heterocycle, unsubstituted or mono- or di-substituted with F, having 1 N heteroatom,
5) $—CR^{13}R^{14}R^{15}$ where $R^{13}$ and $R^{14}$ are independently $CH_3$ or together with the carbon atom to which they are attached form cyclopropyl, and $R^{15}$ is CN or $C_6H_5$,
6)

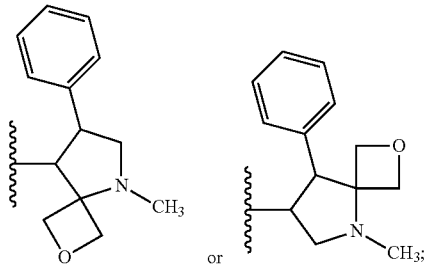 [SMILES: *C1C(c2ccccc2)CN(C)C12COC2 ; *C1CN(C)C2(COC2)C1c1ccccc1]

or $R^3$ is hydrogen, $—OC_{1-4}alkyl$, $—OC_{1-4}alkyl$-OH, or $—CH_2R^{3'}$, wherein $R^{3'}$ is
  1) $—OC_{1-4}alkyl$, 2) 6-membered saturated unsubstituted heterocycle having 1 or 2 heteroatoms independently selected from N and O, 3) $—NHC_{1-4}alkyl$,
  4) $—OC_{1-4}alkyleneR^{3''}$ where $R^{3''}$ is a 4-6-membered saturated unsubstituted heterocycle having 1 or 2 heteroatoms selected from N and O,
  5) $—OC_{1-4}alkylene$-OH, 6) $—OC_{1-4}alkylene$-$OCH_3$, 7) hydrogen,
  8) $—OC_{1-4}alkylene$-$OCH_2C_6H_5$, 9) —OH, 10) $—NHC_{1-4}alkyleneOC_{1-4}alkyl$,
  11) $NH_2$, 12) $—NHC_{1-4}alkyleneN(C_{1-4}alkyl)_2$, 13) $—NHC(O)CH=CH_2$,
  14) $—NHC(O)C_{1-4}alkyl$, 15) $—NHC(O)OC_{1-4}alkyl$, 16) $—OC(O)NHC_{1-4}alkyl$,
  17) $—CH_2NHC(O)CH=CH_2$, 18) $N(CH_3)_2$, or
  19)

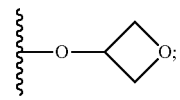 [SMILES: *OC1COC1]

and
$R^4$ is hydrogen or halogen.

3. A compound of claim 2, or a pharmaceutically acceptable salt thereof, wherein
$R^1$ is

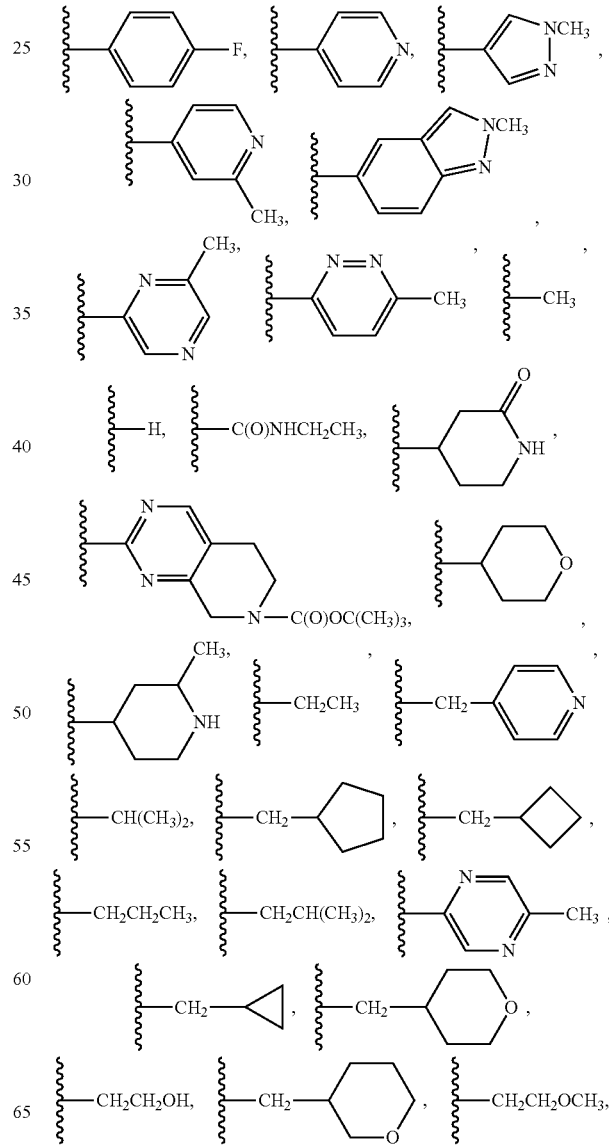

265
-continued
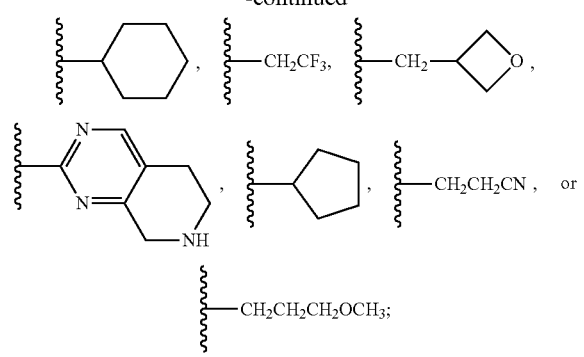
R² is
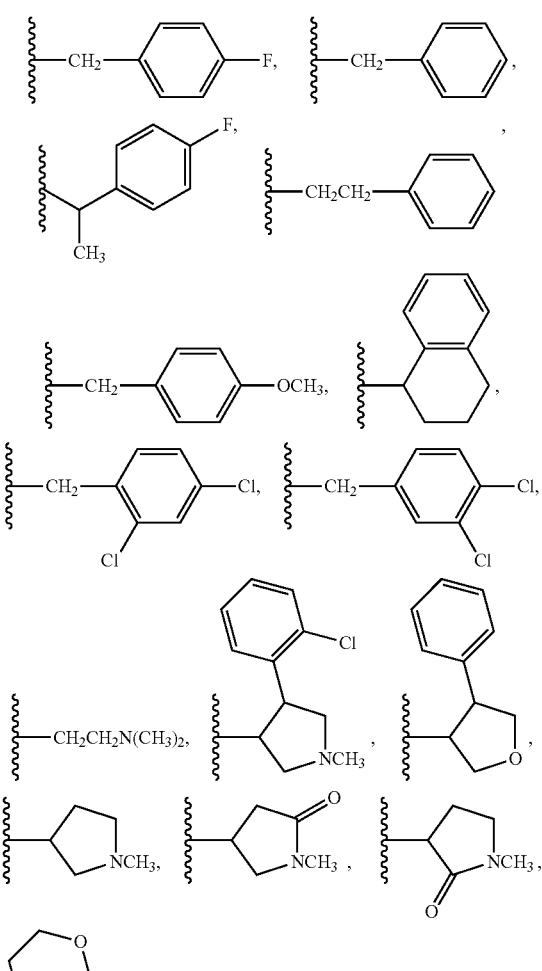
266
-continued
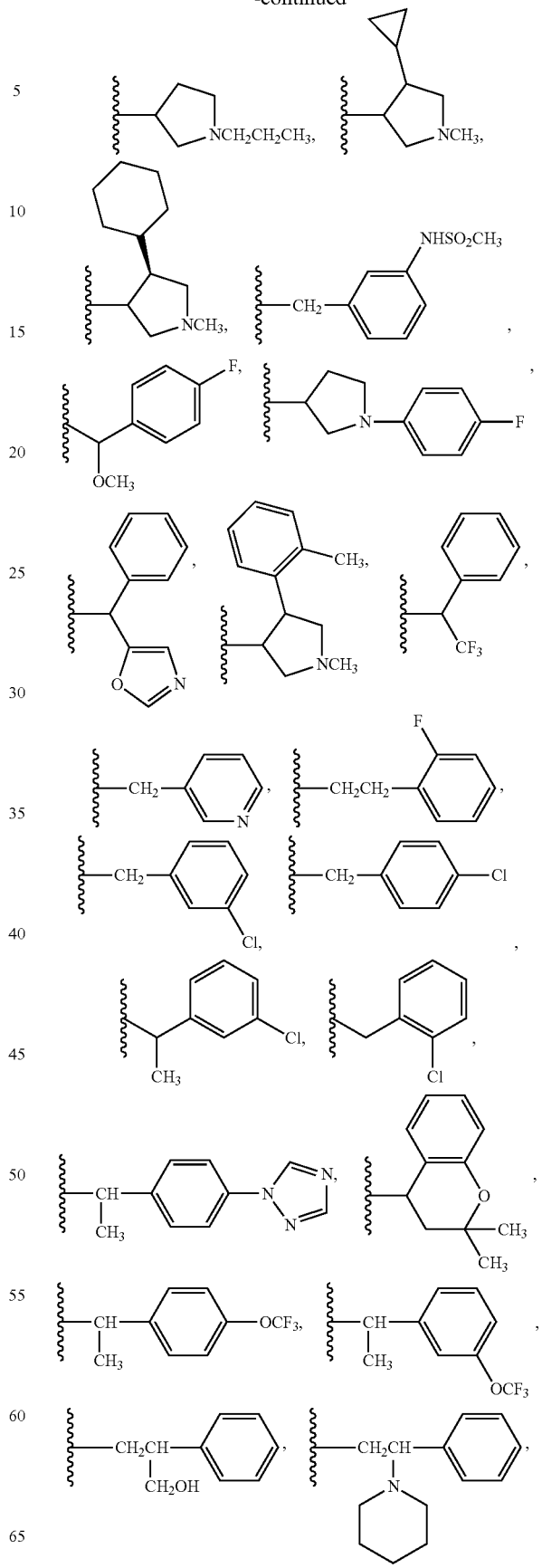

267
-continued
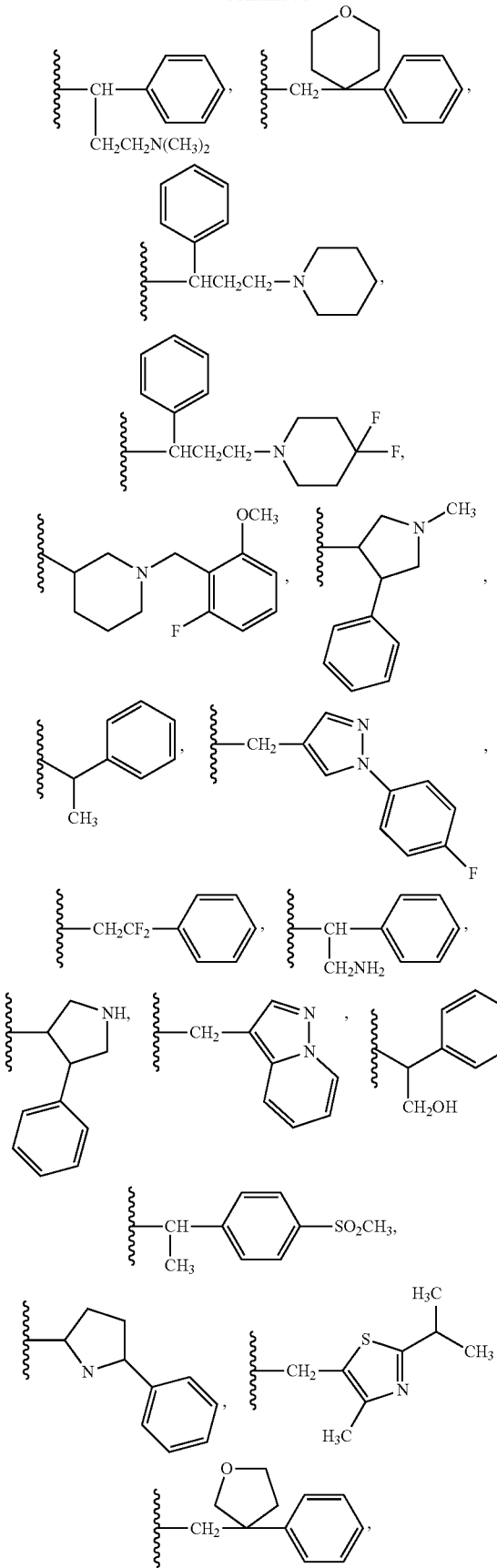
268
-continued
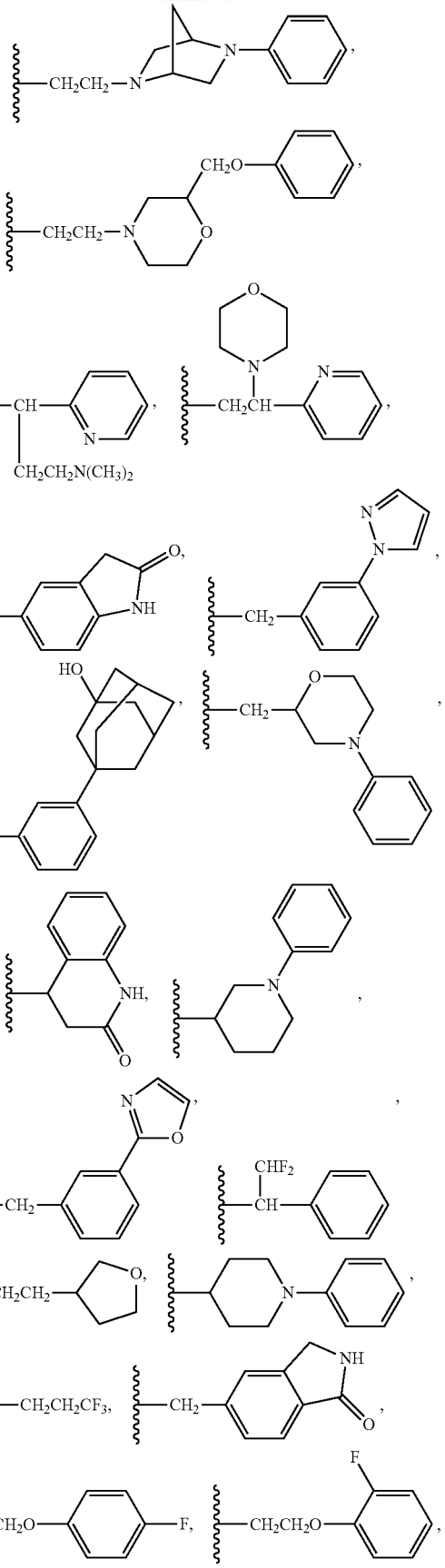

-continued

271
-continued
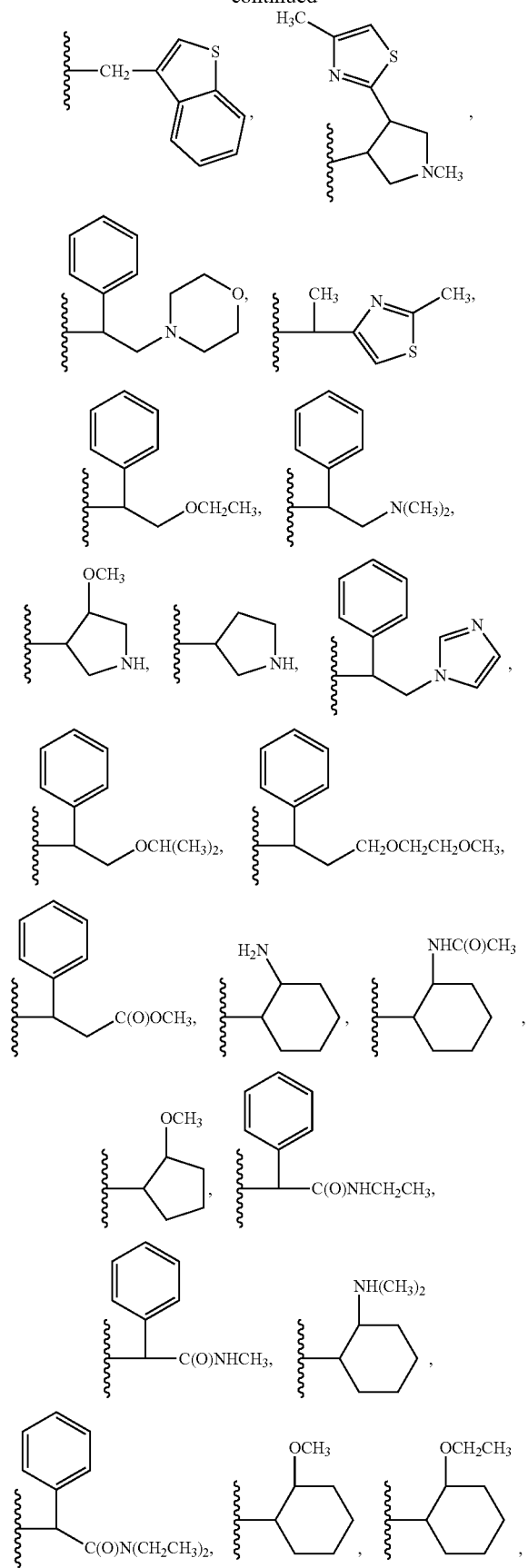
272
-continued
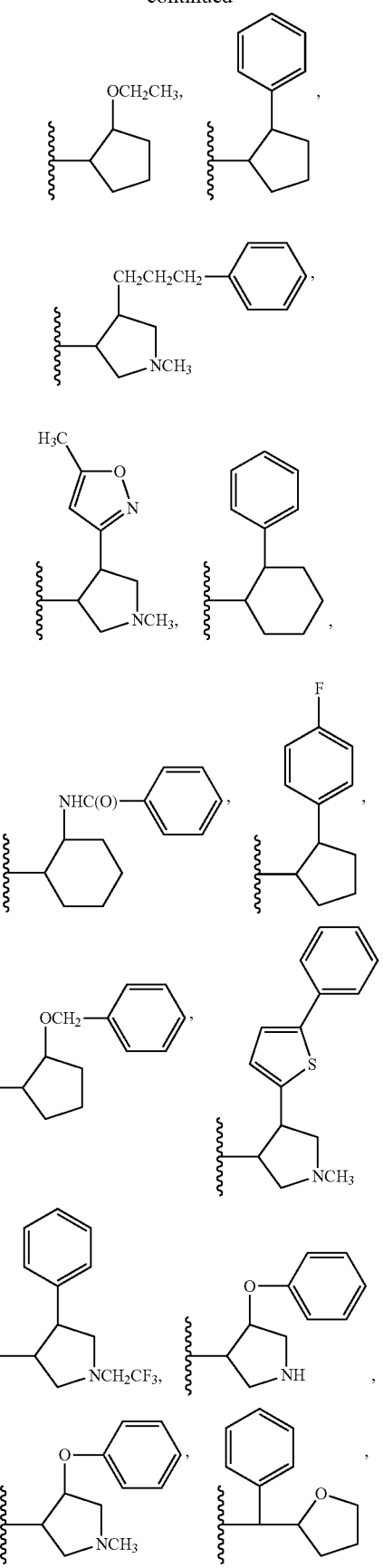

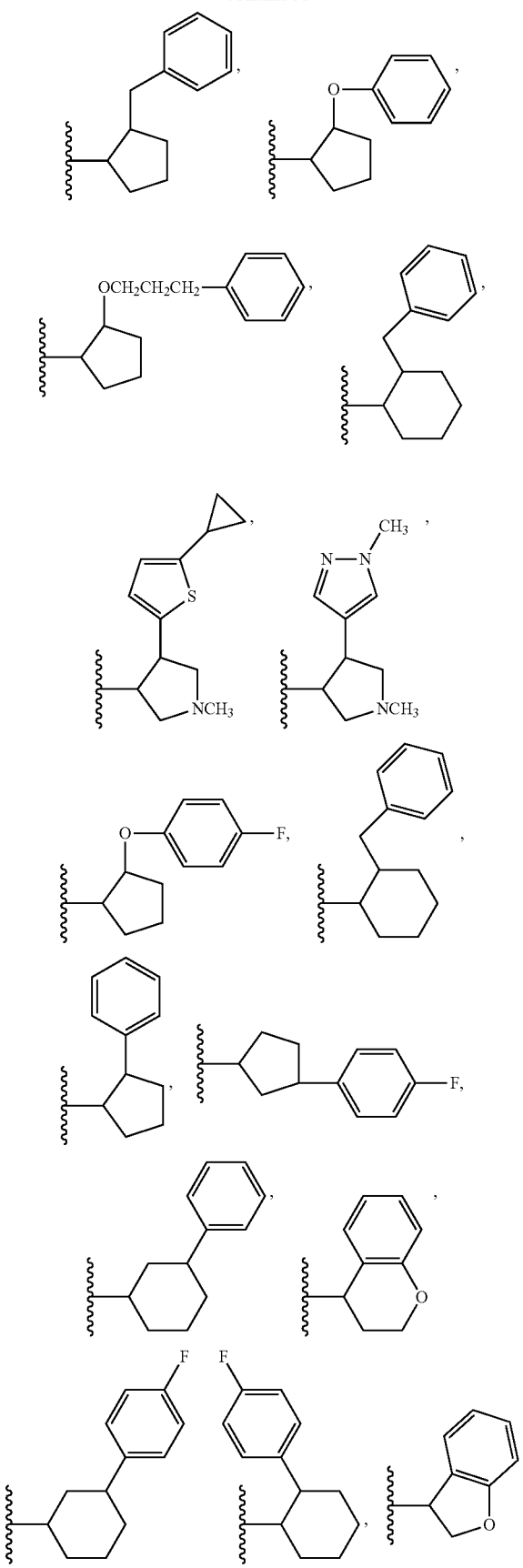
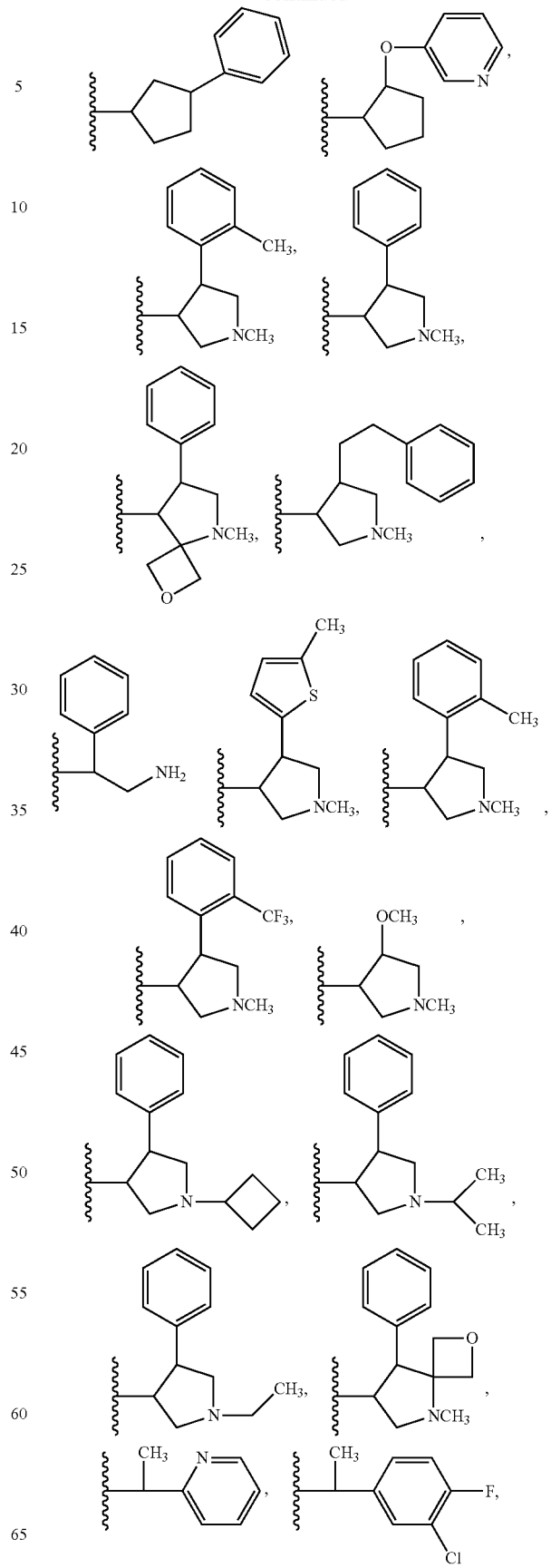

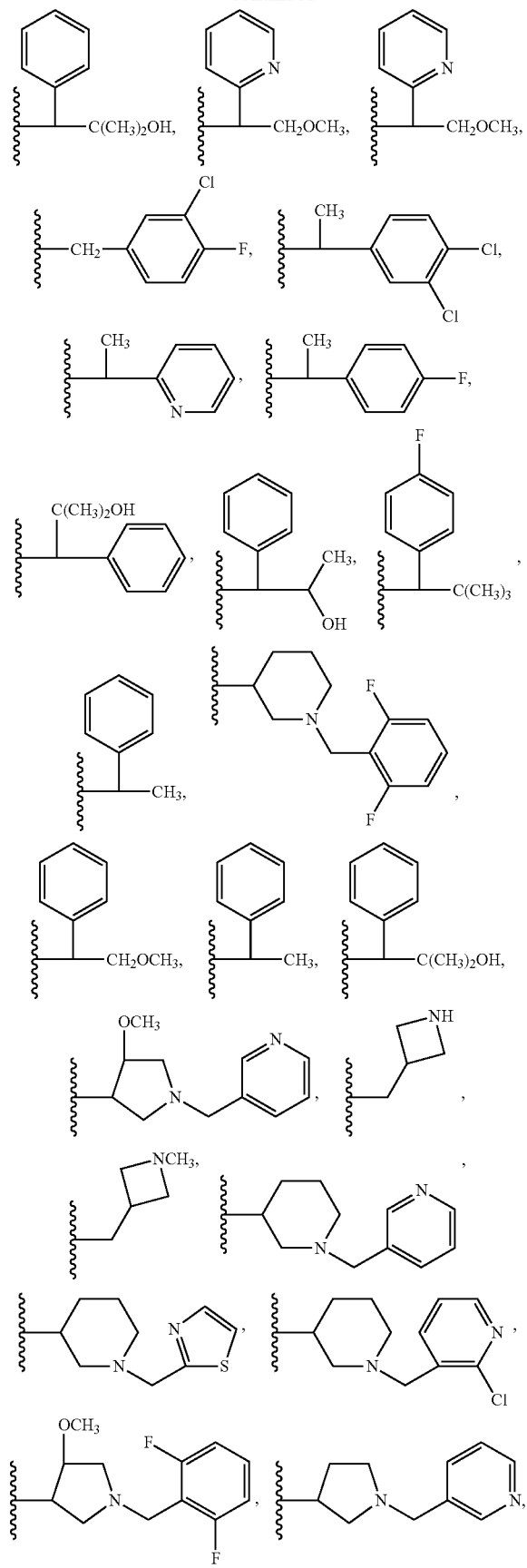
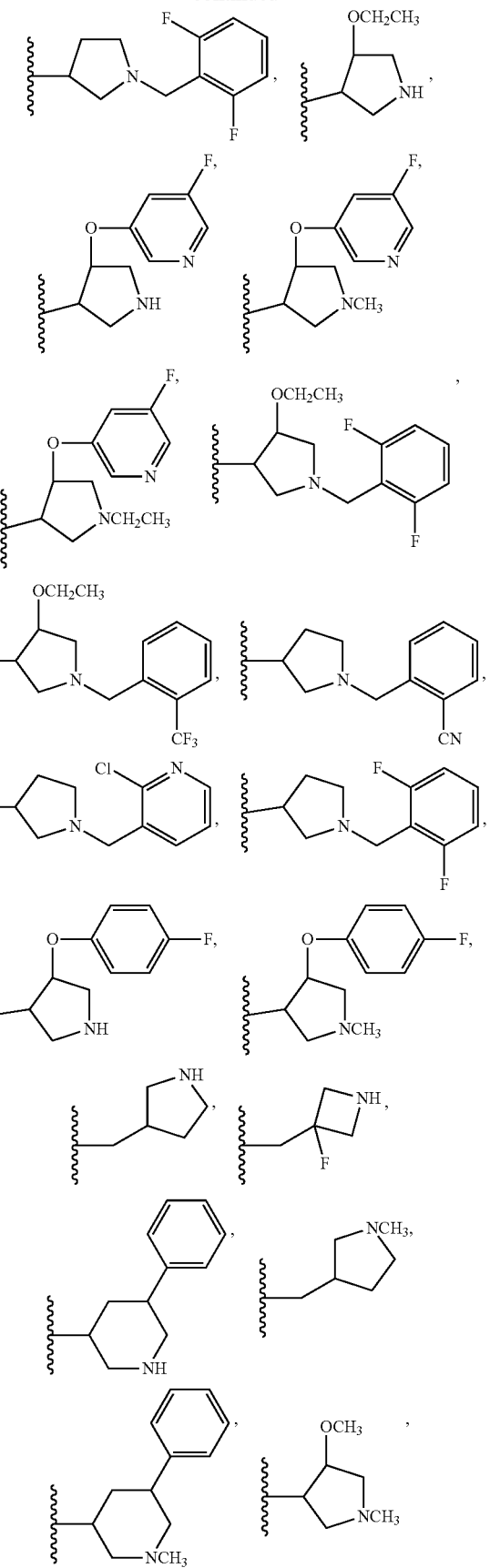

-continued

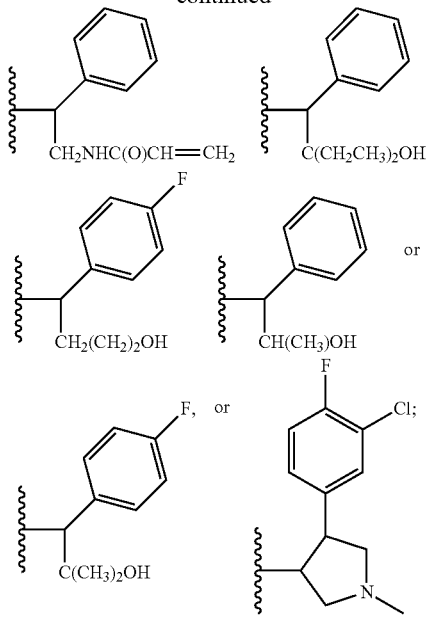

R³ is

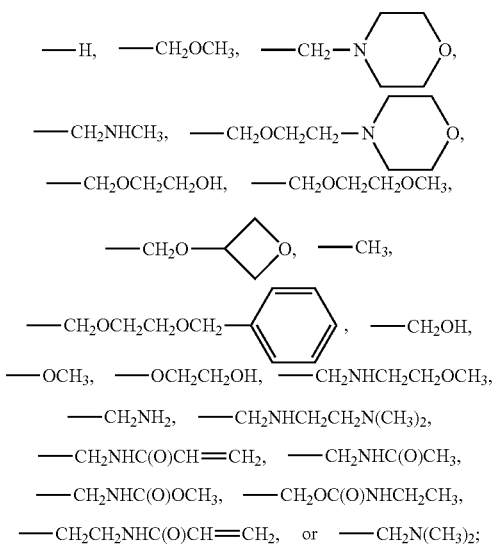

—H, —CH₂OCH₃, —CH₂—N(morpholine),

—CH₂NHCH₃, —CH₂OCH₂CH₂—N(morpholine),

—CH₂OCH₂CH₂OH, —CH₂OCH₂CH₂OCH₃,

—CH₂O—(oxetane), —CH₃,

—CH₂OCH₂CH₂OCH₂—(phenyl), —CH₂OH,

—OCH₃, —OCH₂CH₂OH, —CH₂NHCH₂CH₂OCH₃,

—CH₂NH₂, —CH₂NHCH₂CH₂N(CH₃)₂,

—CH₂NHC(O)CH═CH₂, —CH₂NHC(O)CH₃,

—CH₂NHC(O)OCH₃, —CH₂OC(O)NHCH₂CH₃,

—CH₂CH₂NHC(O)CH═CH₂, or —CH₂N(CH₃)₂;

and
R⁴ is H or F.

4. A compound of claim 3, or a pharmaceutically acceptable salt thereof, selected from the group consisting of
1-(4-fluorobenzyl)-3-(1-(4-fluorophenyl)-1H-pyrazolo[3,4-c]pyridin-5-yl)urea,
1-benzyl-3-(1-pyridin-4-yl-1H-pyrazolo[3,4-c]pyridin-5-yl)urea, 1-[(1R)-1-(4-fluorophenyl)ethyl]-3-[1-(4-fluorophenyl)-1H-pyrazolo[3,4-c]pyridin-5-yl]urea,
1-(4-fluorobenzyl)-3-[1-(1-methyl-1H-pyrazol-4-yl)-1H-pyrazolo[3,4-c]pyridin-5-yl]urea,
1-(4-fluorobenzyl)-3-(1-pyridin-4-yl-1H-pyrazolo[3,4-c]pyridin-5-yl)urea,
1-[(1R)-1-(4-fluorophenyl)ethyl]-3-(1-pyridin-4-yl-1H-pyrazolo[3,4-c]pyridin-5-yl)urea,
1-(2-phenylethyl)-3-(1-pyridin-4-yl-H-pyrazolo[3,4-c]pyridin-5-yl)urea,
1-(4-methoxybenzyl)-3-(1-pyridin-4-yl-1H-pyrazolo[3,4-c]pyridin-5-yl)urea,
1-(1-pyridin-4-yl-1H-pyrazolo[3,4-c]pyridin-5-yl)-3-(1,2,3,4-tetrahydronaphthalen-1-yl)urea,
1-(2,4-dichlorobenzyl)-3-(1-pyridin-4-yl-1H-pyrazolo[3,4-c]pyridin-5-yl)urea,
1-(3,4-dichlorobenzyl)-3-(1-pyridin-4-yl-1H-pyrazolo[3,4-c]pyridin-5-yl)urea,
1-[(3R,4S)-4-(2-chlorophenyl)-1-methylpyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3R,4R)-4-phenyltetrahydrofuran-3-yl]urea,
1-[(3R,4S)-4-(3-chloro-4-fluorophenyl)-1-methylpyrrolidin-3-yl]-3-[1-(2-methylpyridin-4-yl)-1H-pyrazolo[3,4-c]pyridin-5-yl]urea,
1-[(3R,4S)-4-(3-fluorophenyl)-1-methylpyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3R)-1-methylpyrrolidin-3-yl]urea,
1-[1-(2-methylpyridin-4-yl)-1H-pyrazolo[3,4-c]pyridin-5-yl]-3-[(3 S)-1-methylpyrrolidin-3-yl]urea,
1-(1-methyl-5-oxopyrrolidin-3-yl)-3-[1-(2-methylpyridin-4-yl)-1H-pyrazolo[3,4-c]pyridin-5-yl]urea,
1-(1-methyl-2-oxopyrrolidin-3-yl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-{(3R,4S)-1-methyl-4-[(3 S)-tetrahydro-2H-pyran-3-yl]pyrrolidin-3-yl}urea,
1-[(3R,4S)-4-(3-chloro-4-fluorophenyl)-1-methylpyrrolidin-3-yl]-3-[1-(2-methylpyridin-4-yl)-1H-pyrazolo[3,4-c]pyridin-5-yl]urea,
1-[(3R,4S)-4-(3-fluorophenyl)-1-methylpyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3R)-1-methylpyrrolidin-3-yl]urea,
1-[1-(2-methylpyridin-4-yl)-1H-pyrazolo[3,4-c]pyridin-5-yl]-3-[(3 S)-1-methylpyrrolidin-3-yl]urea,
1-(1-methyl-5-oxopyrrolidin-3-yl)-3-[1-(2-methylpyridin-4-yl)-1H-pyrazolo[3,4-c]pyridin-5-yl]urea,
1-(1-methyl-2-oxopyrrolidin-3-yl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-{(3R,4S)-1-methyl-4-[(3 S)-tetrahydro-2H-pyran-3-yl]pyrrolidin-3-yl}urea,
1-[(3R,4S)-1,4-dimethylpyrrolidin-3-yl]-3-[1-(2-methylpyridin-4-yl)-1H-pyrazolo[3,4-c]pyridin-5-yl]urea,
1-[(3R,5S)-1,5-dimethylpyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-{[1-(2,2,2-trifluoro-1-methylethyl)azetidin-3-yl]methyl}urea,
1-[(3R)-1-ethylpyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3R)-1-propylpyrrolidin-3-yl]urea,
1-[(3R,4S)-4-cyclopropyl-1-methylpyrrolidin-3-yl]-3-[1-(2-methylpyridin-4-yl)-1H-pyrazolo[3,4-c]pyridin-5-yl]urea,
1-[(3R,4S)-4-cyclohexyl-1-methylpyrrolidin-3-yl]-3-[1-(2-methylpyridin-4-yl)-1H-pyrazolo[3,4-c]pyridin-5-yl]urea,
N-{3-[({[1-(2-methylpyridin-4-yl)-1H-pyrazolo[3,4-c]pyridin-5-yl]carbamoyl}amino)methyl]phenyl}methanesulfonamide, 1-[(1S)-1-(4-fluorophenyl)-2-methoxyethyl]-3-[1-(2-methylpyridin-4-yl)-1H-pyrazolo[3,4-c]pyridin-5-yl]urea,
1-[(3R)-1-(4-fluorophenyl)pyrrolidin-3-yl]-3-[1-(2-methylpyridin-4-yl)-1H-pyrazolo[3,4-c]pyridin-5-yl]urea,
1-[1-(2-methyl-2H-indazol-5-yl)-1H-pyrazolo[3,4-c]pyridin-5-yl]-3-[1,3-oxazol-5-yl(phenyl)methyl]urea,
1-[(3R,4S) or (3S,4R)-1-methyl-4-(2-methylphenyl)pyrrolidin-3-yl]-3-[1-(2-methylpyridin-4-yl)-1H-pyrazolo[3,4-c]pyridin-5-yl]urea,
1-benzyl-3-[1-(4-fluorophenyl)-1H-pyrazolo[3,4-c]pyridin-5-yl]urea,
1-(1-pyridin-4-yl-1H-pyrazolo[3,4-c]pyridin-5-yl)-3-[(1S)-2,2,2-trifluoro-1-phenylethyl]urea,
1-(pyridin-3-ylmethyl)-3-(1-pyridin-4-yl-1H-pyrazolo[3,4-c]pyridin-5-yl)urea,
1-[2-(2-fluorophenyl)ethyl]-3-(1-pyridin-4-yl-1H-pyrazolo[3,4-c]pyridin-5-yl)urea,
1-(3-chlorobenzyl)-3-(1-pyridin-4-yl-1H-pyrazolo[3,4-c]pyridin-5-yl)urea,
1-(4-chlorobenzyl)-3-(1-pyridin-4-yl-1H-pyrazolo[3,4-c]pyridin-5-yl)urea,
1-[(1R)-1-(3-chlorophenyl)ethyl]-3-[1-(2-methylpyridin-4-yl)-1H-pyrazolo[3,4-c]pyridin-5-yl]urea,
1-[(1R)-1-(2-chlorophenyl)ethyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-{1-[4-(1H-1,2,4-triazol-1-yl)phenyl]ethyl}urea,
1-(2,2-dimethyl-3,4-dihydro-2H-chromen-4-yl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-{1-[4-(trifluoromethoxy)phenyl]ethyl}urea,
1-[1-(2-methylpyridin-4-yl)-1H-pyrazolo[3,4-c]pyridin-5-yl]-3-{1-[3-(trifluoromethoxy)phenyl]ethyl}urea,
1-(3-hydroxy-2-phenylpropyl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(2-phenyl-2-piperidin-1-ylethyl)urea,
1-[3-(dimethylamino)-1-phenylpropyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(4-phenyltetrahydro-2H-pyran-4-yl)methyl]urea,
1-[1-(2-methylpyridin-4-yl)-1H-pyrazolo[3,4-c]pyridin-5-yl]-3-(1-phenyl-3-piperidin-1-ylpropyl)urea,
1-[2-(4-fluorophenyl)-2-piperidin-1-ylethyl]-3-[1-(2-methylpyridin-4-yl)-1H-pyrazolo[3,4-c]pyridin-5-yl]urea,
1-[2-(4,4-difluoropiperidin-1-yl)-2-phenylethyl]-3-[1-(2-methylpyridin-4-yl)-1H-pyrazolo[3,4-c]pyridin-5-yl]urea,
1-[(3R)-1-(2-fluoro-6-methoxybenzyl)piperidin-3-yl]-3-[1-(2-methylpyridin-4-yl)-1H-pyrazolo[3,4-c]pyridin-5-yl]urea,
1-(1-methyl-4-phenylpyrrolidin-3-yl)-3-[1-(2-methylpyridin-4-yl)-1H-pyrazolo[3,4-c]pyridin-5-yl]urea,
1-benzyl-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(1R)-1-phenylethyl]urea,
1-{[1-(4-fluorophenyl)-1H-pyrazol-4-yl]methyl}-3-[1-(2-methylpyridin-4-yl)-1H-pyrazolo[3,4-c]pyridin-5-yl]urea,
1-(2,2-difluoro-2-phenylethyl)-3-[1-(2-methylpyridin-4-yl)-1H-pyrazolo[3,4-c]pyridin-5-yl]urea,
1-(2-amino-1-phenylethyl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(4-phenylpyrrolidin-3-yl)urea,
1-[1-(2-methylpyridin-4-yl)-1H-pyrazolo[3,4-c]pyridin-5-yl]-3-(pyrazolo[1, 5-a]pyridin-3-ylmethyl)urea,
1-[(1S)-2-hydroxy-1-phenylethyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-{1-[4-(methylsulfonyl)phenyl]ethyl}urea,
1-[1-(2-methylpyridin-4-yl)-1H-pyrazolo[3,4-c]pyridin-5-yl]-3-(5-phenylpyrrolidin-3-yl)urea,
1-{[4-methyl-2-(1-methylethyl)-1,3-thiazol-5-yl]methyl}-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3-phenyltetrahydrofuran-3-yl)methyl]urea,
1-[1-(2-methylpyridin-4-yl)-1H-pyrazolo[3,4-c]pyridin-5-yl]-3-[2-(5-phenyl-2,5-diazabicyclo[2.2.1]hept-2-yl)ethyl]urea,
1-[1-(2-methylpyridin-4-yl)-1H-pyrazolo[3,4-c]pyridin-5-yl]-3-{2-[2-(phenoxymethyl)morpholin-4-yl]ethyl}urea,
1-[3-(dimethylamino)-1-pyridin-2-ylpropyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(2-morpholin-4-yl-2-pyridin-2-ylethyl)urea,
1-[1-(2-methylpyridin-4-yl)-1H-pyrazolo[3,4-c]pyridin-5-yl]-3-[(2-oxo-2,3-dihydro-H-indol-5-yl)methyl]urea,
1-[1-(2-methylpyridin-4-yl)-1H-pyrazolo[3,4-c]pyridin-5-yl]-3-[3-(1H-pyrazol-1-yl)benzyl]urea,
1-[1-(2-methylpyridin-4-yl)-1H-pyrazolo[3,4-c]pyridin-5-yl]-3-[4-(1H-pyrazol-1-yl)benzyl]urea,
1-(3-hydroxytricyclo[3.3.1.1~3,7~]dec-1-yl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(1-phenylpiperidin-4-yl)urea,
1-[1-(2-methylpyridin-4-yl)-1H-pyrazolo[3,4-c]pyridin-5-yl]-3-[(4-phenylmorpholin-2-yl)methyl]urea,
1-[1-(2-methylpyridin-4-yl)-1H-pyrazolo[3,4-c]pyridin-5-yl]-3-(2-oxo-1,2,3,4-tetrahydroquinolin-4-yl)urea,
1-[(1S)-2,2-difluoro-1-phenylethyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(1-phenylpiperidin-3-yl)urea,
1-[1-(2-methylpyridin-4-yl)-1H-pyrazolo[3,4-c]pyridin-5-yl]-3-[2-(tetrahydrofuran-3-yl)ethyl]urea,
1-[1-(2-methylpyridin-4-yl)-1H-pyrazolo[3,4-c]pyridin-5-yl]-3-[(1-oxo-2,3-dihydro-1H-isoindol-5-yl)methyl]urea,
1-[2-(4-fluorophenoxy)ethyl]-3-[1-(2-methylpyridin-4-yl)-1H-pyrazolo[3,4-c]pyridin-5-yl]urea,
1-[4-(1-hydroxy-1-methylethyl)benzyl]-3-[1-(2-methylpyridin-4-yl)-1H-pyrazolo[3,4-c]pyridin-5-yl]urea,
1-[2-(2-fluorophenoxy)ethyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(3,3,3-trifluoropropyl)urea,
1-[(1R)-3-hydroxy-1-phenylpropyl]-3-[1-(2-methylpyridin-4-yl)-1H-pyrazolo[3,4-c]pyridin-5-yl]urea,
1-[(1S)-2-methoxy-1-phenylethyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[4-(2-oxopyrrolidin-1-yl)benzyl]urea, N-methyl-4-[({[1-(2-methylpyridin-4-yl)-1H-pyrazolo[3,4-c]pyridin-5-yl]carbamoyl}amino)methyl]benzamide,
1-[1-(2-methylpyridin-4-yl)-1H-pyrazolo[3,4-c]pyridin-5-yl]-3-[3-(methylsulfonyl)benzyl]urea,
1-[1-(2-methylpyridin-4-yl)-1H-pyrazolo[3,4-c]pyridin-5-yl]-3-[3-(1,3-oxazol-2-yl)benzyl]urea,
1-[2-(benzyloxy)ethyl]-3-[1-(2-methylpyridin-4-yl)-1H-pyrazolo[3,4-c]pyridin-5-yl]urea,
1-[2-(benzylamino)ethyl]-3-[1-(2-methylpyridin-4-yl)-1H-pyrazolo[3,4-c]pyridin-5-yl]urea,
N-methyl-3-[({[1-(2-methylpyridin-4-yl)-1H-pyrazolo[3,4-c]pyridin-5-yl]carbamoyl})amino)methyl]benzamide,
1-(3-isoxazol-3-ylbenzyl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(1-methyl-1,2,3,4-tetrahydroquinolin-3-yl)methyl]urea,
1-{[1-(dimethylamino)cyclohexyl]methyl}-3-[1-(2-methylpyridin-4-yl)-1H-pyrazolo[3,4-c]pyridin-5-yl]urea,
1-[(2S,3S,4R)-1,2-dimethyl-4-(2-methylphenyl)pyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3S,4R)-1,2,2-trimethyl-4-(2-methylphenyl)pyrrolidin-3-yl]urea,
1-[1-(2-methylpyridin-4-yl)-1H-pyrazolo[3,4-c]pyridin-5-yl]-3-[(3S,4S)-1,5,5-trimethyl-4-(2-methylphenyl)pyrrolidin-3-yl]urea,
1-[(2R,3S,4R)-1,2-dimethyl-4-(2-methylphenyl)pyrrolidin-3-yl]-3-[1-(2-methylpyridin-4-yl)-1H-pyrazolo[3,4-c]pyridin-5-yl]urea,
1-[(3S,4S,5 S)-1,5-dimethyl-4-(2-methylphenyl)pyrrolidin-3-yl]-3-[1-(2-methylpyridin-4-yl)-1H-pyrazolo[3,4-c]pyridin-5-yl]urea,
1-[(3S,4S,5R)-1,5-dimethyl-4-(2-methylphenyl)pyrrolidin-3-yl]-3-[1-(2-methylpyridin-4-yl)-1H-pyrazolo[3,4-c]pyridin-5-yl]urea,
1-[(7R,8S)-5-methyl-7-phenyl-2-oxa-5-azaspiro[3.4]oct-8-yl]-3-[1-(2-methylpyridin-4-yl)-1H-pyrazolo[3,4-c]pyridin-5-yl]urea,
1-[(1-methyl-1H-imidazol-4-yl)methyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(2-morpholin-4-ylethyl)urea,
1-(2-fluoroethyl)-3-[1-(2-methylpyridin-4-yl)-1H-pyrazolo[3,4-c]pyridin-5-yl]urea,
1-(2-methoxyethyl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3S,4R)-1-methyl-4-pyridin-3-ylpyrrolidin-3-yl]urea,
1-[(3R,4S)-1-methyl-4-(3-methylthiophen-2-yl)pyrrolidin-3-yl]-3-[1-(2-methylpyridin-4-yl)-1H-pyrazolo[3,4-c]pyridin-5-yl]urea,
1-[(5-methyl-3-phenylisoxazol-4-yl)methyl]-3-[1-(2-methylpyridin-4-yl)-1H-pyrazolo[3,4-c]pyridin-5-yl]urea,
1-[(3R,4S)-1-methyl-4-(2-phenylethyl)pyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(1,3,5-trimethyl-1H-pyrazol-4-yl)methyl]urea,
1-[2-(3,5-dimethylisoxazol-4-yl)ethyl]-3-[1-(2-methylpyridin-4-yl)-1H-pyrazolo[3,4-c]pyridin-5-yl]urea,
1-[(4-methyl-1,2,5-oxadiazol-3-yl)methyl]-3-[1-(2-methylpyridin-4-yl)-1H-pyrazolo[3,4-c]pyridin-5-yl]urea,
1-[(1,3-dimethyl-1H-pyrazol-5-yl)methyl]-3-[1-(2-methylpyridin-4-yl)-1H-pyrazolo[3,4-c]pyridin-5-yl]urea,
1-(2-hydroxypropyl)-3-[1-(2-methylpyridin-4-yl)-1H-pyrazolo[3,4-c]pyridin-5-yl]urea,
1-(1-cyanocyclopropyl)-3-[1-(2-methylpyridin-4-yl)-1H-pyrazolo[3,4-c]pyridin-5-yl]urea,
1-(1-methyl-1-phenylethyl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[1-(2-methyl-1,3-thiazol-4-yl)ethyl]urea,
1-[(3S,4R)-1-methyl-4-(5-methylthiophen-2-yl)pyrrolidin-3-yl]-3-[1-(2-methylpyridin-4-yl)-1H-pyrazolo[3,4-c]pyridin-5-yl]urea,
1-(1-benzothiophen-3-ylmethyl)-3-[1-(2-methylpyridin-4-yl)-1H-pyrazolo[3,4-c]pyridin-5-yl]urea,
1-[(3S,4R)-1-methyl-4-(4-methyl-1,3-thiazol-2-yl)pyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(1S)-2-morpholin-4-yl-1-phenylethyl]urea,
1-[1-(2-methylpyridin-4-yl)-1H-pyrazolo[3,4-c]pyridin-5-yl]-3-[1-(2-methyl-1,3-thiazol-4-yl)ethyl]urea,
1-[(1S)-2-ethoxy-1-phenylethyl]-3-[1-(2-methylpyridin-4-yl)-1H-pyrazolo[3,4-c]pyridin-5-yl]urea,
1-[(1S)-2-(dimethylamino)-1-phenylethyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[1-(2-methyl-1,3-thiazol-4-yl)ethyl]urea,
1-[(3S,4S)-4-methoxypyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-pyrrolidin-3-ylurea,
1-[(1S)-2-(1H-imidazol-1-yl)-1-phenylethyl]-3-[1-(2-methylpyridin-4-yl)-1H-pyrazolo[3,4-c]pyridin-5-yl]urea,
1-[(1S)-2-(1-methylethoxy)-1-phenylethyl]-3-[1-(2-methylpyridin-4-yl)-1H-pyrazolo[3,4-c]pyridin-5-yl]urea,
1-[(1S)-2-(2-methoxyethoxy)-1-phenylethyl]-3-[1-(2-methylpyridin-4-yl)-1H-pyrazolo[3,4-c]pyridin-5-yl]urea,
methyl (2S)-({[1-(2-methylpyridin-4-yl)-1H-pyrazolo[3,4-c]pyridin-5-yl]carbamoyl}amino)(phenyl)ethanoate,
1-[(1S,2S)-2-aminocyclohexyl]-3-[1-(2-methylpyridin-4-yl)-1H-pyrazolo[3,4-c]pyridin-5-yl]urea,
N-[(1S,2S)-2-({[1-(2-methylpyridin-4-yl)-1H-pyrazolo[3,4-c]pyridin-5-yl]carbamoyl}amino)cyclohexyl]acetamide,
1-[(1S,2S)-2-methoxycyclopentyl]-3-[1-(2-methylpyridin-4-yl)-1H-pyrazolo[3,4-c]pyridin-5-yl]urea,
(2S)-N-ethyl-2-({[1-(2-methylpyridin-4-yl)-1H-pyrazolo[3,4-c]pyridin-5-yl]carbamoyl}amino)-2-phenylethanamide,
(2S)-N-methyl-2-({[1-(2-methylpyridin-4-yl)-1H-pyrazolo[3,4-c]pyridin-5-yl]carbamoyl}amino)-2-phenylethanamide,
1-[(1S,2S)-2-(dimethylamino)cyclohexyl]-3-[1-(2-methylpyridin-4-yl)-1H-pyrazolo[3,4-c]pyridin-5-yl]urea,
(2S)-N,N-diethyl-2-({[1-(2-methylpyridin-4-yl)-1H-pyrazolo[3,4-c]pyridin-5-yl]carbamoyl}amino)-2-phenylethanamide,
Racemic 1-[(1S,2S) and (1R,2R)-2-methoxycyclohexyl]-3-[1-(2-methylpyridin-4-yl)-1H-pyrazolo[3,4-c]pyridin-5-yl]urea, Racemic 1-[(1S,2S) and (1R,2R)-2-ethoxycyclohexyl]-3-[1-(2-methylpyridin-4-yl)-1H-pyrazolo[3,4-c]pyridin-5-yl]urea,
Racemic 1-[(1S,2S) and (1R,2R)-2-ethoxycyclopentyl]-3-[1-(2-methylpyridin-4-yl)-1H-pyrazolo[3,4-c]pyridin-5-yl]urea,
Racemic 1-[1-(2-methylpyridin-4-yl)-1H-pyrazolo[3,4-c]pyridin-5-yl]-3-[(1S,2S) and (1R,2R)-2-phenylcyclopentyl]urea,
1-[(3R,4S)-1-methyl-4-(3-phenylpropyl)pyrrolidin-3-yl]-3-[1-(2-methylpyridin-4-yl)-1H-pyrazolo[3,4-c]pyridin-5-yl]urea,
1-[(3R,4S)-1-methyl-4-(5-methylisoxazol-3-yl)pyrrolidin-3-yl]-3-[1-(2-methylpyridin-4-yl)-1H-pyrazolo[3,4-c]pyridin-5-yl]urea,
Racemic trans 1-[1-(2-methylpyridin-4-yl)-1H-pyrazolo[3,4-c]pyridin-5-yl]-3-[(1S,2R) and (1R,2S)-2-phenylcyclohexyl]urea,
Racemic Trans N-[(1S,2S) and (1R,2R)-2-({[1-(2-methylpyridin-4-yl)-1H-pyrazolo[3,4-c]pyridin-5-yl]carbamoyl}amino)cyclohexyl]benzamide,
Racemic cis 1-[(1S,2S) and (1R,2R)-2-(4-fluorophenyl)cyclopentyl]-3-[1-(2-methylpyridin-4-yl)-1H-pyrazolo[3,4-c]pyridin-5-yl]urea,
1-[(1S,2S)-2-(benzyloxy)cyclopentyl]-3-[1-(2-methylpyridin-4-yl)-1H-pyrazolo[3,4-c]pyridin-5-yl]urea,
1-[(3R,4S)-1-methyl-4-(5-phenylthiophen-2-yl)pyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3R,4S)-4-phenyl-1-(2,2,2-trifluoroethyl)pyrrolidin-3-yl]urea,
1-[1-(2-methylpyridin-4-yl)-1H-pyrazolo[3,4-c]pyridin-5-yl]-3-[(3S,4S)-4-phenoxypyrrolidin-3-yl]urea,
1-[(3S,4S)-1-methyl-4-phenoxypyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[phenyl(tetrahydrofuran-2-yl)methyl]urea,
1-[(1S,2S)-2-benzylcyclopentyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(1S,2S)-2-phenoxycyclopentyl]urea,
Racemic trans 1-[1-(2-methylpyridin-4-yl)-1H-pyrazolo[3,4-c]pyridin-5-yl]-3-[(1S,2S) and (1R,2R)-2-(3-phenylpropoxy)cyclopentyl]urea,
1-[(1S,2R)-2-benzylcyclohexyl]-3-[1-(2-methylpyridin-4-yl)-1H-pyrazolo[3,4-c]pyridin-5-yl]urea,
1-[(3R,4S)-4-(5-cyclopropylthiophen-2-yl)-1-methylpyrrolidin-3-yl]-3-[1-(2-methylpyridin-4-yl)-1H-pyrazolo[3,4-c]pyridin-5-yl]urea,
1-[(3R,4S)-1-methyl-4-(1-methyl-1H-pyrazol-4-yl)pyrrolidin-3-yl]-3-[1-(2-methylpyridin-4-yl)-1H-pyrazolo[3,4-c]pyridin-5-yl]urea,
Racemic trans 1-[(1S,2S) and (1R,2R)-2-(4-fluorophenoxy)cyclopentyl]-3-[1-(2-methylpyridin-4-yl)-1H-pyrazolo[3,4-c]pyridin-5-yl]urea,
Racemic cis 1-[(1S,2S) and (1R,2R)-2-benzylcyclohexyl]-3-[1-(2-methylpyridin-4-yl)-1H-pyrazolo[3,4-c]pyridin-5-yl]urea,
Racemic trans 1-[1-(2-methylpyridin-4-yl)-1H-pyrazolo[3,4-c]pyridin-5-yl]-3-[(1S,2R) and (1R,2S)-2-phenylcyclopentyl]urea,
Racemic trans 1-[1-(2-methylpyridin-4-yl)-1H-pyrazolo[3,4-c]pyridin-5-yl]-3-[(1S,2R) and (1R,2S)-2-phenylcyclohexyl]urea,
1-[3-(4-fluorophenyl)cyclopentyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(3-phenylcyclohexyl)urea,
1-(3,4-dihydro-2H-chromen-4-yl)-3-[1-(2-methylpyridin-4-yl)-1H-pyrazolo[3,4-c]pyridin-5-yl]urea,
1-[3-(4-fluorophenyl)cyclohexyl]-3-[1-(2-methylpyridin-4-yl)-1H-pyrazolo[3,4-c]pyridin-5-yl]urea,
Racemic cis 1-[(1S,2S) and (1R,2R)-2-(4-fluorophenyl)cyclohexyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(3-phenylcyclohexyl)urea,
1-[3-(4-fluorophenyl)cyclohexyl]-3-[1-(2-methylpyridin-4-yl)-1H-pyrazolo[3,4-c]pyridin-5-yl]urea,
1-(2,3-dihydro-1-benzofuran-3-yl)-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(3-phenylcyclopentyl)urea,
1-((3S,4R)1-methyl-4-phenylpyrrolidin-3-yl)-3-[1-(2-methylpyridin-4-yl)-1H-pyrazolo[3,4-c]pyridin-5-yl]urea,
1-((3R,4S)1-methyl-4-phenylpyrrolidin-3-yl)-3-[1-(2-methylpyridin-4-yl)-1H-pyrazolo[3,4-c]pyridin-5-yl]urea,
1-[(7R,8S)-5-methyl-7-phenyl-2-oxa-5-azaspiro[3.4]oct-8-yl]-3-[1-(2-methylpyridin-4-yl)-1H-pyrazolo[3,4-c]pyridin-5-yl]urea,
1-[(7 S,8R)-5-methyl-7-phenyl-2-oxa-5-azaspiro[3.4]oct-8-yl]-3-[1-(2-methylpyridin-4-yl)-1H-pyrazolo[3,4-c]pyridin-5-yl]urea,
1-[(3R,4S)-1-methyl-4-(2-phenylethyl)pyrrolidin-3-yl]-3-[1-(2-methylpyridin-4-yl)-1H-pyrazolo[3,4-c]pyridin-5-yl]urea,
1-[(1R)-2-amino-1-phenylethyl]-3-[1-(2-methylpyridin-4-yl)-1H-pyrazolo[3,4-c]pyridin-5-yl]urea,
1-[(1S)-2-amino-1-phenylethyl]-3-[1-(2-methylpyridin-4-yl)-1H-pyrazolo[3,4-c]pyridin-5-yl]urea,
1-[(3S,4R)-1-methyl-4-(5-methylthiophen-2-yl)pyrrolidin-3-yl]-3-[1-(2-methylpyridin-4-yl)-1H-pyrazolo[3,4-c]pyridin-5-yl]urea,
1-[(3S,4R)-1-methyl-4-(2-methylphenyl)pyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-{(3R,4S)-1-methyl-4-[2-(trifluoromethyl)phenyl]pyrrolidin-3-yl}urea,
1-[1-(2-methylpyridin-4-yl)-1H-pyrazolo[3,4-c]pyridin-5-yl]-3-{(3S,4R)-1-methyl-4-[2-(trifluoromethyl)phenyl]pyrrolidin-3-yl}urea,
1-[(3S,4S)-4-methoxy-1-methylpyrrolidin-3-yl]-3-[1-(2-methylpyridin-4-yl)-1H-pyrazolo[3,4-c]pyridin-5-yl]urea,
1-[(3R,4R)-4-methoxy-1-methylpyrrolidin-3-yl]-3-[1-(2-methylpyridin-4-yl)-1H-pyrazolo[3,4-c]pyridin-5-yl]urea,
1-[(3R,4S)-1-cyclobutyl-4-phenylpyrrolidin-3-yl]-3-[1-(2-methylpyridin-4-yl)-1H-pyrazolo[3,4-c]pyridin-5-yl]urea,
1-[(3S,4R)-1-cyclobutyl-4-phenylpyrrolidin-3-yl]-3-[1-(2-methylpyridin-4-yl)-1H-pyrazolo[3,4-c]pyridin-5-yl]urea,
1-[(3S,4R)-1-(1-methylethyl)-4-phenylpyrrolidin-3-yl]-3-[1-(2-methylpyridin-4-yl)-1H-pyrazolo[3,4-c]pyridin-5-yl]urea, 1-[(3R,4S)-1-(1-methylethyl)-4-phenylpyrrolidin-3-yl]-3-[1-(2-methylpyridin-4-yl)-1H-pyrazolo[3,4-c]pyridin-5-yl]urea, 1-[(3R,4S)-1-ethyl-4-phenylpyrrolidin-3-yl]-3-[1-(2-methylpyridin-4-yl)-1H-pyrazolo[3,4-c]pyridin-5-yl]urea, 1-[(3S,4R)-1-ethyl-4-phenylpyrrolidin-3-yl]-3-[1-(2-methylpyridin-4-yl)-1H-pyrazolo[3,4-c]pyridin-5-yl]urea, 1-[(7S,8S)-5-methyl-8-phenyl-2-oxa-5-azaspiro[3.4]oct-7-yl]-3-[1-(2-methylpyridin-4-yl)-1H-pyrazolo[3,4-c]pyridin-5-yl]urea, 1-[(7R,8R)-5-methyl-8-phenyl-2-oxa-5-azaspiro[3.4]oct-7-yl]-3-[1-(2-methylpyridin-4-yl)-1H-pyrazolo[3,4-c]pyridin-5-yl]urea, 1-[1-(2-methylpyridin-4-yl)-1H-pyrazolo[3,4-c]pyridin-5-yl]-3-[(1S)-1-pyridin-2-ylethyl]urea, 1-[1-(2-methylpyridin-4-yl)-1H-pyrazolo[3,4-c]pyridin-5-yl]-3-[(1R)-1-pyridin-2-ylethyl]urea, R)-1-(1-(3-chloro-4-fluorophenyl)ethyl)-3-(1-(1-methyl-1H-pyrazol-4-yl)-1H-pyrazolo[3,4-c]pyridin-5-yl)urea, 1-[(1S)-2-hydroxy-2-methyl-1-phenylpropyl]-3-[1-(1-methyl-1H-indazol-6-yl)-1H-pyrazolo[3,4-c]pyridin-5-yl]urea, 1-[(1S)-2-hydroxy-2-methyl-1-phenylpropyl]-3-[1-(2-methyl-2H-indazol-5-yl)-1H-pyrazolo[3,4-c]pyridin-5-yl]urea, 1-[1-(4-fluorophenyl)-1H-pyrazolo[3,4-c]pyridin-5-yl]-3-[(3R,4S)-1-methyl-4-phenylpyrrolidin-3-yl]urea, 1-[(1R)-2-methoxy-1-pyridin-2-ylethyl]-3-[1-(2-methylpyridin-4-yl)-1H-pyrazolo[3,4-c]pyridin-5-yl]urea, 1-[(1S)-2-methoxy-1-pyridin-2-ylethyl]-3-[1-(2-methylpyridin-4-yl)-1H-pyrazolo[3,4-c]pyridin-5-yl]urea, 1-[1-(6-methylpyrazin-2-yl)-1H-pyrazolo[3,4-c]pyridin-5-yl]-3-[(1R)-1-phenylethyl]urea, 1-[1-(5-methylpyrazin-2-yl)-1H-pyrazolo[3,4-c]pyridin-5-yl]-3-[(1R)-1-phenylethyl]urea, 1-[1-(6-methylpyridazin-3-yl)-1H-pyrazolo[3,4-c]pyridin-5-yl]-3-[(1R)-1-phenylethyl]urea, 1-(3-chloro-4-fluorobenzyl)-3-[1-(2-methylpyridin-4-yl)-1H-pyrazolo[3,4-c]pyridin-5-yl]urea, 1-(3-chlorobenzyl)-3-[1-(2-methylpyridin-4-yl)-1H-pyrazolo[3,4-c]pyridin-5-yl]urea, 1-(3-chlorobenzyl)-3-{1-(1-methyl-1H-pyrazol-4-yl)-1H-pyrazolo[3,4-c]pyridin-5-yl]urea, 1-[(1R)-1-(3-chlorophenyl)ethyl]-3-[1-(1-methyl-1H-pyrazol-4-yl)-1H-pyrazolo[3,4-c]pyridin-5-yl]urea, 1-(3-chloro-4-fluorobenzyl)-3-[1-(1-methyl-1H-pyrazol-4-yl)-1H-pyrazolo[3,4-c]pyridin-5-yl]urea, 1-[(1R)-1-(3-chloro-4-fluorophenyl)ethyl]-3-[1-(2-methylpyridin-4-yl)-1H-pyrazolo[3,4-c]pyridin-5-yl]urea, 1-[1-(4-fluorophenyl)-1H-pyrazolo[3,4-c]pyridin-5-yl]-3-[(1S)-1-pyridin-2-ylethyl]urea, 1-[1-(4-fluorophenyl)-1H-pyrazolo[3,4-c]pyridin-5-yl]-3-[(1R)-1-pyridin-2-ylethyl]urea, (R)-1-(1-(4-fluorophenyl)ethyl)-3-(1-(2-methylpyridin-4-yl)-1H-pyrazolo[3,4-c]pyridin-5-yl)urea, (R)-1-(4-Fluoro-1-(2-methylpyridin-4-yl)-1H-pyrazolo[3,4-c]pyridin-5-yl)-3-(1-phenylethyl)urea, (R)-1-(1-methyl-1H-pyrazolo[3,4-c]pyridin-5-yl)-3-(1-phenylethyl)urea, 1-[7-(hydroxymethyl)-1-methyl-1H-pyrazolo[3,4-c]pyridin-5-yl]-3-[(1S)-2-hydroxy-2-methyl-1-phenylpropyl]urea, 1-((1S,2R)-2-Hydroxy-1-phenylpropyl)-3-(1H-pyrazolo[3,4-c]pyridin-5-yl)urea, 1-[(1S)-2-hydroxy-2-methyl-1-phenylpropyl]-3-(1-methyl-1H-pyrazolo[3,4-c]pyridin-5-yl)urea, (R)-1-(7-(hydroxymethyl)-1H-pyrazolo[3,4-c]pyridin-5-yl)-3-(1-phenylethyl)urea, (S)-1-(2-hydroxy-2-methyl-1-phenylpropyl)-3-(1H-pyrazolo[3,4-c]pyridin-5-yl)urea (TFA salt), N-ethyl-5-({[(1R)-1-phenylethyl]carbamoyl}amino)-1H-pyrazolo[3,4-c]pyridine-1-carboxamide, 1-[(1R)-1-(4-fluorophenyl)ethyl]-3-(1-methyl-1H-pyrazolo[3,4-c]pyridin-5-yl)urea, 1-[(1R)-1-(4-fluorophenyl)ethyl]-3-[1-(2-oxopiperidin-4-yl)-1H-pyrazolo[3,4-c]pyridin-5-yl]urea, tert-butyl 2-[5-({[(1S)-1-(4-fluorophenyl)-2-hydroxy-2-methylpropyl]carbamoyl}amino)-1H-pyrazolo[3,4-c]pyridin-1-yl]-5,8-dihydropyrido[3,4-d]pyrimidine-7(6H)-carboxylate, 1-[1-(3-methoxypropyl)-1H-pyrazolo[3,4-c]pyridin-5-yl]-3-[(1R)-1-phenylethyl]urea, 1-[1-(2,6-difluorobenzyl)piperidin-3-yl]-3-(1-methyl-1H-pyrazolo[3,4-c]pyridin-5-yl)urea, 1-[(1S)-2-methoxy-1-phenylethyl]-3-(1-methyl-1H-pyrazolo[3,4-c]pyridin-5-yl)urea, 1-[(1R)-1-phenylethyl]-3-[1-(tetrahydro-2H-pyran-4-yl)-1H-pyrazolo[3,4-c]pyridin-5-yl]urea, 1-[(1S)-2-methoxy-1-phenylethyl]-3-[1-(2-methylpiperidin-4-yl)-1H-pyrazolo[3,4-c]pyridin-5-yl]urea, 1-[1-(4-fluorophenyl)-7-(hydroxymethyl)-1H-pyrazolo[3,4-c]pyridin-5-yl]-3-[(1R)-1-phenylethyl]urea, 1-[1-(4-fluorophenyl)-7-(methoxymethyl)-1H-pyrazolo[3,4-c]pyridin-5-yl]-3-[(1R)-1-phenylethyl]urea, 1-[1-(4-fluorophenyl)-7-(morpholin-4-ylmethyl)-1H-pyrazolo[3,4-c]pyridin-5-yl]-3-[(1R)-1-phenylethyl]urea, 1-{7-[(dimethylamino)methyl]-1-(4-fluorophenyl)-1H-pyrazolo[3,4-c]pyridin-5-yl}-3-[(1R)-1-phenylethyl]urea, 1-{1-(4-fluorophenyl)-7-[(2-morpholin-4-ylethoxy)methyl]-1H-pyrazolo[3,4-c]pyridin-5-yl}-3-[(1R)-1-phenylethyl]urea, 1-[1-(2-methylpyridin-4-yl)-7-(morpholin-4-ylmethyl)-1H-pyrazolo[3,4-c]pyridin-5-yl]-3-[(1R)-1-phenylethyl]urea, 1-{1-(4-fluorophenyl)-7-[(2-hydroxyethoxy)methyl]-1H-pyrazolo[3,4-c]pyridin-5-yl}-3-[(1R)-1-phenylethyl]urea, 1-[7-(methoxymethyl)-1-(2-methylpyridin-4-yl)-1H-pyrazolo[3,4-c]pyridin-5-yl]-3-[(1R)-1-phenylethyl]urea, 1-{7-[(2-methoxyethoxy)methyl]-1-(2-methylpyridin-4-yl)-1H-pyrazolo[3,4-c]pyridin-5-yl}-3-[(1R)-1-phenylethyl]urea, 1-{1-(2-methylpyridin-4-yl)-7-[(2-morpholin-4-ylethoxy)methyl]-1H-pyrazolo[3,4-c]pyridin-5-yl}-3-[(1R)-1-phenylethyl]urea, 1-{1-(2-methylpyridin-4-yl)-7-[(oxetan-3-yloxy)methyl]-1H-pyrazolo[3,4-c]pyridin-5-yl}-3-[(1R)-1-phenylethyl]urea, 1-[7-methyl-1-(2-methylpyridin-4-yl)-1H-pyrazolo[3,4-c]pyridin-5-yl]-3-[(1R)-1-phenylethyl]urea, 1-[7-{[2-(benzyloxy)ethoxy]methyl}-1-(2-methylpyridin-4-yl)-1H-pyrazolo[3,4-c]pyridin-5-yl]-3-[(1R)-1-phenylethyl]urea, 1-{7-[(2-hydroxyethoxy)methyl]-1-(2-methylpyridin-4-yl)-1H-pyrazolo[3,4-c]pyridin-5-yl}-3-[(1R)-1-phenylethyl]urea, 1-[7-(hydroxymethyl)-1-(2-methylpyridin-4-yl)-1H-pyrazolo[3,4-c]pyridin-5-yl]-3-[(1S)-2-hydroxy-2-methyl-1-phenylpropyl]urea,
1-[1-tert-butyl-7-(hydroxymethyl)-1H-pyrazolo[3,4-c]pyridin-5-yl]-3-[(1R)-1-phenylethyl]urea,
1-(1-ethyl-7-methoxy-1H-pyrazolo[3,4-c]pyridin-5-yl)-3-[(1R)-1-phenylethyl]urea,
1-(1-ethyl-7-methoxy-1H-pyrazolo[3,4-c]pyridin-5-yl)-3-[(1S)-2-hydroxy-2-methyl-1-phenylpropyl]urea,
1-[(1S)-2-methoxy-1-phenylethyl]-3-[1-(pyridin-4-ylmethyl)-1H-pyrazolo[3,4-c]pyridin-5-yl]urea,
1-[1-(2-methylpyridin-4-yl)-1H-pyrazolo[3,4-c]pyridin-5-yl]-3-[1-(pyridin-3-ylmethyl)piperidin-3-yl]urea,
1-[1-(2,6-difluorobenzyl)piperidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[1-(1,3-thiazol-2-ylmethyl)piperidin-3-yl]urea,
1-{1-[(2-chloropyridin-3-yl)methyl]piperidin-3-yl}-3-[1-(2-methylpyridin-4-yl)-1H-pyrazolo[3,4-c]pyridin-5-yl]urea,
1-[(3S,4S)-1-(2,6-difluorobenzyl)-4-methoxypyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[1-(pyridin-3-ylmethyl)pyrrolidin-3-yl]urea,
1-[1-(2,6-difluorobenzyl)pyrrolidin-3-yl]-3-[1-(2-methylpyridin-4-yl)-1H-pyrazolo[3,4-c]pyridin-5-yl]urea,
1-[(3S,4S)-4-ethoxypyrrolidin-3-yl]-3-[1-(2-methylpyridin-4-yl)-1H-pyrazolo[3,4-c]pyridin-5-yl]urea,
1-[(3S,4S) or (3R,4R)-1-(2,6-difluorobenzyl)-4-methoxypyrrolidin-3-yl]-3-[1-(2-methylpyridin-4-yl)-1H-pyrazolo[3,4-c]pyridin-5-yl]urea,
1-[(3R,4R) or (3S,4S)-1-(2,6-difluorobenzyl)-4-methoxypyrrolidin-3-yl]-3-[1-(2-methylpyridin-4-yl)-1H-pyrazolo[3,4-c]pyridin-5-yl]urea,
1-{(3S,4S)-4-[(5-fluoropyridin-3-yl)oxy]pyrrolidin-3-yl}-3-[1-(2-methylpyridin-4-yl)-1H-pyrazolo[3,4-c]pyridin-5-yl]urea,
1-{(3S,4S)-4-[(5-fluoropyridin-3-yl)oxy]-1-methylpyrrolidin-3-yl}-3-[1-(2-methylpyridin-4-yl)-1H-pyrazolo[3,4-c]pyridin-5-yl]urea,
1-{(3S,4S)-1-ethyl-4-[(5-fluoropyridin-3-yl)oxy]pyrrolidin-3-yl}-3-[1-(2-methylpyridin-4-yl)-1H-pyrazolo[3,4-c]pyridin-5-yl]urea,
1-[(3S,4S)-1-(2,6-difluorobenzyl)-4-ethoxypyrrolidin-3-yl]-3-[1-(2-methylpyridin-4-yl)-1H-pyrazolo[3,4-c]pyridin-5-yl]urea,
1-{(3S,4S)-4-ethoxy-1-[2-(trifluoromethyl)benzyl]pyrrolidin-3-yl}-3-[1-(2-methylpyridin-4-yl)-1H-pyrazolo[3,4-c]pyridin-5-yl]urea,
1-[1-(2-cyanobenzyl)pyrrolidin-3-yl]-3-[1-(2-methylpyridin-4-yl)-1H-pyrazolo[3,4-c]pyridin-5-yl]urea,
1-{1-[(2-chloropyridin-3-yl)methyl]pyrrolidin-3-yl}-3-[1-(2-methylpyridin-4-yl)-1H-pyrazolo[3,4-c]pyridin-5-yl]urea,
1-[(3 S)-1-(2,6-difluorobenzyl)pyrrolidin-3-yl]-3-[1-(2-methylpyridin-4-yl)-1H-pyrazolo[3,4-c]pyridin-5-yl]urea,
1-[(3R)-1-(2,6-difluorobenzyl)pyrrolidin-3-yl]-3-[1-(2-methylpyridin-4-yl)-1H-pyrazolo[3,4-c]pyridin-5-yl]urea,
1-[(3S,4S)-4-(4-fluorophenoxy)pyrrolidin-3-yl]-3-[1-(2-methylpyridin-4-yl)-1H-pyrazolo[3,4-c]pyridin-5-yl]urea,
1-[(3S,4S)-4-(4-fluorophenoxy)-1-methylpyrrolidin-3-yl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-[(3R)-pyrrolidin-3-ylmethyl]urea,
1-[(3-fluoroazetidin-3-yl)methyl]-3-[1-(2-methylpyridin-4-yl)-1H-pyrazolo[3,4-c]pyridin-5-yl]urea,
1-[1-(2-methylpyridin-4-yl)-1H-pyrazolo[3,4-c]pyridin-5-yl]-3-(5-phenylpiperidin-3-yl)urea,
1-[1-(2-methylpyridin-4-yl)-1H-pyrazolo[3,4-c]pyridin-5-yl]-3-{[(3R)-1-methylpyrrolidin-3-yl]methyl}urea,
1-(1-methyl-5-phenylpiperidin-3-yl)-3-[1-(2-methylpyridin-4-yl)-1H-pyrazolo[3,4-c]pyridin-5-yl]urea,
1-[(1S)-2-ethyl-2-hydroxy-1-phenylbutyl]-3-[1-(2-methylpyridin-4-yl)-1H-pyrazolo[3,4-c]pyridin-5-yl]urea,
1-[(1S)-1-(4-fluorophenyl)-2-hydroxy-2-methylpropyl]-3-[1-(2-methylpyridin-4-yl)-1H-pyrazolo[3,4-c]pyridin-5-yl]urea,
1-[(1S)-1-(4-fluorophenyl)-2-hydroxy-2-methylpropyl]-3-[1-(4-fluorophenyl)-1H-pyrazolo[3,4-c]pyridin-5-yl]urea,
1-[7-(hydroxymethyl)-1-(3-methoxypropyl)-1H-pyrazolo[3,4-c]pyridin-5-yl]-3-[(1R)-1-phenylethyl]urea,
1-[7-(hydroxymethyl)-1-(1-methylethyl)-1H-pyrazolo[3,4-c]pyridin-5-yl]-3-[(1R)-1-phenylethyl]urea,
1-[1-(cyclopentylmethyl)-7-(hydroxymethyl)-1H-pyrazolo[3,4-c]pyridin-5-yl]-3-[(1R)-1-phenylethyl]urea,
1-[1-(cyclobutylmethyl)-7-(hydroxymethyl)-1H-pyrazolo[3,4-c]pyridin-5-yl]-3-[(1R)-1-phenylethyl]urea,
1-[7-(hydroxymethyl)-1-propyl-1H-pyrazolo[3,4-c]pyridin-5-yl]-3-[(1R)-1-phenylethyl]urea,
1-[7-(hydroxymethyl)-1-(2-methylpropyl)-1H-pyrazolo[3,4-c]pyridin-5-yl]-3-[(1R)-1-phenylethyl]urea,
1-[1-cyclopentyl-7-(hydroxymethyl)-1H-pyrazolo[3,4-c]pyridin-5-yl]-3-[(1R)-1-phenylethyl]urea,
1-[1-(cyclopropylmethyl)-7-(hydroxymethyl)-1H-pyrazolo[3,4-c]pyridin-5-yl]-3-[(1R)-1-phenylethyl]urea,
1-[7-(hydroxymethyl)-1-(tetrahydro-2H-pyran-4-ylmethyl)-1H-pyrazolo[3,4-c]pyridin-5-yl]-3-[(1R)-1-phenylethyl]urea,
1-[1-(2-hydroxyethyl)-7-(hydroxymethyl)-1H-pyrazolo[3,4-c]pyridin-5-yl]-3-[(1R)-1-phenylethyl]urea,
1-[7-(hydroxymethyl)-1-(tetrahydrofuran-3-ylmethyl)-1H-pyrazolo[3,4-c]pyridin-5-yl]-3-[(1R)-1-phenylethyl]urea,
1-[7-(hydroxymethyl)-1-(2-methoxyethyl)-1H-pyrazolo[3,4-c]pyridin-5-yl]-3-[(1R)-1-phenylethyl]urea,
1-[1-cyclohexyl-7-(hydroxymethyl)-1H-pyrazolo[3,4-c]pyridin-5-yl]-3-[(1R)-1-phenylethyl]urea,
1-[7-(hydroxymethyl)-1-(2,2,2-trifluoroethyl)-1H-pyrazolo[3,4-c]pyridin-5-yl]-3-[(1R)-1-phenylethyl]urea,
1-[7-(hydroxymethyl)-1-(oxetan-3-ylmethyl)-1H-pyrazolo[3,4-c]pyridin-5-yl]-3-[(1R)-1-phenylethyl]urea,
1-[7-(hydroxymethyl)-1-(tetrahydro-2H-pyran-4-yl)-1H-pyrazolo[3,4-c]pyridin-5-yl]-3-[(1R)-1-phenylethyl]urea,
1-[(1S)-1-(4-fluorophenyl)-2-hydroxy-2-methylpropyl]-3-[1-(5,6,7,8-tetrahydropyrido[3,4-d]pyrimidin-2-yl)-1H-pyrazolo[3,4-c]pyridin-5-yl]urea,
1-[1-(4-Fluorophenyl)-7-{[(2-methoxyethyl)amino]methyl}-1H-pyrazolo[3,4-c]pyridin-5-yl]-3-[(1R)-1-phenylethyl]urea,
1-[7-(aminomethyl)-1-(4-fluorophenyl)-1H-pyrazolo[3,4-c]pyridin-5-yl]-3-[(1R)-1-phenylethyl]urea,
1-[7-({[2-(dimethylamino)ethyl]amino}methyl)-1-(4-fluorophenyl)-1H-pyrazolo[3,4-c]pyridin-5-yl]-3-[(1R)-1-phenylethyl]urea,
1-[7-{[(2-methoxyethyl)amino]methyl}-1-(2-methylpyridin-4-yl)-1H-pyrazolo[3,4-c]pyridin-5-yl]-3-[(1R)-1-phenylethyl]urea, 1-[7-({[2-(dimethylamino)ethyl]amino}methyl)-1-(2-methylpyridin-4-yl)-1H-pyrazolo[3,4-c]pyridin-5-yl]-3-[(1R)-1-phenylethyl]urea, 1-[1-(2-Cyanoethyl)-7-(hydroxymethyl)-1H-pyrazolo[3,4-c]pyridin-5-yl]-3-[(1R)-1-phenylethyl]urea, N-{[1-Methyl-5-({[(1R)-1-phenylethyl]carbamoyl}amino)-1H-pyrazolo[3,4-c]pyridin-7-yl]methyl}prop-2-enamide, N-{[1-(4-Fluorophenyl)-5-({[(1R)-1-phenylethyl]carbamoyl}amino)-1H-pyrazolo[3,4-c]pyridin-7-yl]methyl)}acetamide, Methyl {[1-(4-fluorophenyl)-5-({[(1R)-1-phenylethyl]carbamoyl}amino)-1H-pyrazolo[3,4-c]pyridin-7-yl]methyl}carbamate,

[1-(4-Fluorophenyl)-5-({[(1R)-1-phenylethyl]carbamoyl}amino)-1H-pyrazolo[3,4-c]pyridin-7-yl]methyl ethylcarbamate, N-[(2S)-2-{[(1-Methyl-1H-pyrazolo[3,4-c]pyridin-5-yl)carbamoyl]amino}-2-phenylethyl]prop-2-enamide, and N-{2-[1-Methyl-5-({[(1R)-1-phenylethyl]carbamoyl}amino)-1H-pyrazolo[3,4-c]pyridin-7-yl]ethyl}prop-2-enamide.

5. A composition for treating cancer by inhibiting ERK comprising a compound of claim 1 and a pharmaceutically acceptable carrier.

6. A method for treating cancer by inhibiting ERK comprising administering to ma patient in need there of a composition of claim 5.

* * * * *